(12) United States Patent
Duwenig et al.

(10) Patent No.: US 7,902,423 B2
(45) Date of Patent: Mar. 8, 2011

(54) EXPRESSION CASSETTES FOR SEED-PREFERENTIAL EXPRESSION THAT UTILIZE THE PROMOTER FROM A FLAX TONOPLAST INTRINSIC PROTEIN GENE

(75) Inventors: Elke Duwenig, Ludwigshafen (DE); Linda Patricia Loyall, Mannheim (DE); Christine Müller, Walldorf (DE)

(73) Assignee: BASF Plant Science GmbH, Ludwigshafen (DE)

( * ) Notice: Subject to any disclaimer, the term of this patent is extended or adjusted under 35 U.S.C. 154(b) by 377 days.

(21) Appl. No.: 11/918,837

(22) PCT Filed: Apr. 19, 2006

(86) PCT No.: PCT/EP2006/061666
§ 371 (c)(1),
(2), (4) Date: Oct. 18, 2007

(87) PCT Pub. No.: WO2006/111541
PCT Pub. Date: Oct. 26, 2006

(65) Prior Publication Data
US 2009/0241230 A1    Sep. 24, 2009

(30) Foreign Application Priority Data
Apr. 20, 2005  (EP) .................... 05103195

(51) Int. Cl.
*C12N 15/82* (2006.01)
*C12N 5/04* (2006.01)
*C12N 1/21* (2006.01)
*C07H 21/04* (2006.01)

(52) U.S. Cl. ......... 800/287; 800/278; 800/295; 800/298; 435/419; 435/320.1; 435/468; 435/252.2; 435/252.3; 536/24.1; 536/23.1

(58) Field of Classification Search ................ None
See application file for complete search history.

(56) References Cited

U.S. PATENT DOCUMENTS

| | | |
|---|---|---|
| 4,885,357 A | 12/1989 | Larkins et al. |
| 4,886,878 A | 12/1989 | Larkins et al. |
| 5,003,045 A | 3/1991 | Hoffman |
| 5,057,419 A | 10/1991 | Martin et al. |
| 5,093,249 A | 3/1992 | Nakajima et al. |
| 5,147,792 A | 9/1992 | Perchorowicz et al. |
| 5,215,912 A | 6/1993 | Hoffman |
| 5,229,114 A | 7/1993 | Cregan et al. |
| 5,258,300 A | 11/1993 | Glassman et al. |
| 5,270,200 A | 12/1993 | Sun et al. |
| 5,298,421 A | 3/1994 | Davies et al. |
| 5,304,481 A | 4/1994 | Davies et al. |
| 5,344,771 A | 9/1994 | Davies et al. |
| 5,367,110 A | 11/1994 | Galili et al. |
| 5,443,974 A | 8/1995 | Hitz et al. |
| 5,508,468 A | 4/1996 | Lundquist et al. |
| 5,512,466 A | 4/1996 | Klee et al. |
| 5,512,482 A | 4/1996 | Voelker et al. |
| 5,530,186 A | 6/1996 | Hitz et al. |
| 5,534,421 A | 7/1996 | Livshits et al. |
| 5,543,576 A | 8/1996 | van Ooijen et al. |
| 5,552,306 A | 9/1996 | Thomas et al. |
| 5,576,203 A | 11/1996 | Hoffman |
| 5,589,616 A | 12/1996 | Hoffman |
| 5,608,149 A | 3/1997 | Barry et al. |
| 5,614,393 A | 3/1997 | Thomas et al. |
| 5,633,436 A | 5/1997 | Wandelt |
| 5,639,790 A | 6/1997 | Voelker et al. |
| 5,654,402 A | 8/1997 | Cahoon et al. |
| 5,659,645 A | 8/1997 | Satake |
| 5,663,068 A | 9/1997 | Thomas et al. |
| 5,689,041 A | 11/1997 | Mariani et al. |
| 5,689,050 A | 11/1997 | Thomas et al. |
| 5,705,391 A | 1/1998 | Cahoon et al. |
| 5,750,879 A | 5/1998 | Ohtsuka et al. |
| 5,759,829 A | 6/1998 | Shewmaker et al. |
| 5,760,206 A | 6/1998 | Hitz et al. |
| 5,789,220 A | 8/1998 | Thomas et al. |
| 5,807,893 A | 9/1998 | Voelker et al. |
| 5,850,024 A | 12/1998 | Beach et al. |
| 5,856,157 A | 1/1999 | Craig et al. |
| 5,858,749 A | 1/1999 | Matthews et al. |
| 5,866,789 A | 2/1999 | Hildebrand et al. |
| 5,885,801 A | 3/1999 | Rao |

(Continued)

FOREIGN PATENT DOCUMENTS

WO    WO-90/01869 A1    3/1990

(Continued)

OTHER PUBLICATIONS

Ludevid et al. The expression pattern of the tomoplast intrinic protein gamma-TIP in *Arabidopsis thaliana* is correlated with cell enlargement. (1992) vol. 100; 1633-1639.*
Stalberg, et al. Deletion analysis of a 2S seed storage protein promoter of *Brassic napus* in transgenic tobacco. (1993) PMB; vol. 23, pp. 671-683.*
Gao, Y-P., et al., "Characterization and expression of plasma and tonoplast membrane aquaporins in primed seed of *Brassica napus* during germination under stress conditions", Plant Molecular Biology, 1999, vol. 40, pp. 635-644.
Höfte, H., et al., "Vegetative and seed-specific forms of tonoplast intrinsic protein in the vacuolar membrane of *Arabidopsis thaliana*", Plant Physiol., 1992, vol. 99, pp. 561-570.
Ludevid, D., et al., "The expression pattern of the tonoplast intrinsic protein γ-TIP in *Arabidopsis thaliana* is correlated with cell enlargement", Plant Physiol., 1992, vol. 100, pp. 1633-1639.
Yu, Q., et al., "Cloning of the promoter region of plasma membrane aquaporin *BnPIP1* from *Brassica napus* and its functional analysis", Science in China, 2003, vol. 46, No. 4, pp. 348-357.

(Continued)

*Primary Examiner* — Cathy Kingdon Worley
(74) *Attorney, Agent, or Firm* — Connolly Bove Lodge & Hutz, LLP

(57) ABSTRACT

The present invention relates to expression cassettes comprising transcription regulating nucleotide sequences with seed-preferential or seed-specific expression profiles in plants obtainable from a tonoplast intrinsic protein, said gene being selected from the group consisting of the *Arabidopsis thaliana* tonoplast intrinsic protein alpha described by the GenBank *Arabidopsis thaliana* genome loci At1g73190 and its orthologous genes from *Brassica napus* and *Linum usitatissimum*.

18 Claims, 1 Drawing Sheet

U.S. PATENT DOCUMENTS

| | | | |
|---|---|---|---|
| 5,885,802 A | 3/1999 | Rao | |
| 5,914,450 A | 6/1999 | Blechl et al. | |
| 5,939,599 A | 8/1999 | Chui et al. | |
| 5,942,660 A | 8/1999 | Gruys et al. | |
| 5,945,585 A | 8/1999 | Hitz et al. | |
| 5,952,544 A | 9/1999 | Browse et al. | |
| 5,955,329 A | 9/1999 | Yuan et al. | |
| 5,955,650 A | 9/1999 | Hitz | |
| 5,958,745 A | 9/1999 | Gruys et al. | |
| 5,965,727 A | 10/1999 | Song et al. | |
| 5,985,605 A | 11/1999 | Cheng et al. | |
| 5,990,384 A | 11/1999 | Bagga et al. | |
| 5,990,389 A | 11/1999 | Rao et al. | |
| 5,998,700 A | 12/1999 | Lightfoot et al. | |
| 6,011,199 A | 1/2000 | Speirs et al. | |
| 6,040,160 A | 3/2000 | Kojima et al. | |
| 6,043,411 A | 3/2000 | Nishizawa et al. | |
| 6,051,754 A | 4/2000 | Knutzon | |
| 6,072,103 A | 6/2000 | Wu et al. | |
| 6,075,183 A | 6/2000 | Knutzon et al. | |
| 6,080,560 A | 6/2000 | Russell et al. | |
| 6,100,091 A | 8/2000 | Cahoon et al. | |
| 6,107,051 A | 8/2000 | Job et al. | |
| 6,107,063 A | 8/2000 | Moeckel et al. | |
| 6,110,891 A | 8/2000 | Pusztai et al. | |
| 6,117,677 A | 9/2000 | Thompson et al. | |
| 6,147,279 A | 11/2000 | Poulsen | |
| 6,166,292 A | 12/2000 | Osumi et al. | |
| 6,171,640 B1 | 1/2001 | Bringe | |
| 6,172,106 B1 | 1/2001 | Forse et al. | |
| 6,177,613 B1 * | 1/2001 | Coughlan et al. | 800/287 |
| 6,194,167 B1 | 2/2001 | Browse et al. | |
| 6,194,636 B1 | 2/2001 | McElroy et al. | |
| 6,207,879 B1 | 3/2001 | McElroy et al. | |
| 6,232,122 B1 | 5/2001 | Poulsen | |
| 6,232,526 B1 | 5/2001 | McElroy et al. | |
| 6,380,466 B1 | 4/2002 | Facciotti | |
| 6,388,174 B1 | 5/2002 | Wakasa et al. | |
| 6,426,446 B1 | 7/2002 | McElroy et al. | |
| 6,429,357 B1 | 8/2002 | McElroy et al. | |
| 6,433,252 B1 | 8/2002 | Kriz et al. | |
| 6,437,217 B1 | 8/2002 | McElroy et al. | |
| 6,444,876 B1 | 9/2002 | Lassner et al. | |
| 6,476,295 B2 | 11/2002 | Barry et al. | |
| 6,515,201 B2 | 2/2003 | Anderson et al. | |
| 6,531,648 B1 | 3/2003 | Lanahan et al. | |
| 6,537,750 B1 | 3/2003 | Shorrosh | |
| 6,583,338 B2 | 6/2003 | McElroy et al. | |
| 7,297,847 B1 | 11/2007 | Ludevid et al. | |
| 2003/0028917 A1 | 2/2003 | Gruys et al. | |
| 2003/0028923 A1 | 2/2003 | Lardizabal et al. | |
| 2003/0115632 A1 | 6/2003 | Lardizabal et al. | |

FOREIGN PATENT DOCUMENTS

| | | |
|---|---|---|
| WO | WO-91/13993 A1 | 9/1991 |
| WO | WO-92/14822 A1 | 9/1992 |
| WO | WO-93/08682 A1 | 5/1993 |
| WO | WO-94/20628 A2 | 9/1994 |
| WO | WO-95/19442 A1 | 7/1995 |
| WO | WO-96/17064 A1 | 6/1996 |
| WO | WO-97/22703 A2 | 6/1997 |
| WO | WO-97/26366 A1 | 7/1997 |
| WO | WO-97/28247 A2 | 8/1997 |
| WO | WO-97/35023 A2 | 9/1997 |
| WO | WO-98/26064 A2 | 6/1998 |
| WO | WO-98/55601 A2 | 12/1998 |
| WO | WO-99/02656 | 1/1999 |
| WO | WO-99/06581 A1 | 2/1999 |
| WO | WO-99/11800 A1 | 3/1999 |
| WO | WO-99/40209 A1 | 8/1999 |
| WO | WO-99/49058 A2 | 9/1999 |
| WO | WO-00/10380 A1 | 3/2000 |
| WO | WO-00/19839 A2 | 4/2000 |
| WO | WO-00/32757 A2 | 6/2000 |
| WO | WO-02/057471 A2 | 7/2002 |
| WO | WO-02/102970 A2 | 12/2002 |
| WO | WO-03/008540 A2 | 1/2003 |
| WO | WO-2008/034648 A1 | 3/2008 |

PUBLICATIONS

Johanson, U., et al., "The complete set of genes encoding major intrinsic proteins in *Arabidopsis* provides a framework for a new nomenclature for major intrinsic proteins in plants", Plant Physiology, 2001, vol. 126, pp. 1358-1369.

Sun, M-H., et al., "Distribution of water channel protein RWC3 and its regulation by GA and Sucrose in rice", Acta Botanica Sinica, 2004, vol. 46, No. 9, pp. 1056-1064.

Johnson, K. D., et al., "An abundant, highly conserved tonoplast protein in seeds", Plant Physiol., 1989, vol. 91, pp. 1006-1013.

Van De Loo, F. J., et al., "Expressed sequence tags from developing castor seeds", Plant Physiol., 1995, vol. 108, pp. 1141-1150.

Phillips, A. L., et al., "Cloning of two gibberellin-regulated cDNAs from *Arabidopsis thaliana* by subtractive hybridization: expression of the tonoplast water channel, γ-TIP, is increased by $GA_3$", Plant Molecular Biology, 1994, vol. 24, pp. 603-615.

Daniels, M. J., et al., "Characterization of a new vacuolar membrane aquaporin sensitive to mercury at a unique site", The Plant Cell, 1996, vol. 587-599.

Mitsuhashi, N., et al., "A novel membrane protein that is transported to protein storage vacuoles via precursor-accumulating vesicles", The Plant Cell, 2001, vol. 13, pp. 2361-2372.

Quigley, F., et al., "From genome to function: the *Arabidopsis* aquaporins", Genome Biology, 2001, vol. 3, No. 1, pp. 1-17.

Keegstra, K., "Transport and routing of proteins in to chloroplasts", Cell, 1989, vol. 56, pp. 247-253.

Nawrath, C., et al., "Targeting of the polyhydroxybutyrate biosynthetic pathway to the plastids of *Arabidopsis thaliana* results in high levels of polymer accumulation", Proc. Natl. Acad. Sci. USA, 1994, vol. 91, pp. 12760-12764.

Xia, T., et al., "A monofunctional prephenate dehydrogenase created by cleavage of the 5' 109 bp of the *tyrA* gene from *Erwinia herbicola*", Journal of General Microbiology, 1992, vol. 138, pp. 1309-1316.

Lois, L. M., et al., "Cloning and characterization of a gene from *Escherichia coli* encoding a transketolase-like enzyme that catalyzes the synthesis of D-1-deoxylulose 5-phosphate, a common precursor for isoprenoid, thiamin, and pyridoxol biosynthesis", Proc. Natl. Acad. Sci. USA, 1998, vol. 95, pp. 2105-2110.

Takahashi, S., et al., "A 1-deoxy-D-xylulose 5-phosphate reductoisomerase catalyzing the formation of 2-C-methyl-D-erythritol 4-phosphate in an alternative nonmevalonate pathway for terpenoid biosynthesis", Proc. Natl. Acad. Sci. USA, 1998, vol. 95, pp. 9879-9884.

Norris, S. R., et al., "Complementation of the *Arabidopsis pds 1* mutation with the gene encoding *p-Hydroxyphenylpyruvate* dioxygenase", Plant Physiol., 1998, vol. 117, pp. 1317-1323.

Scolnik, P. A., et al., "Nucleotide sequence of an *Arabidopsis* cDNA for geranylgeranyl pyrophosphate synthase", Plant Physiol., 1994, vol. 104, pp. 1469-1470.

Smith, F. W., et al., "The cloning of two *Arabidopsis* genes belonging to a phosphate transporter family", The Plant Journal, 1997, vol. 11, No. 1, pp. 83-92.

Saint-Guily, A., et al., "Complementary DNA Sequence of an adenylate translocator from *Arabidopsis thaliana*", Plant Physiol., 1992, vol. 100, pp. 1069-1071.

Sato, S., et al., "Structural analysis of *Arabidopsis thaliana* chromosome 5. X. sequence features of the regions of 3,076,755 bp covered by sixty P1 and TAC clones", DNA Research, 2000, vol. 7, pp. 31-63.

Higo, K., et al., "Plant cis-acting regulatory DNA elements (PLACE) database: 1999", Nucleic Acids Research, 1999, vol. 27, No. 1, pp. 297-300.

Jiang, L., et al., "Integral membrane protein sorting to vacuoles in plants cells: evidence for two pathways", The Journal of Cell Biology, 1998, vol. 143, No. 5, pp. 1183-1199.

Waterman, M. D., "Multiple Sequence Alignment", Chapman & Hall, 1995, Chapters 10 & 11, pp. 233-299.

"A. thaliana gene fro tonoplast intrinsic protein alpha-TIP(Ara)", EMBL Database, Accession No. X63551, Jan. 29, 1992.

"*Arabidopsis thaliana* tonoplast intrinsic protein (apla-TIP) gene, complete cds.", EMBL Database, Accession No. M84343 Jan. 27, 1992.

"Phytase gene locus of plasmids pAF 2-3, pAF 2-6, pAF 2-7.", EMBL Database, Accession No. A19451, Jun. 10, 1994.

"N. pseudonarcissus mRNA for phytoene desaturase", EMBL Database, Accession No. X78815, Apr. 18, 1995.

"Medicago sativa acetyl-CoA carboxylase (ACCase) mRNA, complete cds.", EMBL Database, Accession No. L25042, Jun. 28, 1995.

"*Arabidopsis thaliana* chromosome 1 BAC T18K17 genomic sequence, complete sequence", EMBL Database, Accession No. AC010556, Sep. 17, 1999.

"Aquaporin TIP3.1 (Tonoplast intrinsic protein 3.1) (Alpha-tonoplast intrinsic protein) (Alpha-TIP).", Uniprot Database, Accession No. P26587, Aug. 1, 1992.

"Chicken Ig Lambda Light Chain Gene, Silencer, Enhancer and Matrix Associated Region", EMBL Database, Accession No. L26587, Dec. 9, 1993.

Kridl, J. C., et al., "Isolation and Characterization of an Expressed Napin Gene from *Brassica rapa*", Seed Science Research, 1991, vol. 1, pp. 209-219.

Truksa, M., et al., "Molecular Analysis of Flax 2S Storage Protein Conlinin and Seed Specific Activity of its Promoter", Plant Physiology and Biochemistry, 2003, vol. 41, pp. 141-147.

"QGE6H16.yg.ab1 QG_EFGHJ Lettuce serriola Lactuca serriola cDNA Clone, QGE6H16, mRNA Sequence", EMBL Database, Accession No. BQ985310, Aug. 24, 2002.

Partial European Search Report Issued in European Application No. 09 17 2759 Dated Jul. 16, 2010.

* cited by examiner

US 7,902,423 B2

EXPRESSION CASSETTES FOR SEED-PREFERENTIAL EXPRESSION THAT UTILIZE THE PROMOTER FROM A FLAX TONOPLAST INTRINSIC PROTEIN GENE

RELATED APPLICATIONS

This application is a national stage application (under 35 U.S.C. 371) of PCT/EP2006/061666 filed Apr. 19, 2006, which claims benefit of European application 05103195.3 filed Apr. 20, 2005.

SEQUENCE LISTING SUBMISSION

The Sequence Listing associated with this application is filed in electronic format via EFS-Web and hereby incorporated by reference into the specification in its entirety. The name of the text file containing the Sequence Listing is Replacement_Sequence_Listing_13987_00070. The size of the text file is 87 KB, and the text file was created on Dec. 29, 2009.

FIELD OF THE INVENTION

The present invention relates to expression cassettes comprising transcription regulating nucleotide sequences with seed-preferential or seed-specific expression profiles in plants obtainable from a tonoplast intrinsic protein, said gene being selected from the group consisting of the *Arabidopsis thaliana* tonoplast intrinsic protein alpha described by the GenBank *Arabidopsis thaliana* genome loci At1g73190 and its orthologous genes from *Brassica napus* and *Linum usitatissimum*.

BACKGROUND OF THE INVENTION

The Major Intrinsic Protein (MIP) family is large and diverse, possessing over 100 members that all form transmembrane channels. MIPs facilitate the passive transport of small polar molecules across membranes. These channel proteins function in water, small carbohydrate (e.g., glycerol), urea, $NH_3$, $CO_2$ and possibly ion transport by an energy independent mechanism. MIPs constitute a very old family of proteins and are found ubiquitously in all kinds of living organisms, including bacteria, fungi, animals, and plants. Phylogenetic clustering of the proteins is largely according to phylum of the organisms of origin, but one to three clusters are observed for each phylogenetic kingdom (plants, animals, yeast, bacteria and archaea). One of the plant clusters includes only tonoplast (TIP) proteins, with another includes plasma membrane (PIP) proteins (for a review see Urban Johanson (2001) Plant Physiol. 126(4): 1358-1369).

In the genomic sequence of *Arabidopsis*, 35 different MIP-encoding genes were identified. Based on sequence similarity, these 35 proteins are divided into four different subfamilies: plasma membrane intrinsic proteins, tonoplast intrinsic proteins, NOD26-like intrinsic proteins also called NOD26-like MIPs, and the recently discovered small basic intrinsic proteins. In *Arabidopsis*, there are 13 plasma membrane intrinsic proteins, 10 tonoplast intrinsic proteins, nine NOD26-like intrinsic proteins, and three small basic intrinsic proteins. The *Arabidopsis* TIP proteins are encoded by the genes described by the following locii: At2g36830 (TIP1;1 tonoplast intrinsic protein gamma 1), At1g73190 (TIP1;2 tonoplast intrinsic protein alpha), At4g01470 (TIP1;3 tonoplast intrinsic protein gamma 3), At3g16240 (TIP2;1 tonoplast intrinsic protein delta 1), At4g17340 (TIP2;2 tonoplast intrinsic protein delta 2), At5g47450 (TIP2;3 tonoplast intrinsic protein delta 3), At1g73190 (TIP3;1 tonoplast intrinsic protein alpha), At1g17810 (TIP3;2 tonoplast intrinsic protein beta), At2g25810 (TIP4;1 tonoplast intrinsic protein epsilon), At3g47440 (TIP5;1 tonoplast intrinsic protein zeta). For nomenclature of the various TIP proteins see Urban Johanson (2001) Plant Physiol. 126(4): 1358-1369.

With few exceptions, a strict organ-specific expression has not been found for *Arabidopsis* MIP genes. However, preferential expression in seeds/embryos, roots, and shoots has been found for some TIP genes (profiles compared in Urban Johanson (2001) Plant Physiol. 126(4): 1358-1369). AtTIP3;1 (TIP alpha) are described to be seed- and embryo-specific AQP in *Arabidopsis* and other plants such as *Phaseolus vulgaris* and *Ricinus communis* (Johnson K D et al. (1989) Plant Physiol 91:1006-1013; van de Loo F J et al. (1995) Plant Physiol 108:1141-1150). AtTIP1;1 is expressed mainly in the elongation zone of roots and to lower levels in various shoot organs (Höfte H et al. (1992) Plant Physiol 99:561-570; Ludevid D et al. (1992) Plant Physiol 100:1633-1639). It is interesting that this elongation-associated AQP can be induced by gibberellic acid, which is known to promote cell growth in *Arabidopsis* dwarf mutants (Phillips A L et al. (1994) Plant Mol Biol 24:603-615). In contrast, AtTIP2;1 is mainly expressed in shoots and to a lower extent in roots (Daniels M J et al. (1996) Plant Cell 8:587-599). No expression profile is so far reported for the AtTIP1;2 gene. Based on the above described heterogeneity of the expression profiles a prediction of the specificity for that gene does not seem to be possible.

It is however very difficult to distinguish between the certain TIP homologous proteins (e.g., between alpha and beta) and therefore difficult to predict the expression profile for a TIP gene. For example the TIP-alpha und beta genes are very similar on protein level (see FIG. 1) but characterized by distinct expression profiles. While the so-called TIP-alpha proteins are more expressed in seed the TIP-beta proteins are expressed (for *Arabidopsis*) also in rosette leafs and etiolated seedlings (Naoto Mitsuhashi et al. The Plant Cell, Vol. 13, 2361-2372, October 2001; Jiang L, Rogers J C., J Cell Biol. 1998 Nov. 30; 143(5):1183-99; Quigley F et al. Genome Biology 2001, 3(1):research0001.1-0001.17).

Furthermore, it is not guaranteed that the expression profile of an endogenous promoter for its endogenous gene can be easily utilized for transgenic expression techniques. Often essential elements are either in introns or in trans-regions, which are removed during the isolation of the promoter region, thereby significantly changing the expression profile of the promoter.

Manipulation of plants to alter and/or improve phenotypic characteristics (such as productivity or quality) requires the expression of heterologous genes in plant tissues. Such genetic manipulation relies on the availability of a means to drive and to control gene expression as required. For example, genetic manipulation relies on the availability and use of suitable promoters which are effective in plants and which regulate gene expression so as to give the desired effect(s) in the transgenic plant. For numerous applications in plant biotechnology a tissue-specific expression profile is advantageous, since beneficial effects of expression in one tissue may have disadvantages in others. Seed-preferential or seed-specific promoters are useful for expressing genes as well as for producing large quantities of protein, for expressing oils or proteins of interest, e.g., antibodies, genes for increasing the nutritional value of the seed and the like. It is advantageous to have the choice of a variety of different promoters so that the most suitable promoter may be selected for a particular gene, construct, cell, tissue, plant or environment. Moreover, the increasing interest in cotransforming plants with multiple plant transcription units (PTU) and the potential problems associated with using common regulatory sequences for these purposes merit having a variety of promoter sequences available.

There is, therefore, a great need in the art for the identification of novel sequences that can be used for expression of selected transgenes in economically important plants. It is thus an objective of the present invention to provide new and alternative expression cassettes for seed-preferential or seed-specific expression of transgenes in plants. The objective is solved by the present invention.

SUMMARY OF THE INVENTION

A first embodiment of the invention relates to an expression cassette for regulating seed-specific or seed-preferential expression in plants comprising
a) at least one transcription regulating nucleotide sequence derived from a plant tonoplast intrinsic protein gene, said gene being selected from the group consisting of the *Arabidopsis thaliana* tonoplast intrinsic protein alpha described by the GenBank *Arabidopsis thaliana* genome loci At1g73190 and its orthologous genes from *Brassica napus* and *Linum usitatissimum* and functionally linked thereto
b) at least one nucleic acid sequence which is heterologous in relation to said transcription regulating nucleotide sequence.

The transcription nucleotide sequence may be obtained or is obtainable from plant genomic DNA from a gene (e.g., from plant genomic DNA) encoding a polypeptide comprising an amino acid sequence which has at least 90% amino acid sequence identifying to a polypeptide selected from the group described by SEQ ID NO: 13, 15, 17, or 19. Preferably, said orthologous protein has furthermore the same enzymatic activity than the protein encoded by the *Arabidopsis thaliana* locus At1g73190.

Preferably, the transcription regulating nucleotide sequence is selected from the group of sequences consisting of the sequences described by SEQ ID NOs: 1, 2, 3, 4, 5, 6, 7, 8, 9, 10, or 11 or any derivative or fragment thereof. More preferably the transcription regulating nucleotide sequence is selected from the group of sequences consisting of
i) the sequence described by SEQ ID NOs: 1, 2, 3, 4, 5, 6, 7, 8, 9, 10, or 11, and
ii) a fragment of at least 50 consecutive bases, preferably at least 100 consecutive bases, more preferably at least 250 consecutive bases, most preferably at least 500 consecutive bases of a sequence described by any of SEQ ID NO: 1, 2, 3, 4, 5, 6, 7, 8, 9, 10, or 11, and
iii) a nucleotide sequence having substantial similarity (preferably with a sequence identity of at least 50%) to a transcription regulating nucleotide sequence described by SEQ ID NO: 1, 2, 3, 4, 5, 6, 7, 8, 9, 10, or 11, and
iv) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a transcription regulating nucleotide sequence described by SEQ ID NO: 1, 2, 3, 4, 5, 6, 7, 8, 9, 10, or 11, or the complement thereof;
v) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 4, 5, 6, 7, 8, 9, 10, or 11, or the complement thereof;
vi) a nucleotide sequence which is the complement or reverse complement of any of the previously mentioned nucleotide sequences under i) to v).

Preferably, such derivative or fragment (e.g., the sequences specified under ii), iii), iv) v) and vi) above) is capable to modify transcription in a plant cell or organism, more preferably said derivative or fragment (e.g., the sequences specified under ii), iii), iv) v) and vi) above) has substantially the same transcription regulating activity as the transcription regulating nucleotide sequence described by SEQ ID NO: 1, 2, 3, 4, 5, 6, 7, 8, 9, 10, or 11. Preferably, the derivative or fragment (e.g., the sequences specified under iii) above) has a sequence identity of at least 50% or 60%, preferably at least 70% or 80%, more preferably at least 90% or 95%, most preferably at least 98% to a sequence described by SEQ ID NO: 1, 2, 3, 4, 5, 6, 7, 8, 9, 10, or 11. Preferably, the nucleotide sequences identify is determined by using the BlastN program (version 1.4.7 or later) with its default parameters (word length (W) of 11, an expectation (E) of 10, a cutoff of 100, M=5, N=−4, and a comparison of both strands) or any equivalent program.

Preferably, the derivatives or fragments (e.g., the sequences specified under iv) or v) above) are hybridizing under stringent conditions (i.e. low stringent, preferably medium stringent, most preferably high stringent conditions) with the specified target sequence.

Another embodiment of the invention relates to derivatives of the transcription regulating sequences from *Arabidopsis thaliana, Brassica napus* and *Linum usitatissimum* as disclosed herein. A derivative of the *Arabidopsis thaliana* transcription regulating nucleotide sequence (SEQ ID NO: 1) may comprise at least two promoter motifs selected from the group of motifs consisting of the sequences described by SEQ ID NO: 35, 36, 38, 39, 40, 41, 43, 44, 45, 46, 47, 48, 49, 50, 51, 52, and 55. More preferably a derivative of the *Arabidopsis thaliana* transcription regulating nucleotide sequence comprises at least two promoter motifs selected from the group of motifs consisting of the sequences described by SEQ ID NO: 77, 78, 79, 83, 82, 84, 85, 86, 89, 90, 91, 92, 93, 97, 101, 102, 103, 104, 105, 106, 107, 108, 109, 110, and 114. Most preferably a derivative of the *Arabidopsis thaliana* transcription regulating nucleotide sequence comprises at least two promoter motifs selected from the group of motifs consisting of the sequences described by SEQ ID NO: 145, 146, 148, 153, 151, 156, 160, 162, 167, 169, 170, 171, 172, 185, 186, 188, 192, 200, 201, 202, 203, 204, 205, 208, 209, 210, 211, 212, and 216.

A derivative of the *Brassica napus* transcription regulating nucleotide sequence (SEQ ID NO: 3) may comprise at least two promoter motifs selected from the group of motifs consisting of the sequences described by SEQ ID NO: 36, 36, 38, 39, 40, 41, 44, 46, 47, 53, 56, 58, 59, 62, 64, 67, 68, and 71. More preferably a derivative of the *Brassica napus* transcription regulating nucleotide sequence comprises at least two promoter motifs selected from the group of motifs consisting of the sequences described by SEQ ID NO: 78, 80, 82, 83, 84, 85, 86, 90, 94, 97, 98, 99, 111, 115, 117, 118, 119, 122, 128, 132, 134, and 138. Most preferably a derivative of the *Brassica napus* transcription regulating nucleotide sequence comprises at least two promoter motifs selected from the group of motifs consisting of the sequences described by SEQ ID NO: 147, 149, 152, 154, 155, 157, 161, 163, 173, 174, 175, 176, 189, 193, 194, 196, 213, 217, 219, 220, 221, 224, 232, 236, 241, and 245.

A derivative of the *Linum usitatissimum* transcription regulating nucleotide sequence 1 (SEQ ID NO: 6) may comprise at least two promoter motifs selected from the group of motifs consisting of the sequences described by SEQ ID NO: 39, 41, 44, 45, 46, 47, 54, 62, 63, 65, 66, 67, 69, 70, 71, 72, and 73. More preferably a derivative of the *Linum usitatissimum* transcription regulating nucleotide sequence 1 comprises at least two promoter motifs selected from the group of motifs consisting of the sequences described by SEQ ID NO: 84, 87, 90, 92, 95, 96, 98, 100, 112, 123, 126, 127, 129, 130, 131, 133, 135, 137, 139, 140, 141, 142, 143, and 144. Most preferably a derivative of the *Linum usitatissimum* transcription regulating nucleotide sequence 1 comprises at least two promoter motifs selected from the group of motifs consisting of the sequences described by SEQ ID NO: 158, 164, 177, 178, 179, 180, 184, 187, 190, 191, 195, 197, 214, 225, 229, 230, 233, 234, 235, 238, 239, 240, 242, 244, 246, 247, 249, 251, 253, and 254.

A derivative of the *Linum usitatissimum* transcription regulating nucleotide sequence 2 (SEQ ID NO: 9) comprises at least two promoter motifs selected from the group of motifs consisting of the sequences described by SEQ ID NO: 37, 39, 41, 42, 43, 44, 47, 47, 51, 54, 57, 60, 61, 62, 63, 67, 70, 72, 73, and 74. More preferably a derivative of the *Linum usitatissimum* transcription regulating nucleotide sequence 2 comprises at least two promoter motifs selected from the group of motifs consisting of the sequences described by SEQ ID NO: 81, 84, 87, 88, 89, 90, 100, 106, 106, 113, 116, 120, 121, 123, 124, 125, 127, 132, 136, 140, 141, and 142. Most preferably a derivative of the *Linum usitatissimum* transcription regulating nucleotide sequence 2 comprises at least two promoter motifs selected from the group of motifs consisting of the sequences described by SEQ ID NO: 150, 159, 165, 166, 168, 181, 182, 183, 198, 199, 206, 207, 215, 218, 222, 223, 226, 227, 228, 231, 237, 243, 248, 250, and 252.

A derivative of one of the promoters may also comprise motifs from more than one of the promoters disclosed herein. Accordingly another embodiment of the invention a derivative of a transcription regulating nucleotide sequence of the invention comprises at least two promoter motifs selected from the group of motifs consisting of the sequences described by SEQ ID NO: 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, and 76. More preferably a derivative of a transcription regulating nucleotide sequence of the invention comprises at least two promoter motifs selected from the group of motifs consisting of the sequences described by SEQ ID NO: 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 124, 135, 136, 137, 138, 139, 140, 141, 142, 143, and 144. Most preferably a derivative of a transcription regulating nucleotide sequence of the invention comprises at least two promoter motifs selected from the group of motifs consisting of the sequences described by SEQ ID NO: 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 231, 232, 233, 234, 235, 235, 237, 238, 239, 240, 241, 242, 243, 244, 245, 246, 247, 248, 249, 250, 251, 252, 253 and 254.

The transcription regulating sequences of the invention can be utilized to express any kind of nucleic acid sequence. For example, expression of the nucleic acid sequence can result in expression of a protein, or expression of a antisense RNA, sense or double-stranded RNA. Preferably, expression of the nucleic acid sequence confers to the plant an agronomically valuable trait.

Some of the transcription regulating sequences disclosed herein are novel as such (e.g., the sequences from *Brassica napus* and *Linum usitatissimum*). Accordingly, another embodiment of the invention relates to an isolated nucleotide sequence selected from the group of sequences consisting of the sequences described by SEQ ID NOs:3, 4, 5, 6, 7, 8, 9, 10, or 11 or any derivative or fragment thereof. More preferably the isolated nucleotide sequence or its derivative or fragment and is selected from the group of sequences consisting of i) the sequence described by SEQ ID NOs: 3, 4, 5, 6, 7, 8, 9, 10, or 11, and
ii) a fragment of at least 50 consecutive bases, preferably at least 100 consecutive bases, more preferably at least 250 consecutive bases, most preferably at least 500 consecutive bases of a sequence described by any of SEQ ID NO: 3, 4, 5, 6, 7, 8, 9, 10, or 11, and
iii) a nucleotide sequence having substantial similarity (preferably with a sequence identity of at least 50%) to a transcription regulating nucleotide sequence described by SEQ ID NO: 3, 4, 5, 6, 7, 8, 9, 10, or 11, and
iv) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M $NaPO_4$, 1 mM EDTA at 50° C. with washing in 1×SSC, 0.1% SDS at 50° C., more desirably still in 7% sodium dodecyl sulfate (SDS), 0.5 M $NaPO_4$, 1 mM EDTA at 50° C. with washing in 0.5×SSC, 0.1% SDS at 50° C., preferably in 7% sodium dodecyl sulfate (SDS), 0.5 M $NaPO_4$, 1 mM EDTA at 50° C. with washing in 0.1×SSC, 0.1% SDS at 50° C., more preferably in 7% sodium dodecyl sulfate (SDS), 0.5 M $NaPO_4$, 1 mM EDTA at 50° C. with washing in 0.1×SSC, 0.1% SDS at 65° C.) to a transcription regulating nucleotide sequence described by SEQ ID NO: 3, 4, 5, 6, 7, 8, 9, 10, or 11, or the complement thereof;
v) a nucleotide sequence capable of hybridizing (preferably under conditions equivalent to hybridization in 7% sodium dodecyl sulfate (SDS), 0.5 M $NaPO_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 3, 4, 5, 6, 7, 8, 9, 10, or 11, or the complement thereof;

vi) a nucleotide sequence which is the complement or reverse complement of any of the previously mentioned nucleotide sequences under i) to v).

Preferably, such derivative or fragment of said isolated nucleotide sequence (e.g., the sequences specified under ii), iii), iv) v) and vi) above) is capable to modify transcription in a plant cell or organism, more preferably said derivative or fragment (e.g., the sequences specified under ii), iii), iv) v) and vi) above) has substantially the same transcription regulating activity as the transcription regulating nucleotide sequence described by SEQ ID NO: 3, 4, 5, 6, 7, 8, 9, 10, or 11. Preferably, the derivative or fragment (e.g., the sequences specified under iii) above) has a sequence identity of at least 50% or 60%, preferably at least 70% or 80%, more preferably at least 90% or 95%, most preferably at least 98% to a sequence described by SEQ ID NO: 3, 4, 5, 6, 7, 8, 9, 10, or 11. Preferably, the derivative or fragment (e.g., the sequences specified under iv) or v) above) is hybridizing under stringent conditions (i.e. low stringent, preferably medium stringent, most preferably high stringent conditions) with the specified target sequence.

Another embodiment of the invention relates to a vector comprising an isolated nucleic acid sequence or an expression cassette of the invention. Yet another embodiment of the invention relates to a transgenic host cell or non-human organism comprising an expression cassette or a vector of the invention. Yet another embodiment of the invention relates to a transgenic plant or plant cell comprising a expression cassette or a vector of the invention. Preferably, said plant or plant cell is from a plant used for oil production (such as *Brassica napus, Brassica juncea, Linum sativum, Linum usitatissimum, Glycine max*, etc.).

The teachings of this invention (especially the promoter motifs and their orders found in the transcription regulating sequences of the invention) can be employed to generate synthetic promoter sequences. Accordingly another embodiment of the invention relates to a synthetic transcription regulating sequence comprising at least five promoter motifs selected from the group of motifs consisting of the sequences described by SEQ ID NO: 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, and 76. Preferably, said synthetic transcription regulating sequence comprises at least two promoter motifs selected from the group of motifs consisting of the sequences described by SEQ ID NO: 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 124, 135, 136, 137, 138, 139, 140, 141, 142, 143, and 144. More preferably, said synthetic transcription regulating sequence comprises at least five promoter motifs selected from the group of motifs consisting of the sequences described by SEQ ID NO: 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 231, 232, 233, 234, 235, 235, 237, 238, 239, 240, 241, 242, 243, 244, 245, 246, 247, 248, 249, 250, 251, 252, 253 and 254.

Yet another embodiment of the invention relates to a method for providing a synthetic transcription regulating nucleotide sequence characterized that isolated promoter motifs or cluster of promoter motifs are combined, said motifs comprising at least five promoter motifs selected from the group of motifs consisting of the sequences described by SEQ ID NO: 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, and 76. Preferably, for this method isolated promoter motifs or cluster of promoter motifs are combined that motifs comprising at least five promoter motifs selected from the group of motifs consisting of the sequences described by SEQ ID NO: 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 124, 135, 136, 137, 138, 139, 140, 141, 142, 143, and 144. More preferably, for this method isolated promoter motifs or cluster of promoter motifs are combined that motifs comprising at least five promoter motifs selected from the group of motifs consisting of the sequences described by SEQ ID NO: 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 231, 232, 233, 234, 235, 235, 237, 238, 239, 240, 241, 242, 243, 244, 245, 246, 247, 248, 249, 250, 251, 252, 253 and 254.

DEFINITIONS

Figure 1:
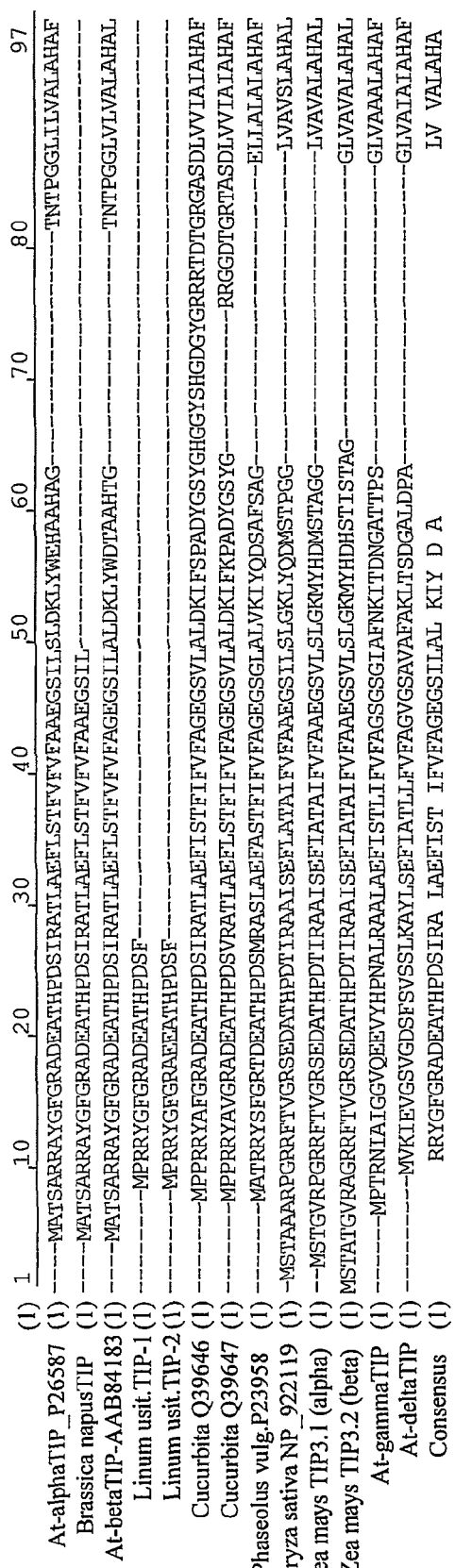
FIG. 1: Multiple sequence alignments of tonoplast intrinsic proteins. As demonstrated *Arabidopsis thaliana* TIP-alpha (At-alphaTIP_P26587) has little to no difference to the *Arabidopsis thaliana* TIP-beta protein (At-betaTIP-AAB84183). Accordingly a clear classification of similar proteins from other species (i.e. either to the alpha or the beta family) is not possible. In contrast the difference to other families (e.g., TIP-gamma) are significant. The sequences shown are: At-alphaTIP_P26587 (SEQ ID NO: 255); *Brassica napus*TIP (SEQ ID NO: 15); At-betaTIP-AAB84183 (SEQ ID NO: 256); *Linum usit.*TIP-1 (SEQ ID NO: 17); *Linum usit.*TIP-2 (SEQ ID NO: 19); *Cucurbita* Q39646 (SEQ ID NO: 257); *Cucurbita* Q39647 (SEQ ID NO: 258); *Phaseolus vulg.*P23958 (SEQ ID NO: 259); *Oryza sativa* NP 922119 (SEQ ID NO: 260); *Zea mays* TIP3.1 (alpha) (SEQ ID NO: 261); *Zea mays* TIP3.2 (beta) (SEQ ID NO: 262); At-gammaTIP (SEQ ID NO: 263); At-deltaTIP (SEQ ID NO: 264).

It is to be understood that this invention is not limited to the particular methodology, protocols, cell lines, plant species or genera, constructs, and reagents described as such. It is also to be understood that the terminology used herein is for the purpose of describing particular embodiments only, and is not intended to limit the scope of the present invention, which will be limited only by the appended claims. It must be noted that as used herein and in the appended claims, the singular forms "a," "and," and "the" include plural reference unless the context clearly dictates otherwise. Thus, for example, reference to "a vector" is a reference to one or more vectors and includes equivalents thereof known to those skilled in the art, and so forth.

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower).

As used herein, the word "or" means any one member of a particular list and also includes any combination of members of that list.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include non-expressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i.e., a cell not having a known mutation.

A "marker gene" encodes a selectable or screenable trait.

The term "chimeric gene" refers to any gene that contains
1) DNA sequences, including regulatory and coding sequences, that are not found together in nature, or
2) sequences encoding parts of proteins not naturally adjoined, or
3) parts of promoters that are not naturally adjoined.

Accordingly, a chimeric gene may comprise regulatory sequences and coding sequences that are derived from different sources, or comprise regulatory sequences, and coding sequences derived from the same source, but arranged in a manner different from that found in nature.

A "transgene" refers to a gene that has been introduced into the genome by transformation and is stably maintained. Transgenes may include, for example, genes that are either heterologous or homologous to the genes of a particular plant to be transformed. Additionally, transgenes may comprise native genes inserted into a non-native organism, or chimeric genes. The term "endogenous gene" refers to a native gene in its natural location in the genome of an organism. A "foreign" gene refers to a gene not normally found in the host organism but that is introduced by gene transfer.

An "oligonucleotide" corresponding to a nucleotide sequence of the invention, e.g., for use in probing or amplification reactions, may be about 30 or fewer nucleotides in length (e.g., 9, 12, 15, 18, 20, 21, 22, 23, or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use processes such as PCR. If required, probing can be done with entire restriction fragments of the gene disclosed herein which may be 100's or even 1000's of nucleotides in length.

The terms "polypeptide", "peptide", "oligopeptide", "polypeptide", "gene product", "expression product" and "protein" are used interchangeably herein to refer to a polymer or oligomer of consecutive amino acid residues. As used herein, the term "amino acid sequence" or a "polypeptide sequence" refers to a list of abbreviations, letters, characters or words representing amino acid residues. Amino acids may be referred to herein by either their commonly known three letter symbols or by the one-letter symbols recommended by the IUPAC-IUB Biochemical Nomenclature Commission. The abbreviations used herein are conventional one letter codes for the amino acids: A, alanine; B, asparagine or aspartic acid; C, cysteine; D aspartic acid; E, glutamate, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine; Z, glutamine or glutamic acid (see L. Stryer, Biochemistry, 1988, W. H. Freeman and Company, New York. The letter "x" as used herein within an amino acid sequence can stand for any amino acid residue.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation of the RNA within the cell to create the mature mRNA that can be translated into a protein.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

A "functional RNA" refers to an antisense RNA, ribozyme, or other RNA that is not translated.

The term "RNA transcript" refers to the product resulting from RNA polymerase catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA" (mRNA) refers to the RNA that is without introns and that can be translated into protein by the cell. "cDNA" refers to a single- or a double-stranded DNA that is complementary to and derived from mRNA.

"Transcription regulating nucleotide sequence", "regulatory sequences", and "suitable regulatory sequences", each refer to nucleotide sequences influencing the transcription, RNA processing or stability, or translation of the associated (or functionally linked) nucleotide sequence to be transcribed. The transcription regulating nucleotide sequence may have various localizations with the respect to the nucleotide sequences to be transcribed. The transcription regulating nucleotide sequence may be located upstream (5' non-coding sequences), within, or downstream (3' non-coding sequences) of the sequence to be transcribed (e.g., a coding sequence). The transcription regulating nucleotide sequences may be selected from the group comprising enhancers, promoters, translation leader sequences, introns, 5'-untranslated sequences, 3'-untranslated sequences, and polyadenylation signal sequences. They include natural and synthetic sequences as well as sequences, which may be a combination of synthetic and natural sequences. As is noted above, the term "transcription regulating nucleotide sequence" is not limited to promoters. However, preferably a transcription regulating nucleotide sequence of the invention comprises at least one promoter sequence (e.g., a sequence localized upstream of the transcription start of a gene capable to induce transcription of the downstream sequences). In one preferred embodiment the transcription regulating nucleotide sequence of the invention comprises the promoter sequence of the corresponding gene and—optionally and preferably—the native 5'-untranslated region of said gene. Furthermore, the 3'-untranslated region and/or the polyadenylation region of said gene may also be employed. As used herein, the term "cis-element" or "promoter motif" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element. The promoters of the present invention desirably contain cis-elements that can confer or modulate gene expression. Cis-elements can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of a cis-element can be further studied by mutagenesis (or substitution) of one or more nucleotides or by other conventional methods. Cis-elements can be obtained by chemical synthesis or by isolation from promoters that include such elements, and they can be synthesized with additional flanking nucleotides that contain useful restriction enzyme sites to facilitate subsequence manipulation.

"5' non-coding sequence" or "5'-untranslated sequence" or "-region" refers to a nucleotide sequence located 5' (upstream) to the coding sequence. It is present in the fully processed mRNA upstream of the initiation codon and may affect processing of the primary transcript to mRNA, mRNA stability or translation efficiency (Turner 1995).

"3' non-coding sequence" or "3'-untranslated sequence" or "-region" refers to nucleotide sequences located 3' (downstream) to a coding sequence and include polyadenylation signal sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., 1989.

The term "translation leader sequence" refers to that DNA sequence portion of a gene between the promoter and coding sequence that is transcribed into RNA and is present in the fully processed mRNA upstream (5') of the translation start codon. The translation leader sequence may affect processing of the primary transcript to mRNA, mRNA stability or translation efficiency.

"Signal peptide" refers to the amino terminal extension of a polypeptide, which is translated in conjunction with the polypeptide forming a precursor peptide and which is required for its entrance into the secretory pathway. The term "signal sequence" refers to a nucleotide sequence that encodes the signal peptide. The term "transit peptide" as used herein refers part of an expressed polypeptide (preferably to the amino terminal extension of a polypeptide), which is translated in conjunction with the polypeptide forming a precursor peptide and which is required for its entrance into a cell organelle (such as the plastids (e.g., chloroplasts) or mitochondria). The term "transit sequence" refers to a nucleotide sequence that encodes the transit peptide.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence, which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements, derived from different promoters found in nature, or even be comprised of synthetic DNA segments. A promoter may also contain DNA sequences that are involved in the binding of protein factors, which control the effectiveness of transcription initiation in response to physiological or developmental conditions.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant. Each of the transcription-activating elements do not exhibit an absolute tissue-specificity, but mediate transcriptional activation in most plant parts at a level of at least 1% of the level reached in the part of the plant in which transcription is most active.

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro et al. (1989). Typical regulated promoters useful in plants include but are not limited to safener-inducible promoters, promoters derived from the tetracycline-inducible system, promoters derived from salicylate-inducible systems, promoters derived from alcohol-inducible systems, promoters derived from glucocorticoid-inducible system, promoters derived from pathogen-inducible systems, and promoters derived from ecdysone-inducible systems.

"Tissue-specific promoter" refers to regulated promoters that are not expressed in all plant cells but only in one or more cell types in specific organs (such as leaves or seeds), specific tissues (such as embryo or cotyledon), or specific cell types (such as leaf parenchyma or seed storage cells). These also include promoters that are temporally regulated, such as in early or late embryogenesis, during fruit ripening in developing seeds or fruit, in fully differentiated leaf, or at the onset of senescence.

"Inducible promoter" refers to those regulated promoters that can be turned on in one or more cell types by an external stimulus, such as a chemical, light, hormone, stress, or a pathogen.

"Operably-linked" or "functionally linked" refers preferably to the association of nucleic acid sequences on single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. For example, in the case of antisense constructs, expression may refer to the transcription of the antisense DNA only. In addition, expression refers to the transcription and stable accumulation of sense (mRNA) or functional RNA. Expression may also refer to the production of protein.

"Specific expression" is the expression of gene products, which is limited to one or a few plant tissues (spatial limitation) and/or to one or a few plant developmental stages (temporal limitation). It is acknowledged that hardly a true specificity exists: promoters seem to be preferably switch on in some tissues, while in other tissues there can be no or only little activity. This phenomenon is known as leaky expression. However, with specific expression in this invention is meant preferable expression in one or a few plant tissues.

The "expression pattern" of a promoter (with or without enhancer) is the pattern of expression levels, which shows where in the plant and in what developmental stage transcription is initiated by said promoter. Expression patterns of a set of promoters are said to be complementary when the expression pattern of one promoter shows little overlap with the expression pattern of the other promoter. The level of expression of a promoter can be determined by measuring the 'steady state' concentration of a standard transcribed reporter mRNA. This measurement is indirect since the concentration of the reporter mRNA is dependent not only on its synthesis rate, but also on the rate with which the mRNA is degraded. Therefore, the steady state level is the product of synthesis rates and degradation rates. The rate of degradation can however be considered to proceed at a fixed rate when the transcribed sequences are identical, and thus this value can serve as a measure of synthesis rates. When promoters are compared in this way techniques available to those skilled in the art are hybridization S1-RNAse analysis, northern blots and competitive RT-PCR. This list of techniques in no way represents all available techniques, but rather describes commonly used procedures used to analyze transcription activity and expression levels of mRNA. The analysis of transcription start points in practically all promoters has revealed that there is usually no single base at which transcription starts, but rather a more or less clustered set of initiation sites, each of which accounts for some start points of the mRNA. Since this distribution varies from promoter to promoter the sequences of the reporter mRNA in each of the populations would differ from each other. Since each mRNA species is more or less prone to degradation, no single degradation rate can be expected for different reporter mRNAs. It has been shown for various eukaryotic promoter sequences that the sequence surrounding the initiation site ('initiator') plays an important role in determining the level of RNA expression directed by that specific promoter. This includes also part of the transcribed sequences. The direct fusion of promoter to reporter sequences would therefore lead to suboptimal levels of transcription. A commonly used procedure to analyze expression patterns and levels is through determination of the 'steady state' level of protein accumulation in a cell. Commonly used candidates for the reporter gene, known to those skilled in the art are beta-glucuronidase (GUS), chloramphenicol acetyl transferase (CAT) and proteins with fluorescent properties, such as green fluorescent protein (GFP) from *Aequora victoria*. In principle, however, many more proteins are suitable for this purpose, provided the protein does not interfere with essential plant functions. For quantification and determination of localization a number of tools are suited. Detection systems can readily be created or are available which are based on, e.g., immunochemical, enzymatic, fluorescent detection and quantification. Protein levels can be determined in plant tissue extracts or in intact tissue using in situ analysis of protein expression. Generally, individual transformed lines with one chimeric promoter reporter construct will vary in their levels of expression of the reporter gene. Also frequently observed is the phenomenon that such transformants do not express any detectable product (RNA or protein). The variability in expression is commonly ascribed to 'position effects', although the molecular mechanisms underlying this inactivity are usually not clear.

"Overexpression" refers to the level of expression in transgenic cells or organisms that exceeds levels of expression in normal or untransformed (non-transgenic) cells or organisms.

"Antisense inhibition" refers to the production of antisense RNA transcripts capable of suppressing the expression of protein from an endogenous gene or a transgene.

"Gene silencing" refers to homology-dependent suppression of viral genes, transgenes, or endogenous nuclear genes. Gene silencing may be transcriptional, when the suppression is due to decreased transcription of the affected genes, or post-transcriptional, when the suppression is due to increased turnover (degradation) of RNA species homologous to the affected genes (English 1996). Gene silencing includes virus-induced gene silencing (Ruiz et al. 1998).

The terms "heterologous DNA sequence", "exogenous DNA segment" or "heterologous nucleic acid," as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide sequence identity refers to the similarity between the nucleotide sequences of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U.K.), or by the comparison of sequence similarity between two nucleic acids or proteins.

The term "substantially similar" refers to nucleotide and amino acid sequences that represent functional and/or structural equivalents or orthologs of *Arabidopsis thaliana* sequences disclosed herein.

In its broadest sense, the term "substantially similar" when used herein with respect to a nucleotide sequence means that the nucleotide sequence is part of a gene which encodes a polypeptide having substantially the same structure and function as a polypeptide encoded by a gene for the reference nucleotide sequence, e.g., the nucleotide sequence comprises a promoter from a gene that is the ortholog of the gene corresponding to the reference nucleotide sequence, as well as promoter sequences that are structurally related the promoter sequences particularly exemplified herein, i.e., the substantially similar promoter sequences hybridize to the complement of the promoter sequences exemplified herein under high or very high stringency conditions. For example, altered nucleotide sequences, which simply reflect the degeneracy of the genetic code but nonetheless encode amino acid sequences that are identical to a particular amino acid sequence are substantially similar to the particular sequences. The term "substantially similar" also includes nucleotide sequences wherein the sequence has been modified, for example, to optimize expression in particular cells, as well as nucleotide sequences encoding a variant polypeptide having one or more amino acid substitutions relative to the (unmodified) polypeptide encoded by the reference sequence, which substitution(s) does not alter the activity of the variant polypeptide relative to the unmodified polypeptide.

In its broadest sense, the term "substantially similar" when used herein with respect to polypeptide means that the polypeptide has substantially the same structure and function as the reference polypeptide. In addition, amino acid sequences that are substantially similar to a particular sequence are those wherein overall amino acid identity is at least 90% or greater to the instant sequences. Modifications that result in equivalent nucleotide or amino acid sequences are well within the routine skill in the art. The percentage of amino acid sequence identity between the substantially similar and the reference polypeptide is at least 90% or more, e.g., 91%, 92%, 93%, 94%, 95%, 96%, 97%, 98%, up to at least 99%, wherein the reference polypeptide is an polypeptide (e.g., from *Arabidopsis thaliana*) encoded by a gene with a promoter having any one of SEQ ID NOs: 1, 2, 3, 4, 5, 6, 7, 8, 9, 10, or 11, a nucleotide sequence comprising an open reading frame comprised in SEQ ID NOs: 12, 14, 16, and 18, which encodes a polypeptide described by SEQ ID NOs: 13, 15, 17, and 19. One indication that two polypeptides are substantially similar to each other, besides having substantially the same function, is that an agent, e.g., an antibody, which specifically binds to one of the polypeptides, also specifically binds to the other.

Sequence comparisons maybe carried out using a Smith-Waterman sequence alignment algorithm (see e.g., Waterman (1995)). The locals program, version 1.16, is preferably used with following parameters: match: 1, mismatch penalty: 0.33, open-gap penalty: 2, extended-gap penalty: 2.

Moreover, a nucleotide sequence that is "substantially similar" to a reference nucleotide sequence is said to be "equivalent" to the reference nucleotide sequence. The skilled artisan recognizes that equivalent nucleotide sequences encompassed by this invention can also be defined by their ability to hybridize, under low, moderate and/or stringent conditions (e.g., 0.1×SSC, 0.1% SDS, 65° C.), with the nucleotide sequences that are within the literal scope of the instant claims.

What is meant by "substantially the same activity" when used in reference to a polynucleotide or polypeptide fragment is that the fragment has at least 90% or more, e.g., 91%, 92%, 93%, 94%, 95%, 96%, 97%, 98%, up to at least 99% of the activity of the full length polynucleotide or full length polypeptide.

"Target gene" refers to a gene on the replicon that expresses the desired target coding sequence, functional RNA, or protein. The target gene is not essential for replicon replication. Additionally, target genes may comprise native non-viral genes inserted into a non-native organism, or chimeric genes, and will be under the control of suitable regulatory sequences. Thus, the regulatory sequences in the target gene may come from any source, including the virus. Target genes may include coding sequences that are either heterologous or homologous to the genes of a particular plant to be transformed. However, target genes do not include native viral genes. Typical target genes include, but are not limited to genes encoding a structural protein, a seed storage protein, a protein that conveys herbicide resistance, and a protein that conveys insect resistance. Proteins encoded by target genes are known as "foreign proteins". The expression of a target gene in a plant will typically produce an altered plant trait.

The term "altered plant trait" means any phenotypic or genotypic change in a trans-genic plant relative to the wild-type or non-transgenic plant host.

"Replication gene" refers to a gene encoding a viral replication protein. In addition to the ORF of the replication protein, the replication gene may also contain other overlapping or non-overlapping ORF(s), as are found in viral sequences in nature. While not essential for replication, these additional ORFs may enhance replication and/or viral DNA accumulation. Examples of such additional ORFs are AC3 and AL3 in ACMV and TGMV geminiviruses, respectively.

"Chimeric trans-acting replication gene" refers either to a replication gene in which the coding sequence of a replication protein is under the control of a regulated plant promoter other than that in the native viral replication gene, or a modified native viral replication gene, for example, in which a site specific sequence(s) is inserted in the 5' transcribed but untranslated region. Such chimeric genes also include insertion of the known sites of replication protein binding between the promoter and the transcription start site that attenuate transcription of viral replication protein gene.

"Chromosomally-integrated" refers to the integration of a foreign gene or DNA construct into the host DNA by covalent bonds. Where genes are not "chromosomally integrated" they may be "transiently expressed." Transient expression of a gene refers to the expression of a gene that is not integrated into the host chromosome but functions independently, either as part of an autonomously replicating plasmid or expression cassette, for example, or as part of another biological system such as a virus.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include *Agrobacterium*-mediated transformation (De Blaere 1987) and particle bombardment technology (U.S. Pat. No. 4,945,050). Whole plants may be regenerated from transgenic cells by methods well known to the skilled artisan (see, for example, Fromm 1990).

"Transformed," "transgenic," and "recombinant" refer to a host organism such as a bacterium or a plant into which a heterologous nucleic acid molecule has been introduced. The nucleic acid molecule can be stably integrated into the genome generally known in the art and are disclosed (Sambrook 1989; Innis 1995; Gelfand 1995; Innis & Gelfand 1999. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as *Agrobacterium*-mediated transformation or biolistic bombardment), but not selected for stable maintenance.

"Stably transformed" refers to cells that have been selected and regenerated on a selection media following transformation.

"Transient expression" refers to expression in cells in which a virus or a transgene is introduced by viral infection or by such methods as *Agrobacterium*-mediated transformation, electroporation, or biolistic bombardment, but not selected for its stable maintenance.

"Genetically stable" and "heritable" refer to chromosomally-integrated genetic elements that are stably maintained in the plant and stably inherited by progeny through successive generations.

"Primary transformant" and "T0 generation" refer to transgenic plants that are of the same genetic generation as the tissue which was initially transformed (i.e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants.

"Wild-type" refers to a virus or organism found in nature without any known mutation.

The terms "genome" or "genomic DNA" is referring to the heritable genetic information of a host organism. Said genomic DNA comprises the DNA of the nucleus (also referred to as chromosomal DNA) but also the DNA of the plastids (e.g., chloroplasts) and other cellular organelles (e.g., mitochondria). Preferably the terms genome or genomic DNA is referring to the chromosomal DNA of the nucleus.

The term "chromosomal DNA" or "chromosomal DNA-sequence" is to be understood as the genomic DNA of the cellular nucleus independent from the cell cycle status. Chromosomal DNA might therefore be organized in chromosomes or chromatids, they might be condensed or uncoiled. An insertion into the chromosomal DNA can be demonstrated and analyzed by various methods known in the art like e.g., polymerase chain reaction (PCR) analysis, Southern blot analysis, fluorescence in situ hybridization (FISH), and in situ PCR.

The term "nucleic acid" refers to deoxyribonucleotides or ribonucleotides and polymers thereof in either single- or double-stranded form, composed of monomers (nucleotides) containing a sugar, phosphate and a base, which is either a purine or pyrimidine. Unless specifically limited, the term encompasses nucleic acids containing known analogs of natural nucleotides, which have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer 1991; Ohtsuka 1985; Rossolini 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The invention encompasses isolated or substantially purified nucleic acid or protein compositions. In the context of the present invention, an "isolated" or "purified" DNA molecule or an "isolated" or "purified" polypeptide is a DNA molecule or polypeptide that, by the hand of man, exists apart from its native environment and is therefore not a product of nature. An isolated DNA molecule or polypeptide may exist in a purified form or may exist in a non-native environment such as, for example, a transgenic host cell. For example, an "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein of interest chemicals. The nucleotide sequences of the invention include both the naturally occurring sequences as well as mutant (variant) forms. Such variants will continue to possess the desired activity, i.e., either promoter activity or the activity of the product encoded by the open reading frame of the non-variant nucleotide sequence.

The term "variant" with respect to a sequence (e.g., a polypeptide or nucleic acid sequence such as—for example—a transcription regulating nucleotide sequence of the invention) is intended to mean substantially similar sequences. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e.g., preferably 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

"Conservatively modified variations" of a particular nucleic acid sequence refers to those nucleic acid sequences that encode identical or essentially identical amino acid sequences, or where the nucleic acid sequence does not encode an amino acid sequence, to essentially identical sequences. Because of the degeneracy of the genetic code, a large number of functionally identical nucleic acids encode any given polypeptide. For instance the codons CGT, CGC, CGA, CGG, AGA, and AGG all encode the amino acid arginine. Thus, at every position where an arginine is specified by a codon, the codon can be altered to any of the corresponding codons described without altering the encoded protein. Such nucleic acid variations are "silent variations" which are one species of "conservatively modified variations." Every nucleic acid sequence described herein, which encodes a polypeptide also describes every possible silent variation, except where otherwise noted. One of skill will recognize that each codon in a nucleic acid (except ATG, which is ordinarily the only codon for methionine) can be modified to yield a functionally identical molecule by standard techniques. Accordingly, each "silent variation" of a nucleic acid, which encodes a polypeptide is implicit in each described sequence.

The nucleic acid molecules of the invention can be "optimized" for enhanced expression in plants of interest (see, for example, WO 91/16432; Perlak 1991; Murray 1989). In this manner, the open reading frames in genes or gene fragments can be synthesized utilizing plant-preferred codons (see, for example, Campbell & Gowri, 1990 for a discussion of host-preferred codon usage). Thus, the nucleotide sequences can be optimized for expression in any plant. It is recognized that all or any part of the gene sequence may be optimized or synthetic. That is, synthetic or partially optimized sequences may also be used. Variant nucleotide sequences and proteins also encompass, sequences and protein derived from a mutagenic and recombinogenic procedure such as DNA shuffling. With such a procedure, one or more different coding sequences can be manipulated to create a new polypeptide possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art (see, for example, Stemmer 1994; Stemmer 1994; Crameri 1997; Moore 1997; Zhang 1997; Crameri 1998; and U.S. Pat. No. 5,605,795,837, 458).

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

Thus, the polypeptides may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art (see, for example, Kunkel 1985; Kunkel 1987; U.S. Pat. No. 4,873,192; Walker & Gaastra, 1983 and the references cited therein). Guidance as to appropriate amino acid substitutions that do not affect biological activity of the protein of interest may be found in the model of Dayhoff et al. (1978). Conservative substitutions, such as exchanging one amino acid with another having similar properties, are preferred. Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). See also, Creighton, 1984. In addition, individual substitutions, deletions or additions which alter, add or delete a single amino acid or a small percentage of amino acids in an encoded sequence are also "conservatively modified variations."

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extracellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. Likewise, a nucleic acid sequence to be expressed may be placed (or inserted) downstream of an endogenous promoter sequence thereby forming an expression cassette. The expression of the nucleotide sequence in the expression cassette may be under the control of a constitutive promoter or of an inducible promoter, which initiates transcription only when the host cell is exposed to some particular external stimulus. In the case of a multicellular organism, the promoter can also be specific to a particular tissue or organ or stage of development (e.g., the seed-specific or seed-preferential promoters of the invention). In a preferred embodiment, such expression cassettes will comprise the transcriptional initiation region of the invention linked to a nucleotide sequence of interest. Such an expression cassette is preferably provided with a plurality of restriction sites for insertion of the gene of interest to be under the transcriptional regulation of the regulatory regions. The expression cassette may additionally contain selectable marker genes. The cassette will include in the 5'-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of *A. tumefaciens*, such as the octopine synthase and nopaline synthase termination regions and others described below (see also, Guerineau 1991; Proudfoot 1991; Sanfacon 1991; Mogen 1990; Munroe 1990; Ballas 1989; Joshi 1987).

"Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication).

Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

Preferably the nucleic acid in the vector is under the control of, and operably linked to, an appropriate promoter or other regulatory elements for transcription in a host cell such as a microbial, e.g. bacterial, or plant cell. The vector may be a bifunctional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller, 1988; the local homology algorithm of Smith et al. 1981; the homology alignment algorithm of Needleman and Wunsch 1970; the search-for-similarity-method of Pearson and Lipman 1988; the algorithm of Karlin and Altschul, 1990, modified as in Karlin and Altschul, 1993.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575

Science Drive, Madison, Wis., USA). Alignments using these programs can be performed using the default parameters. The CLUSTAL program is well described (Higgins 1988, 1989; Corpet 1988; Huang 1992; Pearson 1994). The ALIGN program is based on the algorithm of Myers and Miller, supra. The BLAST programs of Altschul et al., 1990, are based on the algorithm of Karlin and Altschul, supra. Multiple aligments (i.e. of more than 2 sequences) are preferably performed using the Clustal W algorithm (Thompson 1994; e.g., in the software VectorNTI™, version 9; Invitrogen Inc.) with the scoring matrix BLOSUM62MT2 with the default settings (gap opening penalty 15/19, gap extension penalty 6.66/0.05; gap separation penalty range 8; % identity for alignment delay 40; using residue specific gaps and hydrophilic residue gaps).

Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences (see, e.g., Karlin & Altschul (1993). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

To obtain gapped alignments for comparison purposes, Gapped BLAST (in BLAST 2.0) can be utilized as described in Altschul et al. 1997. Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, 1989). See http://www.ncbi.nlm.nih.gov. Alignment may also be performed manually by inspection.

For purposes of the present invention, comparison of nucleotide sequences for determination of percent sequence identity to the promoter sequences disclosed herein is preferably made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the preferred program.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e) (i) The term "substantial identity" of polynucleotide sequences means that a polynucleotide comprises a sequence that has at least 90%, 91%, 92%, 93%, or 94%, and most preferably at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 90%, 95%, and most preferably at least 98%.

Another indication that nucleotide sequences are substantially identical is if two molecules hybridize to each other under stringent conditions (see below). Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(ii) The term "substantial identity" in the context of a peptide indicates that a peptide comprises a sequence with at least 90%, 91%, 92%, 93%, or 94%, or even more preferably, 95%, 96%, 97%, 98% or 99%, sequence identity to the reference sequence over a specified comparison window. Preferably, optimal alignment is conducted using the homology alignment algorithm of Needleman and Wunsch (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridization are sequence dependent, and are different under different environmental parameters. The $T_m$ is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl, 1984:

$$T_m = 81.5°\text{ C.} + 16.6(\log_{10} M) + 0.41(\% \ GC) - 0.61(\% \text{ form}) - 500/L$$

where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point I for the specific sequence and its complement at a defined ionic strength and pH. However, severely stringent conditions can utilize a hybridization and/or wash at 1, 2, 3, 4, 5, 6, 7, 8, 9, 10, or 11° C. lower than the thermal melting point I; moderately stringent conditions can utilize a hybridization and/or wash at 6, 7, 8, 9, or 10° C. lower than the thermal melting point I; low stringency conditions can utilize a hybridization and/or wash at 11, 12, 13, 14, 15, or 20° C. lower than the thermal melting point I. Using the equation, hybridization and wash compositions, and desired T, those of ordinary skill will understand that variations in the stringency of hybridization and/or wash solutions are inherently described. If the desired degree of mismatching results in a T of less than 45° C. (aqueous solution) or 32° C. (formamide solution), it is preferred to increase the SSC concentration so that a higher temperature can be used. An extensive guide to the hybridization of nucleic acids is found in Tijssen, 1993. Generally, highly stringent hybridization and wash conditions are selected to be about 5° C. lower than the thermal melting point $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4 to 6×SSC at 40° C. for 15 minutes. For short probes (e.g., about 10 to 50 nucleotides), stringent conditions typically involve salt concentrations of less than about 1.5 M, more preferably about 0.01 to 1.0 M, Na ion concentration (or other salts) at pH 7.0 to 8.3, and the temperature is typically at least about 30° C. and at least about 60° C. for long robes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids which have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

The following are examples of sets of hybridization/wash conditions that may be used to clone orthologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1× SSC, 0.1% SDS at 65° C.

"DNA shuffling" is a method to introduce mutations or rearrangements, preferably randomly, in a DNA molecule or to generate exchanges of DNA sequences between two or more DNA molecules, preferably randomly. The DNA molecule resulting from DNA shuffling is a shuffled DNA molecule that is a non-naturally occurring DNA molecule derived from at least one template DNA molecule. The shuffled DNA preferably encodes a variant polypeptide modified with respect to the polypeptide encoded by the template DNA, and may have an altered biological activity with respect to the polypeptide encoded by the template DNA.

"Recombinant DNA molecule" is a combination of DNA sequences that are joined together using recombinant DNA technology and procedures used to join together DNA sequences as described, for example, in Sambrook et al., 1989.

The word "plant" refers to any plant, particularly to agronomically useful plants (e.g., seed plants), and "plant cell" is a structural and physiological unit of the plant, which comprises a cell wall but may also refer to a protoplast. The plant cell may be in form of an isolated single cell or a cultured cell, or as a part of higher organized unit such as, for example, a plant tissue, or a plant organ differentiated into a structure that is present at any stage of a plant's development. Such structures include one or more plant organs including, but are not limited to, fruit, shoot, stem, leaf, flower petal, etc. Preferably, the term "plant" includes whole plants, shoot vegetative organs/structures (e.g. leaves, stems and tubers), roots, flowers and floral organs/structures (e.g. bracts, sepals, petals, stamens, carpels, anthers and ovules), seeds (including embryo, endosperm, and seed coat) and fruits (the mature ovary), plant tissues (e.g. vascular tissue, ground tissue, and the like) and cells (e.g. guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid and hemizygous. Included within the scope of the invention are all genera and species of higher and lower plants of the plant kingdom. Included are furthermore the mature plants, seed, shoots and seedlings, and parts, propagation material (for example seeds and fruit) and cultures, for example cell cultures, derived therefrom. Preferred are plants and plant materials of the following plant families: Amaranthaceae, Brassicaceae, Carophyllaceae, Chenopodiaceae, Compositae, Cucurbitaceae, Labiatae, Leguminosae, Papilionoideae, Liliaceae, Linaceae, Malvaceae, Rosaceae, Saxifragaceae, Scrophulariaceae, Solanaceae, Tetragoniaceae. Annual, perennial, monocotyledonous and dicotyledonous plants are preferred host organisms for the generation of transgenic plants. The use of the recombination system, or method according to the invention is furthermore advantageous in all ornamental plants, forestry, fruit, or ornamental trees, flowers, cut flowers, shrubs or turf. Said plant may include—but shall not be limited to—bryophytes such as, for example, Hepaticae (hepaticas) and Musci (mosses); pteridophytes such as ferns, horsetail and clubmosses; gymnosperms such as conifers, cycads, ginkgo and Gnetaeae; algae such as Chlorophyceae, Phaeophpyceae, Rhodophyceae, Myxophyceae, Xanthophyceae, Bacillariophyceae (diatoms) and Euglenophyceae. Plants for the purposes of the invention may comprise the families of the Rosaceae such as rose, Ericaceae such as rhododendrons and azaleas, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as gladioli, iris, freesia and crocus, Compositae such as marigold, Geraniaceae such as geraniums, Liliaceae such as Drachaena, Moraceae such as ficus, Araceae such as philodendron and many others. The transgenic plants according to the invention are furthermore selected in particular from among dicotyledonous crop plants such as, for example, from the families of the Leguminosae such as pea, alfalfa and soybean; the family of the Umbelliferae, particularly the genus *Daucus* (very particularly the species carota (carrot)) and *Apium* (very particularly the species *graveolens* var. *dulce* (celery)) and many others; the family of the Solanaceae, particularly the genus *Lycopersicon*, very particularly the species *esculentum* (tomato) and the genus *Solanum*, very particularly the species *tuberosum* (potato) and *melongena* (aubergine), tobacco and many others; and the genus *Capsicum*, very particularly the species *annum* (pepper) and many others; the family of the Leguminosae, particularly the genus *Glycine*, very particularly the species *max* (soybean) and many others; and the family of the Cruciferae, particularly the genus *Brassica*, very particularly the species *napus* (oilseed rape), *campestris* (beet), *oleracea* cv Tastie (cabbage), *oleracea* cv Snowball Y (cauliflower) and *oleracea* cv Emperor (broccoli); and the genus *Arabidopsis*, very particularly the species *thaliana* and many others; the family of the Compositae, particularly the genus *Lactuca*, very particularly the species *sativa* (lettuce) and many others. The transgenic plants according to the invention may be selected among monocotyledonous crop plants, such as, for example, cereals such as wheat, barley, sorghum and millet, rye, triticale, maize, rice or oats, and sugarcane. Further preferred are trees such as apple, pear, quince, plum, cherry, peach, nectarine, apricot, papaya, mango, and other woody species including coniferous and deciduous trees such as poplar, pine, sequoia, cedar, oak, etc. Especially preferred are *Arabidopsis thaliana, Nicotiana tabacum*, oilseed rape, soybean, corn (maize), wheat, *Linum usitatissimum* (linseed and flax), *Camelina sativa, Brassica juncea*, potato and tagetes.

"Significant increase" is an increase that is larger than the margin of error inherent in the measurement technique, preferably an increase by about 2-fold or greater.

"Significantly less" means that the decrease is larger than the margin of error inherent in the measurement technique, preferably a decrease by about 2-fold or greater.

DETAILED DESCRIPTION OF THE INVENTION

The present invention thus provides for isolated nucleic acid molecules comprising a plant nucleotide sequence that directs seed-preferential or seed-specific transcription of an operably linked nucleic acid fragment in a plant cell.

Specifically, the present invention provides transgenic expression cassettes for regulating seed-specific or seed-preferential expression in plants comprising
a) at least one transcription regulating nucleotide sequence derived from a plant tonoplast intrinsic protein gene, said gene being selected from the group consisting of the *Arabidopsis thaliana* tonoplast intrinsic protein alpha described by the GenBank *Arabidopsis thaliana* genome loci At1g73190 and its orthologous genes from *Brassica napus* and *Linum usitatissimum* and functionally linked thereto
b) at least one nucleic acid sequence which is heterologous in relation to said transcription regulating nucleotide sequence.

The seed-preferential or seed-specific promoters may be useful for expressing genes as well as for producing large quantities of protein, for expressing oils or proteins of interest, e.g., antibodies, genes for increasing the nutritional value of the seed and the like.

The term "seed" in the context of the inventions means a seed of a plant in any stage of its development i.e. starting from the fusion of pollen and oocyte, continuing over the embryo stage and the stage of the dormant seed, until the germinating seed, ending with early seedling organs, as e.g. cotyledons and hypocotyl.

"Seed-specific transcription" in the context of this invention means the transcription of a nucleic acid sequence by a transcription regulating element in a way that transcription of said nucleic acid sequence in seeds contribute to more than 90%, preferably more than 95%, more preferably more than 99% of the entire quantity of the RNA transcribed from said nucleic acid sequence in the entire plant during any of its developmental stage. The transcription regulating nucleotide sequences specifically disclosed herein are considered to be seed-specific transcription regulating nucleotide sequences.

"Seed-preferential transcription" in the context of this invention means the transcription of a nucleic acid sequence by a transcription regulating element in a way that transcription of said nucleic acid sequence in seeds contribute to more than 50%, preferably more than 70%, more preferably more than 80% of the entire quantity of the RNA transcribed from said nucleic acid sequence in the entire plant during any of its developmental stage.

Preferably a transcription regulating nucleotide sequence of the invention comprises at least one promoter sequence of the respective gene (e.g., a sequence localized upstream of the transcription start of the respective gene capable to induce transcription of the downstream sequences). Said transcription regulating nucleotide sequence may comprise the promoter sequence of said genes but may further comprise other elements such as the 5'-untranslated sequence, enhancer, introns etc. Preferably, said promoter sequence directs seed-preferential or seed-specific transcription of an operably linked nucleic acid segment in a plant or plant cell e.g., a linked plant DNA comprising an open reading frame for a structural or regulatory gene.

The following Table 1 illustrates the genes from which the promoters of the invention are preferably isolated, the function of said genes, the cDNA encoded by said genes, and the protein (ORF) encoded by said genes.

TABLE 1

Genes, from which the promoters of the invention are preferably isolated, putative function of said genes, cDNA and the protein encoded by said genes.

| Gene Locus | Putative function | Promoter SEQ ID | mRNA locus ID cDNA SEQ ID | Protein ID Protein SEQ ID |
|---|---|---|---|---|
| At1g73190 | *Arabidopsis thaliana* putative *Arabidopsis thaliana* alpha-tonoplast intrinsic protein | SEQ ID NO: 1, 2 | NM_10597 SEQ ID NO: 12 | P26587 SEQ ID NO: 13 |
| — | *Brassica napus* tonoplast intrinsic protein; otholog of *Arabidopsis thaliana* At1g73190 protein | 3, 4, 5 | SEQ ID NO. 14 | SEQ ID NO. 15 |
| — | *Linum usitatissimum* tonoplast intrinsic protein 1; otholog of *Arabidopsis thaliana* At1g73190 protein | 6, 7, 8 | SEQ ID NO. 16 | SEQ ID NO. 17 |
| — | *Linum usitatissimum* tonoplast intrinsic protein 2; otholog of *Arabidopsis thaliana* At1g73190 protein | 9, 10, 11 | SEQ ID NO. 18 | SEQ ID NO. 19 |

Some of the transcription regulating sequences disclosed herein are novel as such (e.g., the sequences from *Brassica napus* and *Linum usitatissimum*). Accordingly, another embodiment of the invention relates to an isolated nucleotide sequence selected from the group of sequences consisting of the sequences described by SEQ ID NOs:3, 4, 5, 6, 7, 8, 9, 10, or 11 or any derivative or fragment thereof. More preferably the isolated nucleotide sequence or its derivative or fragment and is selected from the group of sequences consisting of i) the sequence described by SEQ ID NOs: 3, 4, 5, 6, 7, 8, 9, 10, or 11, and ii) a fragment of at least 50 consecutive bases, preferably at least 100 consecutive bases, more preferably at least 250 consecutive bases, most preferably at least 500 consecutive bases of a sequence described by any of SEQ ID NO: 3, 4, 5, 6, 7, 8, 9, 10, or 11, and iii) a nucleotide sequence having substantial similarity (preferably with a sequence identity of at least 50%) to a transcription regulating nucleotide sequence described by SEQ ID NO: 3, 4, 5, 6, 7, 8, 9, 10, or 11, and iv) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a transcription regulating nucleotide sequence described by SEQ ID NO: 3, 4, 5, 6, 7, 8, 9, 10, or 11, or the complement thereof;

v) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 3, 4, 5, 6, 7, 8, 9, 10, or 11, or the complement thereof;

vi) a nucleotide sequence which is the complement or reverse complement of any of the previously mentioned nucleotide sequences under i) to v).

Preferably, such derivative or fragment of said isolated nucleotide sequence (e.g., the sequences specified under ii), iii), iv) v) and vi) above) is capable to modify transcription in a plant cell or organism, more preferably said derivative or fragment (e.g., the sequences specified under ii), iii), iv) v) and vi) above) has substantially the same transcription regulating activity as the transcription regulating nucleotide sequence described by SEQ ID NO: 3, 4, 5, 6, 7, 8, 9, 10, or 11. Preferably, the derivative or fragment (e.g., the sequences specified under iii) above) has a sequence identity of at least 50% or 60%, preferably at least 70% or 80%, more preferably at least 90% or 95%, most preferably at least 98% to a sequence described by SEQ ID NO: 3, 4, 5, 6, 7, 8, 9, 10, or 11. As specified above in the DEFINITION section, identities between nucleotide sequences are preferably measured by the BLASTN program using default parameters with a wordlength (W) of 11, an expectation (E) of 10, a cutoff of 100, M=5, N=−4, and a comparison of both strands. For measuring identity between amino acid sequences, the BLASTP program is used with default parameters with a wordlength (W) of 3, an expectation (E) of 10, and the BLOSUM62 scoring matrix (see Henikoff & Henikoff, 1989). The BLAST Program version 1.4.7 or later is used. Preferably, the derivative or fragment (e.g., the sequences specified under iv) or v) above) is hybridizing under stringent conditions (i.e. low stringent, preferably medium stringent, most preferably high stringent conditions) with the specified target sequence.

Preferably, the transcription regulating nucleotide sequence employed in the expression cassettes of the invention is selected from the group of sequences consisting of the sequences described by SEQ ID NOs: 1, 2, 3, 4, 5, 6, 7, 8, 9, 10, or 11 or any derivative or fragment thereof. More preferably the transcription regulating nucleotide sequence employed in the expression cassette of the invention is selected from the group of sequences consisting of i) the sequence described by SEQ ID NOs: 1, 2, 3, 4, 5, 6, 7, 8, 9, 10, or 11, and ii) a fragment of at least 50 consecutive bases, preferably at least 100 consecutive bases, more preferably at least 250 consecutive bases, most preferably at least 500 consecutive bases of a sequence described by any of SEQ ID NO: 1, 2, 3, 4, 5, 6, 7, 8, 9, 10, or 11, and iii) a nucleotide sequence having substantial similarity (preferably with a sequence identity of at least 50%) to a transcription regulating nucleotide sequence described by SEQ ID NO: 1, 2, 3, 4, 5, 6, 7, 8, 9, 10, or 11, and iv) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a transcription regulating nucleotide sequence described by SEQ ID NO: 1, 2, 3, 4, 5, 6, 7, 8, 9, 10, or 11, or the complement thereof;

v) a nucleotide sequence capable of hybridizing (preferably under conditions equivalent to hybridization in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.) to a nucleic acid comprising 50 to 200 or more consecutive nucleotides of a transcription regulating nucleotide sequence described by SEQ ID NO: 1, 2, 3, 4, 5, 6, 7, 8, 9, 10, or 11, or the complement thereof;

vi) a nucleotide sequence which is the complement or reverse complement of any of the previously mentioned nucleotide sequences under i) to v).

Preferably, such derivative or fragment of the transcription regulating nucleotide sequence to be employed in the expression cassette of the invention (e.g., the sequences specified under ii), iii), iv) v) and vi) above) is capable to modify transcription in a plant cell or organism, more preferably said derivative or fragment (e.g., the sequences specified under ii), iii), iv) v) and vi) above) has substantially the same transcription regulating activity as the transcription regulating nucleotide sequence described by SEQ ID NO: 1, 2, 3, 4, 5, 6, 7, 8, 9, 10, or 11. Preferably, the derivative or fragment (e.g., the sequences specified under iii) above) has a sequence identity of at least 50% or 60%, preferably at least 70% or 80%, more preferably at least 90% or 95%, most preferably at least 98% to a sequence described by SEQ ID NO: 1, 2, 3, 4, 5, 6, 7, 8, 9, 10, or 11. As specified above in the DEFINITION section, identities between nucleotide sequences are preferably measured by the BLASTN program using default parameters with a wordlength (W) of 11, an expectation (E) of 10, a cutoff of 100, M=5, N=4, and a comparison of both strands. For measuring identity between amino acid sequences, the BLASTP program is used with default parameters with a wordlength (W) of 3, an expectation (E) of 10, and the BLOSUM62 scoring matrix (see Henikoff & Henikoff, 1989). The BLAST Program version 1.4.7 or later is used. Preferably, the derivatives or fragments (e.g., the sequences specified under iv) or v) above) are hybridizing under stringent conditions (i.e. low stringent, preferably medium stringent, most preferably high stringent conditions) with the specified target sequence.

The derivatives or fragments of the transcription regulating nucleotide sequence of the invention (e.g., the sequence described by any of SEQ ID NO: 1, 2, 3, 4, 5, 6, 7, 8, 9, 10, or 11) may be obtained or is obtainable from plant genomic DNA from a gene encoding a tonoplast intrinsic protein polypeptide (preferably from an orthologous gene i.e., encoding an orthologous protein; more preferably a TIP-alpha protein) which is comprising a amino acid sequence having at least 90% amino acid sequence identity, more preferably at least 90% or 95%, most preferably at least 97% or 98% amino acid sequence identity, to a polypeptide as described by SEQ ID NO: 13, 15, 17, or 19. Preferably, said orthologous protein has furthermore the same enzymatic activity than the protein encoded by the *Arabidopsis thaliana* locus At1g73190 or. More preferably the functional equivalent transcription regulating sequence exhibits promoter activity in a seed-preferential or seed-specific fashion.

The activity of a transcription regulating nucleotide sequence is considered equivalent if transcription is initiated in a seed-preferential or seed-specific fashion (as defined above). Such expression profile is preferably demonstrated using reporter genes operably linked to said transcription regulating nucleotide sequence. Preferred reporter genes (Schenborn 1999) in this context are green fluorescence protein (GFP) (Chui 1996; Leffel 1997), chloramphenicol transferase, luciferase (Millar 1992), β-glucuronidase or β-galactosidase. Especially preferred is β-glucuronidase (Jefferson 1987).

Beside this the transcription regulating activity of a function equivalent derivative of fragment of the transcription regulating nucleotide sequence may vary from the activity of its parent sequence, especially with respect to expression level. The expression level may be higher or lower than the expression level of the parent sequence. Both derivations may be advantageous depending on the nucleic acid sequence of interest to be expressed. Preferred are such functional equivalent sequences, which—in comparison with its parent sequence—does, not derivate from the expression level of said parent sequence by more than 50%, preferably 25%, more preferably 10% (as to be preferably judged by either mRNA expression or protein (e.g., reporter gene) expression). Furthermore preferred are equivalent sequences which demonstrate an increased expression in comparison to its parent sequence, preferably an increase my at least 50%, more preferably by at least 100%, most preferably by at least 500%.

Preferably a functional equivalent of the transcription regulating nucleotide sequence of the invention can be obtained or is obtainable from plant genomic DNA from a gene expressing a mRNA described by a cDNA comprising a sequence which is substantially similar and preferably has at least 90%, preferably at least 92% or 95%, more preferably at least 96% or 97%, most preferably at least 99% sequence identity to a sequence described by any SEQ ID NOs: 12, 14, 16, or 18. Preferably said transcription regulating nucleotide sequence exhibits promoter activity in a seed-preferential or seed-specific fashion.

Such functional equivalent of the transcription regulating nucleotide sequence may be obtained from other plant species by using the seed-preferential or seed-specific *Arabidopsis thaliana*, *Brassica napus*, or *Linum usitatissimum* promoter sequences described herein as probes to screen for homologous structural genes in other plants by hybridization under low, moderate or stringent hybridization conditions. Regions of the seed-preferential or seed-specific promoter sequences of the present invention which are conserved among species could also be used as PCR primers to amplify a segment from a species other than *Arabidopsis thaliana*, *Brassica napus*, or *Linum usitatissimum*, and that segment used as a hybridization probe (the latter approach permitting higher stringency screening) or in a transcription assay to determine promoter activity. Moreover, the seed-preferential or seed-specific promoter sequences could be employed to identify structurally related sequences in a database using computer algorithms.

More specifically, based on the nucleic acid sequences of the present invention, orthologs may be identified or isolated from the genome of any desired organism, preferably from another plant, according to well known techniques based on their sequence similarity to the *Arabidopsis thaliana*, *Brassica napus*, or *Linum usitatissimum* nucleic acid sequences, e.g., hybridization, PCR or computer generated sequence comparisons. For example, all or a portion of a particular *Arabidopsis thaliana*, *Brassica napus*, or *Linum usitatissimum* nucleic acid sequence is used as a probe that selectively hybridizes to other gene sequences present in a population of cloned genomic DNA fragments or cDNA fragments (i.e., genomic or cDNA libraries) from a chosen source organism. Further, suitable genomic and cDNA libraries may be prepared from any cell or tissue of an organism. Such techniques include hybridization screening of plated DNA libraries (either plaques or colonies; see, e.g., Sambrook 1989) and amplification by PCR using oligonucleotide primers preferably corresponding to sequence domains conserved among related polypeptide or subsequences of the nucleotide sequences provided herein (see, e.g., Innis 1990). These methods are particularly well suited to the isolation of gene sequences from organisms closely related to the organism from which the probe sequence is derived. The application of these methods using the *Arabidopsis thaliana*, *Brassica napus*, or *Linum usitatissimum* sequences as probes is well suited for the isolation of gene sequences from any source organism, preferably other plant species. In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism.

The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the sequence of the invention. Methods for preparation of probes for hybridization and for construction of cDNA and genomic libraries are generally known in the art and are disclosed in Sambrook et al. (1989). In general, sequences that hybridize to the sequences disclosed herein will have at least about 50% to 70% and even about 80% 85%, 90%, 95% to 98% or more identity with the disclosed sequences. That is, the sequence similarity of sequences may range, sharing at least about 50% to 70%, and even about 80%, 85%, 90%, 95% to 98% sequence similarity.

The nucleic acid molecules of the invention can also be identified by, for example, a search of known databases for genes encoding polypeptides having a specified amino acid sequence identity or DNA having a specified nucleotide sequence identity. Methods of alignment of sequences for comparison are well known in the art and are described hereinabove.

Hence, the isolated nucleic acid molecules of the invention include the orthologs of the *Arabidopsis thaliana*, *Brassica napus*, or *Linum usitatissimum* sequences disclosed herein, i.e., the corresponding nucleotide sequences in organisms other than *Arabidopsis thaliana*, *Brassica napus*, or *Linum usitatissimum* including, but not limited to, plants other than *Arabidopsis thaliana*, *Brassica napus*, or *Linum usitatissimum*, preferably dicotyledonous plants, e.g., alfalfa, sunflower, soybean, cotton, peanut, tobacco, or sugar beet, but also cereal plants such as corn, wheat, rye, turfgrass, sorghum, millet, sugarcane, barley and banana. An orthologous gene is a gene from a different species that encodes a product having the same or similar function, e.g., catalyzing the same reaction as a product encoded by a gene from a reference organism. Thus, an ortholog includes polypeptides having less than, e.g., 50% amino acid sequence identity, but which ortholog encodes a polypeptide having the same or similar function. Databases such GenBank may be employed to identify sequences related to the *Arabidopsis thaliana*, *Brassica napus*, or *Linum usitatissimum* sequences, e.g., orthologs in other dicotyledonous plants. Alternatively, recombinant DNA techniques such as hybridization or PCR may be employed to identify sequences related to the *Arabidopsis thaliana*, *Brassica napus*, or *Linum usitatissimum* sequences or to clone the equivalent sequences from different DNAs.

The transcription regulating nucleotide sequences of the invention or their functional equivalents can be obtained or isolated from any plant or non-plant source, or produced synthetically by purely chemical means. Preferred sources include, but are not limited to the plants defined in the DEFINITION section above.

Thus, another preferred embodiment of the invention relates to a method for identifying and/or isolating a transcription regulating nucleotide sequence (preferably with seed-preferential or seed-specific transcription regulating activity; more preferably from a tonoplast intrinsic protein alpha) characterized that said identification and/or isolation utilizes a nucleic acid sequence encoding a polypeptide (preferably the *Arabidopsis thaliana*, *Brassica napus*, or *Linum usitatissimum* tonoplast intrinsic proteins) comprising a sequence as described by SEQ ID NO: 13, 15, 17, or 19, or a part of said nucleic acid sequence. Preferred are nucleic acid sequences described by or comprising any of SEQ ID NO: 12, 14, 16, or 18 or parts thereof. "Part" in this context means a nucleic acid sequence of at least 15 consecutive nucleotides, preferably at least 25 consecutive nucleotides, more preferably at least 50 consecutive nucleotides.

The method for identification and/or isolation can be based on (but is not limited to) the methods described above such as polymerase chain reaction, hybridization or database screening. Preferably, this method of the invention is based on a polymerase chain reaction, wherein said nucleic acid sequence or its part is utilized as oligonucleotide primer. The person skilled in the art is aware of several methods to amplify and isolate the promoter of a gene starting from part of its coding sequence (such as, for example, part of a cDNA). Such methods may include but are not limited to method such as inverse PCR ("iPCR") or "thermal asymmetric interlaced PCR" ("TAIL PCR").

Thus, another embodiment of the invention relates to a method for providing or producing a transgenic expression cassette for heterologous expression in plants comprising the steps of:

I. isolating of a transcription regulating nucleotide sequence of a plant gene (preferably encoding a tonoplast intrinsic protein alpha) utilizing at least one nucleic acid sequence encoding the tonoplast intrinsic protein comprising any of SEQ ID NO: 13, 15, 17, or 19, or a part of at least 15 consecutive nucleotides of said nucleic acid sequence, and II. functionally linking said transcription regulating nucleotide sequence to another nucleotide sequence of interest, which is heterologous in relation to said transcription regulating nucleotide sequence.

Still another embodiment of the invention relates to a method for providing a transgenic expression cassette for seed-specific or seed-preferential expression comprising the steps of:

I. isolating of a seed-preferential or seed-specific transcription regulating nucleotide sequence utilizing at least one nucleic acid sequence or a part thereof, wherein said sequence is encoding a tonoplast intrinsic protein comprising any of SEQ ID NO: 13, 15, 17, or 19, or a part of at least 15 consecutive nucleotides thereof, and II. functionally linking said seed-preferential or seed-specific transcription regulating nucleotide sequence to another nucleotide sequence of interest, which is heterologous in relation to said seed-preferential or seed-specific transcription regulating nucleotide sequence.

Preferably, the nucleic acid sequence employed for the isolation comprises at least 15 consecutive nucleotides, preferably at least 25 consecutive nucleotides, more preferably at least 50 consecutive nucleotides of a sequence described by any of SEQ ID NO: 12, 14, 16, or 18. Preferably, the isolation of the seed-preferential or seed-specific transcription regulating nucleotide sequence is realized by a polymerase chain reaction utilizing said nucleic acid sequence as a primer. The operable linkage can be realized by standard cloning method known in the art such as ligation-mediated cloning or recombination-mediated cloning.

Preferably, the transcription regulating nucleotide sequences and promoters of the invention include a consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 4, 5, 6, 7, 8, 9, 10, and 11, or the promoter orthologs thereof, which include the minimal promoter region.

Preferably, the transcription regulating nucleotide sequences and promoters of the invention include a consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 4, 5, 6, 7, 8, 9, 10, or 11, or the promoter orthologs thereof, which include the minimal promoter region. In a particular embodiment of the invention said consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, has at least 50% or 60%, preferably at least 70% or 80%, more preferably at least 90% and most preferably at least 95%, nucleic acid sequence identity with a corresponding consecutive stretch of about 25 to 2000, including 50 to 500 or 100 to 250, and up to 1000 or 1500, contiguous nucleotides, e.g., 40 to about 743, 60 to about 743, 125 to about 743, 250 to about 743, 400 to about 743, 600 to about 743, of any one of SEQ ID NOs: 1, 2, 3, 4, 5, 6, 7, 8, 9, 10, or 11, or the promoter orthologs thereof, which include the minimal promoter region. The above-defined stretch of contiguous nucleotides preferably comprises one or more promoter motifs selected from the group consisting of TATA box, GC-box, CAAT-box and a transcription start site.

The transcription regulating nucleotide sequences of the invention or their functional equivalents are capable of driving seed-preferential or seed-specific expression of a coding sequence in a target cell, particularly in a plant cell. The promoter sequences and methods disclosed herein are useful in regulating seed-preferential or seed-specific expression, respectively, of any heterologous nucleotide sequence in a host plant in order to vary the phenotype of that plant. These promoters can be used with combinations of enhancer, upstream elements, and/or activating sequences from the 5' flanking regions of plant expressible structural genes. Similarly the upstream element can be used in combination with various plant promoter sequences.

The transcription regulating nucleotide sequences and promoters of the invention are useful to modify the phenotype of a plant. Various changes in the phenotype of a transgenic plant are desirable, i.e., modifying the fatty acid composition in a plant, altering the amino acid content of a plant, altering a plant's pathogen defense mechanism, and the like. These results can be achieved by providing expression of heterologous products or increased expression of endogenous products in plants. Alternatively, the results can be achieved by providing for a reduction of expression of one or more endogenous products, particularly enzymes or cofactors in the plant. These changes result in an alteration in the phenotype of the transformed plant.

Generally, the transcription regulating nucleotide sequences and promoters of the invention may be employed to express a nucleic acid segment that is operably linked to said promoter such as, for example, an open reading frame, or a portion thereof, an anti-sense sequence, a sequence encoding for a double-stranded RNA sequence, or a transgene in plants.

An operable linkage may—for example—comprise an sequential arrangement of the transcription regulating nucleotide sequence of the invention (for example a sequence as described by SEQ ID NO: 1, 2, 3, 4, 5, 6, 7, 8, 9, 10, or 11) with a nucleic acid sequence to be expressed, and—optionally— additional regulatory elements such as for example polyadenylation or transcription termination elements, enhancers, introns etc, in a way that the transcription regulating nucleotide sequence can fulfill its function in the process of expression the nucleic acid sequence of interest under the appropriate conditions. The term "appropriate conditions" mean preferably the presence of the expression cassette in a plant cell. Preferred are arrangements, in which the nucleic acid sequence of interest to be expressed is placed down-stream (i.e., in 3'-direction) of the transcription regulating nucleotide sequence of the invention in a way, that both sequences are covalently linked. Optionally additional sequences may be inserted inbetween the two sequences. Such sequences may be for example linker or multiple cloning sites. Furthermore, sequences can be inserted coding for parts of fusion proteins (in case a fusion protein of the protein encoded by the nucleic acid of interest is intended to be expressed). Preferably, the distance between the nucleic acid sequence of interest to be expressed and the transcription regulating nucleotide sequence of the invention is not more than 200 base pairs, preferably not more than 100 base pairs, more preferably no more than 50 base pairs.

An operable linkage in relation to any expression cassette or of the invention may be realized by various methods known in the art, comprising both in vitro and in vivo procedure. Thus, an expression cassette of the invention or an vector comprising such expression cassette may by realized using standard recombination and cloning techniques well known in the art (see e.g., Maniatis 1989; Silhavy 1984; Ausubel 1987).

An expression cassette may also be assembled by inserting a transcription regulating nucleotide sequence of the invention (for example a sequence as described by SEQ ID NO: 1, 2, 3, 4, 5, 6, 7, 8, 9, 10, or 11) into the plant genome. Such insertion will result in an operable linkage to a nucleic acid sequence of interest which as such already existed in the genome. By the insertion the nucleic acid of interest is expressed in a seed-preferential or seed-specific way due to the transcription regulating properties of the transcription regulating nucleotide sequence. The insertion may be directed or by chance. Preferably the insertion is directed and realized by for example homologous recombination. By this procedure a natural promoter may be exchanged against the transcription regulating nucleotide sequence of the invention, thereby modifying the expression profile of an endogenous gene. The transcription regulating nucleotide sequence may also be inserted in a way, that antisense mRNA of an endogenous gene is expressed, thereby inducing gene silencing.

Similar, a nucleic acid sequence of interest to be expressed may by inserted into a plant genome comprising the transcription regulating nucleotide sequence in its natural genomic environment (i.e. linked to its natural gene) in a way that the inserted sequence becomes operably linked to the transcription regulating nucleotide sequence, thereby forming an expression cassette of the invention.

The expression cassette may be employed for numerous expression purposes such as for example expression of a protein, or expression of a antisense RNA, sense or double-stranded RNA. Preferably, expression of the nucleic acid sequence confers to the plant an agronomically valuable trait.

The open reading frame to be linked to the transcription regulating nucleotide sequence of the invention may be obtained from an insect resistance gene, a disease resistance gene such as, for example, a bacterial disease resistance gene, a fungal disease resistance gene, a viral disease resistance gene, a nematode disease resistance gene, a herbicide resistance gene, a gene affecting grain composition or quality, a nutrient utilization gene, a mycotoxin reduction gene, a male sterility gene, a selectable marker gene, a screenable marker gene, a negative selectable marker, a positive selectable marker, a gene affecting plant agronomic characteristics, i.e., yield, standability, and the like, or an environment or stress resistance gene, i.e., one or more genes that confer herbicide resistance or tolerance, insect resistance or tolerance, disease resistance or tolerance (viral, bacterial, fungal, oomycete, or nematode), stress tolerance or resistance (as exemplified by resistance or tolerance to drought, heat, chilling, freezing, excessive moisture, salt stress, or oxidative stress), increased yields, food content and makeup, physical appearance, male sterility, drydown, standability, prolificacy, starch properties or quantity, oil quantity and quality, amino acid or protein composition, and the like. By "resistant" is meant a plant, which exhibits substantially no phenotypic changes as a consequence of agent administration, infection with a pathogen, or exposure to stress. By "tolerant" is meant a plant, which, although it may exhibit some phenotypic changes as a consequence of infection, does not have a substantially decreased reproductive capacity or substantially altered metabolism.

Seed-preferential or seed-specific transcription regulating nucleotide sequences (e.g., promoters) are useful for expressing a wide variety of genes including those which alter metabolic pathways, confer disease resistance, for protein production, e.g., antibody production, or to improve nutrient uptake and the like. Seed-preferential or seed-specific transcription regulating nucleotide sequences (e.g., promoters) may be modified so as to be regulatable, e.g., inducible. The genes and transcription regulating nucleotide sequences (e.g., promoters) described hereinabove can be used to identify orthologous genes and their transcription regulating nucleotide sequences (e.g., promoters) which are also likely expressed in a particular tissue and/or development manner. Moreover, the orthologous transcription regulating nucleotide sequences (e.g., promoters) are useful to express linked open reading frames. In addition, by aligning the transcription regulating nucleotide sequences (e.g., promoters) of these orthologs, novel cis elements can be identified that are useful to generate synthetic transcription regulating nucleotide sequences (e.g., promoters).

The expression regulating nucleotide sequences specified above may be optionally operably linked to other suitable regulatory sequences, e.g., a transcription terminator sequence, operator, repressor-binding site, transcription factor binding site and/or an enhancer.

The present invention further provides a recombinant vector containing the expression cassette of the invention, and host cells comprising the expression cassette or vector, e.g., comprising a plasmid. The expression cassette or vector may augment the genome of a transformed plant or may be maintained extra chromosomally. The expression cassette or vector of the invention may be present in the nucleus, chloroplast, mitochondria and/or plastid of the cells of the plant. Preferably, the expression cassette or vector of the invention is comprised in the chromosomal DNA of the plant nucleus. The present invention also provides a transgenic plant prepared by this method, a seed from such a plant and progeny plants from such a plant including hybrids and inbreds. The expression cassette may be operatively linked to a structural gene, the open reading frame thereof, or a portion thereof. The expression cassette may further comprise a Ti plasmid and be contained in an *Agrobacterium tumefaciens* cell; it may be carried on a microparticle, wherein the microparticle is suitable for ballistic transformation of a plant cell; or it may be contained in a plant cell or protoplast. Further, the expression cassette or vector can be contained in a transformed plant or cells thereof, and the plant may be a dicot or a monocot. In particular, the plant may be a dicotyledonous plant. Preferred transgenic plants are transgenic maize, soybean, barley, alfalfa, sunflower, canola, soybean, cotton, peanut, sorghum, tobacco, sugarbeet, rice, wheat, rye, turfgrass, millet, sugarcane, tomato, or potato.

The invention also provides a method of plant breeding, e.g., to prepare a crossed fertile transgenic plant. The method comprises crossing a fertile transgenic plant comprising a particular expression cassette of the invention with itself or with a second plant, e.g., one lacking the particular expression cassette, to prepare the seed of a crossed fertile transgenic plant comprising the particular expression cassette. The seed is then planted to obtain a crossed fertile transgenic plant. The plant may be a monocot or a dicot. In a particular embodiment, the plant is a dicotyledonous plant. The crossed fertile transgenic plant may have the particular expression cassette inherited through a female parent or through a male parent. The second plant may be an inbred plant. The crossed fertile transgenic may be a hybrid. Also included within the present invention are seeds of any of these crossed fertile transgenic plants.

The transcription regulating nucleotide sequences of the invention further comprise sequences which are complementary to one (hereinafter "test" sequence) which hybridizes under stringent conditions with a nucleic acid molecule as described by SEQ ID NO: 1, 2, 3, 4, 5, 6, 7, 8, 9, 10, or 11, as well as RNA which is transcribed from the nucleic acid molecule. When the hybridization is performed under stringent conditions, either the test or nucleic acid molecule of invention is preferably supported, e.g., on a membrane or DNA chip. Thus, either a denatured test or nucleic acid molecule of the invention is preferably first bound to a support and hybridization is effected for a specified period of time at a temperature of, e.g., between 55 and 70° C., in double strength citrate buffered saline (SC) containing 0.1% SDS followed by rinsing of the support at the same temperature but with a buffer having a reduced SC concentration. Depending upon the degree of stringency required such reduced concentration buffers are typically single strength SC containing 0.1% SDS, half strength SC containing 0.1% SDS and one-tenth strength SC containing 0.1% SDS. More preferably hybridization is carried out under high stringency conditions (as defined above).

Virtually any DNA composition may be used for delivery to recipient plant cells, e.g., dicotyledonous cells, to ultimately produce fertile transgenic plants in accordance with the present invention. For example, DNA segments or fragments in the form of vectors and plasmids, or linear DNA segments or fragments, in some instances containing only the DNA element to be expressed in the plant, and the like, may be employed. The construction of vectors, which may be employed in conjunction with the present invention, will be known to those of skill of the art in light of the present disclosure (see, e.g., Sambrook 1989; Gelvin 1990).

Vectors, plasmids, cosmids, YACs (yeast artificial chromosomes), BACs (bacterial artificial chromosomes) and DNA segments for use in transforming such cells will, of course, generally comprise the cDNA, gene or genes which one desires to introduce into the cells. These DNA constructs can further include structures such as promoters, enhancers, polylinkers, or even regulatory genes as desired. The DNA segment, fragment or gene chosen for cellular introduction will often encode a protein which will be expressed in the resultant recombinant cells, such as will result in a screenable or selectable trait and/or which will impart an improved phenotype to the regenerated plant. However, this may not always be the case, and the present invention also encompasses transgenic plants incorporating non-expressed transgenes.

In certain embodiments, it is contemplated that one may wish to employ replication-competent viral vectors in monocot transformation. Such vectors include, for example, wheat dwarf virus (WDV) "shuttle" vectors, such as pW1-11 and PW1-GUS (Ugaki 1991). These vectors are capable of autonomous replication in maize cells as well as E. coli, and as such may provide increased sensitivity for detecting DNA delivered to transgenic cells. A replicating vector may also be useful for delivery of genes flanked by DNA sequences from transposable elements such as Ac, Ds, or Mu. It has been proposed (Laufs 1990) that transposition of these elements within the maize genome requires DNA replication. It is also contemplated that transposable elements would be useful for introducing DNA segments or fragments lacking elements necessary for selection and maintenance of the plasmid vector in bacteria, e.g., antibiotic resistance genes and origins of DNA replication. It is also proposed that use of a transposable element such as Ac, Ds, or Mu would actively promote integration of the desired DNA and hence increase the frequency of stably transformed cells. The use of a transposable element such as Ac, Ds, or Mu may actively promote integration of the DNA of interest and hence increase the frequency of stably transformed cells. Transposable elements may be useful to allow separation of genes of interest from elements necessary for selection and maintenance of a plasmid vector in bacteria or selection of a transformant. By use of a transposable element, desirable and undesirable DNA sequences may be transposed apart from each other in the genome, such that through genetic segregation in progeny, one may identify plants with either the desirable undesirable DNA sequences.

The nucleotide sequence of interest linked to one or more of the transcription regulating nucleotide sequences of the invention can, for example, code for a ribosomal RNA, an antisense RNA or any other type of RNA that is not translated into protein. In another preferred embodiment of the invention, said nucleotide sequence of interest is translated into a protein product. The transcription regulating nucleotide sequence and/or nucleotide sequence of interest linked thereto may be of homologous or heterologous origin with respect to the plant to be transformed. A recombinant DNA molecule useful for introduction into plant cells includes that which has been derived or isolated from any source, that may be subsequently characterized as to structure, size and/or function, chemically altered, and later introduced into plants. An example of a nucleotide sequence or segment of interest "derived" from a source, would be a nucleotide sequence or segment that is identified as a useful fragment within a given organism, and which is then chemically synthesized in essentially pure form. An example of such a nucleotide sequence or segment of interest "isolated" from a source, would be nucleotide sequence or segment that is excised or removed from said source by chemical means, e.g., by the use of restriction endonucleases, so that it can be further manipulated, e.g., amplified, for use in the invention, by the methodology of genetic engineering. Such a nucleotide sequence or segment is commonly referred to as "recombinant."

Therefore a useful nucleotide sequence, segment or fragment of interest includes completely synthetic DNA, semi-synthetic DNA, DNA isolated from biological sources, and DNA derived from introduced RNA. Generally, the introduced DNA is not originally resident in the plant genotype which is the recipient of the DNA, but it is within the scope of the invention to isolate a gene from a given plant genotype, and to subsequently introduce multiple copies of the gene into the same genotype, e.g., to enhance production of a given gene product such as a storage protein or a protein that confers tolerance or resistance to water deficit.

The introduced recombinant DNA molecule includes but is not limited to, DNA from plant genes, and non-plant genes such as those from bacteria, yeasts, animals or viruses. The introduced DNA can include modified genes, portions of genes, or chimeric genes, including genes from the same or different genotype. The term "chimeric gene" or "chimeric DNA" is defined as a gene or DNA sequence or segment comprising at least two DNA sequences or segments from species which do not combine DNA under natural conditions, or which DNA sequences or segments are positioned or linked in a manner which does not normally occur in the native genome of untransformed plant.

The introduced recombinant DNA molecule used for transformation herein may be circular or linear, double-stranded or single-stranded. Generally, the DNA is in the form of chimeric DNA, such as plasmid DNA that can also contain coding regions flanked by regulatory sequences, which promote the expression of the recombinant DNA present in the resultant plant. Generally, the introduced recombinant DNA molecule will be relatively small, i.e., less than about 30 kb to minimize any susceptibility to physical, chemical, or enzymatic degradation which is known to increase as the size of the nucleotide molecule increases. As noted above, the number of proteins, RNA transcripts or mixtures thereof, which is introduced into the plant genome, is preferably preselected and defined, e.g., from one to about 5-10 such products of the introduced DNA may be formed.

Two principal methods for the control of expression are known, viz.: overexpression and underexpression. Overexpression can be achieved by insertion of one or more than one extra copy of the selected gene. It is, however, not unknown for plants or their progeny, originally transformed with one or more than one extra copy of a nucleotide sequence, to exhibit the effects of underexpression as well as overexpression. For underexpression there are two principle methods, which are commonly referred to in the art as "antisense downregulation" and "sense downregulation" (sense downregulation is also referred to as "cosuppression"). Generically these processes are referred to as "gene silencing". Both of these methods lead to an inhibition of expression of the target gene.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed.

It is specifically contemplated by the inventors that one could mutagenize a promoter to potentially improve the utility of the elements for the expression of transgenes in plants. The mutagenesis of these elements can be carried out at random and the mutagenized promoter sequences screened for activity in a trial-by-error procedure. Alternatively, particular sequences which provide the promoter with desirable expression characteristics, or the promoter with expression enhancement activity, could be identified and these or similar sequences introduced into the sequences via mutation. It is further contemplated that one could mutagenize these sequences in order to enhance their expression of transgenes in a particular species.

The means for mutagenizing a DNA segment encoding a promoter sequence of the current invention are well known to those of skill in the art. As indicated, modifications to promoter or other regulatory element may be made by random, or site-specific mutagenesis procedures. The promoter and other regulatory element may be modified by altering their structure through the addition or deletion of one or more nucleotides from the sequence which encodes the corresponding unmodified sequences.

Mutagenesis may be performed in accordance with any of the techniques known in the art, such as, and not limited to, synthesizing an oligonucleotide having one or more mutations within the sequence of a particular regulatory region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

In general, the technique of site-specific mutagenesis is well known in the art, as exemplified by various publications. As will be appreciated, the technique typically employs a phage vector, which exists in both a single stranded and double stranded form. Typical vectors useful in site-directed mutagenesis include vectors such as the M13 phage. These phages are readily commercially available and their use is generally well known to those skilled in the art. Double stranded plasmids also are routinely employed in site directed mutagenesis, which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the promoter. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and cells are selected which include recombinant vectors bearing the mutated sequence arrangement. Vector DNA can then be isolated from these cells and used for plant transformation. A genetic selection scheme was devised by Kunkel et al. (1987) to enrich for clones incorporating mutagenic oligonucleotides. Alternatively, the use of PCR with commercially available thermostable enzymes such as Taq polymerase may be used to incorporate a mutagenic oligonucleotide primer into an amplified DNA fragment that can then be cloned into an appropriate cloning or expression vector. The PCR-mediated mutagenesis procedures of Tomic et al. (1990) and Upender et al. (1995) provide two examples of such protocols. A PCR employing a thermostable ligase in addition to a thermostable polymerase also may be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting, as there are other ways in which sequence variants of DNA sequences may be obtained. For example, recombinant vectors encoding the desired promoter sequence may be treated with mutagenic agents, such as hydroxylamine, to obtain sequence variants.

As used herein; the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson and Rarnstad, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224. A number of template-dependent processes are available to amplify the target sequences of interest present in a sample, such methods being well known in the art and specifically disclosed herein below.

Where a clone comprising a promoter has been isolated in accordance with the instant invention, one may wish to delimit the essential promoter regions within the clone. One efficient, targeted means for preparing mutagenizing promoters relies upon the identification of putative regulatory elements within the promoter sequence. This can be initiated by comparison with promoter sequences known to be expressed in similar tissue-specific or developmentally unique manner. Sequences, which are shared among promoters with similar expression patterns, are likely candidates for the binding of transcription factors and are thus likely elements that confer expression patterns. Confirmation of these putative regulatory elements can be achieved by deletion analysis of each putative regulatory region followed by functional analysis of each deletion construct by assay of a reporter gene, which is functionally attached to each construct. As such, once a starting promoter sequence is provided, any of a number of different deletion mutants of the starting promoter could be readily prepared.

Functionally equivalent fragments of a transcription regulating nucleotide sequence of the invention can also be obtained by removing or deleting non-essential sequences without deleting the essential one. Narrowing the transcription regulating nucleotide sequence to its essential, transcription mediating elements can be realized in vitro by trial-and-arrow deletion mutations, or in silico using promoter element search routines. Regions essential for promoter activity often demonstrate clusters of certain, known promoter elements. Such analysis can be performed using available computer algorithms such as PLACE ("Plant Cis-acting Regulatory DNA Elements"; Higo 1999), the BIOBASE database "Transfac" (Biologische Datenbanken GmbH, Braunschweig; Wingender 2001) or the database PlantCARE (Lescot 2002).

Preferably, functional equivalent fragments of one of the transcription regulating nucleotide sequences of the invention comprises at least 100 base pairs, preferably, at least 200 base pairs, more preferably at least 500 base pairs of a transcription regulating nucleotide sequence as described by SEQ ID NO:

1, 2, 3, 4, 5, 6, 7, 8, 9, 10, or 11. More preferably this fragment is starting from the 3'-end of the indicated sequences.

Especially preferred are equivalent fragments of transcription regulating nucleotide sequences, which are obtained by deleting the region encoding the 5'-untranslated region of the mRNA, thus only providing the (untranscribed) promoter region. The 5'-untranslated region can be easily determined by methods known in the art (such as 5'-RACE analysis). Accordingly, some of the transcription regulating nucleotide sequences of the invention are equivalent fragments of other sequences (see Table 2 below).

TABLE 2

Relationship of transcription regulating nucleotide sequences of the invention

| Transcription regulating sequence | Equivalent fragment |
|---|---|
| SEQ ID NO: 1 (529 bp) | SEQ ID NO: 2 (320 bp) |
| SEQ ID NO: 3 (1510 bp) | SEQ ID NO: 4 (1112 bp) |
|  | SEQ ID NO: 5 (578 bp) |
| SEQ ID NO: 6 (1521 bp) | SEQ ID NO: 7 (1086 bp) |
|  | SEQ ID NO: 8 (400 bp) |
| SEQ ID NO: 9 (1751 bp) | SEQ ID NO: 10 (901 bp) |
|  | SEQ ID NO: 11 (384 bp) |

As indicated above, deletion mutants, deletion mutants of the promoter of the invention also could be randomly prepared and then assayed. With this strategy, a series of constructs are prepared, each containing a different portion of the clone (a subclone), and these constructs are then screened for activity. A suitable means for screening for activity is to attach a deleted promoter or intron construct, which contains a deleted segment to a selectable or screenable marker, and to isolate only those cells expressing the marker gene. In this way, a number of different, deleted promoter constructs are identified which still retain the desired, or even enhanced, activity. The smallest segment, which is required for activity, is thereby identified through comparison of the selected constructs. This segment may then be used for the construction of vectors for the expression of exogenous genes.

A promoter motif analysis can be done for example by using the Genomatix software MatInspector Release professional 7.3 (August 2004) (see Example 8). Motifs found in the transcription regulating sequences of the invention are listed in Table 5 below. The term "motif" means a nucleotide sequence which is predictive for promoter activity and/or binding of certain transcription regulating factors. However, the individual nucleotides of a complete motif matrix (e.g., atgatcaAACActtgaaat; SEQ ID NO: 145) are of different relevance. The motif comprises a conserved region e.g., tcnAACActtga; SEQ ID NO: 77), —which consists of a core region (e.g., AACA; SEQ ID NO: 35, bold capital letters) and a less conserved part (bold small letters). The motifs described above may be present in one or more copies in the respective region (see Example 8 and Table 3 below).

In the three promoter sequences characterized herein various promoter motifs were identified. In the tables below (Table 3 to 7) these promoter motifs are prioritized according to the following principles:

Priority 1: Putative seed-specific motifs, which are found in all of the promoter sequences disclosed herein. Putative seed-specific motifs include motifs which were described to be seed-specific for other known seed-specific promoters such as the beta-phaseolin promoter (e.g., opaque-2, G-Box) and motifs such as RY and Sph motifs.

Priority 2: Putative seed-specific motifs, which are not present in all promoters disclosed herein.

Priority 3: Motifs, which are not putative seed-specific but are having a conserved position or conserved order in all the promoters disclosed herein.

Priority 4: Motifs, which are not putative seed-specific but are present in all promoters disclosed herein.

Priority 5: Motifs, which are not putative seed-specific and are not present in all promoters disclosed herein.

Accordingly another embodiment of the invention a derivative of the *Arabidopsis thaliana* transcription regulating nucleotide sequence comprises at least two promoter motifs (preferably at least 3, 4, 5, 6 or 7, more preferably at least 8, 9, 10 or 11, most preferably at least 12, 13, 14, 15, 16, 17 or all motifs) selected from the group of motifs consisting of the sequences described by SEQ ID NO: 35, 36, 38, 39, 40, 41, 43, 44, 45, 46, 47, 48, 49, 50, 51, 52, and 55. More preferably the promoter elements are selected from the group of elements described with priority 1, 2, 3 or 4 (preferably priority 1, 2, or 3; more preferably priority 1 or 2; most preferably priority 1) in Table 3 or 4 below. Most preferably the order (in 5'-3' direction) of the selected motifs is as indicated in Table 3 (column 3 or 4) or Table 4 (column 1 and 2) giving the order of the motifs in the transcription regulating sequence of the invention as described by SEQ ID NO: 1. Even more preferably the distance between the selected motifs is substantially the same as in the transcription regulating sequence of the invention as described by SEQ ID NO: 1. Substantially identical means that the distance does not deviate by more than 100, preferably 50, more preferably 25, most preferably 10 nucleotides from the distance as in the transcription regulating sequence of the invention as described by SEQ ID NO: 1.

More preferably a derivative of the *Arabidopsis thaliana* transcription regulating nucleotide sequence comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22, 23, 24, 25 or all motifs) selected from the group of motifs consisting of the sequences described by SEQ ID NO: 77, 78, 79, 83, 82, 84, 85, 86, 89, 90, 91, 92, 93, 97, 101, 102, 103, 104, 105, 106, 107, 108, 109, 110, and 114. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 or 4 below. Most preferably the order (in 5'-3' direction) of the selected motifs is as indicated in Table 3 (column 3 or 4) or Table 4 (column 1 and 2) giving the order of the motifs in the transcription regulating sequence of the invention as described by SEQ ID NO: 1. Even more preferably the distance between the selected motifs is substantially the same as in the transcription regulating sequence of the invention as described by SEQ ID NO: 1. Substantially identical means that the distance does not deviate by more than 100, preferably 50, more preferably 25, most preferably 10 nucleotides from the distance as in the transcription regulating sequence of the invention as described by SEQ ID NO: 1.

Most preferably a derivative of the *Arabidopsis thaliana* transcription regulating nucleotide sequence comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22, 23, 24, 25, 26, 27, 28, 29, 30 or all motifs) selected from the group of motifs consisting of the sequences described by SEQ ID NO: 145, 146, 148, 153, 151, 156, 160, 162, 167, 169, 170, 171, 172, 185, 186, 188, 192, 200, 201, 202, 203, 204, 205, 208, 209, 210, 211, 212, and 216. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 or 4 below. Most preferably the order (in 5'-3' direction) of the selected motifs is as indicated Table 3 (column 3 or 4) or Table 4 (column 1 and 2) giving the order of the motifs in the transcription regulating sequence of the invention as described by SEQ ID NO: 1. Even more preferably the distance between the selected motifs is substantially the same as in the transcription regulating sequence of the invention as described by SEQ ID NO: 1. Substantially identical means that the distance does not deviate by more than 100, preferably 50, more preferably 25, most preferably 10 nucleotides from the distance as in the transcription regulating sequence of the invention as described by SEQ ID NO: 1.

Another embodiment of the invention a derivative of the *Brassica napus* transcription regulating nucleotide sequence comprises at least two promoter motifs (preferably at least 3, 4, 5, 6 or 7, more preferably at least 8, 9, 10 or 11, most preferably at least 12, 13, 14, 15, 16, 17, 18 or all motifs) selected from the group of motifs consisting of the sequences described by SEQ ID NO: 36, 36, 38, 39, 40, 41, 44, 46, 47, 53, 56, 58, 59, 62, 64, 67, 68, and 71. More preferably the promoter elements are selected from the group of elements described with priority 1, 2, 3 or 4 (preferably priority 1, 2, or 3; more preferably priority 1 or 2; most preferably priority 1) in Table 3 or 5 below. Most preferably the order (in 5'-3' direction) of the selected motifs is as indicated Table 3 (column 3 or 4) or Table 5 (column 1 and 2) giving the order of the motifs in the transcription regulating sequence of the invention as described by SEQ ID NO: 3. Even more preferably the distance between the selected motifs is substantially the same as in the transcription regulating sequence of the invention as described by SEQ ID NO: 3. Substantially identical means that the distance does not deviate by more than 100, preferably 50, more preferably 25, most preferably 10 nucleotides from the distance as in the transcription regulating sequence of the invention as described by SEQ ID NO: 3.

More preferably a derivative of the *Brassica napus* transcription regulating nucleotide sequence comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22 or all motifs) selected from the group of motifs consisting of the sequences described by SEQ ID NO: 78, 80, 82, 83, 84, 85, 86, 90, 94, 97, 98, 99, 111, 115, 117, 118, 119, 122, 128, 132, 134, and 138. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 or 5 below. Most preferably the order (in 5'-3' direction) of the selected motifs is as indicated Table 3 (column 3 or 4) or Table 5 (column 1 and 2) giving the order of the motifs in the transcription regulating sequence of the invention as described by SEQ ID NO: 3. Even more preferably the distance between the selected motifs is substantially the same as in the transcription regulating sequence of the invention as described by SEQ ID NO: 3. Substantially identical means that the distance does not deviate by more than 100, preferably 50, more preferably 25, most preferably 10 nucleotides from the distance as in the transcription regulating sequence of the invention as described by SEQ ID NO: 3.

Most preferably a derivative of the *Brassica napus* transcription regulating nucleotide sequence comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22, 23, 24, 25, 26 or all motifs) selected from the group of motifs consisting of the sequences described by SEQ ID NO: 147, 149, 152, 154, 155, 157, 161, 163, 173, 174, 175, 176, 189, 193, 194, 196, 213, 217, 219, 220, 221, 224, 232, 236, 241, and 245. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 or 5 below. Most preferably the order (in 5'-3' direction) of the selected motifs is as indicated in Table 3 (column 3 or 4) or Table 5 (column 1 and 2) giving the order of the motifs in the transcription regulating sequence of the invention as described by SEQ ID NO: 3. Even more preferably the distance between the selected motifs is substantially the same as in the transcription regulating sequence of the invention as described by SEQ ID NO: 3. Substantially identical means that the distance does not deviate by more than 100, preferably 50, more preferably 25, most preferably 10 nucleotides from the distance as in the transcription regulating sequence of the invention as described by SEQ ID NO: 3.

Another embodiment of the invention a derivative of the *Linum usitatissimum* transcription regulating nucleotide sequence 1 comprises at least two promoter motifs (preferably at least 3, 4, 5, 6 or 7, more preferably at least 8, 9, 10 or 11, most preferably at least 12, 13, 14, 15, 16, 17 or all motifs) selected from the group of motifs consisting of the sequences described by SEQ ID NO: 39, 41, 44, 45, 46, 47, 54, 62, 63, 65, 66, 67, 69, 70, 71, 72, and 73. More preferably the promoter elements are selected from the group of elements described with priority 1, 2, 3 or 4 (preferably priority 1, 2, or 3; more preferably priority 1 or 2; most preferably priority 1) in Table 3 or 6 below. Most preferably the order (in 5'-3' direction) of the selected motifs is as indicated in Table 3 (column 3 or 4) or Table 6 (column 1 and 2) giving the order of the motifs in the transcription regulating sequence of the invention as described by SEQ ID NO: 6. Even more preferably the distance between the selected motifs is substantially the same as in the transcription regulating sequence of the invention as described by SEQ ID NO: 6. Substantially identical means that the distance does not deviate by more than 100, preferably 50, more preferably 25, most preferably 10 nucleotides from the distance as in the transcription regulating sequence of the invention as described by SEQ ID NO: 6.

More preferably a derivative of the *Linum usitatissimum* transcription regulating nucleotide sequence 1 comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22, 23, 24 or all motifs) selected from the group of motifs consisting of the sequences described by SEQ ID NO: 84, 87, 90, 92, 95, 96, 98, 100, 112, 123, 126, 127, 129, 130, 131, 133, 135, 137, 139, 140, 141, 142, 143, and 144. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 or 6 below. Most preferably the order (in 5'-3' direction) of the selected motifs is as indicated in Table 3 (column 3 or 4) or Table 6 (column 1 and 2) giving the order of the motifs in the transcription regulating sequence of the invention as described by SEQ ID NO: 6. Even more preferably the distance between the selected motifs is substantially the same as in the transcription regulating sequence of the invention as described by SEQ ID NO: 6. Substantially identical means that the distance does not deviate by more than 100, preferably 50, more preferably 25, most preferably 10 nucleotides from the distance as in the transcription regulating sequence of the invention as described by SEQ ID NO: 6.

Most preferably a derivative of the *Linum usitatissimum* transcription regulating nucleotide sequence 1 comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22, 23, 24, 25, 26, 27, 28, 29, 30, 31, 32 or all motifs) selected from the group of motifs consisting of the sequences described by SEQ ID NO: 158, 164, 177, 178, 179, 180, 184, 187, 190, 191, 195, 197, 214, 225, 229, 230, 233, 234, 235, 238, 239, 240, 242, 244, 246, 247, 249, 251, 253, and 254. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 or 6 below. Most preferably the order (in 5'-3' direction) of the selected motifs is as indicated in Table 3 (column 3 or 4) or Table 6 (column 1 and 2) giving the order of the motifs in the transcription regulating sequence of the invention as described by SEQ ID NO: 6. Even more preferably the distance between the selected motifs is substantially the same as in the transcription regulating sequence of the invention as described by SEQ ID NO: 6. Substantially identical means that the distance does not deviate by more than 100, preferably 50, more preferably 25, most preferably 10 nucleotides from the distance as in the transcription regulating sequence of the invention as described by SEQ ID NO: 6.

Another embodiment of the invention a derivative of the *Linum usitatissimum* transcription regulating nucleotide sequence 2 comprises at least two promoter motifs (preferably at least 3, 4, 5, 6 or 7, more preferably at least 8, 9, 10 or 11, most preferably at least 12, 13, 14, 15, 16, 17, 18, 19, 20 or all motifs) selected from the group of motifs consisting of the sequences described by SEQ ID NO: 37, 39, 41, 42, 43, 44, 47, 47, 51, 54, 57, 60, 61, 62, 63, 67, 70, 72, 73, and 74. More preferably the promoter elements are selected from the group of elements described with priority 1, 2, 3 or 4 (preferably priority 1, 2, or 3; more preferably priority 1 or 2; most preferably priority 1) in Table 3 or 7 below. Most preferably the order (in 5'-3' direction) of the selected motifs is as indicated in Table 3 (column 3 or 4) or Table 7 (column 1 and 2) giving the order of the motifs in the transcription regulating sequence of the invention as described by SEQ ID NO: 9. Even more preferably the distance between the selected motifs is substantially the same as in the transcription regulating sequence of the invention as described by SEQ ID NO: 9. Substantially identical means that the distance does not deviate by more than 100, preferably 50, more preferably 25, most preferably 10 nucleotides from the distance as in the transcription regulating sequence of the invention as described by SEQ ID NO: 9.

More preferably a derivative of the *Linum usitatissimum* transcription regulating nucleotide sequence 2 comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22 or all motifs) selected from the group of motifs consisting of the sequences described by SEQ ID NO: 81, 84, 87, 88, 89, 90, 100, 106, 106, 113, 116, 120, 121, 123, 124, 125, 127, 132, 136, 140, 141, and 142. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 or 7 below. Most preferably the order (in 5'-3' direction) of the selected motifs is as indicated in Table 3 (column 3 or 4) or Table 7 (column 1 and 2) giving the order of the motifs in the transcription regulating sequence of the invention as described by SEQ ID NO: 9. Even more preferably the distance between the selected motifs is substantially the same as in the transcription regulating sequence of the invention as described by SEQ ID NO: 9. Substantially identical means that the distance does not deviate by more than 100, preferably 50, more preferably 25, most preferably 10 nucleotides from the distance as in the transcription regulating sequence of the invention as described by SEQ ID NO: 9.

Most preferably a derivative of the *Linum usitatissimum* transcription regulating nucleotide sequence 2 comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22, 23, 24, 25 or all motifs) selected from the group of motifs consisting of the sequences described by SEQ ID NO: 150, 159, 165, 166, 168, 181, 182, 183, 198, 199, 206, 207, 215, 218, 222, 223, 226, 227, 228, 231, 237, 243, 248, 250, and 252. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 or 7 below. Most preferably the order (in 5'-3' direction) of the selected motifs is as indicated in Table 3 (column 3 or 4) or Table 7 (column 1 and 2) giving the order of the motifs in the transcription regulating sequence of the invention as described by SEQ ID NO: 9. Even more preferably the distance between the selected motifs is substantially the same as in the transcription regulating sequence of the invention as described by SEQ ID NO: 9. Substantially identical means that the distance does not deviate by more than 100, preferably 50, more preferably 25, most preferably 10 nucleotides from the distance as in the transcription regulating sequence of the invention as described by SEQ ID NO: 9.

A derivative of one of the promoters may also comprise motifs from more than one of the promoters disclosed herein. Accordingly another embodiment of the invention a derivative of a transcription regulating nucleotide sequence of the invention comprises at least two promoter motifs (preferably at least 3, 4, 5, 6 or 7, more preferably at least 8, 9, 10 or 11, most preferably at least 12, 13, 14, 15, 16, 17, 18, 19, 20, 25, 30, 35 or all motifs) selected from the group of motifs consisting of the sequences described by SEQ ID NO: 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, and 76. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

More preferably a derivative of a transcription regulating nucleotide sequence of the invention comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22, 30, 35, 40, 45, 50, 55, 60, 70 or all motifs) selected from the group of motifs consisting of the sequences described by SEQ ID NO: 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 124, 135, 136, 137, 138, 139, 140, 141, 142, 143, and 144. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

Most preferably a derivative of a transcription regulating nucleotide sequence of the invention comprises at least two promoter motifs (preferably at least 3, 4, 5, 6 or 7, more preferably at least 8, 9, 10 or 11, most preferably at least 12, 13, 14, 15, 16, 17, 18, 19, 20, 21, 22, 23, 24, 25, 30, 40, 50, 60, 70, 80, 90, 100 or all motifs) selected from the group of motifs consisting of the sequences described by SEQ ID NO: 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 231, 232, 233, 234, 235, 235, 237, 238, 239, 240, 241, 242, 243, 244, 245, 246, 247, 248, 249, 250, 251, 252, 253 and 254. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

TABLE 3

Promoter elements found in tonoplast intrinsic protein promoters, sorted first by the potential importance of the element (column 1, "Priority"; 1: more essential and preferred to be present in the promoter to 5: less essential) and sorted second by the specific plant promoter from which the element is derived from (column 2; either Arabidopsis "At", Brassica napus "Bn", Linum usitatissium promoter 1 "Lu-1", Linum usitatissium promoter 2 "Lu-2") and the SEQ ID NO for this promoter (column 3). Given is also the Order No. of the motif within one promoter sequence starting with "1" closest to translation start 'ATG' (column 4), the exact position in the promoter (column 5; referring to promoter motif matrix), the type of the promoter element (column 6), and the sequences for the core region, conserved region and entire matrix for the promoter element.

| Priority | Plant | SEQ ID No. of promoter | Motif Order No. in promoter | Motif position in promoter | Further Information | Promoter Motif Matrix | conserved SEQ motif ID matrix No region | core region SEQ of ID motif No matrix | SEQ ID matrix No |
|---|---|---|---|---|---|---|---|---|---|
| 1 | At | 1 | 4 | 383-403 | G-box binding proteins | ttaaagctACGTgtccagctt | 153 tACGT | 83 ACGT | 38 |
| 1 | At | 1 | 5 | 382-402 | G-box binding proteins | agctggacACGTagctttaaa | 156 cACGT | 84 ACGT | 39 |
| 1 | At | 1 | 9 | 367-393 | RY and Sph motifs conserved in seed-specific promoters | agtaattgCATGcaatttaaagctacg | 169 CATGca | 90 CATG | 44 |
| 1 | At | 1 | 10 | 360-386 | RY and Sph motifs conserved in seed-specific promoters | ttaaattgCATGcaattacttaaccat | 170 CATGca | 90 CATG | 44 |

TABLE 3-continued

Promoter elements found in tonoplast intrinsic protein promoters, sorted first by the potential importance of the element (column 1, "Priority"; 1: more essential and preferred to be present in the promoter to 5: less essential) and sorted second by the specific plant promoter from which the element is derived from (column 2; either *Arabidopsis* "At", *Brassica napus* "Bn", *Linum usitatissium* promoter 1 "Lu-1", *Linum usitatissium* promoter 2 "Lu-2") and the SEQ ID NO for this promoter (column 3). Given is also the Order No. of the motif within one promoter sequence starting with "1" closest to translation start 'ATG' (column 4), the exact position in the promoter (column 5; referring to promoter motif matrix), the type of the promoter element (column 6), and the sequences for the core region, conserved region and entire matrix for the promoter element.

| Priority | Plant | SEQ ID No. of promoter | Motif Order No. in promoter | Motif position in promoter | Further Information | Promoter Motif Matrix | conserved SEQ ID No motif matrix region | core region SEQ ID No of motif matrix | SEQ ID No |
|---|---|---|---|---|---|---|---|---|---|
| 1 | At | 1 | 16 | 192-218 | RY and Sph motifs conserved in seed-specific promoters | ttggcacaCATGca tgcttagtcaaca | 171 CATGca | 90 CATG | 44 |
| 1 | At | 1 | 17 | 189-215 | RY and Sph motifs conserved in seed-specific promoters | tgactaagCATGca tgtgtgccaagta | 172 CATGca | 90 CATG | 44 |
| 1 | At | 1 | 13 | 246-262 | Recognition site for BZIP transcription factors that belong to the group of Opaque-2 like proteins | cacgaggACATgt atta | 192 gnACnTgnnt | 97 AcnT | 47 |
| 1 | Bn | 3 | 3 | 1379-1399 | G-box binding proteins | ttcaagctACGTgtc catctc | 154 tACGT | 83 ACGT | 38 |
| 1 | Bn | 3 | 7 | 1379-1399 | G-box binding proteins | ttcaagctACGTgtc catctc | 155 tACGT | 83 ACGT | 38 |
| 1 | Bn | 3 | 5 | 1378-1398 | G-box binding proteins | agatggacACGTa gcttgaaa | 157 cACGT | 84 ACGT | 39 |
| 1 | Bn | 3 | 8 | 1363-1389 | RY and Sph motifs conserved in seed-specific promoters | gtaacatgCATGca gtttcaagctacg | 173 CATGca | 90 CATG | 44 |
| 1 | Bn | 3 | 9 | 1359-1385 | RY and Sph motifs conserved in seed-specific promoters | ttaagtaaCATGcat gcagtttcaagc | 174 CATGca | 90 CATG | 44 |
| 1 | Bn | 3 | 10 | 1356-1382 | RY and Sph motifs conserved in seed-specific promoters | tgaaactgCATGca tgttacttaacca | 175 CATGca | 90 CATG | 44 |
| 1 | Bn | 3 | 17 | 1243-1269 | RY and Sph motifs conserved in seed-specific promoters | gttaagtaCATGcat aaagtttaagga | 176 CATGca | 90 CATG | 44 |
| 1 | Bn | 3 | 16 | 1253-1269 | Recognition site for BZIP transcription factors that belong to the group of Opaque-2 like proteins | GttaagtACATgca taa | 193 gnACnTgnnt | 97 AcnT | 47 |
| 1 | Bn | 3 | 11 | 1359-1375 | Recognition site for BZIP transcription factors that belong to the group of Opaque-2 like proteins | ttaagtaACATgcat gc | 194 tnACnTgnnt | 98 AcnT | 47 |
| 1 | Bn | 3 | 12 | 1342-1358 | Recognition site for BZIP transcription factors that belong to the group of Opaque-2 like proteins | gaaaatgACATac atgg | 196 tnACnTannt | 99 AcnT | 47 |
| 1 | Lu1 | 6 | 10 | 1268-1288 | G-box binding proteins | ggatagccACGTa gaattaaa | 158 cACGT | 84 ACGT | 39 |
| 1 | Lu1 | 6 | 4 | 1372-1398 | RY and Sph motifs conserved in seed-specific Promoters | ctcccatcCATGcat aaacctcatttc | 177 CATGca | 90 CATG | 44 |

TABLE 3-continued

Promoter elements found in tonoplast intrinsic protein promoters, sorted first by the potential importance of the element (column 1, "Priority"; 1: more essential and preferred to be present in the promoter to 5: less essential) and sorted second by the specific plant promoter from which the element is derived from (column 2; either *Arabidopsis* "At", *Brassica napus* "Bn", *Linum usitatissium* promoter 1 "Lu-1", *Linum usitatissium* promoter 2 "Lu-2") and the SEQ ID NO for this promoter (column 3). Given is also the Order No. of the motif within one promoter sequence starting with "1" closest to translation start 'ATG' (column 4), the exact position in the promoter (column 5; referring to promoter motif matrix), the type of the promoter element (column 6), and the sequences for the core region, conserved region and entire matrix for the promoter element.

| Priority | Plant | SEQ ID No. of promoter | Motif Order No. in promoter | Motif position in promoter | Further Information | Promoter Motif Matrix | conserved SEQ ID No motif region | core region SEQ ID No of motif matrix | SEQ ID No |
|---|---|---|---|---|---|---|---|---|---|
| 1 | Lu1 | 6 | 5 | 1282-1308 | RY and Sph motifs conserved in seed-specific promoters | gctatcccCATGca tgaaattccaaaa | 178 CATGca | 90 CATG | 44 |
| 1 | Lu1 | 6 | 6 | 1279-1305 | RY and Sph motifs conserved in seed-specific promoters | tggaatttCATGcat ggggatagccac | 179 CATGca | 90 CATG | 44 |
| 1 | Lu1 | 6 | 12 | 1204-1230 | RY and Sph motifs conserved in seed-specific promoters | gagaagaaCATGc atttacagaggata | 180 CATGca | 90 CATG | 44 |
| 1 | Lu1 | 6 | 29 | 446-472 | RY and Sph motifs conserved in seed-specific promoters | aacgccacCATGc atccataattttt | 184 CATGca | 90 CATG | 44 |
| 1 | Lu1 | 6 | 1 | 1505-1521 | Recognition site for BZIP transcription factors that belong to the group of Opaque-2 like proteins | gatgatgACTTgttt gt | 195 tnACnTgnnt | 98 AcnT | 47 |
| 1 | Lu1 | 6 | 9 | 1270-1286 | Recognition site for BZIP transcription factors that belong to the group of Opaque-2 like proteins | taattctACGTggct at | 197 cnACnTgnnt | 100 AcnT | 47 |
| 1 | Lu-2 | 9 | 11 | 1515-1535 | G-box binding proteins | ggatagccACGTa gaaactaa | 159 cACGT | 84 ACGT | 39 |
| 1 | Lu-2 | 9 | 3 | 1617-1643 | RY and Sph motifs conserved in seed-specific promoters | tcccatccCATGcat acacctcaattg | 181 CATGca | 90 CATG | 44 |
| 1 | Lu-2 | 9 | 6 | 1529-1555 | RY and Sph motifs conserved in seed-specific promoters | gctatccaCATGca tgaaattccaaaa | 182 CATGca | 90 CATG | 44 |
| 1 | Lu-2 | 9 | 7 | 1526-1552 | RY and Sph motifs conserved in seed-specific promoters | tggaatttCATGcat gtggatagccac | 183 CATGca | 90 CATG | 44 |
| 1 | Lu-2 | 9 | 5 | 1529-1545 | Recognition site for BZIP transcription factors that belong to the group of Opaque-2 like proteins | gctatccACATGca tga | 198 cnACnTgnnt | 100 AcnT | 47 |
| 1 | Lu-2 | 9 | 9 | 1517-1533 | Recognition site for BZIP transcription factors that belong to the group of Opaque-2 like proteins | agtttctACGTggct at | 199 cnACnTgnnt | 100 AcnT | 47 |
| 2 | At | 1 | 3 | 385-401 | Rice transcription activator-1 (RITA), basic leucin zipper protein, highly expressed during seed development | gctggacACGTag cttt | 151 cACGT | 82 ACGT | 38 |
| 2 | At | 1 | 12 | 292-308 | GCN4, conserved in cereal seed storage protein gene promoters, similar to yeast GCN4 and vertebrate AP-1 | tcttggTGAGttatttt | 188 gTGAGtta | 93 TGAG | 46 |

TABLE 3-continued

Promoter elements found in tonoplast intrinsic protein promoters, sorted first by the potential importance of the element (column 1, "Priority"; 1: more essential and preferred to be present in the promoter to 5: less essential) and sorted second by the specific plant promoter from which the element is derived from (column 2; either *Arabidopsis* "At", *Brassica napus* "Bn", *Linum usitatissium* promoter 1 "Lu-1", *Linum usitatissium* promoter 2 "Lu-2") and the SEQ ID NO for this promoter (column 3). Given is also the Order No. of the motif within one promoter sequence starting with "1" closest to translation start 'ATG' (column 4), the exact position in the promoter (column 5; referring to promoter motif matrix), the type of the promoter element (column 6), and the sequences for the core region, conserved region and entire matrix for the promoter element.

| Priority | Plant | SEQ ID No. of promoter | Motif Order No. in promoter | Motif position in promoter | Further Information | Promoter Motif Matrix | conserved SEQ ID No | motif matrix region | core region SEQ ID No | of motif matrix | SEQ ID No |
|---|---|---|---|---|---|---|---|---|---|---|---|
| 2 | Bn | 3 | 2 | 1381-1397 | Rice transcription activator-1 (RITA), basic leucin zipperprotein, highly expressed during seed development 1397 | gatggacACGTagcttg | 152 | cACGT | 82 | ACGT | 38 |
| 2 | Bn | 3 | 27 | 205-221 | GCN4, conserved in cereal seed storage protein gene promoters, similar to yeast GCN4 and vertebrate AP-1 | atgaacTGAGtcactgt | 189 | cTGAGtca | 94 | TGAG | 46 |
| 2 | Bn | 3 | 15 | 1262-1288 | Legumin box, highly conserved sequence element about 100 bp upstream of the TSS in legumin genes | tacttaaCCATgagattccaacaaaga | 219 | acttaaCCATgagntnccaacaaag | 117 | CCAT | 58 |
| 2 | Bn | 3 | 23 | 432-458 | Legumin box, highly conserved sequence element about 100 bp upstream of the TSS in legumin genes | tgaataaCCATggaaccttagtaaggc | 220 | gaataaCCATggancnttagtaagg | 118 | CCAT | 58 |
| 2 | Bn | 3 | 22 | 627-653 | Legumin box, highly conserved sequence element about 100 bp upstream of the TSS in legumin genes | aagataaCCGTtgaagaacaatagtgt | 221 | agataaCCGTtgangnacaatagtg | 119 | CCGT | 59 |
| 2 | Bn | 3 | 18 | 1058-1074 | Opaque-2 | TCATtacagagagatga | 224 | TCATtacagagagat | 122 | TCAT | 62 |
| 2 | Bn | 3 | 26 | 360-376 | Opaque-2 | TTATttcaagaagatgt | 232 | TTATttcaagaagat | 128 | TTAT | 64 |
| 2 | Bn | 3 | 19 | 966-980 | SEF3, Soybean embryo factor 3 | aggaaACCCagcagg | 236 | aACCCanc | 132 | ACCC | 67 |
| 2 | Bn | 3 | 20 | 941-957 | Prolamin box, conserved in cereal seed storage protein gene promoters | tgatttgcAAATgcagt | 241 | tgnnntgcAAATnnng | 134 | AAAT | 68 |
| 2 | Bn | 3 | 28 | 175-191 | Prolamin box, conserved in cereal seed storage protein gene promoters | ggtcatgaAAAGataca | 245 | ggnnntgaAAAGnnnc | 138 | AAAG | 71 |
| 2 | Lu1 | 6 | 22 | 841-857 | GCN4, conserved in cereal seed storage protein gene promoters, similar to yeast GCN4 and vertebrate AP-1 | aagtgtTGAGtcagaat | 190 | tTGAGtca | 95 | TGAG | 46 |
| 2 | Lu1 | 6 | 26 | 598-614 | GCN4, conserved in cereal seed storage protein gene promoters, similar to yeast GCN4 and vertebrate AP-1 | ttatgaTGAGtcgtact | 191 | aTGAGtcg | 96 | TGAG | 46 |
| 2 | Lu1 | 6 | 2 | 1504-1520 | Opaque-2 | aacaaacaagTCATcat | 225 | cannTCATc | 123 | TCAT | 62 |
| 2 | Lu1 | 6 | 23 | 680-696 | Opaque-2 | TCATttaacctcgagtc | 229 | TCATttaacctcgag | 126 | TCAT | 62 |

TABLE 3-continued

Promoter elements found in tonoplast intrinsic protein promoters, sorted first by the potential importance of the element (column 1, "Priority"; 1: more essential and preferred to be present in the promoter to 5: less essential) and sorted second by the specific plant promoter from which the element is derived from (column 2; either *Arabidopsis* "At", *Brassica napus* "Bn", *Linum usitatissium* promoter 1 "Lu-1", *Linum usitatissium* promoter 2 "Lu-2") and the SEQ ID NO for this promoter (column 3). Given is also the Order No. of the motif within one promoter sequence starting with "1" closest to translation start 'ATG' (column 4), the exact position in the promoter (column 5; referring to promoter motif matrix), the type of the promoter element (column 6), and the sequences for the core region, conserved region and entire matrix for the promoter element.

| Priority | Plant | SEQ ID No. of promoter | Motif Order No. in promoter | Motif position in promoter | Further Information | Promoter Motif Matrix | SEQ ID No | conserved motif region | SEQ ID No | core region of motif matrix | SEQ ID No |
|---|---|---|---|---|---|---|---|---|---|---|---|
| 2 | Lu1 | 6 | 7 | 1271-1287 | Opaque-2 | gatagccACGTagaatt | 230 | ACGTa | 127 | ACGT | 63 |
| 2 | Lu1 | 6 | 24 | 616-632 | Opaque-2 | CCATtctacataggga | 233 | CCATtctacatagg | 129 | CCAT | 65 |
| 2 | Lu1 | 6 | 32 | 385-401 | Opaque-2 | TCAAtccatcttaattt | 234 | TCAAtccatctta at | 130 | TCAA | 66 |
| 2 | Lu1 | 6 | 37 | 172-188 | Opaque-2 | caaacccattTCAAcaa | 235 | cattTCAAc | 131 | TCAA | 66 |
| 2 | Lu1 | 6 | 17 | 1055-1069 | SEF3, Soybean embryo factor 3 | gtctaACCCaattca | 238 | aACCCant | 133 | ACCC | 67 |
| 2 | Lu1 | 6 | 25 | 609-623 | SEF3, Soybean embryo factor 3 | tcataACCCattcta | 239 | aACCCant | 133 | ACCC | 67 |
| 2 | Lu1 | 6 | 36 | 176-190 | SEF3, Soybean embryo factor 3 | tacaaACCCatttca | 240 | aACCCant | 133 | ACCC | 67 |
| 2 | Lu1 | 6 | 19 | 977-993 | Prolamin box, conserved in cereal seed storage protein gene promoters | tgttgtttAAACtaaat | 242 | tgnnntttAAACnnna | 135 | AAAC | 69 |
| 2 | Lu1 | 6 | 31 | 394-410 | Prolamin box, conserved in cereal seed storage protein gene promoters | tggattgaAAAAgagaa | 244 | tgnnntgaAAAAnnna | 137 | AAAA | 70 |
| 2 | Lu1 | 6 | 28 | 466-482 | Prolamin box, conserved in cereal seed storage protein gene promoters | tggcgttgAAAGctcag | 246 | tgnnnttgAAAGnnna | 139 | AAAG | 71 |
| 2 | Lu1 | 6 | 3 | 1435-1445 | Soybean embryo factor 4 | ggTTTTtgata | 247 | TTTTtg | 140 | TTTT | 72 |
| 2 | Lu-2 | 9 | 4 | 1533-1559 | Legumin box, highly conserved sequence element about 100 bp upstream of the TSS in legumin genes | tccacatGCATgaaattccaaaacagg | 222 | ccacatGCATgaantccaaaacag | 120 | GCAT | 60 |
| 2 | Lu-2 | 9 | 20 | 973-999 | Legumin box, highly conserved sequence element about 100 bp upstream of the TSS in legumin genes | tctaaatCCTTtcactaaaaagaatca | 223 | ctaaatCCTTtcantnaaaagaatc | 121 | CCTT | 61 |
| 2 | Lu2 | 9 | 24 | 891-907 | Opaque-2 | TCATtgaaaatatattt | 228 | TCATtgaaaatat at | 125 | TCAT | 62 |
| 2 | Lu-2 | 9 | 1 | 1734-1750 | Opaque-2 | tatcaacaagTCATcat | 226 | cannTCATc | 123 | TCAT | 62 |
| 2 | Lu-2 | 9 | 16 | 1247-1263 | Opaque-2 | TCATtcaactcaaatca | 227 | TCATtcaactcaa at | 124 | TCAT | 62 |
| 2 | Lu-2 | 9 | 8 | 1518-1534 | Opaque-2 | gatagccACGTagaaac | 231 | ACGTa | 127 | ACGT | 63 |
| 2 | Lu2 | 9 | 26 | 400-414 | SEF3, Soybean embryo factor 3 | accgaACCCagccgg | 237 | aACCCanc | 132 | ACCC | 67 |

TABLE 3-continued

Promoter elements found in tonoplast intrinsic protein promoters, sorted first by the potential importance of the element (column 1, "Priority"; 1: more essential and preferred to be present in the promoter to 5: less essential) and sorted second by the specific plant promoter from which the element is derived from (column 2; either *Arabidopsis* "At", *Brassica napus* "Bn", *Linum usitatissium* promoter 1 "Lu-1", *Linum usitatissium* promoter 2 "Lu-2") and the SEQ ID NO for this promoter (column 3). Given is also the Order No. of the motif within one promoter sequence starting with "1" closest to translation start 'ATG' (column 4), the exact position in the promoter (column 5; referring to promoter motif matrix), the type of the promoter element (column 6), and the sequences for the core region, conserved region and entire matrix for the promoter element.

| Priority | Plant | SEQ ID No. of promoter | Motif Order No. in promoter | Motif position in promoter | Further Information | Promoter Motif Matrix | SEQ ID No | conserved motif region | SEQ ID No | core region of motif matrix | SEQ ID No |
|---|---|---|---|---|---|---|---|---|---|---|---|
| 2 | Lu-2 | 9 | 18 | 1221-1237 | Prolamin box, conserved in cereal seed storage protein gene promoters | tcatatgtAAAAtttga | 243 | tcnnntgtAAAAnnng | 136 | AAAA | 70 |
| 2 | Lu-2 | 9 | 2 | 1680-1690 | Soybean embryo factor 4 | ggTTTTtgata | 248 | TTTTtg | 140 | TTTT | 72 |
| 4 | At | 1 | 7 | 379-405 | ABA response elements | caatttaaagctACGTgtccagcttaa | 162 | annnACGTg | 86 | ACGT | 41 |
| 4 | Bn | 3 | 6 | 1375-1401 | ABA response elements | cagtttcaagctACGTgtccatctcaa | 163 | annnACGTg | 86 | ACGT | 41 |
| 4 | Lu1 | 6 | 11 | 1265-1291 | ABA response elements | tagtttaattctACGTggctatcccca | 164 | tnnnACGTg | 87 | ACGT | 41 |
| 4 | Lu-2 | 9 | 12 | 1512-1538 | ABA response elements | caattagtttctACGTggctatccaca | 165 | tnnnACGTg | 87 | ACGT | 41 |
| 5 | At | 1 | 1 | 510-528 | CA-rich element | atgatcaAACActtgaaat | 145 | tcnAACActtga | 77 | AACA | 35 |
| 5 | At | 1 | 2 | 448-462 | Heat shock element | AgaaaccaaaAGAAg | 146 | gannnnaanAGAA | 78 | AGAA | 36 |
| 5 | At | 1 | 20 | 80-94 | Heat shock element | caaatcataaAGAAc | 148 | aannnntanAGAA | 79 | AGAA | 36 |
| 5 | At | 1 | 6 | 380-406 | ABA (abscisic acid) inducible transcriptional activator | cttaagctggACACgtagctttaaatt | 160 | gnACACgtagc | 85 | ACAC | 40 |
| 5 | At | 1 | 8 | 377-393 | Dof3-single zinc finger transcription factor | tgcaatttAAAGctacg | 167 | AAAGc | 89 | AAAG | 43 |
| 5 | At | 1 | 11 | 331-345 | CAACTC regulatory elements, GA-inducible | ccttaagAGTTggtg | 185 | angAGTTggtg | 91 | AGTT | 45 |
| 5 | At | 1 | 19 | 155-169 | CAACTC regulatory elements, GA-inducible | cttctagAGTTggga | 186 | tngAGTTg | 92 | AGTT | 45 |
| 5 | At | 1 | 14 | 239-259 | OCS-like elements | acacgtacacgaggACATgta | 200 | gtacnngnnnACAT | 101 | ACAT | 48 |
| 5 | At | 1 | 21 | 79-99 | OCS-like elements | tcaaatcataaagaACATatt | 201 | atcannannnACAT | 102 | ACAT | 48 |
| 5 | At | 1 | 26 | 24-44 | OCS-like elements | ttagttcaagcataACATgtg | 202 | ttcanncnnnACAT | 103 | ACAT | 48 |
| 5 | At | 1 | 15 | 238-258 | OCS-like elements | acatgtcctcgtgtACGTgtt | 203 | gtccnngnnnACGT | 104 | ACGT | 49 |
| 5 | At | 1 | 18 | 184-194 | Motif involved in carotenoid and tocopherol biosynthesis and in the expression of photosynthesis-related genes | ttATCTacttg | 204 | ttATCTacttg | 105 | ATCT | 50 |

TABLE 3-continued

Promoter elements found in tonoplast intrinsic protein promoters, sorted first by the potential importance of the element (column 1, "Priority"; 1: more essential and preferred to be present in the promoter to 5: less essential) and sorted second by the specific plant promoter from which the element is derived from (column 2; either *Arabidopsis* "At", *Brassica napus* "Bn", *Linum usitatissium* promoter 1 "Lu-1", *Linum usitatissium* promoter 2 "Lu-2") and the SEQ ID NO for this promoter (column 3). Given is also the Order No. of the motif within one promoter sequence starting with "1" closest to translation start 'ATG' (column 4), the exact position in the promoter (column 5; referring to promoter motif matrix), the type of the promoter element (column 6), and the sequences for the core region, conserved region and entire matrix for the promoter element.

| Priority | Plant | SEQ ID No. of promoter | Motif Order No. in promoter | Motif position in promoter | Further Information | Promoter Motif Matrix | conserved SEQ motif ID matrix No region | core region SEQ of ID motif No matrix | SEQ ID No matrix |
|---|---|---|---|---|---|---|---|---|---|
| 5 | At | 1 | 22 | 50-66 | WRKY plant specific zinc-finger-type factor associated with pathogen defence, W box | aattaTTGActtgca ga | 205 TTGAc | 106 TTGA | 51 |
| 5 | At | 1 | 23 | 46-58 | HDZip class I protein ATHB5 | TcaATAAttattt | 208 aATAAtt | 107 AtnA | 52 |
| 5 | At | 1 | 24 | 45-57 | HDZip class I protein ATHB5 | gaaATAAttattg | 209 aATAAtt | 107 AtnA | 52 |
| 5 | At | 1 | 25 | 43-55 | HDZip class I protein ATHB5 | ataATTAtttctt | 210 aATTAtt | 108 AtnA | 52 |
| 5 | At | 1 | 28 | 12-24 | HDZip class I protein ATHB5 | aaaATCAtttgtc | 211 aATCAtt | 109 AtnA | 52 |
| 5 | At | 1 | 29 | 10-22 | HDZip class I protein ATHB5 | caaATGAttttca | 212 aATGAtt | 110 AtnA | 52 |
| 5 | At | 1 | 27 | 18-30 | Auxin Response Element | attTGTCacatgt | 216 TGTCnc | 114 TGTC | 55 |
| 5 | Bn | 3 | 1 | 1430-1444 | Heat shock element | agaatttaaaAGA Ag | 147 gannnnaanAGA A | 78 AGAA | 36 |
| 5 | Bn | 3 | 21 | 785-799 | Heat shock element | ataatcatagAGAA g | 149 tannnntanAGA A | 80 AGAA | 36 |
| 5 | Bn | 3 | 4 | 1376-1402 | ABA (abscisic acid) inducible transcriptional activator | cttgagatggACAC gtagcttgaaact | 161 gnACACgtagc | 85 ACAC | 40 |
| 5 | Bn | 3 | 13 | 1305-1319 | Storekeeper (STK), plant specific DNA binding protein important for tuber-specific and sucrose-inducible gene expression | gtcCAAAaaattac c | 213 CAAAnaatt | 111 CAAA | 53 |
| 5 | Bn | 3 | 14 | 1292-1306 | Cis-element in the GAPDH promoters conferring light inducibility | acggATTAagaca aa | 217 ATTAananna | 115 ATTA | 56 |
| 5 | Lu1 | 6 | 15 | 1080-1094 | CAACTC regulatory elements, GA-inducible | ttagtcgAGTTgaa a | 187 tngAGTTg | 92 AGTT | 45 |
| 5 | Lu1 | 6 | 18 | 986-1000 | Storekeeper (STK), plant specific DNA binding protein important for tuber-specific and sucrose-inducible gene expression | aacTAAAtaatctat | 214 TAAAnaatc | 112 TAAA | 54 |
| 5 | Lu1 | 6 | 8 | 1269-1289 | *Oryza sativa* bZIP protein 8 | ttaattctACGTggc tatccc | 249 ACGTggC | 141 ACGT | 73 |
| 5 | Lu1 | 6 | 13 | 1154-1164 | *Arabidopsis thaliana* signal-responsive gene 1, Ca2+/calmodulin binding protein homolog to NtER1 (tobacco early ethylene-responsive gene) | tgcCGCGtaca | 251 CGCGta | 142 CGCG | 74 |

TABLE 3-continued

Promoter elements found in tonoplast intrinsic protein promoters, sorted first by the potential importance of the element (column 1, "Priority"; 1: more essential and preferred to be present in the promoter to 5: less essential) and sorted second by the specific plant promoter from which the element is derived from (column 2; either *Arabidopsis* "At", *Brassica napus* "Bn", *Linum usitatissium* promoter 1 "Lu-1", *Linum usitatissium* promoter 2 "Lu-2") and the SEQ ID NO for this promoter (column 3). Given is also the Order No. of the motif within one promoter sequence starting with "1" closest to translation start 'ATG' (column 4), the exact position in the promoter (column 5; referring to promoter motif matrix), the type of the promoter element (column 6), and the sequences for the core region, conserved region and entire matrix for the promoter element.

| Priority | Plant | SEQ ID No. of promoter | Motif Order No. in promoter | Motif position in promoter | Further Information | Promoter Motif Matrix | SEQ ID No | conserved motif region | SEQ ID No | core region of motif matrix | SEQ ID No |
|---|---|---|---|---|---|---|---|---|---|---|---|
| 5 | Lu1 | 6 | 14 | 1134-1150 | Trihelix DNA-binding factor GT-3a | agctagGTTAcatttat | 253 | tnnGTTAcnnnt | 143 | GTTA | 75 |
| 5 | Lu1 | 6 | 16 | 1074-1088 | Putative cis-acting element in various PAL and 4CL gene promoters | taGAGGttagtcgag | 254 | GnGGtnngtnnng | 144 | GnGG | 76 |
| 5 | Lu-2 | 9 | 23 | 926-940 | Heat shock element | tgaactatctTGAAa | 150 | gannnntnnTGAA | 81 | TGAA | 37 |
| 5 | Lu-2 | 9 | 13 | 1489-1515 | ABA (absoisic acid) inducible transcriptional activator | attgtcttgatgCCGTgacgaagtttt | 166 | gntgCCGTgacnnnnnt | 88 | CCGT | 42 |
| 5 | Lu-2 | 9 | 21 | 962-978 | Dof3-single zinc finger transcription factor | gaatcagaAAAGcagga | 168 | AAAGc | 89 | AAAG | 43 |
| 5 | Lu-2 | 9 | 19 | 1083-1099 | WRKY plant specific zinc-finger-type factor associated with pathogen defence, W box | ttactTTGAcccttgag | 206 | TTGAc | 106 | TTGA | 51 |
| 5 | Lu-2 | 9 | 22 | 949-965 | WRKY plant specific zinc-finger-type factor associated with pathogen defence, W box | aaagtTTGActattcct | 207 | TTGAc | 106 | TTGA | 51 |
| 5 | Lu-2 | 9 | 17 | 1235-1249 | Storekeeper (STK), plant specific DNA binding protein important for tuber-specific and sucrose-inducible gene expression | tcaTAAAaaatttca | 215 | TAAAnaatt | 113 | TAAA | 54 |
| 5 | Lu-2 | 9 | 15 | 1327-1341 | Cis-element in the GAPDH promoters conferring light inducibility | ggttATGAatagtaa | 218 | ATGAananna | 116 | ATGA | 57 |
| 5 | Lu-2 | 9 | 10 | 1516-1536 | *Oryza sativa* bZIP protein 8 | tagtttctACGTggctatcca | 250 | ACGTggc | 141 | ACGT | 73 |
| 5 | Lu-2 | 9 | 14 | 1400-1410 | *Arabidopsis thaliana* signal-responsive gene1, Ca2+/calmodulin binding protein homolog to NtER1 (tobacco early ethylene-responsive gene) | tgcCGCGtaca | 252 | CGCGta | 142 | CGCG | 74 |

TABLE 4

Promoter elements found in the *Arabidopsis* tonoplast intrinsic protein alpha promoter (SEQ ID NO.: 1) sorted by their Order No. in the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | conserved region motif region | SEQ ID No | core region of motif matrix | SEQ ID No |
|---|---|---|---|---|---|---|---|---|---|
| 1 | 510-528 | 5 | CA-rich element | atgatcaAACActtgaaat | 145 | tcnAACActtga | 77 | AACA | 35 |
| 2 | 448-462 | 5 | Heat shock element | agaaaccaaaAGAAg | 146 | gannnnaanAGAA | 78 | AGAA | 36 |
| 3 | 385-401 | 2 | Rice transcription activator-1 (RITA), basic leucin zipper protein, highly expressed during seed development | gctggacACGTagcttt | 151 | cACGT | 82 | ACGT | 38 |
| 4 | 383-403 | 1 | G-box binding proteins | ttaaagctACGTgtccagctt | 153 | tACGT | 83 | ACGT | 38 |
| 5 | 382-402 | 1 | G-box binding proteins | agctggacACGTagctttaaa | 156 | cACGT | 84 | ACGT | 39 |
| 6 | 380-406 | 5 | ABA (abscisic acid) inducible transcriptional activator | cttaagctggACACgtagcttaaatt | 160 | gnACACgtagc | 85 | ACAC | 40 |
| 7 | 379-405 | 4 | ABA response elements | caatttaaagctACGTgtccagcttaa | 162 | annnACGTg | 86 | ACGT | 41 |
| 8 | 377-393 | 5 | Dof3 - single zinc finger transcription factor | tgcaatttAAAGctacg | 167 | AAAGc | 89 | AAAG | 43 |
| 9 | 367-393 | 1 | RY and Sph motifs conserved in seed-specific promoters | agtaattgCATGcaatttaaagctacg | 169 | CATGca | 90 | CATG | 44 |
| 10 | 360-386 | 1 | RY and Sph motifs conserved in seed-specific promoters | ttaaattgCATGcaattacttaaccat | 170 | CATGca | 90 | CATG | 44 |
| 11 | 331-345 | 5 | CAACTC regulatory elements, GA-inducible | ccttaagAGTTggtg | 185 | angAGTTg | 91 | AGTT | 45 |
| 12 | 292-308 | 2 | GCN4, conserved in cereal seed storage protein gene promoters, similar to yeast GCN4 and vertebrate AP-1 | tcttggTGAGttatttt | 188 | gTGAGtta | 93 | TGAG | 46 |
| 13 | 246-262 | 1 | Recognition site for BZIP transcription factors that belong to the group of Opaque-2 like proteins | cacgaggACATgtatta | 192 | gnACnTgnnt | 97 | AcnT | 47 |
| 14 | 239-259 | 5 | OCS-like elements | acacgtacacgaggACATgta | 200 | gtacnngnnnACAT | 101 | ACAT | 48 |
| 15 | 238-258 | 5 | OCS-like elements | acatgtcctcgtgtACGTgtt | 203 | gtccnngnnnACGT | 104 | ACGT | 49 |
| 16 | 192-218 | 1 | RY and Sph motifs conserved in seed-specific promoters | ttggcacaCATGcatgcttagtcaaca | 171 | CATGca | 90 | CATG | 44 |
| 17 | 189-215 | 1 | RY and Sph motifs conserved in seed-specific promoters | tgactaagCATGcatgtgtccaagta | 172 | CATGca | 90 | CATG | 44 |

TABLE 4-continued

Promoter elements found in the *Arabidopsis* tonoplast intrinsic protein alpha promoter (SEQ ID NO.: 1) sorted by their Order No. in the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | conserved SEQ motif ID matrix No region | core region SEQ of ID motif No matrix | SEQ ID No |
|---|---|---|---|---|---|---|---|
| 18 | 184-194 | 5 | Motif involved in carotenoid and tocopherol biosynthesis and in the expression of photosynthesis-related genes | ttATCTacttg | 204 ttATCTacttg | 105 ATCT | 50 |
| 19 | 155-169 | 5 | CAACTC regulatory elements, GA-inducible | cttctagAGTTggga | 186 tngAGTTg | 92 AGTT | 45 |
| 20 | 80-94 | 5 | Heat shock element | caaatcataaAGAAc | 148 aannnntanAGAA | 79 AGAA | 36 |
| 21 | 79-99 | 5 | OCS-like elements | tcaaatcataaagaACATat t | 201 atcannannnAC AT | 102 ACAT | 48 |
| 22 | 50-66 | 5 | WRKY plant specific zinc-finger-type factor associated with pathogen defence, W box | aattaTTGActtgcaga | 205 TTGAc | 106 TTGA | 51 |
| 23 | 46-58 | 5 | HDZip class I protein ATHB5 | TcaATAAttattt | 208 aATAAtt | 107 AtnA | 52 |
| 24 | 45-57 | 5 | HDZip class I protein ATHB5 | gaaATAAttattg | 209 aATAAtt | 107 AtnA | 52 |
| 25 | 43-55 | 5 | HDZip class I protein ATHB5 | ataATTAtttctt | 210 aATTAtt | 108 AtnA | 52 |
| 26 | 24-44 | 5 | OCS-like elements | ttagttcaagcataACATgt g | 202 ttcanncnnnACA T | 103 ACAT | 48 |
| 27 | 18-30 | 5 | Auxin Response Element | attTGTCacatgt | 216 TGTCnc | 114 TGTC | 55 |
| 28 | 12-24 | 5 | HDZip class I protein ATHB5 | aaaATCAtttgtc | 211 aATCAtt | 109 AtnA | 52 |
| 29 | 10-22 | 5 | HDZip class I protein ATHB5 | caaATGAtttca | 212 aATGAtt | 110 AtnA | 52 |

TABLE 5

Promoter elements found in the *Brassica napus* intrinsic protein promoter (SEQ ID NO.: 3) sorted by their Order No. in the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | conserved SEQ motif ID matrix No region | core region SEQ of ID motif No matrix | SEQ ID No |
|---|---|---|---|---|---|---|---|
| 1 | 1430-1444 | 5 | Heat shock element | agaatttaaaAGAAg | 147 gannnnaanA-GAA | 78 AGAA | 36 |
| 2 | 1381-1397 | 2 | Rice transcription activator-1 (RITA), basic leucin zip-perprotein, highly expressed during seed development 1397 | gatggacACGTagcttg | 152 cACGT | 82 ACGT | 38 |

TABLE 5-continued

Promoter elements found in the *Brassica napus* intrinsic protein promoter (SEQ ID NO.: 3) sorted by their Order No. in the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | conserved motif region | SEQ ID No | core region of motif matrix | SEQ ID No |
|---|---|---|---|---|---|---|---|---|---|
| 3 | 1379-1399 | 1 | G-box binding proteins | ttcaagctACGTgtccatctc | 154 | tACGT | 83 | ACGT | 38 |
| 4 | 1376-1402 | 5 | ABA (abscisic acid) inducible transcriptional activator | cttgagatggACACgtagcttgaaact | 161 | gnACACgtagc | 85 | ACAC | 40 |
| 5 | 1378-1398 | 1 | G-box binding proteins | agatggacACGTagcttgaaa | 157 | cACGT | 84 | ACGT | 39 |
| 6 | 1375-1401 | 4 | ABA response elements | cagtttcaagctACGTgtccatctcaa | 163 | annnACGTg | 86 | ACGT | 41 |
| 7 | 1379-1399 | 1 | G-box binding proteins | ttcaagctACGTgtccatctc | 155 | tACGT | 83 | ACGT | 38 |
| 8 | 1363-1389 | 1 | RY and Sph motifs conserved in seed-specific promoters | gtaacatgCATGcagtttcaagctacg | 173 | CATGca | 90 | CATG | 44 |
| 9 | 1359-1385 | 1 | RY and Sph motifs conserved in seed-specific promoters | ttaagtaaCATGcatgcagtttcaagc | 174 | CATGca | 90 | CATG | 44 |
| 10 | 1356-1382 | 1 | RY and Sph motifs conserved in seed-specific promoters | tgaaactgCATGcatgttacttaacca | 175 | CATGca | 90 | CATG | 44 |
| 11 | 1359-1375 | 1 | Recognition site for BZIP transcription factors that belong to the group of Opaque-2 like proteins | ttaagtaACATgcatgc | 194 | tnACnTgnnt | 98 | AcnT | 47 |
| 12 | 1342-1358 | 1 | Recognition site for BZIP transcription factors that belong to the group of Opaque-2 like proteins | gaaaatgACATacatgg | 196 | tnACnTannt | 99 | AcnT | 47 |
| 13 | 1305-1319 | 5 | Storekeeper (STK), plant specific DNA binding protein important for tuber-specific and sucrose-inducible gene expression | gtcCAAAaaattacc | 213 | CAAAnaatt | 111 | CAAA | 53 |
| 14 | 1292-1306 | 5 | Cis-element in the GAPDH promoters conferring light inducibility | acggATTAagacaaa | 217 | ATTAananna | 115 | ATTA | 56 |
| 15 | 1262-1288 | 2 | Legumin box, highly conserved sequence element about 100 bp upstream of the TSS in legumin genes | tacttaaCCATgagattccaacaaaga | 219 | acttaaCCATgagntncaacaaag | 117 | CCAT | 58 |
| 16 | 1253-1269 | 1 | Recognition site for BZiP transcription factors that belong to the group of Opaque-2 like proteins | gttaagtACATgcataa | 193 | gnACnTgnnt | 97 | AcnT | 47 |
| 17 | 1243-1269 | 1 | RY and Sph motifs conserved in seed-specific promoters | gttaagtaCATGcataaagtttaagga | 176 | CATGca | 90 | CATG | 44 |
| 18 | 1058-1074 | 2 | Opaque-2 | TCATtacagagagatga | 224 | TCATtacagagagat | 122 | TCAT | 62 |

TABLE 5-continued

Promoter elements found in the *Brassica napus* intrinsic protein promoter (SEQ ID NO.: 3) sorted by their Order No. in the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | conserved motif region | SEQ ID No | core region of motif matrix | SEQ ID No |
|---|---|---|---|---|---|---|---|---|---|
| 19 | 966-980 | 2 | SEF3, Soybean embryo factor 3 | aggaaACCCagcagg | 236 | aACCCanc | 132 | ACCC | 67 |
| 20 | 941-957 | 2 | Prolamin box, conserved in cereal seed storage protein gene promoters | tgatttgcAAATgcagt | 241 | tgnnntgcAAATnnng | 134 | AAAT | 68 |
| 21 | 785-799 | 5 | Heat shock element | ataatcatagAGAAg | 149 | tannnntanAGAA | 80 | AGAA | 36 |
| 22 | 627-653 | 2 | Legumin box, highly conserved sequence element about 100 bp upstream of the TSS in legumin genes | aagataaCCGTgaagaacaatagtgt | 221 | aga-taaCCGTgang-nacaatagtg | 119 | CCGT | 59 |
| 23 | 432-458 | 2 | Legumin box, highly conserved sequence element about 100 bp upstream of the TSS in legumin genes | tgaataaC-CATggaaccttag-taaggc | 220 | gaataaC-CATggancnttag-taagg | 118 | CCAT | 58 |
| 26 | 360-376 | 2 | Opaque-2 | TTATttcaagaagatgt | 232 | TTATttcaagaa-gat | 128 | TTAT | 64 |
| 27 | 205-221 | 2 | GCN4, conserved in cereal seed storage protein gene promoters, similar to yeast GCN4 and vertebrate AP-1 | atgaacTGAGtcactgt | 189 | cTGAGtca | 94 | TGAG | 46 |
| 28 | 175-191 | 2 | Prolamin box, conserved in cereal seed storage protein gene promoters | ggtcatgaAAAGataca | 245 | ggnnntgaAA-AGnnnc | 138 | AAAG | 71 |

TABLE 6

Promoter elements found in the *Linum usitatissimum* tonoplast intrinsic protein promoter 1 (SEQ ID NO.: 6) sorted by their Order No. in the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | conserved motif matrix region | SEQ ID No | core region of motif matrix | SEQ ID No |
|---|---|---|---|---|---|---|---|---|---|
| 1 | 1505-1521 | 1 | Recognition site for BZIP transcription factors that belong to the group of Opaque-2 like proteins | gatgatgACTTgtttgt | 195 | tnACnTgnnt | 98 | AcnT | 47 |
| 2 | 1504-1520 | 2 | Opaque-2 | aacaaacaagTCATcat | 225 | cannTCATc | 123 | TCAT | 62 |
| 3 | 1435-1445 | 2 | Soybean embryo factor 4 | ggTTTTtg ata | 247 | TTTTtg | 140 | TTTT | 72 |
| 4 | 1372-1398 | 1 | RY and Sph motifs conserved in seed-specific Promoters | ctcccatcCATGcataaacctcatttc | 177 | CATGca | 90 | CATG | 44 |

TABLE 6-continued

Promoter elements found in the *Linum usitatissimum* tonoplast intrinsic protein promoter 1 (SEQ ID NO.: 6) sorted by their Order No. in the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | conserved motif matrix region | SEQ ID No | core region of motif matrix | SEQ ID No |
|---|---|---|---|---|---|---|---|---|---|
| 5 | 1282-1308 | 1 | RY and Sph motifs conserved in seed-specific promoters | gctatcccCATGcatgaaattccaaaa | 178 | CATGca | 90 | CATG | 44 |
| 6 | 1279-1305 | 1 | RY and Sph motifs conserved in seed-specific promoters | tggaatttCATGcatgggg atagccac | 179 | CATGca | 90 | CATG | 44 |
| 7 | 1271-1287 | 2 | Opaque-2 | gatagccACGTagaatt | 230 | ACGTa | 127 | ACGT | 63 |
| 8 | 1269-1289 | 5 | Oryza sativa bZIP protein 8 | ttaattctACGTggctatcc c | 249 | ACGTggc | 141 | ACGT | 73 |
| 9 | 1270-1286 | 1 | Recognition site for BZIP transcription factors that belong to the group of Opaque-2 like proteins | taattctACGTggctat | 197 | cnACnTgnnt | 100 | AcnT | 47 |
| 10 | 1268-1288 | 1 | G-box binding proteins | ggatagccACGTagaatt aaa | 158 | cACGT | 84 | ACGT | 39 |
| 11 | 1265-1291 | 4 | ABA response elements | tagtttaattctACGTggct atcccca | 164 | tnnnACGTg | 87 | ACGT | 41 |
| 12 | 1204-1230 | 1 | RY and Sph motifs conserved in seed-specific promoters | gagaagaaCATGcattta cagaggata | 180 | CATGCa | 90 | CATG | 44 |
| 13 | 1154-1164 | 5 | *Arabidopsis thaliana* signal-responsive gene1, Ca2+/calmodulin binding protein homolog to NtER1 (tobacco early ethylene-responsive gene) | tgcCGCGtaca | 251 | CGCGta | 142 | CGCG | 74 |
| 14 | 1134-1150 | 5 | Trihelix DNA-binding factor GT-3a | agctagGTTAcatttat | 253 | tnnGTTAcnnt | 143 | GTTA | 75 |
| 15 | 1080-1094 |  | CMCTC regulatory elements, GA-inducible | ttagtcgAGTTgaaa | 187 | tngAGTTg | 92 | AGTT | 45 |
| 16 | 1074-1088 | 5 | Putative cis-acting element in various PAL and 4CL gene promoters | taGAGGttagtcgag | 254 | GnGGtnngtnnng | 144 | GnGG | 76 |
| 17 | 1055-1069 | 2 | SEF3, Soybean embryo factor 3 | gtctaACCCaattca | 238 | aACCCant | 133 | ACCC | 67 |
| 18 | 986-1000 | 5 | Storekeeper (STK), plant specific DNA binding protein important for tuber-specific and sucrose-inducible gene expression | aacTAAAtaatctat | 214 | TAAAnaatc | 112 | TAAA | 54 |
| 19 | 977-993 | 2 | Prolamin box, conserved in cereal seed storage protein gene promoters | tgttgtttAAACtaaat | 242 | tgnnntttAAACnnna | 135 | AAAC | 69 |
| 22 | 841-857 | 2 | GCN4, conserved in cereal seed storage protein gene promoters, similar to yeast GCN4 and vertebrate AP-1 | aagtgtTGAGtcagaat | 190 | tTGAGtca | 95 | TGAG | 46 |

TABLE 6-continued

Promoter elements found in the *Linum usitatissimum* tonoplast intrinsic protein promoter 1 (SEQ ID NO.: 6) sorted by their Order No. in the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | conserved motif matrix region | SEQ ID No | core region of motif matrix | SEQ ID No |
|---|---|---|---|---|---|---|---|---|---|
| 23 | 680-696 | 2 | Opaque-2 | TCATttaacctcgagtc | 229 | TCATttaacctcg ag | 126 | TCAT | 62 |
| 24 | 616-632 | 2 | Opaque-2 | CCATctacataggga | 233 | CCATctacatag gg | 129 | CCAT | 65 |
| 25 | 609-623 | 2 | SEF3, Soybean embryo factor 3 | tcataACCCattcta | 239 | aACCCant | 133 | ACCC | 67 |
| 26 | 598-614 | 2 | GCN4, conserved in cereal seed storage protein gene promoters similar to yeast GCN4 and vertebrate AP-1 | ttatgaTGAGtcgtact | 191 | aTGAGtcg | 96 | TGAG | 46 |
| 28 | 466-482 | 2 | Prolamin box, conserved in cereal seed storage protein gene promoters | tggcgttgAAAGctcag | 246 | tgnnnttgAAAG nnna | 139 | AAAG | 71 |
| 29 | 446-472 | 1 | RY and Sph motifs conserved in seed-specific promoters | aacgccacCATGcatcc ataatttttt | 184 | CATGca | 90 | CATG | 44 |
| 31 | 394-410 | 2 | Prolamin box, conserved in cereal seed storage protein gene promoters | tggattgaAAAAgagaa | 244 | tgnnntgaAAAA nnna | 137 | AAAA | 70 |
| 32 | 385-401 | 2 | Opaque-2 | TCAAtccatcttaattt | 234 | TCAAtccatctta at | 130 | TCAA | 66 |
| 36 | 176-190 | 2 | SEF3, Soybean embryo factor 3 | tacaaACCCattcca | 240 | aACCCant | 133 | ACCC | 67 |
| 37 | 172-188 | 2 | Opaque-2 | caaacccattTCAAcaa | 235 | cattTCAAc | 131 | TCAA | 66 |

TABLE 7

Promoter elements found in the *Linum usitatissimum* tonoplast intrinsic protein promoter 2 (SEQ ID NO: 9) sorted by their Order No. In the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | Conserved motif matrix region | SEQ ID No | core region of motif matrix | SEQ ID No |
|---|---|---|---|---|---|---|---|---|---|
| 1 | 1734-1750 | 2 | Opaque-2 | tatcaacaagTCATcat | 226 | cannTCATc | 123 | TCAT | 62 |
| 2 | 1680-1690 | 2 | Soybean embryo factor 4 | ggTTTTtgata | 248 | TTTTtg | 140 | TTTT | 72 |
| 3 | 1617-1643 | 1 | RY and Sph motifs conserved in seed-specific promoters | tcccatccCATGcataca cctcaattg | 181 | CATGca | 90 | CATG | 44 |

TABLE 7-continued

Promoter elements found in the *Linum usitatissimum* tonoplast intrinsic protein promoter 2 (SEQ ID NO: 9) sorted by their Order No. In the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | Conserved motif matrix region | SEQ ID No | core region of motif matrix | SEQ ID No |
|---|---|---|---|---|---|---|---|---|---|
| 4 | 1533-1559 | 2 | Legumin box, highly conserved sequence element about 100 bp upstream of the TSS in legumin genes | tccacatGCATgaaattccaaaacagg | 222 | ccacatGCATgaantccaaaacag | 120 | GCAT | 60 |
| 5 | 1529-1545 | 1 | Recognition site for BZIP transcription factors that belong to the group of Opaque-2 like proteins | gctatccACATgcatga | 198 | cnACnTgnnt | 100 | AcnT | 47 |
| 6 | 1529-1555 | 1 | RY and Sph motifs conserved in seed-specific promoters | gctatccaCATGcatgaattccaaaa | 182 | CATGca | 90 | CATG | 44 |
| 7 | 1526-1552 | 1 | RY and Sph motifs conserved in seed-specific promoters | tggaattCATGcatgtggatagccac | 183 | CATGCa | 90 | CATG | 44 |
| 8 | 1518-1534 | 2 | Opaque-2 | gatagccACGTagaaac | 231 | ACGTa | 127 | ACGT | 63 |
| 9 | 1517-1533 | 1 | Recognition site for BZIP transcription factors that belong to the group of Opaque-2 like proteins | agtttctACGTggctat | 199 | cnACnTgnnt | 100 | AcnT | 47 |
| 10 | 1516-1536 | 5 | Oryza sativa bZIP protein 8 | tagtttctACGTggctatcca | 250 | ACGTggc | 141 | ACGT | 73 |
| 11 | 1515-1535 | 1 | G-box binding proteins | ggatagccACGTagaaactaa | 159 | cACGT | 84 | ACGT | 39 |
| 12 | 1512-1538 | 4 | ABA response elements | caattagtttctACGTggctatccaca | 165 | tnnnACGTg | 87 | ACGT | 41 |
| 13 | 1489-1515 | 5 | ABA (abscisic acid) inducible transcriptional activator | attgtcttgatgCCGTgacgaagtttt | 166 | gntgCCGTgacnnnnnt | 88 | CCGT | 42 |
| 14 | 1400-1410 | 5 | *Arabidopsis thaliana* signal-responsive gene1, Ca2+/calmodulin binding protein homolog to NtER1 (tobacco early ethylene-responsive gene) | tgcCGCGtaca | 252 | CGCGta | 142 | CGCG | 74 |
| 15 | 1327-1341 | 5 | Cis-element in the GAPDH promoters conferring light inducibility | ggttATGAatagtaa | 218 | ATGAananna | 116 | ATGA | 57 |
| 16 | 1247-1263 | 2 | Opaque-2 | TCATtcaactcaaatca | 227 | TCATtcaactcaaat | 124 | TCAT | 62 |
| 17 | 1235-1249 | 5 | Storekeeper (STK), plant specific DNA binding protein important for tuber-specific and sucrose-inducible gene expression | tcaTAAAaaatttca | 215 | TAAAnaatt | 113 | TAAA | 54 |
| 18 | 1221-1237 | 2 | Prolamin box, conserved in cereal seed storage protein gene promoters | tcatatgtAAAAtttga | 243 | tcnnntgtAAAAnnng | 136 | AAAA | 70 |

TABLE 7-continued

Promoter elements found in the *Linum usitatissimum* tonoplast intrinsic protein promoter 2 (SEQ ID NO: 9) sorted by their Order No. In the sequence with "1" closest to translation start 'ATG' (column 1). Given is also the exact position of the element (column 2; referring to promoter motif matrix), the potential importance of the element (column 3, "Priority"; 1: more essential and preferred to be present in the promoter to 5: less essential), the type of the promoter element (column 4), and the sequences for the core region, conserved region and entire matrix for the promoter element.

| Motif Order No. in promoter | Motif position in promoter | Priority | Further Information | Promoter Motif Matrix | SEQ ID No | Conserved motif matrix region | SEQ ID No | core region of motif matrix | SEQ ID No |
|---|---|---|---|---|---|---|---|---|---|
| 19 | 1083-1099 | 5 | WRKY plant specific zinc-finger-type factor associated with pathogen defence, W box | ttactTTGAcccttgag | 206 | TTGAc | 106 | TTGA | 51 |
| 20 | 973-999 | 2 | Legumin box, highly conserved sequence element about 100 bp up-stream of the TSS in legumin genes | tpb ctaaatCCTTtcactaaa aagaatca | 223 | ctaaatCCTTtcantn aaaagaatc | 121 | CCTT | 61 |
| 21 | 962-978 | 5 | Dof3 - single zinc finger transcription factor | gaatcagaAAAGcagga | 168 | AAAGc | 89 | AAAG | 43 |
| 22 | 949-965 | 5 | WRKY plant specific zinc-finger-type factor associated with pathogen defence, W box | aaagtTTGActattcct | 207 | TTGAc | 106 | TTGA | 51 |
| 23 | 926-940 | 5 | Heat shock element | tgaactatctTGAAa | 150 | gannnntnnTGAA | 81 | TGAA | 37 |
| 24 | 891-907 | 2 | Opaque-2 | TCATgaaaatatattt | 228 | TCATgaaaatatat | 125 | TCAT | 62 |
| 26 | 400-414 | 2 | SEF3, Soybean embryo factor 3 | accgaACCCagccgg | 237 | aCCCanc | 132 | ACCC | 67 |

The motifs of the promoters disclosed herein can also be employed to construct a synthetic promoter by fusing said motifs together by standard cloning techniques. Accordingly another embodiment of the invention relates to a synthetic transcription regulating sequence comprising at least five promoter motifs (preferably at least 6 or 7, more preferably at least 8, 9, 10 or 11, most preferably at least 12, 13, 14, 15, 16, 17, 18, 19, 20, 25, 30, 35 or all motifs) selected from the group of motifs consisting of the sequences described by SEQ ID NO: 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, and 76. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

Preferably, the synthetic transcription regulating sequence comprises at least five promoter motifs (preferably at least 6 or 7, more preferably at least 8, 9, 10 or 11, most preferably at least 12, 13, 14, 15, 16, 17, 18, 19, 20, 21, 22, 30, 35, 40, 45, 50, 55, 60, 70 or all motifs) selected from the group of motifs consisting of the sequences described by SEQ ID NO: 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 124, 135, 136, 137, 138, 139, 140, 141, 142, 143, and 144. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

More preferably, the synthetic transcription regulating sequence comprises at least five promoter motifs (preferably at least 6 or 7, more preferably at least 8, 9, 10 or 11, most preferably at least 12, 13, 14, 15, 16, 17, 18, 19, 20, 21, 22, 23, 24, 25, 30, 40, 50, 60, 70, 80, 90, 100 or all motifs) selected from the group of motifs consisting of the sequences described by SEQ ID NO: 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 231, 232, 233, 234, 235, 235, 237, 238, 239, 240, 241, 242, 243, 244, 245, 246, 247, 248, 249, 250, 251, 252, 253 and 254. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

Synthetic in this context means a sequence, which as such does not exist in nature and which—preferably—is assembled and made by act of man (e.g., by DNA synthesis). Preferably, said synthetic transcription regulating sequence does not comprise a sequence stretch of consecutive nucleotides being identical to a natural occurring sequence of more than 100 nucleotides, preferably or more than 50 nucleotides.

Still another embodiment of the invention relates to a method for providing a synthetic transcription regulating nucleotide sequence characterized that isolated promoter motifs or cluster of promoter motifs are combined (preferably by man e.g., by standard cloning techniques such as ligation or recombination), said motifs comprising at least five promoter motifs (preferably at least 6 or 7, more preferably at least 8, 9, 10 or 11, most preferably at least 12, 13, 14, 15, 16, 17, 18, 19, 20, 25, 30, 35 or all motifs) selected from the group of motifs consisting of the sequences described by SEQ ID NO: 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, and 76. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

Preferably, the method for providing a synthetic transcription regulating nucleotide sequences characterized that isolated promoter motifs or cluster of promoter motifs are combined (e.g., by standard cloning techniques such as ligation or recombination) that motifs comprising at least five promoter motifs (preferably at least 6 or 7, more preferably at least 8, 9, 10 or 11, most preferably at least 12, 13, 14, 15, 16, 17, 18, 19, 20, 21, 22, 30, 35, 40, 45, 50, 55, 60, 70 or all motifs) selected from the group of motifs consisting of the sequences described by SEQ ID NO: 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 124, 135, 136, 137, 138, 139, 140, 141, 142, 143, and 144. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

More preferably, the method for providing a synthetic transcription regulating nucleotide sequences characterized that isolated promoter motifs or cluster of promoter motifs are combined (e.g., by standard cloning techniques such as ligation or recombination) that motifs comprising at least five promoter motifs (preferably at least 6 or 7, more preferably at least 8, 9, 10 or 11, most preferably at least 12, 13, 14, 15, 16, 17, 18, 19, 20, 21, 22, 23, 24, 25, 30, 40, 50, 60, 70, 80, 90, 100 or all motifs) selected from the group of motifs consisting of the sequences described by SEQ ID NO: 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 231, 232, 233, 234, 235, 235, 237, 238, 239, 240, 241, 242, 243, 244, 245, 246, 247, 248, 249, 250, 251, 252, 253 and 254. Some of the motifs are variants of one conserved region of a motif matrix and in general (but not necessarily) only one of these is selected. More preferably the promoter elements are selected from the group of elements described with priority 1, 2, 3 or 4 (preferably priority 1, 2, or 3; more preferably priority 1 or 2; most preferably priority 1) in Table 3 to 7 below. Most preferably the order (in 5'-3' direction) of the selected motifs is as indicated in Table 3 (column 3 or 4) or Table 4 to 7 (column 1 and 2) giving the order of the motifs in the transcription regulating sequence of the invention as described by any of SEQ ID NO: 1, 3, 6, or 9. Even more preferably the distance between the selected motifs is substantially the same as in the transcription regulating sequence of the invention as described by any of SEQ ID NO: 1, 3, 6, or 9. Substantially identical means that the distance does not deviate by more than 100, preferably 50, more preferably 25, most preferably 10 nucleotides from the distance as in the transcription regulating sequence of the invention as described by any of SEQ ID NO: 1, 3, 6, or 9.

An expression cassette of the invention may comprise further regulatory elements. The term in this context is to be understood in a broad meaning comprising all sequences, which may influence construction or function of the expression cassette. Regulatory elements may for example modify transcription and/or translation in prokaryotic or eukaryotic organism. In an preferred embodiment the expression cassette of the invention comprised downstream (in 3'-direction) of the nucleic acid sequence to be expressed a transcription termination sequence and—optionally additional regulatory elements—each operably liked to the nucleic acid sequence to be expressed (or the transcription regulating nucleotide sequence).

Additional regulatory elements may comprise additional promoter, minimal promoters, or promoter elements, which may modify the expression regulating properties. For example the expression may be made depending on certain stress factors such water stress, abscisin (Lam 1991) or heat stress (Schoffl 1989). Furthermore additional promoters or promoter elements may be employed, which may realize expression in other organisms (such as *E. coli* or *Agrobacterium*). Such regulatory elements can be found in the promoter sequences or bacteria such as amy and SPO2 or in the promoter sequences of yeast or fungal promoters (such as ADC1, MFa, AC, P-60, CYC1, GAPDH, TEF, rp28, and ADH).

Furthermore, it is contemplated that promoters combining elements from more than one promoter may be useful. For example, U.S. Pat. No. 5,491,288 discloses combining a Cauliflower Mosaic Virus promoter with a histone promoter. Thus, the elements from the promoters disclosed herein may be combined with elements from other promoters. Promoters, which are useful for plant transgene expression include those that are inducible, viral, synthetic, constitutive (Odell 1985), temporally regulated, spatially regulated, tissue-specific, and spatial-temporally regulated.

Where expression in specific tissues or organs is desired, tissue-specific promoters may be used. In contrast, where gene expression in response to a stimulus is desired, inducible promoters are the regulatory elements of choice. Where continuous expression is desired throughout the cells of a plant, constitutive promoters are utilized. Additional regulatory sequences upstream and/or downstream from the core promoter sequence may be included in expression constructs of transformation vectors to bring about varying levels of expression of heterologous nucleotide sequences in a transgenic plant.

A variety of 5' and 3' transcriptional regulatory sequences are available for use in the present invention. Transcriptional terminators are responsible for the termination of transcription and correct mRNA polyadenylation. The 3' nontranslated regulatory DNA sequence preferably includes from about 50 to about 1,000, more preferably about 100 to about 1,000, nucleotide base pairs and contains plant transcriptional and translational termination sequences. Appropriate transcriptional terminators and those which are known to function in plants include the CaMV 35S terminator, the tml terminator, the nopaline synthase terminator, the pea rbcS E9 terminator, the terminator for the T7 transcript from the octopine synthase gene of *Agrobacterium tumefaciens*, and the 3' end of the protease inhibitor I or II genes from potato or tomato, although other 3' elements known to those of skill in the art can also be employed. Alternatively, one also could use a gamma coixin, oleosin 3 or other terminator from the genus *Coix*.

Preferred 3' elements include those from the nopaline synthase gene of *Agrobacterium tumefaciens* (Bevan 1983), the terminator for the T7 transcript from the octopine synthase gene of *Agrobacterium tumefaciens*, and the 3' end of the protease inhibitor I or II genes from potato or tomato.

As the DNA sequence between the transcription initiation site and the start of the coding sequence, i.e., the untranslated leader sequence, can influence gene expression, one may also wish to employ a particular leader sequence. Preferred leader sequences are contemplated to include those, which include sequences, predicted to direct optimum expression of the attached gene, i.e., to include a preferred consensus leader sequence, which may increase or maintain mRNA stability and prevent inappropriate initiation of translation. The choice of such sequences will be known to those of skill in the art in light of the present disclosure. Sequences that are derived from genes that are highly expressed in plants will be most preferred.

Preferred regulatory elements also include the 5'-untranslated region, introns and the 3'-untranslated region of genes. Such sequences that have been found to enhance gene expression in transgenic plants include intron sequences (e.g., from Adh1, bronze1, actin1, actin 2 (WO 00/760067), or the sucrose synthase intron; see: The Maize Handbook, Chapter 116, Freeling and Walbot, Eds., Springer, New York (1994)) and viral leader sequences (e.g., from TMV, MCMV and AMV; Gallie 1987). For example, a number of non-translated leader sequences derived from viruses are known to enhance expression. Specifically, leader sequences from Tobacco Mosaic Virus (TMV), Maize Chlorotic Mottle Virus (MCMV), and Alfalfa Mosaic Virus (AMV) have been shown to be effective in enhancing expression (e.g., Gallie 1987; Skuzeski 1990). Other leaders known in the art include but are not limited to: Picornavirus leaders, for example, EMCV leader (Encephalomyocarditis 5' noncoding region) (Elroy-Stein 1989); Potyvirus leaders, for example, TEV leader (Tobacco Etch Virus); MDMV leader (Maize Dwarf Mosaic Virus); Human immunoglobulin heavy-chain binding protein (BiP) leader, (Macejak 1991); Untranslated leader from the coat protein mRNA of alfalfa mosaic virus (AMV RNA 4), (Jobling 1987; Tobacco mosaic virus leader (TMV), (Gallie 1989; and Maize Chlorotic Mottle Virus leader (MCMV) (Lommel 1991. See also, Della-Cioppa 1987. Regulatory elements such as Adh intron 1 (Callis 1987), sucrose synthase intron (Vasil 1989) or TMV omega element (Gallie 1989), may further be included where desired. Especially preferred are the 5'-untranslated region, introns and the 3'-untranslated region selected from a) the gene described by the GenBank *Arabidopsis thaliana* genome locii At1g73190 and b) orthologous genes of the gene described by the GenBank *Arabidopsis thaliana* genome locii At1g73190.

Most preferred are the 5'-untranslated sequences comprised in the sequences as described by SEQ ID NO: 1, 3, 5, 7, 9, 10, or 11 (see sequence listing for specification of the localization).

Additional preferred regulatory elements are enhancer sequences or polyadenylation sequences. Preferred polyadenylation sequences are those from plant genes or *Agrobacte-*

*rium* T-DNA genes (such as for example the terminator sequences of the OCS (octopine synthase) or NOS (nopaline synthase) genes).

Examples of enhancers include elements from the CaMV 35S promoter, octopine synthase genes (Ellis et al., 1987), the rice actin I gene, the maize alcohol dehydrogenase gene (Callis 1987), the maize shrunken I gene (Vasil 1989), TMV Omega element (Gallie 1989) and promoters from non-plant eukaryotes (e.g. yeast; Ma 1988). Vectors for use in accordance with the present invention may be constructed to include the ocs enhancer element. This element was first identified as a 16 bp palindromic enhancer from the octopine synthase (ocs) gene of ultilane (Ellis 1987), and is present in at least 10 other promoters (Bouchez 1989). The use of an enhancer element, such as the ocs elements and particularly multiple copies of the element, will act to increase the level of transcription from adjacent promoters when applied in the context of plant transformation.

An expression cassette of the invention (or a vector derived therefrom) may comprise additional functional elements, which are to be understood in the broad sense as all elements, which influence construction, propagation, or function of an expression cassette or a vector or a transgenic organism comprising them. Such functional elements may include origin of replications (to allow replication in bacteria; for the ORI of pBR322 or the P15A ori; Sambrook 1989), or elements required for *Agrobacterium* T-DNA transfer (such as for example the left and/or rights border of the T-DNA).

Ultimately, the most desirable DNA segments for introduction into, for example, a dicot genome, may be homologous genes or gene families which encode a desired trait (e.g., increased yield per acre) and which are introduced under the control of novel promoters or enhancers, etc., or perhaps even homologous or tissue specific (e.g., root-, collar/sheath-, whorl-, stalk-, earshank-, kernel- or leaf-specific) promoters or control elements. Indeed, it is envisioned that a particular use of the present invention will be the expression of a gene in a seed-preferential or seed-specific manner.

Additionally, vectors may be constructed and employed in the intracellular targeting of a specific gene product within the cells of a transgenic plant or in directing a protein to the extracellular environment. This will generally be achieved by joining a DNA sequence encoding a transit or signal peptide sequence to the coding sequence of a particular gene. The resultant transit or signal peptide will transport the protein to a particular intracellular or extracellular destination, respectively, and will then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane.

A particular example of such a use concerns the direction of a herbicide resistance gene, such as the EPSPS gene, to a particular organelle such as the chloroplast rather than to the cytoplasm. This is exemplified by the use of the rbcs transit peptide which confers plastid-specific targeting of proteins. In addition, it is proposed that it may be desirable to target certain genes responsible for male sterility to the mitochondria, or to target certain genes for resistance to phytopathogenic organisms to the extracellular spaces, or to target proteins to the vacuole.

By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. Targeting of certain proteins may be desirable in order to enhance the stability of the protein (U.S. Pat. No. 5,545,818).

It may be useful to target DNA itself within a cell. For example, it may be useful to target introduced DNA to the nucleus as this may increase the frequency of transformation. Within the nucleus itself it would be useful to target a gene in order to achieve site-specific integration. For example, it would be useful to have a gene introduced through transformation replace an existing gene in the cell. Other elements include those that can be regulated by endogenous or exogenous agents, e.g., by zinc finger proteins, including naturally occurring zinc finger proteins or chimeric zinc finger proteins (see, e.g., U.S. Pat. No. 5,789,538, WO 99/48909; WO 99/45132; WO 98/53060; WO 98/53057; WO 98/53058; WO 00/23464; WO 95/19431; and WO 98/54311) or myb-like transcription factors. For example, a chimeric zinc finger protein may include amino acid sequences, which bind to a specific DNA sequence (the zinc finger) and amino acid sequences that activate (e.g., GAL 4 sequences) or repress the transcription of the sequences linked to the specific DNA sequence.

It is one of the objects of the present invention to provide recombinant DNA molecules comprising a nucleotide sequence according to the invention operably linked to a nucleotide segment of interest.

A nucleotide segment of interest is reflective of the commercial markets and interests of those involved in the development of the crop. Crops and markets of interest changes, and as developing nations open up world markets, new crops and technologies will also emerge. In addition, as the understanding of agronomic traits and characteristics such as yield and heterosis increase, the choice of genes for transformation will change accordingly. General categories of nucleotides of interest include, for example, genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in starch, oil, carbohydrate, or nutrient metabolism, as well as those affecting kernel size, sucrose loading, zinc finger proteins, see, e.g., U.S. Pat. No. 5,789,538, WO 99/48909; WO 99/45132; WO 98/53060; WO 98/53057; WO 98/53058; WO 00/23464; WO 95/19431; and WO 98/54311, and the like.

One skilled in the art recognizes that the expression level and regulation of a transgene in a plant can vary significantly from line to line. Thus, one has to test several lines to find one with the desired expression level and regulation. Once a line is identified with the desired regulation specificity of a chimeric Cre transgene, it can be crossed with lines carrying different inactive replicons or inactive transgene for activation.

Other sequences, which may be linked to the gene of interest, which encodes a polypeptide, are those which can target to a specific organelle, e.g., to the mitochondria, nucleus, or plastid, within the plant cell. Targeting can be achieved by providing the polypeptide with an appropriate targeting peptide sequence, such as a secretory signal peptide (for secretion or cell wall or membrane targeting, a plastid transit peptide, a chloroplast transit peptide, e.g., the chlorophyll a/b binding protein, a mitochondrial target peptide, a vacuole targeting peptide, or a nuclear targeting peptide, and the like. For example, the small subunit of ribulose bisphosphate carboxylase transit peptide, the EPSPS transit peptide or the dihydrodipicolinic acid synthase transit peptide may be used, for examples of plastid organelle targeting sequences (see WO 00/12732). Plastids are a class of plant organelles derived from proplastids and include chloroplasts, leucoplasts, amyloplasts, and chromoplasts. The plastids are major sites of biosynthesis in plants. In addition to photosynthesis in the chloroplast, plastids are also sites of lipid biosynthesis, nitrate reduction to ammonium, and starch storage. And while plastids contain their own circular, genome, most of the proteins localized to the plastids are encoded by the nuclear genome and are imported into the organelle from the cytoplasm.

Transgenes used with the present invention will often be genes that direct the expression of a particular protein or polypeptide product, but they may also be non-expressible DNA segments, e.g., transposons such as Ds that do no direct their own transposition. As used herein, an "expressible gene" is any gene that is capable of being transcribed into RNA (e.g., mRNA, antisense RNA, etc.) or translated into a protein, expressed as a trait of interest, or the like, etc., and is not limited to selectable, screenable or non-selectable marker genes. The invention also contemplates that, where both an expressible gene that is not necessarily a marker gene is employed in combination with a marker gene, one may employ the separate genes on either the same or different DNA segments for transformation. In the latter case, the different vectors are delivered concurrently to recipient cells to maximize cotransformation.

The choice of the particular DNA segments to be delivered to the recipient cells will often depend on the purpose of the transformation. One of the major purposes of trans-formation of crop plants is to add some commercially desirable, agronomically important traits to the plant. Such traits include, but are not limited to, herbicide resistance or tolerance; insect resistance or tolerance; disease resistance or tolerance (viral, bacterial, fungal, nematode); stress tolerance and/or resistance, as exemplified by resistance or tolerance to drought, heat, chilling, freezing, excessive moisture, salt stress; oxidative stress; increased yields; food content and makeup; physical appearance; male sterility; drydown; standability; prolificacy; starch properties; oil quantity and quality; and the like. One may desire to incorporate one or more genes conferring any such desirable trait or traits, such as, for example, a gene or genes encoding pathogen resistance.

In certain embodiments, the present invention contemplates the transformation of a recipient cell with more than one advantageous transgene. Two or more transgenes can be supplied in a single transformation event using either distinct transgene-encoding vectors, or using a single vector incorporating two or more gene coding sequences. For example, plasmids bearing the bar and aroA expression units in either convergent, divergent, or collinear orientation, are considered to be particularly useful. Further preferred combinations are those of an insect resistance gene, such as a Bt gene, along with a protease inhibitor gene such as pinII, or the use of bar in combination with either of the above genes. Of course, any two or more transgenes of any description, such as those conferring herbicide, insect, disease (viral, bacterial, fungal, nematode) or drought resistance, male sterility, drydown, standability, prolificacy, starch properties, oil quantity and quality, or those increasing yield or nutritional quality may be employed as desired.

1. Exemplary Transgenes
1.1. Herbicide Resistance

The genes encoding phosphinothricin acetyltransferase (bar and pat), glyphosate tolerant EPSP synthase genes, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar and pat genes code for an enzyme, phosphinothricin acetyltransferase (PAT), which inactivates the herbicide phosphinothricin and prevents this compound from inhibiting glutamine synthetase enzymes. The enzyme 5-enolpyruvylshikimate 3-phosphate synthase (EPSP Synthase), is normally inhibited by the herbicide N-(phosphonomethyl)glycine (glyphosate). However, genes are known that encode glyphosate-resistant EPSP Synthase enzymes. The deh gene encodes the enzyme dalapon dehalogenase and confers resistance to the herbicide dalapon. The bxn gene codes for a specific nitrilase enzyme that converts bromoxynil to a non-herbicidal degradation product.

1.2 Insect Resistance

An important aspect of the present invention concerns the introduction of insect resistance-conferring genes into plants. Potential insect resistance genes, which can be introduced, include *Bacillus thuringiensis* crystal toxin genes or Bt genes (Watrud 1985). Bt genes may provide resistance to lepidopteran or coleopteran pests such as European Corn Borer (ECB) and corn rootworm (CRW). Preferred Bt toxin genes for use in such embodiments include the CryIA(b) and CryIA (c) genes. Endotoxin genes from other species of *B. thuringiensis*, which affect insect growth or development, may also be employed in this regard. Protease inhibitors may also provide insect resistance (Johnson 1989), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered by the present inventors to produce synergistic insecticidal activity. Other genes, which encode inhibitors of the insects' digestive system, or those that encode enzymes or co-factors that facilitate the production of inhibitors, may also be useful. Cystatin and amylase inhibitors, such as those from wheat and barley, may exemplify this group.

Also, genes encoding lectins may confer additional or alternative insecticide properties. Lectins (originally termed phytohemagglutinins) are multivalent carbohydrate-binding proteins, which have the ability to agglutinate red blood cells from a range of species. Lectins have been identified recently as insecticidal agents with activity against weevils, ECB and rootworm (Murdock 1990; Czapla & Lang, 1990). Lectin genes contemplated to be useful include, for example, barley and wheat germ agglutinin (WGA) and rice lectins (Gatehouse 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated, that the expression of juvenile hormone esterase, directed towards specific insect pests, may also result in insecticidal activity, or perhaps cause cessation of metamorphosis (Hammock 1990).

Transgenic plants expressing genes, which encode enzymes that affect the integrity of the insect cuticle form yet another aspect of the invention. Such genes include those encoding, e.g., chitinase, proteases, lipases and also genes for the production of nik-komycin, a compound that inhibits chitin synthesis, the introduction of any of which is contemplated to produce insect resistant maize plants. Genes that code for activities that affect insect molting, such those affecting the production of ecdysteroid UDP-glucosyl transferase, also fall within the scope of the useful transgenes of the present invention.

Genes that code for enzymes that facilitate the production of compounds that reduce the nutritional quality of the host plant to insect pests are also encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti-nutritional effects on insects and to reduce the nutritional quality of their diet. Therefore, further embodiments of the invention concern transgenic plants with enhanced lipoxygenase activity which may be resistant to insect feeding.

The present invention also provides methods and compositions by which to achieve qualitative or quantitative changes in plant secondary metabolites. One example concerns transforming plants to produce DIMBOA which, it is contemplated, will confer resistance to European corn borer, rootworm and several other maize insect pests. Candidate genes that are particularly considered for use in this regard include those genes at the bx locus known to be involved in the synthetic DIMBOA pathway (Dunn 1981). The introduction of genes that can regulate the production of maysin, and genes involved in the production of dhurrin in sorghum, is also contemplated to be of use in facilitating resistance to earworm and rootworm, respectively.

*Tripsacum dactyloides* is a species of grass that is resistant to certain insects, including corn rootworm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson & Guss, 1972).

Further genes encoding proteins characterized as having potential insecticidal activity may also be used as transgenes in accordance herewith. Such genes include, for example, the cowpea trypsin inhibitor (CpTI; Hilder 1987), which may be used as a rootworm deterrent; genes encoding avermectin (Campbell 1989; Ikeda 1987) which may prove particularly useful as a corn rootworm deterrent; ribosome inactivating protein genes; and even genes that regulate plant structures. Transgenic maize including anti-insect antibody genes and genes that code for enzymes that can covert a non-toxic insecticide (pro-insecticide) applied to the outside of the plant into an insecticide inside the plant are also contemplated.

1.3 Environment or Stress Resistance

Improvement of a plant's ability to tolerate various environmental stresses such as, but not limited to, drought, excess moisture, chilling, freezing, high temperature, salt, and oxidative stress, can also be effected through expression of heterologous, or overexpression of homologous genes. Benefits may be realized in terms of increased resistance to freezing temperatures through the introduction of an "antifreeze" protein such as that of the Winter Flounder (Cutler 1989) or synthetic gene derivatives thereof. Improved chilling tolerance may also be conferred through increased expression of glycerol-3-phosphate acetyltransferase in chloroplasts (Murata 1992; Wolter 1992). Resistance to oxidative stress (often exacerbated by conditions such as chilling temperatures in combination with high light intensities) can be conferred by expression of superoxide dismutase (Gupta 1993), and may be improved by glutathione reductase (Bowler 1992). Such strategies may allow for tolerance to freezing in newly emerged fields as well as extending later maturity higher yielding varieties to earlier relative maturity zones.

Expression of novel genes that favorably effect plant water content, total water potential, osmotic potential, and turgor can enhance the ability of the plant to tolerate drought. As used herein, the terms "drought resistance" and "drought tolerance" are used to refer to a plants increased resistance or tolerance to stress induced by a reduction in water availability, as compared to normal circumstances, and the ability of the plant to function and survive in lower-water environments, and perform in a relatively superior manner. In this aspect of the invention it is proposed, for example, that the expression of a gene encoding the biosynthesis of osmotically active solutes can impart protection against drought. Within this class of genes are DNAs encoding mannitol dehydrogenase (Lee and Saier, 1982) and trehalose-6-phosphate synthase (Kaasen 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski 1992).

Similarly, the efficacy of other metabolites in protecting either enzyme function (e.g. alanopine or propionic acid) or membrane integrity (e.g., alanopine) has been documented (Loomis 1989), and therefore expression of gene encoding the biosynthesis of these compounds can confer drought resistance in a manner similar to or complimentary to mannitol. Other examples of naturally occurring metabolites that are osmotically active and/or provide some direct protective effect during drought and/or desiccation include sugars and sugar derivatives such as fructose, erythritol (Coxson 1992), sorbitol, dulcitol (Karsten 1992), glucosylglycerol (Reed 1984; Erdmann 1992), sucrose, stachyose (Koster & Leopold 1988; Blackman 1992), ononitol and pinitol (Vernon & Bohnert 1992), and raffinose (Bernal-Lugo & Leopold 1992). Other osmotically active solutes, which are not sugars, include, but are not limited to, proline and glycine-betaine (Wyn-Jones and Storey, 1981). Continued canopy growth and increased reproductive fitness during times of stress can be augmented by introduction and expression of genes such as those controlling the osmotically active compounds discussed above and other such compounds, as represented in one exemplary embodiment by the enzyme myoinositol 0-methyltransferase.

It is contemplated that the expression of specific proteins may also increase drought tolerance. Three classes of Late Embryogenic Proteins have been assigned based on structural similarities (see Dure 1989). All three classes of these proteins have been demonstrated in maturing (i.e., desiccating) seeds. Within these 3 types of proteins, the Type-II (dehydrin-type) have generally been implicated in drought and/or desiccation tolerance in vegetative plant parts (e.g. Mundy and Chua, 1988; Piatkowski 1990; Yamaguchi-Shinozaki 1992). Recently, expression of a Type-III LEA (HVA-1) in tobacco was found to influence plant height, maturity and drought tolerance (Fitzpatrick, 1993). Expression of structural genes from all three groups may therefore confer drought tolerance. Other types of proteins induced during water stress include thiol proteases, aldolases and transmembrane transporters (Guerrero 1990), which may confer various protective and/or repair-type functions during drought stress. The expression of a gene that effects lipid biosynthesis and hence membrane composition can also be useful in conferring drought resistance on the plant.

Many genes that improve drought resistance have complementary modes of action. Thus, combinations of these genes might have additive and/or synergistic effects in improving drought resistance in maize. Many of these genes also improve freezing tolerance (or resistance); the physical stresses incurred during freezing and drought are similar in nature and may be mitigated in similar fashion. Benefit may be conferred via constitutive expression or tissue-specific of these genes, but the preferred means of expressing these novel genes may be through the use of a turgor-induced promoter (such as the promoters for the turgor-induced genes described in Guerrero et al. 1990 and Shagan 1993). Spatial and temporal expression patterns of these genes may enable maize to better withstand stress.

Expression of genes that are involved with specific morphological traits that allow for increased water extractions from drying soil would be of benefit. For example, introduction and expression of genes that alter root characteristics may enhance water uptake. Expression of genes that enhance reproductive fitness during times of stress would be of significant value. For example, expression of DNAs that improve the synchrony of pollen shed and receptiveness of the female flower parts, i.e., silks, would be of benefit. In addition, expression of genes that minimize kernel abortion during times of stress would increase the amount of grain to be harvested and hence be of value. Regulation of cytokinin levels in monocots, such as maize, by introduction and expression of an isopentenyl transferase gene with appropriate regulatory sequences can improve monocot stress resistance and yield (Gan 1995).

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Improved protection of the plant to abiotic stress factors such as drought, heat or chill, can also be achieved—for example—by overexpressing antifreeze polypeptides from *Myoxocephalus Scorpius* (WO 00/00512), *Myoxocephalus octodecemspinosus*, the *Arabidopsis thaliana* transcription activator CBF-1, glutamate dehydrogenases (WO 97/12983, WO 98/11240), calcium-dependent protein kinase genes (WO 98/26045), calcineurins (WO 99/05902), casein kinase from yeast (WO 02/052012), farnesyltransferases (WO 99/06580; Pei Z M et al. (1998) Science 282:287-290), ferritin (Deak M et al. (1999) Nature Biotechnology 17:192-196), oxalate oxidase (WO 99/04013; Dunwell J M (1998) Biotechn Genet Eng Rev 15:1-32), DREB1A factor ("dehydration response element B 1A"; Kasuga M et al. (1999) Nature Biotech 17:276-286), genes of mannitol or trehalose synthesis such as trehalose-phosphate synthase or trehalose-phosphate phosphatase (WO 97/42326) or by inhibiting genes such as trehalase (WO 97/50561).

1.4 Disease Resistance

It is proposed that increased resistance to diseases may be realized through introduction of genes into plants period. It is possible to produce resistance to diseases caused, by viruses, bacteria, fungi, root pathogens, insects and nematodes. It is also contemplated that control of mycotoxin producing organisms may be realized through expression of introduced genes.

Resistance to viruses may be produced through expression of novel genes. For example, it has been demonstrated that expression of a viral coat protein in a transgenic plant can impart resistance to infection of the plant by that virus and perhaps other closely related viruses (Cuozzo 1988, Hemenway 1988, Abel 1986). It is contemplated that expression of antisense genes targeted at essential viral functions may impart resistance to said virus. For example, an antisense gene targeted at the gene responsible for replication of viral nucleic acid may inhibit said replication and lead to resistance to the virus. It is believed that interference with other viral functions through the use of antisense genes may also increase resistance to viruses. Further it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so-called "peptide antibiotics," pathogenesis related (PR) proteins, toxin resistance, and proteins affecting host-pathogen interactions such as morphological characteristics will be useful. Peptide antibiotics are polypeptide sequences, which are inhibitory to growth of bacteria and other microorganisms. For example, the classes of peptides referred to as cecropins and magainins inhibit growth of many species of bacteria and fungi. It is proposed that expression of PR proteins in plants may be useful in conferring resistance to bacterial disease. These genes are induced following pathogen attack on a host plant and have been divided into at least five classes of proteins (Bol 1990). Included amongst the PR proteins are beta-1,3-glucanases, chitinases, and osmotin and other proteins that are believed to function in plant resistance to disease organisms. Other genes have been identified that have antifungal properties, e.g., UDA (stinging nettle lectin) and hevein (Broakgert 1989; Barkai-Golan 1978). It is known that certain plant diseases are caused by the production of phytotoxins. Resistance to these diseases could be achieved through expression of a novel gene that encodes an enzyme capable of degrading or otherwise inactivating the phytotoxin. Expression novel genes that alter the interactions between the host plant and pathogen may be useful in reducing the ability the disease organism to invade the tissues of the host plant, e.g., an increase in the waxiness of the leaf cuticle or other morphological characteristics.

Plant parasitic nematodes are a cause of disease in many plants. It is proposed that it would be possible to make the plant resistant to these organisms through the expression of novel genes. It is anticipated that control of nematode infestations would be accomplished by altering the ability of the nematode to recognize or attach to a host plant and/or enabling the plant to produce nematicidal compounds, including but not limited to proteins.

Furthermore, a resistance to fungi, insects, nematodes and diseases, can be achieved by targeted accumulation of certain metabolites or proteins. Such proteins include but are not limited to glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further examples are nucleic acids which encode the *Trichoderma harzianum* chit42 endochitinase (GenBank Acc. No.: S78423) or the N-hydroxylating, multi-functional cytochrome P450 (CYP79) protein from *Sorghum bi-color* (GenBank Acc. No.: U32624), or functional equivalents of these. The accumulation of glucosinolates as protection from pests (Rask L et al. (2000) Plant Mol Biol 42:93-113; Menard R et al. (1999) Phytochemistry 52:29-35), the expression of *Bacillus thuringiensis* endotoxins (Vaeck et al. (1987) Nature 328:33-37) or the protection against attack by fungi, by expression of chitinases, for example from beans (Broglie et al. (1991) Science 254:1194-1197), is advantageous. Resistance to pests such as, for example, the rice pest *Nilaparvata lugens* in rice plants can be achieved by expressing the snowdrop (*Galanthus nivalis*) lectin agglutinin (Rao et al. (1998) Plant J 15(4):469-77). The expression of synthetic cryIA(b) and cryIA(c) genes, which encode lepidoptera-specific *Bacillus thuringiensis* D-endotoxins can bring about a resistance to insect pests in various plants (Goyal R K et al. (2000) Crop Protection 19(5):307-312). Further target genes which are suitable for pathogen defense comprise "polygalacturonase-inhibiting protein" (PGIP), thaumatine, invertase and antimicrobial peptides such as lactoferrin (Lee T J et al. (2002) J Amer Soc Horticult Sci 127(2):158-164). Other nucleic acid sequences which may be advantageously used herein include traits for insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407; and 6,506,962), virus resistance (U.S. Pat. Nos. 5,304,730 and 6,013,864), nematode resistance (U.S. Pat. No. 6,228,992), and bacterial disease resistance (U.S. Pat. No. 5,516,671).

1.5 Mycotoxin Reduction/Elimination

Production of mycotoxins, including aflatoxin and fumonisin, by fungi associated with plants is a significant factor in rendering the grain not useful. These fungal organisms do not cause disease symptoms and/or interfere with the growth of the plant, but they produce chemicals (mycotoxins) that are toxic to animals. Inhibition of the growth of these fungi would reduce the synthesis of these toxic substances and, therefore, reduce grain losses due to mycotoxin contamination. Novel genes may be introduced into plants that would inhibit synthesis of the mycotoxin without interfering with fungal growth. Expression of a novel gene, which encodes an enzyme capable of rendering the mycotoxin nontoxic, would be useful in order to achieve reduced mycotoxin contamination of grain. The result of any of the above mechanisms would be a reduced presence of mycotoxins on grain.

1.6 Grain Composition or Quality

Genes may be introduced into plants, particularly commercially important cereals such as maize, wheat or rice, to improve the grain for which the cereal is primarily grown. A wide range of novel transgenic plants produced in this manner may be envisioned depending on the particular end use of the grain.

For example, the largest use of maize grain is for feed or food. Introduction of genes that alter the composition of the grain may greatly enhance the feed or food value. The primary components of maize grain are starch, protein, and oil. Each of these primary components of maize grain may be improved by altering its level or composition. Several examples may be mentioned for illustrative purposes but in no way provide an exhaustive list of possibilities.

The protein of many cereal grains is suboptimal for feed and food purposes especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after the grain is supplemented with other inputs for feed formulations. For example, when the grain is supplemented with soybean meal to meet lysine requirements, methionine becomes limiting. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

One mechanism for increasing the biosynthesis of the amino acids is to introduce genes that deregulate the amino acid biosynthetic pathways such that the plant can no longer adequately control the levels that are produced. This may be done by deregulating or bypassing steps in the amino acid biosynthetic pathway that are normally regulated by levels of the amino acid end product of the pathway. Examples include the introduction of genes that encode deregulated versions of the enzymes aspartokinase or dihydrodipicolinic acid (DHDP)-synthase for increasing lysine and threonine production, and anthranilate synthase for increasing tryptophan production. Reduction of the catabolism of the amino acids may be accomplished by introduction of DNA sequences that reduce or eliminate the expression of genes encoding enzymes that catalyse steps in the catabolic pathways such as the enzyme lysine-ketoglutarate reductase.

The protein composition of the grain may be altered to improve the balance of amino acids in a variety of ways including elevating expression of native proteins, decreasing expression of those with poor composition, changing the composition of native proteins, or introducing genes encoding entirely new proteins possessing superior composition. DNA may be introduced that decreases the expression of members of the zein family of storage proteins. This DNA may encode ribozymes or antisense sequences directed to impairing expression of zein proteins or expression of regulators of zein expression such as the opaque-2 gene product. The protein composition of the grain may be modified through the phenomenon of cosuppression, i.e., inhibition of expression of an endogenous gene through the expression of an identical structural gene or gene fragment introduced through transformation (Goring 1991). Additionally, the introduced DNA may encode enzymes, which degrade zeines. The decreases in zein expression that are achieved may be accompanied by increases in proteins with more desirable amino acid composition or increases in other major seed constituents such as starch. Alternatively, a chimeric gene may be introduced that comprises a coding sequence for a native protein of adequate amino acid composition such as for one of the globulin proteins or 10 kD zein of maize and a promoter or other regulatory sequence designed to elevate expression of said protein. The coding sequence of said gene may include additional or replacement codons for essential amino acids. Further, a coding sequence obtained from another species, or, a partially or completely synthetic sequence encoding a completely unique peptide sequence designed to enhance the amino acid composition of the seed may be employed.

The introduction of genes that alter the oil content of the grain may be of value. Increases in oil content may result in increases in metabolizable energy content and density of the seeds for uses in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, beta-ketoacyl-ACP synthase, plus other well-known fatty acid biosynthetic activities. Other possibilities are genes that encode proteins that do not possess enzymatic activity such as acyl carrier protein. Additional examples include 2-acetyltransferase, oleosin pyruvate dehydrogenase complex, acetyl CoA synthetase, ATP citrate lyase, ADP-glucose pyrophosphorylase and genes of the carnitine-CoA-acetyl-CoA shuttles. It is anticipated that expression of genes related to oil biosynthesis will be targeted to the plastid, using a plastid transit peptide sequence and preferably expressed in the seed embryo. Genes may be introduced that alter the balance of fatty acids present in the oil providing a more healthful or nutritive feedstuff. The introduced DNA may also encode sequences that block expression of enzymes involved in fatty acid biosynthesis, altering the proportions of fatty acids present in the grain such as described below.

Genes may be introduced that enhance the nutritive value of the starch component of the grain, for example by increasing the degree of branching, resulting in improved utilization of the starch in cows by delaying its metabolism.

Besides affecting the major constituents of the grain, genes may be introduced that affect a variety of other nutritive, processing, or other quality aspects of the grain as used for feed or food. For example, pigmentation of the grain may be increased or decreased. Enhancement and stability of yellow pigmentation is desirable in some animal feeds and may be achieved by introduction of genes that result in enhanced production of xanthophylls and carotenes by eliminating rate-limiting steps in their production. Such genes may encode altered forms of the enzymes phytoene synthase, phytoene desaturase, or lycopene synthase. Alternatively, unpigmented white corn is desirable for production of many food products and may be produced by the introduction of DNA, which blocks or eliminates steps in pigment production pathways.

Feed or food comprising some cereal grains possesses insufficient quantities of vitamins and must be supplemented to provide adequate nutritive value. Introduction of genes that enhance vitamin biosynthesis in seeds may be envisioned including, for example, vitamins A, E, $B_{12}$, choline, and the like. For example, maize grain also does not possess sufficient mineral content for optimal nutritive value. Genes that affect the accumulation or availability of compounds containing phosphorus, sulfur, calcium, manganese, zinc, and iron among others would be valuable. An example may be the introduction of a gene that reduced phytic acid production or encoded the enzyme phytase, which enhances phytic acid breakdown. These genes would increase levels of available phosphate in the diet, reducing the need for supplementation with mineral phosphate.

Numerous other examples of improvement of cereals for feed and food purposes might be described. The improvements may not even necessarily involve the grain, but may, for example, improve the value of the grain for silage. Introduction of DNA to accomplish this might include sequences that alter lignin production such as those that result in the "brown midrib" phenotype associated with superior feed value for cattle.

In addition to direct improvements in feed or food value, genes may also be introduced which improve the processing of grain and improve the value of the products resulting from the processing. The primary method of processing certain grains such as maize is via wetmilling. Maize may be improved though the expression of novel genes that increase the efficiency and reduce the cost of processing such as by decreasing steeping time.

Improving the value of wetmilling products may include altering the quantity or quality of starch, oil, corn gluten meal, or the components of corn gluten feed. Elevation of starch may be achieved through the identification and elimination of rate limiting steps in starch biosynthesis or by decreasing levels of the other components of the grain resulting in proportional increases in starch. An example of the former may be the introduction of genes encoding ADP-glucose pyrophosphorylase enzymes with altered regulatory activity or which are expressed at higher level. Examples of the latter may include selective inhibitors of, for example, protein or oil biosynthesis expressed during later stages of kernel development.

The properties of starch may be beneficially altered by changing the ratio of amylose to amylopectin, the size of the starch molecules, or their branching pattern. Through these changes a broad range of properties may be modified which include, but are not limited to, changes in gelatinization temperature, heat of gelatinization, clarity of films and pastes, Theological properties, and the like. To accomplish these changes in properties, genes that encode granule-bound or soluble starch synthase activity or branching enzyme activity may be introduced alone or combination. DNA such as antisense constructs may also be used to decrease levels of endogenous activity of these enzymes. The introduced genes or constructs may possess regulatory sequences that time their expression to specific intervals in starch biosynthesis and starch granule development. Furthermore, it may be advisable to introduce and express genes that result in the in vivo derivatization, or other modification, of the glucose moieties of the starch molecule. The covalent attachment of any molecule may be envisioned, limited only by the existence of enzymes that catalyze the derivatizations and the accessibility of appropriate substrates in the starch granule. Examples of important derivations may include the addition of functional groups such as amines, carboxyls, or phosphate groups, which provide sites for subsequent in vitro derivatizations or affect starch properties through the introduction of ionic charges. Examples of other modifications may include direct changes of the glucose units such as loss of hydroxyl groups or their oxidation to aldehyde or carboxyl groups.

Oil is another product of wetmilling of corn and other grains, the value of which may be improved by introduction and expression of genes. The quantity of oil that can be extracted by wetmilling may be elevated by approaches as described for feed and food above. Oil properties may also be altered to improve its performance in the production and use of cooking oil, shortenings, lubricants or other oil-derived products or improvement of its health attributes when used in the food-related applications. Novel fatty acids may also be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids and the lipids possessing them or by increasing levels of native fatty acids while possibly reducing levels of precursors. Alternatively DNA sequences may be introduced which slow or block steps in fatty acid biosynthesis resulting in the increase in precursor fatty acid intermediates. Genes that might be added include desaturases, epoxidases, hydratases, dehydratases, and other enzymes that catalyze reactions involving fatty acid intermediates. Representative examples of catalytic steps that might be blocked include the desaturations from stearic to oleic acid and oleic to linolenic acid resulting in the respective accumulations of stearic and oleic acids.

Improvements in the other major cereal wetmilling products, gluten meal and gluten feed, may also be achieved by the introduction of genes to obtain novel plants. Representative possibilities include but are not limited to those described above for improvement of food and feed value.

In addition it may further be considered that the plant be used for the production or manufacturing of useful biological compounds that were either not produced at all, or not produced at the same level, in the plant previously. The novel plants producing these compounds are made possible by the introduction and expression of genes by transformation methods. The possibilities include, but are not limited to, any biological compound which is presently produced by any organism such as proteins, nucleic acids, primary and intermediary metabolites, carbohydrate polymers, etc. The compounds may be produced by the plant, extracted upon harvest and/or processing, and used for any presently recognized useful purpose such as pharmaceuticals, fragrances, industrial enzymes to name a few.

Further possibilities to exemplify the range of grain traits or properties potentially encoded by introduced genes in transgenic plants include grain with less breakage susceptibility for export purposes or larger grit size when processed by dry milling through introduction of genes that enhance gamma-zein synthesis, popcorn with improved popping, quality and expansion volume through genes that increase pericarp thickness, corn with whiter grain for food uses though introduction of genes that effectively block expression of enzymes involved in pigment production pathways, and improved quality of alcoholic beverages or sweet corn through introduction of genes which affect flavor such as the shrunken gene (encoding sucrose synthase) for sweet corn.

1.7 Tuber or Seed Composition or Quality

Various traits can be advantageously expressed especially in seeds or tubers to improve composition or quality. Useful nucleic acid sequences that can be combined with the promoter nucleic acid sequence of the present invention and provide improved end-product traits include, without limitation, those encoding seed storage proteins, fatty acid pathway enzymes, tocopherol biosynthetic enzymes, amino acid biosynthetic enzymes, and starch branching enzymes. A discussion of exemplary heterologous DNAs useful for the modification of plant phenotypes may be found in, for example, U.S. Pat. Nos. 6,194,636; 6,207,879; 6,232,526; 6,426,446; 6,429,357; 6,433,252; 6,437,217; 6,515,201; and 6,583,338 and PCT Publication WO 02/057471, each of which is specifically incorporated herein by reference in its entirety. Such traits include but are not limited to:

Expression of metabolic enzymes for use in the food-and-feed sector, for example of phytases and cellulases. Especially preferred are nucleic acids such as the artificial cDNA, which encodes a microbial phytase (GenBank Acc. No.: A19451) or functional equivalents thereof.

Expression of genes, which bring about an accumulation of fine chemicals such as of tocopherols, tocotrienols or carotenoids. An example, which may be mentioned is phytoene desaturase. Preferred are nucleic acids, which encode the *Narcissus pseudonarcissus* photoene desaturase (GenBank Acc. No.: X78815) or functional equivalents thereof. Preferred tocopherol biosynthetic enzymes include tyrA, slr1736, ATPT2, dxs, dxr, GGPPS, HPPD, GMT, MT1, tMT2, AANT1, slr 1737, and an antisense construct for homogentisic acid dioxygenase (Kridl et al., Seed Sci. Res., 1:209:219 (1991); Keegstra, Cell, 56(2):247-53 (1989); Nawrath et al., Proc. Natl. Acad. Sci. USA, 91:12760-12764 (1994); Xia et al., J. Gen. Microbiol., 138:1309-1316 (1992); Lois et al., Proc. Natl. Acad. Sci. USA, 95(5):2105-2110 (1998); Takahashi et al., Proc. Natl. Acad. Sci. USA, 95(17):9879-9884 (1998); Norris et al., Plant Physiol., 117:1317-1323 (1998); Bartley and Scolnik, Plant Physiol., 104:1469-1470 (1994); Smith et al., Plant J., 11:83-92 (1997); WO 00/32757; WO 00/10380; Saint Guily et al., Plant Physiol., 100(2):1069-1071 (1992); Sato et al., J. DNA Res., 7(1):31-63 (2000)) all of which are incorporated herein by reference.

starch production (U.S. Pat. Nos. 5,750,876 and 6,476,295), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. No. 5,958,745 and U.S. Patent Publication No. 2003/0028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648), low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements and transgenes described in the patents listed above are herein incorporated by reference. Preferred starch branching enzymes (for modification of starch properties) include those set forth in U.S. Pat. Nos. 6,232,122 and 6,147,279; and PCT Publication WO 97/22703, all of which are incorporated herein by reference.

Modified oils production (U.S. Pat. No. 6,444,876), high oil production (U.S. Pat. Nos. 5,608,149 and 6,476,295), or modified fatty acid content (U.S. Pat. No. 6,537,750). Preferred fatty acid pathway enzymes include thioesterases (U.S. Pat. Nos. 5,512,482; 5,530,186; 5,945,585; 5,639,790; 5,807,893; 5,955,650; 5,955,329; 5,759,829; 5,147,792; 5,304,481; 5,298,421; 5,344,771; and 5,760,206), diacylglycerol acyltransferases (U.S. Patent Publications 20030115632A1 and 20030028923A1), and desaturases (U.S. Pat. Nos. 5,689,050; 5,663,068; 5,614,393; 5,856,157; 6,117,677; 6,043,411; 6,194,167; 5,705,391; 5,663,068; 5,552,306; 6,075,183; 6,051,754; 5,689,050; 5,789,220; 5,057,419; 5,654,402; 5,659,645; 6,100,091; 5,760,206; 6,172,106; 5,952,544; 5,866,789; 5,443,974; and 5,093,249) all of which are incorporated herein by reference.

Preferred amino acid biosynthetic enzymes include anthranilate synthase (U.S. Pat. No. 5,965,727 and PCT Publications WO 97/26366, WO 99/11800, WO 99/49058), tryptophan decarboxylase (PCT Publication WO 99/06581), threonine decarboxylase (U.S. Pat. Nos. 5,534,421 and 5,942,660; PCT Publication WO 95/19442), threonine deaminase (PCT Publications WO 99/02656 and WO 98/55601), dihydrodipicolinic acid synthase (U.S. Pat. No. 5,258,300), and aspartate kinase (U.S. Pat. Nos. 5,367,110; 5,858,749; and 6,040,160) all of which are incorporated herein by reference.

Production of nutraceuticals such as, for example, polyunsaturated fatty acids (for example arachidonic acid, eicosapentaenoic acid or docosahexaenoic acid) by expression of fatty acid elongases and/or desaturases, or production of proteins with improved nutritional value such as, for example, with a high content of essential amino acids (for example the high-methionine 2S albumin gene of the brazil nut). Preferred are nucleic acids which encode the *Bertholletia excelsa* high-methionine 2S albumin (GenBank Acc. No.: AB044391), the *Physcomitrella patens* Δ6-acyl-lipid desaturase (GenBank Acc. No.: Acc. 222980; Girke et al. (1998) Plant J 15:39-48), the *Mortierella alpina* Δ6-desaturase (Sakuradani et al. 1999 Gene 238:445-453), the *Caenorhabditis elegans* Δ5-desaturase (Michaelson et al. 1998, FEBS Letters 439:215-218), the *Caenorhabditis elegans* Δ5-fatty acid desaturase (des-5) (GenBank Acc. No.: AF078796), the *Mortierella alpina* Δ5-desaturase (Michaelson et al. JBC 273:19055-19059), the *Caenorhabditis elegans* Δ6-elongase (Beaudoin et al. 2000, PNAS 97:6421-6426), the *Physcomitrella patens* A6-elongase (Zank et al. 2000, Biochemical Society Transactions 28:654-657), or functional equivalents of these.

Production of high-quality proteins and enzymes for industrial purposes (for example enzymes, such as lipases) or as pharmaceuticals (such as, for example, antibodies, blood clotting factors, interferons, lymphokines, colony stimulation factor, plasminogen activators, hormones or vaccines, as described by Hood E E, Jilka J M (1999) Curr Opin Biotechnol 10(4): 382-6; Ma J K, Vine N D (1999) Curr Top Microbiol Immunol 236:275-92). For example, it has been possible to produce recombinant avidin from chicken albumen and bacterial β-glucuronidase (GUS) on a large scale in transgenic maize plants (Hood et al. (1999) Adv Exp Med Biol 464:127-47. Review).

Obtaining an increased storability in cells which normally comprise fewer storage proteins or storage lipids, with the purpose of increasing the yield of these substances, for example by expression of acetyl-CoA carboxylase. Preferred nucleic acids are those, which encode the *Medicago sativa* acetyl-CoA carboxylase (ACCase) (GenBank Acc. No.: L25042), or functional equivalents thereof. Alternatively, in some scenarios an increased storage protein content might be advantageous for high-protein product production. Preferred seed storage proteins include zeins (U.S. Pat. Nos. 4,886,878; 4,885,357; 5,215,912; 5,589,616; 5,508,468; 5,939,599; 5,633,436; and 5,990,384; PCT Publications WO 90/01869, WO 91/13993, WO 92/14822, WO 93/08682, WO 94/20628, WO 97/28247, WO 98/26064, and WO 99/40209), 7S proteins (U.S. Pat. Nos. 5,003,045 and 5,576,203), brazil nut protein (U.S. Pat. No. 5,850,024), phenylalanine free proteins (PCT Publication WO 96/17064), albumin (PCT Publication WO 97/35023), b-conglycinin (PCT Publication WO 00/19839), 11S (U.S. Pat. No. 6,107, 051), alpha-hordothionin (U.S. Pat. Nos. 5,885,802 and 5,88,5801), arcelin seed storage proteins (U.S. Pat. No. 5,270,200), lectins (U.S. Pat. No. 6,110,891), and glutenin (U.S. Pat. Nos. 5,990,389 and 5,914,450) all of which are incorporated herein by reference.

Reducing levels of α-glucan L-type tuber phosphorylase (GLTP) or α-glucan H-type tuber phosphorylase (GHTP) enzyme activity preferably within the potato tuber (see U.S. Pat. No. 5,998,701). The conversion of starches to sugars in potato tubers, particularly when stored at temperatures below 7° C., is reduced in tubers exhibiting reduced GLTP or GHTP enzyme activity. Reducing cold-sweetening in potatoes allows for potato storage at cooler temperatures, resulting in prolonged dormancy, reduced incidence of disease, and increased storage life. Reduction of GLTP or GHTP activity within the potato tuber may be accomplished by such techniques as suppression of gene expression using homologous antisense or double-stranded RNA, the use of co-suppression, regulatory silencing sequences. A potato plant having improved cold-storage characteristics, comprising a potato plant transformed with an expression cassette having a TPT promoter sequence operably linked to a DNA sequence comprising at least 20 nucleotides of a gene encoding an α-glucan phosphorylase selected from the group consisting of α-glucan L-type tuber phosphorylase (GLTP) and α-glucan H-type phosphorylase (GHTP).

Further examples of advantageous genes are mentioned for example in Dunwell J M, Transgenic approaches to crop improvement, J Exp Bot. 2000; 51 Spec No; pages 487-96.

1.8 Plant Agronomic Characteristics

Two of the factors determining where plants can be grown are the average daily temperature during the growing season and the length of time between frosts. Within the areas where it is possible to grow a particular plant, there are varying limitations on the maximal time it is allowed to grow to maturity and be harvested. The plant to be grown in a particular area is selected for its ability to mature and dry down to harvestable moisture content within the required period of time with maximum possible yield. Therefore, plants of varying maturities are developed for different growing locations. Apart from the need to dry down sufficiently to permit harvest is the desirability of having maximal drying take place in the field to minimize the amount of energy required for additional drying post-harvest. Also the more readily the grain can dry down, the more time there is available for growth and kernel fill. Genes that influence maturity and/or dry down can be identified and introduced into plant lines using transformation techniques to create new varieties adapted to different growing locations or the same growing location but having improved yield to moisture ratio at harvest. Expression of genes that are involved in regulation of plant development may be especially useful, e.g., the liguleless and rough sheath genes that have been identified in plants.

Genes may be introduced into plants that would improve standability and other plant growth characteristics. For example, expression of novel genes, which confer stronger stalks, improved root systems, or prevent or reduce ear droppage would be of great value to the corn farmer. Introduction and expression of genes that increase the total amount of photoassimilate available by, for example, increasing light distribution and/or interception would be advantageous. In addition the expression of genes that increase the efficiency of photosynthesis and/or the leaf canopy would further increase gains in productivity. Such approaches would allow for increased plant populations in the field.

Delay of late season vegetative senescence would increase the flow of assimilates into the grain and thus increase yield.

Overexpression of genes within plants that are associated with "stay green" or the expression of any gene that delays senescence would be advantageous. For example, a non-yellowing mutant has been identified in *Festuca pratensis* (Davies 1990). Expression of this gene as well as others may prevent premature breakdown of chlorophyll and thus maintain canopy function.

1.9 Nutrient Utilization

The ability to utilize available nutrients and minerals may be a limiting factor in growth of many plants. It is proposed that it would be possible to alter nutrient uptake, tolerate pH extremes, mobilization through the plant, storage pools, and availability for metabolic activities by the introduction of novel genes. These modifications would allow a plant to more efficiently utilize available nutrients. It is contemplated that an increase in the activity of, for example, an enzyme that is normally present in the plant and involved in nutrient utilization would increase the availability of a nutrient. An example of such an enzyme would be phytase. It is also contemplated that expression of a novel gene may make a nutrient source available that was previously not accessible, e.g., an enzyme that releases a component of nutrient value from a more complex molecule, perhaps a macromolecule.

1.10 Male Sterility

Male sterility is useful in the production of hybrid seed. It is proposed that male sterility may be produced through expression of novel genes. For example, it has been shown that expression of genes that encode proteins that interfere with development of the male inflorescence and/or gametophyte result in male sterility. Chimeric ribonuclease genes that express in the anthers of transgenic tobacco and oilseed rape have been demonstrated to lead to male sterility (Mariani 1990). For example, a number of mutations were discovered in maize that confer cytoplasmic male sterility. One mutation in particular, referred to as T cytoplasm, also correlates with sensitivity to Southern corn leaf blight. A DNA sequence, designated TURF-13 (Levings 1990), was identified that correlates with T cytoplasm. It would be possible through the introduction of TURF-13 via transformation to separate male sterility from disease sensitivity. As it is necessary to be able to restore male fertility for breeding purposes and for grain production, it is proposed that genes encoding restoration of male fertility may also be introduced.

1.11. Non-Protein-Expressing Sequences 1.11.1 RNA-Expressing

DNA may be introduced into plants for the purpose of expressing RNA transcripts that function to affect plant phenotype yet are not translated into protein. Two examples are antisense RNA and RNA with ribozyme activity. Both may serve possible functions in reducing or eliminating expression of native or introduced plant genes.

Genes may be constructed or isolated, which when transcribed, produce antisense RNA or double-stranded RNA that is complementary to all or part(s) of a targeted messenger RNA(s). The antisense RNA reduces production of the polypeptide product of the messenger RNA. The polypeptide product may be any protein encoded by the plant genome. The aforementioned genes will be referred to as antisense genes. An antisense gene may thus be introduced into a plant by transformation methods to produce a novel transgenic plant with reduced expression of a selected protein of interest. For example, the protein may be an enzyme that catalyzes a reaction in the plant. Reduction of the enzyme activity may reduce or eliminate products of the reaction which include any enzymatically synthesized compound in the plant such as fatty acids, amino acids, carbohydrates, nucleic acids and the like. Alternatively, the protein may be a storage protein, such as a zein, or a structural protein, the decreased expression of which may lead to changes in seed amino acid composition or plant morphological changes respectively. The possibilities cited above are provided only by way of example and do not represent the full range of applications.

Expression of antisense-RNA or double-stranded RNA by one of the expression cassettes of the invention is especially preferred. Also expression of sense RNA can be employed for gene silencing (co-suppression). This RNA is preferably a non-translatable RNA. Gene regulation by double-stranded RNA ("double-stranded RNA interference"; dsRNAi) is well known in the art and described for various organism including plants (e.g., Matzke 2000; Fire A et al 1998; WO 99/32619; WO 99/53050; WO 00/68374; WO 00/44914; WO 00/44895; WO 00/49035; WO 00/63364).

Genes may also be constructed or isolated, which when transcribed produce RNA enzymes, or ribozymes, which can act as endoribonucleases and catalyze the cleavage of RNA molecules with selected sequences. The cleavage of selected messenger RNA's can result in the reduced production of their encoded polypeptide products. These genes may be used to prepare novel transgenic plants, which possess them. The transgenic plants may possess reduced levels of polypeptides including but not limited to the polypeptides cited above that may be affected by antisense RNA.

It is also possible that genes may be introduced to produce novel transgenic plants, which have reduced expression of a native gene product, by a mechanism of cosuppression. It has been demonstrated in tobacco, tomato, and petunia (Goring 1991; Smith 1990; Napoli 1990; van der Krol 1990) that expression of the sense transcript of a native gene will reduce or eliminate expression of the native gene in a manner similar to that observed for antisense genes. The introduced gene may encode all or part of the targeted native protein but its translation may not be required for reduction of levels of that native protein.

1.11.2 Non-RNA-Expressing

For example, DNA elements including those of transposable elements such as Ds, Ac, or Mu, may be, inserted into a gene and cause mutations. These DNA elements may be inserted in order to inactivate (or activate) a gene and thereby "tag" a particular trait. In this instance the transposable element does not cause instability of the tagged mutation, because the utility of the element does not depend on its ability to move in the genome. Once a desired trait is tagged, the introduced DNA sequence may be used to clone the corresponding gene, e.g., using the introduced DNA sequence as a PCR primer together with PCR gene cloning techniques (Shapiro, 1983; Dellaporta 1988). Once identified, the entire gene(s) for the particular trait, including control or regulatory regions where desired may be isolated, cloned and manipulated as desired. The utility of DNA elements introduced into an organism for purposed of gene tagging is independent of the DNA sequence and does not depend on any biological activity of the DNA sequence, i.e., transcription into RNA or translation into protein. The sole function of the DNA element is to disrupt the DNA sequence of a gene.

It is contemplated that unexpressed DNA sequences, including novel synthetic sequences could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Another possible element, which may be introduced, is a matrix attachment region element (MAR), such as the chicken lysozyme A element (Stief 1989), which can be positioned around an expressible gene of interest to effect an increase in overall expression of the gene and diminish position dependant effects upon incorporation into the plant genome (Stief 1989; Phi-Van 1990).

Further nucleotide sequences of interest that may be contemplated for use within the scope of the present invention in operable linkage with the promoter sequences according to the invention are isolated nucleic acid molecules, e.g., DNA or RNA, comprising a plant nucleotide sequence according to the invention comprising an open reading frame that is preferentially expressed in a specific tissue, i.e., seed-, root, green tissue (leaf and stem), panicle-, or pollen, or is expressed constitutively.

2. Marker Genes

In order to improve the ability to identify transformants, one may desire to employ a selectable or screenable marker gene as, or in addition to, the expressible gene of interest. "Marker genes" are genes that impart a distinct phenotype to cells expressing the marker gene and thus allow such transformed cells to be distinguished from cells that do not have the marker. Such genes may encode either a selectable or screenable marker, depending on whether the marker confers a trait which one can 'select' for by chemical means, i.e., through the use of a selective agent (e.g., a herbicide, antibiotic, or the like), or whether it is simply a trait that one can identify through observation or testing, i.e., by 'screening' (e.g., the R-locus trait, the green fluorescent protein (GFP)). Of course, many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers, which encode a secretable antigen that can be identified by antibody interaction, or even secretable enzymes, which can be detected by their catalytic activity. Secretable proteins fall into a number of classes, including small, diffusible proteins detectable, e.g., by ELISA; small active enzymes detectable in extracellular solution (e.g., alpha-amylase, beta-lactamase, phosphinothricin acetyltransferase); and proteins that are inserted or trapped in the cell wall (e.g., proteins that include a leader sequence such as that found in the expression unit of extensin or tobacco PR-S).

With regard to selectable secretable markers, the use of a gene that encodes a protein that becomes sequestered in the cell wall, and which protein includes a unique epitope is considered to be particularly advantageous. Such a secreted antigen marker would ideally employ an epitope sequence that would provide low background in plant tissue, a promoter-leader sequence that would impart efficient expression and targeting across the plasma membrane, and would produce protein that is bound in the cell wall and yet accessible to antibodies. A normally secreted wall protein modified to include a unique epitope would satisfy all such requirements.

One example of a protein suitable for modification in this manner is extensin, or hydroxyproline rich glycoprotein (HPRG). For example, the maize HPRG (Steifel 1990) molecule is well characterized in terms of molecular biology, expression and protein structure. However, any one of a variety of ultilane and/or glycine-rich wall proteins (Keller 1989) could be modified by the addition of an antigenic site to create a screenable marker.

One exemplary embodiment of a secretable screenable marker concerns the use of a maize sequence encoding the wall protein HPRG, modified to include a 15 residue epitope from the pro-region of murine interleukin, however, virtually any detectable epitope may be employed in such embodiments, as selected from the extremely wide variety of antigen-antibody combinations known to those of skill in the art. The unique extracellular epitope can then be straightforwardly detected using antibody labeling in conjunction with chromogenic or fluorescent adjuncts.

Elements of the present disclosure may be exemplified in detail through the use of the bar and/or GUS genes, and also through the use of various other markers. Of course, in light of this disclosure, numerous other possible selectable and/or screenable marker genes will be apparent to those of skill in the art in addition to the one set forth herein below. Therefore, it will be understood that the following discussion is exemplary rather than exhaustive. In light of the techniques disclosed herein and the general recombinant techniques which are known in the art, the present invention renders possible the introduction of any gene, including marker genes, into a recipient cell to generate a transformed plant.

2.1 Selectable Markers

Various selectable markers are known in the art suitable for plant transformation. Such markers may include but are not limited to:

2.1.1 Negative Selection Markers

Negative selection markers confer a resistance to a biocidal compound such as a metabolic inhibitor (e.g., 2-deoxyglucose-6-phosphate, WO 98/45456), antibiotics (e.g., kanamycin, G 418, bleomycin or hygromycin) or herbicides (e.g., phosphinothricin or glyphosate). Transformed plant material (e.g., cells, tissues or plantlets), which express marker genes, are capable of developing in the presence of concentrations of a corresponding selection compound (e.g., antibiotic or herbicide), which suppresses growth of an untransformed wild type tissue. Especially preferred negative selection markers are those, which confer resistance to herbicides. Examples, which may be mentioned, are:

Phosphinothricin acetyltransferases (PAT; also named Bialophos® resistance; bar; de Block 1987; Vasil 1992, 1993; Weeks 1993; Becker 1994; Nehra 1994; Wan & Lemaux 1994; EP 0 333 033; U.S. Pat. No. 4,975,374). Preferred are the bar gene from *Streptomyces hygroscopicus* or the pat gene from *Streptomyces viridochromogenes*. PAT inactivates the active ingredient in the herbicide bialaphos, phosphinothricin (PPT). PPT inhibits glutamine synthetase, (Murakami 1986; Twell 1989) causing rapid accumulation of ammonia and cell death.

altered 5-enolpyruvylshikimate-3-phosphate synthase (EPSPS) conferring resistance to Glyphosate® (N-(phosphonomethyl)glycine) (Hinchee 1988; Shah 1986; Della-Cioppa 1987). Where a mutant EPSP synthase gene is employed, additional benefit may be realized through the incorporation of a suitable chloroplast transit peptide, CTP (EP-A1 0 218 571).

Glyphosate® degrading enzymes (Glyphosate® oxidoreductase; gox),

Dalapon® inactivating dehalogenases (deh)

sulfonylurea- and/or imidazolinone-inactivating acetolactate synthases (ahas or ALS; for example mutated ahas/ALS variants with, for example, the S4, XI12, XA17, and/or Hra mutation (EP-A1 154 204)

Bromoxynil® degrading nitrilases (bxn; Stalker 1988)
Kanamycin- or geneticin (G418) resistance genes (NPTII; NPT or neo; Potrykus 1985) coding e.g., for neomycin phosphotransferases (Fraley 1983; Nehra 1994)
2-Desoxyglucose-6-phosphate phosphatase ($DOG^R1$-Gene product; WO 98/45456; EP 0 807 836) conferring resistance against 2-desoxyglucose (Randez-Gil 1995).
hygromycin phosphotransferase (HPT), which mediates resistance to hygromycin (Vanden Elzen 1985).
altered dihydrofolate reductase (Eichholtz 1987) conferring resistance against methotrexat (Thillet 1988);
mutated anthranilate synthase genes that confers resistance to 5-methyl tryptophan.

Additional negative selectable marker genes of bacterial origin that confer resistance to antibiotics include the aadA gene, which confers resistance to the antibiotic spectinomycin, gentamycin acetyl transferase, streptomycin phosphotransferase (SPT), aminoglycoside-3-adenyl transferase and the bleomycin resistance determinant (Hayford 1988; Jones 1987; Svab 1990; Hille 1986).

Especially preferred are negative selection markers that confer resistance against the toxic effects imposed by D-amino acids like e.g., D-alanine and D-serine (WO 03/060133; Erikson 2004). Especially preferred as negative selection marker in this contest are the daoI gene (EC: 1.4.3.3: GenBank Acc.-No.: U60066) from the yeast *Rhodotorula gracilis* (*Rhodosporidium toruloides*) and the *E. coli* gene dsdA (D-serine dehydratase (D-serine deaminase) [EC: 4.3.1.18; GenBank Acc.-No.: J01603).

Transformed plant material (e.g., cells, embryos, tissues or plantlets) which express such marker genes are capable of developing in the presence of concentrations of a corresponding selection compound (e.g., antibiotic or herbicide) which suppresses growth of an untransformed wild type tissue. The resulting plants can be bred and hybridized in the customary fashion. Two or more generations should be grown in order to ensure that the genomic integration is stable and hereditary. Corresponding methods are described (Jenes 1993; Potrykus 1991).

Furthermore, reporter genes can be employed to allow visual screening, which may or may not (depending on the type of reporter gene) require supplementation with a substrate as a selection compound.

Various time schemes can be employed for the various negative selection marker genes. In case of resistance genes (e.g., against herbicides or D-amino acids) selection is preferably applied throughout callus induction phase for about 4 weeks and beyond at least 4 weeks into regeneration. Such a selection scheme can be applied for all selection regimes. It is furthermore possible (although not explicitly preferred) to remain the selection also throughout the entire regeneration scheme including rooting.

For example, with the phosphinotricin resistance gene (bar) as the selective marker, phosphinotricin at a concentration of from about 1 to 50 mg/l may be included in the medium. For example, with the daoI gene as the selective marker, D-serine or D-alanine at a concentration of from about 3 to 100 mg/l may be included in the medium. Typical concentrations for selection are 20 to 40 mg/l. For example, with the mutated ahas genes as the selective marker, PURSUIT™ at a concentration of from about 3 to 100 mg/l may be included in the medium. Typical concentrations for selection are 20 to 40 mg/l.

2.1.2 Positive Selection Marker

Furthermore, positive selection marker can be employed. Genes like isopentenyltransferase from *Agrobacterium tumefaciens* (strain: PO22; Genbank Acc.-No.: AB025109) may—as a key enzyme of the cytokinin biosynthesis—facilitate regeneration of trans-formed plants (e.g., by selection on cytokinin-free medium). Corresponding selection methods are described (Ebinuma 2000a,b). Additional positive selection markers, which confer a growth advantage to a transformed plant in comparison with a non-transformed one, are described e.g., in EP-A 0 601 092. Growth stimulation selection markers may include (but shall not be limited to) β-Glucuronidase (in combination with e.g., a cytokinin glucuronide), mannose-6-phosphate isomerase (in combination with mannose), UDP-galactose-4-epimerase (in combination with e.g., galactose), wherein mannose-6-phosphate isomerase in combination with mannose is especially preferred.

2.1.3 Counter-Selection Marker

Counter-selection markers are especially suitable to select organisms with defined deleted sequences comprising said marker (Koprek 1999). Examples for counter-selection marker comprise thymidin kinases (TK), cytosine deaminases (Gleave 1999; Perera 1993; Stougaard 1993), cytochrom P450 proteins (Koprek 1999), haloalkan dehalogenases (Naested 1999), iaaH gene products (Sundaresan 1995), cytosine deaminase codA (Schlaman & Hooykaas 1997), tms2 gene products (Fedoroff & Smith 1993), or α-naphthalene acetamide (NAM; Depicker 1988). Counter selection markers may be useful in the construction of transposon tagging lines. For example, by marking an autonomous transposable element such as Ac, Master Mu, or En/Spn with a counter selection marker, one could select for transformants in which the autonomous element is not stably integrated into the genome. This would be desirable, for example, when transient expression of the autonomous element is desired to activate in trans the transposition of a defective transposable element, such as Ds, but stable integration of the autonomous element is not desired. The presence of the autonomous element may not be desired in order to stabilize the defective element, i.e., prevent it from further transposing. However, it is proposed that if stable integration of an autonomous transposable element is desired in a plant the presence of a negative selectable marker may make it possible to eliminate the autonomous element during the breeding process.

2.2. Screenable Markers

Screenable markers that may be employed include, but are not limited to, a beta-glucuronidase (GUS) or uidA gene which encodes an enzyme for which various chromogenic substrates are known; an R-locus gene, which encodes a product that regulates the production of anthocyanin pigments (red color) in plant tissues (Dellaporta 1988); a beta-lactamase gene (Sutcliffe 1978), which encodes an enzyme for which various chromogenic substrates are known (e.g., PADAC, a chromogenic cephalosporin); a xylE gene (Zukowsky 1983) which encodes a catechol dioxygenase that can convert chromogenic catechols; an α-amylase gene (Ikuta 1990); a tyrosinase gene (Katz 1983) which encodes an enzyme capable of oxidizing tyrosine to DOPA and dopaquinone which in turn condenses to form the easily detectable compound melanin; β-galactosidase gene, which encodes an enzyme for which there are chromogenic substrates; a luciferase (lux) gene (Ow 1986), which allows for bioluminescence detection; or even an aequorin gene (Prasher 1985), which may be employed in calcium-sensitive bioluminescence detection, or a green fluorescent protein gene (Niedz 1995).

Genes from the maize R gene complex are contemplated to be particularly useful as screenable markers. The R gene complex in maize encodes a protein that acts to regulate the production of anthocyanin pigments in most seed and plant tissue. A gene from the R gene complex was applied to maize transformation, because the expression of this gene in transformed cells does not harm the cells. Thus, an R gene introduced into such cells will cause the expression of a red pigment and, if stably incorporated, can be visually scored as a red sector. If a maize line is dominant for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 which contains the rg-Stadler allele and TR112, a K55 derivative which is r-g, b, P1. Alternatively any genotype of maize can be utilized if the C1 and R alleles are introduced together.

It is further proposed that R gene regulatory regions may be employed in chimeric constructs in order to provide mechanisms for controlling the expression of chimeric genes. More diversity of phenotypic expression is known at the R locus than at any other locus (Coe 1988). It is contemplated that regulatory regions obtained from regions 5' to the structural R gene would be valuable in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, the most preferred will generally be Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for populational screening for bioluminescence, such as on tissue culture plates, or even for whole plant screening. Where use of a screenable marker gene such as lux or GFP is desired, benefit may be realized by creating a gene fusion between the screenable marker gene and a selectable marker gene, for example, a GFP-NPTII gene fusion. This could allow, for example, selection of transformed cells followed by screening of transgenic plants or seeds.

3. Exemplary DNA Molecules

The invention provides an isolated nucleic acid molecule, e.g., DNA or RNA, comprising a plant nucleotide sequence comprising an open reading frame that is preferentially expressed in a specific plant tissue, i.e., in seeds, roots, green tissue (leaf and stem), panicles or pollen, or is expressed constitutively, or a promoter thereof.

These promoters include, but are not limited to, constitutive, inducible, temporally regulated, developmentally regulated, spatially-regulated, chemically regulated, stress-responsive, tissue-specific, viral and synthetic promoters. Promoter sequences are known to be strong or weak. A strong promoter provides for a high level of gene expression, whereas a weak promoter provides for a very low level of gene expression. An inducible promoter is a promoter that provides for the turning on and off of gene expression in response to an exogenously added agent, or to an environmental or developmental stimulus. A bacterial promoter such as the $P_{tac}$ promoter can be induced to varying levels of gene expression depending on the level of isothiopropylgalactoside added to the transformed bacterial cells. An isolated promoter sequence that is a strong promoter for heterologous nucleic acid is advantageous because it provides for a sufficient level of gene expression to allow for easy detection and selection of trans-formed cells and provides for a high level of gene expression when desired.

Within a plant promoter region there are several domains that are necessary for full function of the promoter. The first of these domains lies immediately upstream of the structural gene and forms the "core promoter region" containing consensus sequences, normally 70 base pairs immediately upstream of the gene. The core promoter region contains the characteristic CAAT and TATA boxes plus surrounding sequences, and represents a transcription initiation sequence that defines the transcription start point for the structural gene.

The presence of the core promoter region defines a sequence as being a promoter: if the region is absent, the promoter is non-functional. Furthermore, the core promoter region is insufficient to provide full promoter activity. A series of regulatory sequences upstream of the core constitute the remainder of the promoter. The regulatory sequences determine expression level, the spatial and temporal pattern of expression and, for an important subset of promoters, expression under inductive conditions (regulation by external factors such as light, temperature, chemicals, hormones).

Regulated expression of the chimeric transacting viral replication protein can be further regulated by other genetic strategies. For example, Cre-mediated gene activation as described by Odell et al. 1990. Thus, a DNA fragment containing 3' regulatory sequence bound by lox sites between the promoter and the replication protein coding sequence that blocks the expression of a chimeric replication gene from the promoter can be removed by Cre-mediated excision and result in the expression of the trans-acting replication gene. In this case, the chimeric Cre gene, the chimeric trans-acting replication gene, or both can be under the control of tissue- and developmental-specific or inducible promoters. An alternate genetic strategy is the use of tRNA suppressor gene. For example, the regulated expression of a tRNA suppressor gene can conditionally control expression of a trans-acting replication protein coding sequence containing an appropriate termination codon as described by Ulmasov et al. 1997. Again, either the chimeric tRNA suppressor gene, the chimeric transacting replication gene, or both can be under the control of tissue- and developmental-specific or inducible promoters.

Frequently it is desirable to have continuous or inducible expression of a DNA sequence throughout the cells of an organism in a tissue-independent manner. For example, increased resistance of a plant t6 infection by soil- and airborne-pathogens might be accomplished by genetic manipulation of the plant's genome to comprise a continuous promoter operably linked to a heterologous pathogen-resistance gene such that pathogen-resistance proteins are continuously expressed throughout the plant's tissues.

Alternatively, it might be desirable to inhibit expression of a native DNA sequence within the seeds of a plant to achieve a desired phenotype. In this case, such inhibition might be accomplished with transformation of the plant to comprise a promoter operably linked to an antisense nucleotide sequence, such that seed-preferential or seed-specific expression of the antisense sequence produces an RNA transcript that interferes with translation of the mRNA of the native DNA sequence.

To define a minimal promoter region, a DNA segment representing the promoter region is removed from the 5' region of the gene of interest and operably linked to the coding sequence of a marker (reporter) gene by recombinant DNA techniques well known to the art. The reporter gene is operably linked downstream of the promoter, so that transcripts initiating at the promoter proceed through the reporter gene. Reporter genes generally encode proteins, which are easily measured, including, but not limited to, chloramphenicol acetyl transferase (CAT), beta-glucuronidase (GUS), green fluorescent protein (GFP), beta-galactosidase (beta-GAL), and luciferase.

The construct containing the reporter gene under the control of the promoter is then introduced into an appropriate cell type by transfection techniques well known to the art. To assay for the reporter protein, cell lysates are prepared and appropriate assays, which are well known in the art, for the reporter protein are performed. For example, if CAT were the reporter gene of choice, the lysates from cells transfected with constructs containing CAT under the control of a promoter under study are mixed with isotopically labeled chloramphenicol and acetyl-coenzyme A (acetyl-CoA). The CAT enzyme transfers the acetyl group from acetyl-CoA to the 2- or 3-position of chloramphenicol. The reaction is monitored by thin-layer chromatography, which separates acetylated chloramphenicol from unreacted material. The reaction products are then visualized by autoradiography.

The level of enzyme activity corresponds to the amount of enzyme that was made, which in turn reveals the level of expression from the promoter of interest. This level of expression can be compared to other promoters to determine the relative strength of the promoter under study. In order to be sure that the level of expression is determined by the promoter, rather than by the stability of the mRNA, the level of the reporter mRNA can be measured directly, such as by Northern blot analysis.

Once activity is detected, mutational and/or deletional analyses may be employed to determine the minimal region and/or sequences required to initiate transcription. Thus, sequences can be deleted at the 5' end of the promoter region and/or at the 3' end of the promoter region, and nucleotide substitutions introduced. These constructs are then introduced to cells and their activity determined.

In one embodiment, the promoter may be a gamma zein promoter, an oleosin ole16 promoter, a globulins promoter, an actin I promoter, an actin cl promoter, a sucrose synthetase promoter, an INOPS promoter, an EXM5 promoter, a globulin2 promoter, a b-32, ADPG-pyrophosphorylase promoter, an Ltp1 promoter, an Ltp2 promoter, an oleosin ole17 promoter, an oleosin ole18 promoter, an actin 2 promoter, a pollen-specific protein promoter, a pollen-specific pectate lyase promoter, an anther-specific protein promoter, an anther-specific gene RTS2 promoter, a pollen-specific gene promoter, a tapetum-specific gene promoter, tapeturn-specific gene RAB24 promoter, a anthranilate synthase alpha subunit promoter, an alpha zein promoter, an anthranilate synthase beta subunit promoter, a dihydrodipicolinate synthase promoter, a Thi1 promoter, an alcohol dehydrogenase promoter, a cab binding protein promoter, an H3C4 promoter, a RUBISCO SS starch branching enzyme promoter, an ACCase promoter, an actin3 promoter, an actin7 promoter, a regulatory protein GF14-12 promoter, a ribosomal protein L9 promoter, a cellulose biosynthetic enzyme promoter, an S-adenosyl-L-homocysteine hydrolase promoter, a superoxide dismutase promoter, a C-kinase receptor promoter, a phosphoglycerate mutase promoter, a root-specific RCc3 mRNA promoter, a glucose-6 phosphate isomerase promoter, a pyrophosphate-fructose 6-phosphatelphosphotransferase promoter, an ubiquitin promoter, a beta-ketoacyl-ACP synthase promoter, a 33 kDa photosystem 11 promoter, an oxygen evolving protein promoter, a 69 kDa vacuolar ATPase subunit promoter, a metallothionein-like protein promoter, a glyceraldehyde-3-phosphate dehydrogenase promoter, an ABA- and ripening-inducible-like protein promoter, a phenylalanine ammonia lyase promoter, an adenosine triphosphatase S-adenosyl-L-homocysteine hydrolase promoter, an a-tubulin promoter, a cab promoter, a PEPCase promoter, an R gene promoter, a lectin promoter, a light harvesting complex promoter, a heat shock protein promoter, a chalcone synthase promoter, a zein promoter, a globulin-1 promoter, an ABA promoter, an auxin-binding protein promoter, a UDP glucose flavonoid glycosyl-transferase gene promoter, an NTI promoter, an actin promoter, an opaque 2 promoter, a b70 promoter, an oleosin promoter, a CaMV 35S promoter, a CaMV 34S promoter, a CaMV 19S promoter, a histone promoter, a turgor-inducible promoter, a pea small subunit RuBP carboxylase promoter, a Ti plasmid mannopine synthase promoter, Ti plasmid nopaline synthase promoter, a petunia chalcone isomerase promoter, a bean glycine rich protein I promoter, a CaMV 35S transcript promoter, a potato patatin promoter, or a S-E9 small subunit RuBP carboxylase promoter.

4. Transformed (Transgenic) Plants of the Invention and Methods of Preparation

Plant species may be transformed with the DNA construct of the present invention by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis," as used herein, means a process by which shoots and roots are developed sequentially from meristematic centers; the term "embryogenesis," as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and ultilane meristem).

Plants of the present invention may take a variety of forms. The plants may be chimeras of transformed cells and non-transformed cells; the plants may be clonal transformants (e.g., all cells transformed to contain the expression cassette); the plants may comprise grafts of transformed and untransformed tissues (e.g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) plant cell, in planta or ex planta, including a transformed plastid or other organelle, e.g., nucleus, mitochondria or chloroplast. The present invention may be used for transformation of any plant species, including, but not limited to, cells from the plant species specified above in the DEFINITION section. Preferably, transgenic plants of the present invention are crop plants and in particular cereals (for example, corn, alfalfa, sunflower, rice, Brassica, canola, soybean, barley, soybean, sugarbeet, cotton, safflower, peanut, sorghum, wheat, millet, tobacco, Linum usitatissimum (linseed and fax), Camelina sativa, Brassica juncea, etc.), and even more preferably corn, rice and soybean. Other embodiments of the invention are related to cells, cell cultures, tissues, parts (such as plants organs, leaves, roots, etc.) and propagation material (such as seeds) of such plants.

The transgenic expression cassette of the invention may not only be comprised in plants or plant cells but may advantageously also be containing in other organisms such for example bacteria. Thus, another embodiment of the invention relates to trans-genic cells or non-human, transgenic organisms comprising an expression cassette of the invention. Preferred are prokaryotic and eukaryotic organisms. Both microorganism and higher organisms are comprised. Preferred microorganisms are bacteria, yeast, algae, and fungi. Preferred bacteria are those of the genus Escherichia, Erwinia, Agrobacterium, Flavobacterium, Alcaligenes, Pseudomonas, Bacillus or Cyanobacterim such as—for example—Synechocystis and other bacteria described in Brock Biology of Microorganisms Eighth Edition (pages A-8, A-9, A10 and A11). Most preferably the transgenic cells or non-human, transgenic organisms comprising an expression cassette of the invention is a plant cell or plant (as defined above), more preferably a plant used for oil production such as—for example—Brassica napus, Brassica juncea, Linum usitatissimum, soybean, Camelina or sunflower.

Especially preferred are microorganisms capable to infect plants and to transfer DNA into their genome, especially bacteria of the genus Agrobacterium, preferably Agrobacterium tumefaciens and rhizogenes. Preferred yeasts are Candida, Saccharomyces, Hansenula and Pichia. Preferred fungi are Aspergillus, Trichoderma, Ashbya, Neurospora, Fusarium, and Beauveria. Most preferred are plant organisms as defined above.

Transformation of plants can be undertaken with a single DNA molecule or multiple DNA molecules (i.e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

A variety of techniques are available and known to those skilled in the art for introduction of constructs into a plant cell host. These techniques generally include transformation with DNA employing A. tumefaciens or A. rhizogenes as the transforming agent, liposomes, PEG precipitation, electroporation, DNA injection, direct DNA uptake, microprojectile bombardment, particle acceleration, and the like (See, for example, EP 295959 and EP 138341) (see below). However, cells other than plant cells may be transformed with the expression cassettes of the invention. The general descriptions of plant expression vectors and reporter genes, and Agrobacterium and Agrobacterium-mediated gene transfer, can be found in Gruber et al. (1993).

Expression vectors containing genomic or synthetic fragments can be introduced into protoplasts or into intact tissues or isolated cells. Preferably expression vectors are introduced into intact tissue. General methods of culturing plant tissues are provided for example by Maki et al., (1993); and by Phillips et al. (1988). Preferably, expression vectors are introduced into maize or other plant tissues using a direct gene transfer method such as microprojectile-mediated delivery, DNA injection, electroporation and the like. More preferably expression vectors are introduced into plant tissues using the microprojectile media delivery with the biolistic device. See, for example, Tomes et al. (1995). The vectors of the invention can not only be used for expression of structural genes but may also be used in exon-trap cloning, or promoter trap procedures to detect differential gene expression in varieties of tissues (Lindsey 1993; Auch & Reth 1990).

It is particularly preferred to use the binary type vectors of Ti and Ri plasmids of Agrobacterium spp. Ti-derived vectors transform a wide variety of higher plants, including monocotyledonous and dicotyledonous plants, such as soybean, cotton, rape, tobacco, and rice (Pacciotti 1985: Byrne 1987; Sukhapinda 1987; Lorz 1985; Potrykus, 1985; Park 1985: Hiei 1994). The use of T-DNA to transform plant cells has received extensive study and is amply described (EP 120516; Hoekema, 1985; Knauf, 1983; and An 1985). For introduction into plants, the chimeric genes of the invention can be inserted into binary vectors as described in the examples.

Other transformation methods are available to those skilled in the art, such as direct uptake of foreign DNA constructs (see EP 295959), techniques of electroporation (Fromm 1986) or high velocity ballistic bombardment with metal particles coated with the nucleic acid constructs (Kline 1987, and U.S. Pat. No. 4,945,050). Once transformed, the cells can be regenerated by those skilled in the art. Of particular relevance are the recently described methods to transform foreign genes into commercially important crops, such as rapeseed (De Block 1989), sunflower (Everett 1987), soybean (McCabe 1988; Hinchee 1988; Chee 1989; Christou 1989; EP 301749), rice (Hiei 1994), and corn (Gordon-Kamm 1990; Fromm 1990).

Those skilled in the art will appreciate that the choice of method might depend on the type of plant, i.e., monocotyledonous or dicotyledonous, targeted for transformation. Suitable methods of transforming plant cells include, but are not limited to, microinjection (Crossway 1986), electroporation (Riggs 1986), Agrobacterium-mediated transformation (Hinchee 1988), direct gene transfer (Paszkowski 1984), and ballistic particle acceleration using devices available from Agracetus, Inc., Madison, Wis. And BioRad, Hercules, Calif. (see, for example, U.S. Pat. No. 4,945,050; and McCabe 1988). Also see, Weissinger 1988; Sanford 1987 (onion); Christou 1988 (soybean); McCabe 1988 (soybean); Datta 1990 (rice); Klein 1988 (maize); Klein 1988 (maize); Klein 1988 (maize); Fromm 1990 (maize); and Gordon-Kamm 1990 (maize); Svab 1990 (tobacco chloroplast); Koziel 1993 (maize); Shimamoto 1989 (rice); Christou 1991 (rice); European Patent Application EP 0 332 581 (orchardgrass and other Pooideae); Vasil 1993 (wheat); Weeks 1993 (wheat).

In another embodiment, a nucleotide sequence of the present invention is directly transformed into the plastid genome. Plastid transformation technology is extensively described in U.S. Pat. Nos. 5,451,513, 5,545,817, and 5,545,818, in PCT application no. WO 95/16783, and in McBride et al., 1994. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate orthologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (Svab 1990; Staub 1992). This resulted in stable homoplasmic transformants at a frequency of approximately one per 100 bombardments of target leaves. The presence of cloning sites between these markers allowed creation of a plastid-targeting vector for introduction of foreign genes (Staub 1993). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3N-adenyltransferase (Svab 1993). Other selectable markers useful for plastid transformation are known in the art and encompassed within the scope of the invention. Typically, approximately 15-20 cell division cycles following transformation are required to reach a homoplastidic state. Plastid expression, in which genes are inserted by orthologous recombination into all of the several thousand copies of the circular plastid genome present in each plant cell, takes advantage of the enormous copy number advantage over nuclear-expressed genes to permit expression levels that can readily exceed 10% of the total soluble plant protein. In a preferred embodiment, a nucleotide sequence of the present invention is inserted into a plastid-targeting vector and transformed into the plastid genome of a desired plant host. Plants homoplastic for plastid genomes containing a nucleotide sequence of the present invention are obtained, and are preferentially capable of high expression of the nucleotide sequence.

Agrobacterium tumefaciens cells containing a vector comprising an expression cassette of the present invention, wherein the vector comprises a Ti plasmid, are useful in methods of making transformed plants. Plant cells are infected with an Agrobacterium tumefaciens as described above to produce a transformed plant cell, and then a plant is regenerated from the transformed plant cell. Numerous Agrobacterium vector systems useful in carrying out the present invention are known.

Various Agrobacterium strains can be employed, preferably disarmed Agrobacterium tumefaciens or rhizogenes strains. In a preferred embodiment, Agrobacterium strains for use in the practice of the invention include octopine strains, e.g., LBA4404 or agropine strains, e.g., EHA101 or EHA105. Suitable strains of A. tumefaciens for DNA transfer are for example EHA101[pEHA101] (Hood 1986), EHA105 [pEHA105] (Li 1992), LBA4404[pAL4404] (Hoekema 1983), C58C1[pMP90] (Koncz & Schell 1986), and C58C1 [pGV2260] (Deblaere 1985). Other suitable strains are Agrobacterium tumefaciens C58, a nopaline strain. Other suitable strains are A. tumefaciens C58C1 (Van Larebeke 1974), A136 (Watson 1975) or LBA4011 (Klapwijk 1980). In another preferred embodiment the soil-borne bacterium is a disarmed variant of Agrobacterium rhizogenes strain K599 (NCPPB 2659). Preferably, these strains are comprising a disarmed plasmid variant of a Ti- or Ri-plasmid providing the functions required for T-DNA transfer into plant cells (e.g., the vir genes). In a preferred embodiment, the Agrobacterium strain used to transform the plant tissue pre-cultured with the plant phenolic compound contains a L,L-succinamopine type Ti-plasmid, preferably disarmed, such as pEHA101. In another preferred embodiment, the Agrobacterium strain used to trans-form the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated (Jarschow 1991).

The method of the invention can also be used in combination with particular Agrobacterium strains, to further increase the transformation efficiency, such as Agrobacterium strains wherein the vir gene expression and/or induction thereof is altered due to the presence of mutant or chimeric virA or virG genes (e.g. Hansen 1994; Chen and Winans 1991; Scheeren-Groot, 1994). Preferred are further combinations of Agrobacterium tumefaciens strain LBA4404 (Hiei 1994) with super-virulent plasmids. These are preferably pTOK246-based vectors (Ishida 1996). A binary vector or any other vector can be modified by common DNA recombination techniques, multiplied in E. coli, and introduced into Agrobacterium by e.g., electroporation or other transformation techniques (Mozo & Hooykaas 1991).

Agrobacterium is grown and used in a manner similar to that described in Ishida (1996). The vector comprising Agrobacterium strain may, for example, be grown for 3 days on YP medium (5 g/l yeast extract, 10 g/l peptone, 5 g/l NaCl, 15 g/l agar, pH 6.8) supplemented with the appropriate antibiotic (e.g., 50 mg/l spectinomycin). Bacteria are collected with a loop from the solid medium and resuspended. In a preferred embodiment of the invention, Agrobacterium cultures are started by use of aliquots frozen at −80° C.

The transformation of the target tissue (e.g., an immature embryo) by the Agrobacterium may be carried out by merely contacting the target tissue with the Agrobacterium. The concentration of Agrobacterium used for infection and co-cultivation may need to be varied. For example, a cell suspension of the Agrobacterium having a population density of approximately from $10^5$-$10^{11}$, preferably $10^6$ to $10^{10}$, more preferably about $10^8$ cells or cfu/ml is prepared and the target tissue is immersed in this suspension for about 3 to 10 minutes. The resulting target tissue is then cultured on a solid medium for several days together with the Agrobacterium.

Preferably, the bacterium is employed in concentration of $10^6$ to $10^{10}$ cfu/ml. In a preferred embodiment for the co-cultivation step about 1 to 10 µl of a suspension of the soil-borne bacterium (e.g., Agrobacteria) in the co-cultivation medium are directly applied to each target tissue explant and air-dried. This is saving labor and time and is reducing unintended Agrobacterium-mediated damage by excess Agrobacterium usage.

For Agrobacterium treatment, the bacteria are resuspended in a plant compatible co-cultivation medium. Supplementation of the co-culture medium with antioxidants (e.g., silver nitrate), phenol-absorbing compounds (like polyvinylpyrrolidone, Perl 1996) or thiol compounds (e.g., dithiothreitol, L-cysteine, Olhoft 2001) which can decrease tissue necrosis due to plant defense responses (like phenolic oxidation) may further improve the efficiency of Agrobacterium-mediated transformation. In another preferred embodiment, the co-cultivation medium of comprises least one thiol compound, preferably selected from the group consisting of sodium thiolsulfate, dithiotrietol (DTT) and cysteine. Preferably the concentration is between about 1 mM and 10 mM of L-Cysteine, 0.1 mM to 5 mM DTT, and/or 0.1 mM to 5 mM sodium thiolsulfate. Preferably, the medium employed during co-cultivation comprises from about 1 µM to about 10 µM of silver nitrate and from about 50 mg/L to about 1,000 mg/L of L-Cystein. This results in a highly reduced vulnerability of the target tissue against Agrobacterium-mediated damage (such as induced necrosis) and highly improves overall transformation efficiency.

Various vector systems can be used in combination with Agrobacteria. Preferred are binary vector systems. Common binary vectors are based on "broad host range"-plasmids like pRK252 (Bevan 1984) or pTJS75 (Watson 1985) derived from the P-type plasmid RK2. Most of these vectors are derivatives of pBIN19 (Bevan 1984). Various binary vectors are known, some of which are commercially available such as, for example, pBI101.2 or pBIN19 (Clontech Laboratories, Inc. USA). Additional vectors were improved with regard to size and handling (e.g. pPZP; Hajdukiewicz 1994). Improved vector systems are described also in WO 02/00900.

Methods using either a form of direct gene transfer or Agrobacterium-mediated transfer usually, but not necessarily, are undertaken with a selectable marker, which may provide resistance to an antibiotic (e.g., kanamycin, hygromycin or methotrexate) or a herbicide (e.g., phosphinothricin). The choice of selectable marker for plant transformation is not, however, critical to the invention.

For certain plant species, different antibiotic or herbicide selection markers may be preferred. Selection markers used routinely in transformation include the nptII gene which confers resistance to kanamycin and related antibiotics (Messing & Vierra, 1982; Bevan 1983), the bar gene which confers resistance to the herbicide phosphinothricin (White 1990, Spencer 1990), the hph gene which confers resistance to the antibiotic hygromycin (Blochlinger & Diggelmann), and the dhfr gene, which confers resistance to methotrexate (Bourouis 1983).

5. Production and Characterization of Stably Transformed Plants

Transgenic plant cells are then placed in an appropriate selective medium for selection of transgenic cells, which are then grown to callus. Shoots are grown from callus. Plantlets are generated from the shoot by growing in rooting medium. The various constructs normally will be joined to a marker for selection in plant cells. Conveniently, the marker may be resistance to a biocide (particularly an antibiotic, such as kanamycin, G418, bleomycin, hygromycin, chloramphenicol, herbicide, or the like). The particular marker used will allow for selection of transformed cells as compared to cells lacking the DNA, which has been introduced. Components of DNA constructs including transcription cassettes of this invention may be prepared from sequences, which are native (endogenous) or foreign (exogenous) to the host. By "foreign" it is meant that the sequence is not found in the wild-type host into which the construct is introduced. Heterologous constructs will contain at least one region, which is not native to the gene from which the transcription-initiation-region is derived.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR or TaqMan; "biochemical" assays, such as detecting the presence of a protein product, e.g., by immunological means (ELISAs and Western blots) or by enzymatic function; plant part assays, such as seed assays; and also, by analyzing the phenotype of the whole regenerated plant, e.g., for disease or pest resistance.

DNA may be isolated from cell lines or any plant parts to determine the presence of the preselected nucleic acid segment through the use of techniques well known to those skilled in the art. Note that intact sequences will not always be present, presumably due to rearrangement or deletion of sequences in the cell.

The presence of nucleic acid elements introduced through the methods of this invention may be determined by polymerase chain reaction (PCR). Using these technique discreet fragments of nucleic acid are amplified and detected by gel electrophoresis. This type of analysis permits one to determine whether a preselected nucleic acid segment is present in a stable transformant, but does not prove integration of the introduced preselected nucleic acid segment into the host cell genome. In addition, it is not possible using PCR techniques to determine whether transformants have exogenous genes introduced into different sites in the, genome, i.e., whether transformants are of independent origin. It is contemplated that using PCR techniques it would be possible to clone fragments of the host genomic DNA adjacent to an introduced preselected DNA segment.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced preselected DNA segments in high molecular weight DNA, i.e., confirm that the introduced preselected, DNA segment has been integrated into the host cell genome. The technique of Southern hybridization provides information that is obtained using PCR, e.g., the presence of a preselected DNA segment, but also demonstrates integration into the genome and characterizes each individual transformant.

It is contemplated that using the techniques of dot or slot blot hybridization which are modifications of Southern hybridization techniques one could obtain the same information that is derived from PCR, e.g., the presence of a preselected DNA segment. Both PCR and Southern hybridization techniques can be used to demonstrate transmission of a preselected DNA segment to progeny. In most instances the characteristic Southern hybridization pattern for a given transformant will segregate in progeny as one or more Mendelian genes (Spencer 1992); Laursen 1994) indicating stable inheritance of the gene. The non-chimeric nature of the callus and the parental transformants ($R_O$) was suggested by germine transmission and the identical Southern blot hybridization patterns and intensities of the transforming DNA in callus, $R_0$ plants and $R_1$ progeny that segregated for the transformed gene.

Whereas DNA analysis techniques may be conducted using DNA isolated from any part of a plant, RNA may only be expressed in particular cells or tissue types and hence it will be necessary to prepare RNA for analysis from these tissues. PCR techniques may also be used for detection and quantitation of RNA produced from introduced preselected DNA segments. In this application of PCR it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and will only demonstrate the presence or absence of an RNA species.

While Southern blotting and PCR may be used to detect the preselected DNA segment in question, they do not provide information as to whether the preselected DNA segment is being expressed. Expression may be evaluated by specifically identifying the protein products of the introduced preselected DNA segments or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures may also be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed.

Very frequently the expression of a gene product is determined by evaluating the phenotypic results of its expression. These assays also may take many forms including but not limited to analyzing changes in the chemical composition, morphology, or physiological properties of the plant. Morphological changes may include greater stature or thicker stalks. Most often changes in response of plants or plant parts to imposed treatments are evaluated under carefully controlled conditions termed bioassays.

6. Uses of Transgenic Plants

Once an expression cassette of the invention has been transformed into a particular plant species, it may be propagated in that species or moved into other varieties of the same species, particularly including commercial varieties, using traditional breeding techniques. Particularly preferred plants of the invention include the agronomically important crops listed above. The genetic properties engineered into the transgenic seeds and plants described above are passed on by sexual reproduction and can thus be maintained and propagated in progeny plants. The present invention also relates to a transgenic plant cell, tissue, organ, seed or plant part obtained from the transgenic plant. Also included within the invention are transgenic descendants of the plant as well as transgenic plant cells, tissues, organs, seeds and plant parts obtained from the descendants.

Preferably, the expression cassette in the transgenic plant is sexually transmitted. In one preferred embodiment, the coding sequence is sexually transmitted through a complete normal sexual cycle of the R0 plant to the R1 generation. Additionally preferred, the expression cassette is expressed in the cells, tissues, seeds or plant of a transgenic plant in an amount that is different than the amount in the cells, tissues, seeds or plant of a plant, which only differs in that the expression cassette is absent. The transgenic plants produced herein are thus expected to be useful for a variety of commercial and research purposes. Transgenic plants can be created for use in traditional agriculture to possess traits beneficial to the grower (e.g., agronomic traits such as resistance to water deficit, pest resistance, herbicide resistance or increased yield), beneficial to the consumer of the grain harvested from the plant (e.g., improved nutritive content in human food or animal feed; increased vitamin, amino acid, and antioxidant content; the production of antibodies (passive immunization) and nutraceuticals), or beneficial to the food processor (e.g., improved processing traits). In such uses, the plants are generally grown for the use of their grain in human or animal foods. Additionally, the use of root-specific promoters in transgenic plants can provide beneficial traits that are localized in the consumable (by animals and humans) roots of plants such as carrots, parsnips, and beets. However, other parts of the plants, including stalks, husks, vegetative parts, and the like, may also have utility, including use as part of animal silage or for ornamental purposes. Often, chemical constituents (e.g., oils or starches) of maize and other crops are extracted for foods or industrial use and trans-genic plants may be created which have enhanced or modified levels of such components.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules. The transgenic plants may also be used in commercial breeding programs, or may be crossed or bred to plants of related crop species. Improvements encoded by the expression cassette may be transferred, e.g., from maize cells to cells of other species, e.g., by protoplast fusion. The transgenic plants may have many uses in research or breeding, including creation of new mutant plants through insertional mutagenesis, in order to identify beneficial mutants that might later be created by traditional mutation and selection. An example would be the introduction of a recombinant DNA sequence encoding a transposable element that may be used for generating genetic variation. The methods of the invention may also be used to create plants having unique "signature sequences" or other marker sequences which can be used to identify proprietary lines or varieties.

Thus, the transgenic plants and seeds according to the invention can be used in plant breeding, which aims at the development of plants with improved properties conferred by the expression cassette, such as tolerance of drought, disease, or other stresses. The various breeding steps are characterized by well-defined human intervention such as selecting the lines to be crossed, directing pollination of the parental lines, or selecting appropriate descendant plants. Depending on the desired properties different breeding measures are taken. The relevant techniques are well known in the art and include but are not limited to hybridization, inbreeding, backcross breeding, multilane breeding, variety blend, interspecific hybridization, aneuploid techniques, etc. Hybridization techniques also include the sterilization of plants to yield male or female sterile plants by mechanical, chemical or biochemical means. Cross-pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines, which for example increase the effectiveness of conventional methods such as herbicide or pesticide treatment or allow dispensing with said methods due to their modified genetic properties. Alternatively new crops with improved stress tolerance can be obtained which, due to their optimized genetic "equipment", yield harvested product of better quality than products, which were not able to tolerate comparable adverse developmental conditions.

EXAMPLES

Materials and General Methods

Unless indicated otherwise, chemicals and reagents in the Examples were obtained from Sigma Chemical Company (St. Louis, Mo.), restriction endonucleases were from New England Biolabs (Beverly, Mass.) or Roche (Indianapolis, Ind.), oligonucleotides were synthesized by MWG Biotech Inc. (High Point, N.C.), and other modifying enzymes or kits regarding biochemicals and molecular biological assays were from Clontech (Palo Alto, Calif.), Pharmacia Biotech (Piscataway, N.J.), Promega Corporation (Madison, Wis.), or Stratagene (La Jolla, Calif.). Materials for cell culture media were obtained from Gibco/BRL (Gaithersburg, Md.) or DIFCO (Detroit, Mich.). The cloning steps carried out for the purposes of the present invention, such as, for example, restriction cleavages, agarose gel electrophoresis, purification of DNA fragments, transfer of nucleic acids to nitrocellulose and nylon membranes, linking DNA fragments, transformation of E. coli cells, growing bacteria, multiplying phages and sequence analysis of recombinant DNA, are carried out as described by Sambrook (1989). The sequencing of recombinant DNA molecules is carried out using ABI laser fluorescence DNA sequencer following the method of Sanger (Sanger 1977).

Example 1

Generation of Transgenic Plants 1.1 Generation of Transgenic *Arabidopsis thaliana* Plants For generating transgenic *Arabidopsis* plants *Agrobacterium tumefaciens* (strain C58C1-[pMP90]) is transformed with the various promoter::GUS vector constructs (see below). Resulting *Agrobacterium* strains are subsequently employed to obtain trans-genic plants. For this purpose a isolated transformed *Agrobacterium* colony is incubated in 4 ml culture (Medium: YEB medium with 50 µg/ml Kanamycin and 25 µg/ml Rifampicin) over night at 28° C. With this culture a 400 ml culture of the same medium is inoculated and incubated over night (28° C., 220 rpm). The bacteria a precipitated by centrifugation (GSA-Rotor, 8.000 U/min, 20 min) and the pellet is resuspended in infiltration medium (½ MS-Medium; 0.5 g/l MES, pH 5.8; 50 g/l sucrose). The suspension is placed in a plant box (Duchefa) and 100 ml SILVET L-77 (Osi Special-ties Inc., Cat. P030196) are added to a final concentration of 0.02%. The plant box with 8 to 12 Plants is placed into an exsiccator for 10 to 15 min. under vacuum with subsequent, spontaneous ventilation (expansion). This process is repeated 2-3 times. Thereafter all plants are transferred into pods with wet-soil and grown under long daytime conditions (16 h light; day temperature 22-24° C., night temperature 19° C.; 65% rel. humidity). Seeds are harvested after 6 weeks.

1.2 Generation of Transgenic Linseed

Transgenic linseed plants can be generated for example by the method of Bell et al., 1999, In Vitro Cell. Dev. Biol.-Plant. 35(6): 456-465 by means of particle bombardment. Agrobacteria-mediated transformations can be generated for example by the method of Mlynarova et al. (1994), Plant Cell Report 13: 282-285.

1.3 *Agrobacterium*-Mediated Transformation of *Brassica napus*

Oilseed rape can be transformed by cotyledonary petiole or hypocotyl transformation (Moloney 1989; De Block 1989). The use of antibiotics for the selection of Agrobacteria and plants depends on the binary vector and the *Agrobacterium* strain used for the transformation. The selection of oilseed rape is generally carried out using kanamycin as selectable plant marker.

More specifically oilseed rape can be transformed as follows: *Agrobacterium* strains transformed with the plasmid of interest s grown in 50 mL YEB medium at 28° C. overnight. The *Agrobacterium* solution is mixed with liquid co-cultivation medium (double concentrated MSB5 salts (Duchefa), 30 g/L sucrose (Duchefa), 3.75 mg/LI BAP (6-benzylamino purine, Duchefa), 0.5 g/L MES (Duchefa), 0.5 mg/L GA3 (Gibberellic Acid, Duchefa); pH5.2) until $OD_{650}$ of 0.5 is reached. Petiols of 4 days old seedlings of *Brassica napus* cv. Westar grown on growth medium B (MSB5 salts (Duchefa), 3% sucrose (Duchefa), 0.8% oxoidagar (Oxoid GmbH); pH 5.8) are cut. Petiols are dipped for 2-3 seconds in the *Agrobacterium* solution and afterwards put into solid medium for co-cultivation (co-cultivation medium supplemented with 1.6% Oxoidagar). The co-cultivation lasts 3 days (at 24° C. and about 50 µMol/m²s light intensity). Afterwards petiols are transferred to co-cultivation medium supplemented with the appropriate selection agent (18 mg/L kanamycin (Duchefa) for plants comprising the nptII marker kanamycin for plants carrying the nptII resistance marker, or 0.3 to 30 mM D-amino acids; as described below) for plants comprising an expression cassette for the dao1 gene from *Rhodotorula gracilis*) and 300 mg/L Timentin (Duchefa)

Transformed petioles are incubated on the selection medium for four weeks at 24° C. This step is repeated until shoots appear. Shoots are transferred to A6 medium (MS salts (Sigma Aldrich), 20 g/L sucrose, 100 mg/L myo-inositol (Duchefa), 40 mg/L adeninesulfate (Sigma Aldrich), 500 mg/L MES, 0.0025 mg/L BAP (Sigma), 5 g/L oxoidagar (Oxoid GmbH), 150 mg/L timetin (Duchefa), 0.1 mg/L IBA (indol butyric acid, Duchefa); pH 5.8) supplemented with the appropriate selection agent (18 mg/L kanamycin (Duchefa) for plants comprising the nptII marker kanamycin for plants carrying the nptII resistance marker, or 0.3 to 30 mM D-amino acids; as described below) until they elongated. Elongated shoots are cultivated in A7 medium (A6 medium without BAP) for rooting. Rooted plants are transferred to soil and grown in the greenhouse.

Example 2

Growth Conditions for Plants for Tissue-Specific Expression Analysis

To obtain 4 and 7 days old seedlings, about 400 seeds (*Arabidopsis thaliana* ecotype Columbia) are sterilized with a 80% (v/v) ethanol:water solution for 2 minutes, treated with a sodium hypochlorite solution (0.5% v/v) for 5 minutes, washed three times with distillated water and incubated at 4° C. for 4 days to ensure a standardized germination. Subsequently, seeds are incubated on Petri dishes with MS medium (Sigma M5519) supplemented with 1% sucrose, 0.5 g/l MES (Sigma M8652), 0.8% Difco-BactoAgar (Difco 0140-01), adjusted to pH 5.7. The seedlings are grown under 16 h light/8 h dark cyklus (Philips 58W/33 white light) at 22° C. and harvested after 4 or 7 days, respectively.

To obtain root tissue, 100 seeds are sterilized as described above, incubated at 4° C. for 4 days, and transferred into 250 ml flasks with MS medium (Sigma M5519) supplemented with additional 3% sucrose and 0.5 g/l MES (Sigma M8652), adjusted to pH 5.7 for further growing. The seedlings are grown at a 16 h light/8 h dark cycle (Philips 58W/33 white light) at 22° C. and 120 rpm and harvested after 3 weeks. For all other plant organs employed, seeds are sown on standard soil (Type VM, Manna-Italia, Via S. Giacomo 42, 39050 San Giacomo/Laives, Bolzano, Italien), incubated for 4 days at 4° C. to ensure uniform germination, and subsequently grown under a 16 h light/8 darkness regime (OSRAM Lumi-lux Daylight 36W/12) at 22° C. Young rosette leaves are harvested at the 8-leaf stage (after about 3 weeks), mature rosette leaves are harvested after 8 weeks briefly before stem formation. Apices of out-shooting stems are harvested briefly after out-shooting. Stem, stem leaves, and flower buds are harvested in development stage 12 (Bowmann J (ed.), *Arabidopsis*, Atlas of Morphology, Springer New York, 1995) prior to stamen development. Open flowers are harvested in development stage 14 immediately after stamen development. Wilting flowers are harvested in stage 15 to 16. Green and yellow shoots used for the analysis have a length of 10 to 13 mm.

The regenerated transgenic linseed and rape seed plants are tested in tissue culture for early leakiness. For the detailed analyses 3 individual plants per single or multi insertion line (5-15 lines in total per construct) are analyzed in the T1 to T3 generation regarding the potential expression of the promoter candidates in all non-seed tissues as well as in different phases of seed development:

Mature seeds 3 d old seedlings: root base, root tip, main root, side root, other root areas, cotyledon, hypocotyl 10 d old seedlings: root base, root tip, main root, side root, other root areas, cotyledon, hypocotyl, primary leaves, following leaves 17 d old seedlings: root base, root tip, main root, side root, other root areas, cotyledon, hypocotyl, primary leaves, following leaves Adult plant: root, young leaves, mature leaves, stem Flower 0, 1 daf, 3 daf capsula/siliques/fruit, 3 daf seed/embryo, 6 daf capsula/siliques/fruit, 6 daf seed/embryo, 9 daf capsula/siliques/fruit, 9 daf seed/embryo, 12 daf capsula/siliques/fruit, 12 daf seed/embryo, 15 daf capsula/siliques/fruit, 15 daf seed/embryo, 18 daf capsula/siliques/fruit, 18 daf seed/embryo, 21 daf capsula/siliques/fruit, 21 daf seed/embryo, 24 daf capsula/siliques/fruit, 24 daf seed/embryo alternatively, embryos from e.g. linseed capsule and rapeseed siliques are isolated from different stages of fruit development based on visual parameters and sorted to the following stages of embryo development: early, young, medium, late and mature.

The promoters are also checked for their inducibility by biotic and abiotic stress via ABA spraying on leaves.

Example 3

Demonstration of Expression Profile

To demonstrate and analyze the transcription regulating properties of a promoter of the useful to operably link the promoter or its fragments to a reporter gene, which can be employed to monitor its expression both qualitatively and quantitatively. Preferably bacterial β-glucuronidase is used (Jefferson 1987). β-glucuronidase activity can be monitored in planta with chromogenic substrates such as 5-bromo4-Chloro-3-indolyl-β-D-glucuronic acid during corresponding activity assays (Jefferson 1987). For determination of promoter activity and tissue specificity plant tissue is dissected, embedded, stained and analyzed as described (e.g., Bäumlein 1991).

For quantitative β-glucuronidase activity analysis MUG (methylumbelliferyl glucuronide) is used as a substrate, which is converted into MU (methylumbelliferone) and glucuronic acid. Under alkaline conditions this conversion can be quantitatively monitored fluorometrically (excitation at 365 nm, measurement at 455 nm; SpectroFluorimeter Thermo Life Sciences Fluoroscan) as described (Bustos 1989).

Example 4

Cloning of the Promoter Fragments

To isolate the promoter fragments described by SEQ ID NO: 1, 2, 3, 4, 5, 6, 7, 8, 9, 10, and 11, genomic DNA is isolated from *Arabidopsis thaliana* (ecotype Columbia), *Brassica napus*, or *Linum usitatissimum* as described (Galbiati 2000). The isolated genomic DNA is employed as matrix DNA for a polymerase chain reaction (PCR) mediated amplification using the oligonucleotide primers and protocols indicated below (Table 6).

TABLE 6

PCR oligonucleotide primers for amplification of the various transcription regulating nucleotide sequences and restriction enzymes for modifying the resulting PCR products

| SEQ ID | Promoter | Forward Primer | Reverse Primer | Restriktion enzym |
|---|---|---|---|---|
| SEQ ID NO: 1 | AtTIP-529 aus GenBank mit 5'UTR | AtTIP-529 SEQ ID NO: 20 | AtTIP-529 SEQ ID NO: 21 | SalI/BamHI |
| SEQ ID NO: 2 | AtTIP-320 aus GenBank ohne 5'UTR | AtTIP-320 SEQ ID NO: 20 | AtTIP-320 SEQ ID NO: 22 | SalI/BamHI |
| SEQ ID NO: 3 | BnTIP-1510 bp- aus Lo445 | BnTIP-1510-Lo445 SEQ ID NO: 23 | BnTIP-Lo445 SEQ ID NO: 24 | HindIII/BamHI |
| SEQ ID NO: 4 | BnTIP-1112 bp- ausLo445 | BnTIP-1112-Lo445 SEQ ID NO: 25 | BnTIP-Lo445 SEQ ID NO: 24 | HindIII/BamHI |
| SEQ ID NO: 5 | BnTIP-578 bp- aus Lo445 | BnTIP-578-Lo445 SEQ ID NO: 26 | BnTIP-Lo445 SEQ ID NO: 24 | HindIII/BamHI |
| SEQ ID NO: 6 | LuTIP-1-1521 bp- aus Lo401 | LuTIP-1-1521-Lo401 SEQ ID NO: 27 | LuTIP-1-Lo401 SEQ ID NO: 28 | HindIII/SpeI |
| SEQ ID NO: 7 | LuTIP-1-1086 bp- aus Lo401 | LuTIP-1-1086-Lo401 SEQ ID NO: 29 | LuTIP-1-Lo401 SEQ ID NO: 28 | HindIII/SpeI |
| SEQ ID NO: 8 | LuTIP-1-400 bp- aus Lo401 | LuTIP-1-400-Lo401 SEQ ID NO: 30 | LuTIP-1-Lo401 SEQ ID NO: 28 | HindIII/SpeI |
| SEQ ID NO: 9 | LuTIP-2-1751 bp- aus Lo402 | LuTIP-2-1751-Lo402 SEQ ID NO: 31 | LuTIP-2-Lo402 SEQ ID NO: 32 | HindIII/SpeI |
| SEQ ID | LuTIP-2-901 bp- | LuTIP-2-901-Lo402 | LuTIP-2-Lo402 | HindIII/SpeI |

TABLE 6-continued

PCR oligonucleotide primers for amplification of the various transcription regulating
nucleotide sequences and restriction enzymes for modifying the resulting PCR products

| SEQ ID | Promoter | Forward Primer | Reverse Primer | Restriktion enzym |
|---|---|---|---|---|
| NO: 10 | aus Lo402 | SEQ ID NO: 33 | SEQ ID NO: 32 | |
| SEQ ID NO: 11 | LuTIP-2-384 bp- aus Lo402 | LuTIP-2-384-Lo402 SEQ ID NO: 34 | LuTIP-2-Lo402 SEQ ID NO: 32 | HindIII/SpeI |

Amplification is carried out as follows:
100 ng genomic DNA
1×PCR buffer
2.5 mM MgCl$_2$,
200 μM each of dATP, dCTP, dGTP und dTTP
10 pmol of each oligonucleotide primers
2.5 Units Pfu DNA Polymerase (Stratagene)
in a final volume of 50 μl The following temperature program is employed for the various amplifications (BIORAD Thermocycler).
1. 95° C. for 5 min
2. 54° C. for 1 min, followed by 72° C. for 5 min and 95° C. for 30 sec. Repeated 25 times.
3. 54° C. for 1 min, followed by 72° C. for 10 min.
4. Storage at 4° C.

The resulting PCR-products are digested with the restriction endonucleases specified in the Table above (Table 3) and cloned into the vector pSUN0301 (SEQ ID NO: 147) (pre-digested with the same enzymes) upstream and in operable linkage to the glucuronidase (GUS) gene. Following stable transformation of each of these constructs into *Arabidopsis thaliana* tissue specificity and expression profile was analyzed by a histochemical and quantitative GUS-assay, respectively.

Example 5

Expression Profile of the Various Promoter::GUS Constructs in Stably Transformed *A. thaliana*, Rapeseed and Linseed Plants The glucuronidase (GUS) expression pattern of the tonoplast intrinsic protein alpha promoters (SEQ ID NO: 1, 2, 3, 4, 5, 6, 7, 8, 9, 10 and 11) are investigated in *Arabidopsis*, rapeseed and linseed.

The *Arabidopsis thaliana* TIP-alpha promoter (SEQ ID NO: 1) demonstrated to be seed-specific in *Brassica napus* and seed-preferential in *Linum sativum* (having slight expression also in roots, flowers, leafs, and capsula).

The *Brassica napus* TIP promoter (SEQ ID NO: 3) demonstrated to be seed-specific in *Linum sativum*.

The *Linum usitatissimum* TIP promoter (SEQ ID NO: 6) demonstrated to be seed-specific in *Brassica napus* and seed-preferential in *Linum sativum* (having slight expression also in roots in some of the assessed lines).

Example 7

Vector Construction for Overexpression and Gene "Knockout" Experiments 7.1 Overexpression Vectors used for expression of full-length "candidate genes" of interest in plants (over-expression) are designed to overexpress the protein of interest and are of two general types, biolistic and binary, depending on the plant transformation method to be used. For biolistic transformation (biolistic vectors), the requirements are as follows:
1. a backbone with a bacterial selectable marker (typically, an antibiotic resistance gene) and origin of replication functional in *Escherichia coli* (*E. coli*; e.g., ColE1), and
2. a plant-specific portion consisting of:
   a. a gene expression cassette consisting of a promoter (eg. ZmUBIint MOD), the gene of interest (typically, a full-length cDNA) and a transcriptional terminator (e.g., *Agrobacterium tumefaciens* nos terminator);
   b. a plant selectable marker cassette, consisting of a suitable promoter, selectable marker gene (e.g., D-amino acid oxidase; dao1) and transcriptional terminator (eg. nos terminator).

Vectors designed for transformation by *Agrobacterium tumefaciens* (*A. tumefaciens*; binary vectors) consist of:
1. a backbone with a bacterial selectable marker functional in both *E. coli* and *A. tumefaciens* (e.g., spectinomycin resistance mediated by the aadA gene) and two origins of replication, functional in each of aforementioned bacterial hosts, plus the *A. tumefaciens* virG gene;
2. a plant-specific portion as described for biolistic vectors above, except in this instance this portion is flanked by *A. tumefaciens* right and left border sequences which mediate transfer of the DNA flanked by these two sequences to the plant.

7.2 Gene Silencing Vectors

Vectors designed for reducing or abolishing expression of a single gene or of a family or related genes (gene silencing vectors) are also of two general types corresponding to the methodology used to downregulate gene expression: antisense or double-stranded RNA interference (dsRNAi).

(a) Anti-Sense

For antisense vectors, a full-length or partial gene fragment (typically, a portion of the cDNA) can be used in the same vectors described for full-length expression, as part of the gene expression cassette. For antisense-mediated down-regulation of gene expression, the coding region of the gene or gene fragment will be in the opposite orientation relative to the promoter; thus, mRNA will be made from the non-coding (antisense) strand in planta.

(b) dsRNAi

For dsRNAi vectors, a partial gene fragment (typically, 300 to 500 basepairs long) is used in the gene expression cassette, and is expressed in both the sense and antisense orientations, separated by a spacer region (typically, a plant intron, eg. the OsSH1 intron 1, or a selectable marker, eg. conferring kanamycin resistance). Vectors of this type are designed to form a double-stranded mRNA stem, resulting from the basepairing of the two complementary gene fragments in planta.

Biolistic or binary vectors designed for overexpression or knockout can vary in a number of different ways, including eg. the selectable markers used in plant and bacteria, the transcriptional terminators used in the gene expression and plant selectable marker cassettes, and the methodologies used for cloning in gene or gene fragments of interest (typically, conventional restriction enzyme-mediated or Gateway™ recombinase-based cloning).

Example 8

Promoter Element Analysis

Promoter motif analysis of the tonoplast intrinsic protein promoters was done using the Genomatix software MatInspector Release professional 7.3 (August 2004). The results are given above in Table 3 to 7.

REFERENCES

1. Abel et al., Science, 232:738 (1986).
2. Altschul et al., Nucleic Acids Res., 25:3389 (1997).
3. Altschul et al., J. Mol. Biol., 215:403 (1990).
4. An et al., EMBO J., 4:277 (1985).
5. Auch & Reth, Nucleic Acids Research, 18:6743 (1990).
6. Ausubel et al. (1987) Current Protocols in Molecular Biology, Greene Publishing Assoc. and Wiley Interscience
7. Ballas et al., Nucleic Acids Res., 17:7891 (1989).
8. Barkai-Golan et al., Arch. Microbiol., 116:119 (1978).
9. Batzer et al., Nucleic Acid Res., 19:5081 (1991).
10. Bäumlein et al. Mol Gen Genet 225:121-128 (1991)
11. Becker et al. (1994) Plant J., 5:299-307,
12. Bernal-Lugo and Leopold, Plant Physiol., 98:1207 (1992).
13. Bevan et al., Nature, 304:184 (1983).
14. Bevan et al., Nucl. Acids Res., 11:369 (1983).
15. Bevan, Nucl. Acids Res., 12:8711 (1984).
16. Blackman et al., Plant Physiol., 100:225 (1992).
17. Blochlinger & Diggelmann, Mol Cell Biol, 4:2929 (1984).
18. Bol et al., Ann. Rev. Phytopath., 28:113 (1990).
19. Bouchez et al., EMBO J., 8:4197 (1989).
20. Bourouis et al., EMBO J., 2:1099 (1983).
21. Bowler et al., Ann. Rev. Plant Physiol., 43:83 (1992).
22. Branson and Guss, Proc. North Central Branch Entomological Society of America (1972).
23. Broakgert et al., Science, 245:110 (1989).
24. Bustos M M et al. (1989) Plant Gell 1:839-853
25. Byrne et al. Plant Cell Tissue and Organ Culture, 8:3 (1987).
26. Callis et al., Genes and Develop., 1:1183 (1987).
27. Campbell and Gowri, Plant Physiol., 92:1 (1990).
28. Campbell, W. C., ed. Ivermectin and Abamectin, Springer-Verlag, New York, 1989.
29. Chee et al. Plant Physiol., 91:1212 (1989).
30. Chen and Winans (1991) J. Bacteriol. 173: 1139-1144
31. Christou et al. Proc. Natl. Acad. Sci USA, 86:7500 (1989).
32. Christou et al., Biotechnology, 9:957 (1991).
33. Christou et al., Plant Physiol., 87:671 (1988).
34. Chui et al. (1996) Curr Biol 6:325-330
35. Coe et al., In: Corn and Corn Improvement, Sprague et al. (eds.) pp. 81-258 (1988).
36. Corpet et al. Nucleic Acids Res., 16:10881 (1988).
37. Coxson et al., Biotropica, 24:121 (1992).
38. Crameri et al., Nature Biotech., 15:436 (1997).
39. Crameri et al., Nature, 391:288 (1998).
40. Crossway et al., BioTechniques, 4:320 (1986).
41. Cuozzo et al., Bio/Technology, 6:549 (1988).
42. Cutler et al., J. Plant Physiol., 135:351 (1989).
43. Czapla and Lang, J. Econ. Entomol., 83:2480 (1990).
44. Datta et al., Bio/Technology, 8:736 (1990).
45. Davies et al., Plant Physiol., 93:588 (1990).
46. Dayhoff et al., Atlas of Protein Sequence and Structure, Natl. Biomed. Res. Found., Washington, C. D. (1978).
47. De Blaere et al., Meth. Enzymol., 143:277 (1987).
48. De Block et al. Plant Physiol., 91:694 (1989).
49. De Block et al., EMBO Journal, 6:2513 (1987).
50. Deblaere et al. Nucl Acids Res 13:4777-4788 (1985)
51. Della-Cioppa et al. Bio/Technology 5:579-584 (1987)
52. Della-Cioppa et al., Plant Physiology, 84:965-968 (1987).
53. Dellaporta et al., in Chromosome Structure and Function, Plenum Press, 263-282 (1988).
54. Depicker et al., Plant Cell Reports, 7:63 (1988).
55. Dunn et al., Can. J. Plant Sci., 61:583 (1981).
56. Dure et al., Plant Mol. Biol., 12:475 (1989).
57. Ebinuma et al. Proc Natl Acad Sci USA 94:2117-2121 (2000a)
58. Ebinuma et al. Selection of Marker-free transgenic plants using the oncogenes (ipt, rol A, B, C) of *Agrobacterium* as selectable markers, In Molecular Biology of Woody Plants. Kluwer Academic Publishers (2000b)
59. Eichholtz et al. Somatic Cell and Molecular Genetics 13, 67-76 (1987)
60. Ellis et al., EMBO Journal, 6:3203 (1987).
61. Elroy-Stein et al., Proc. Natl. Acad. Sci. U.S.A., 86:6126 (1989).
62. English et al., Plant Cell, 8:179 (1996).
63. Erdmann et al., J. Gen. Microbiol., 138:363 (1992).
64. Erikson et al. Nat Biotechnol. 22(4):455-8 (2004)
65. Everett et al., Bio/Technology, 5:1201 (1987).
66. Fedoroff N V & Smith D L Plant J 3:273-289 (1993)
67. Fire A et al Nature 391:806-811 (1998)
68. Fitzpatrick, Gen. Engineering News, 22:7 (1993).
69. Fraley et al. Proc Natl Acad Sci USA 80:4803 (1983)
70. Fromm et al., Bio/Technology, 8:833 (1990).
71. Fromm et al., Nature (London), 319:791 (1986).
72. Galbiati et al. Funct. Integr Genozides 2000, 20 1:25-34
73. Gallie et al. Nucl Acids Res 15:8693-8711 (1987)
74. Gallie et al., Nucleic Acids Res., 15:3257 (1987).
75. Gallie et al., The Plant Cell, 1:301 (1989).
76. Gan et al., Science, 270:1986 (1995).
77. Gatehouse et al., J. Sci. Food Agric., 35:373 (1984).
78. Gelfand, eds., PCR Strategies Academic Press, New York (1995).
79. Gelvin et al., Plant Molecular Biology Manual, (1990).
80. Gleave et al. Plant Mol Biol. 40(2):223-35 (1999)
81. Gordon-Kamm et al., Plant Cell, 2:603 (1990).
82. Goring et al, PNAS, 88:1770 (1991).
83. Gruber, et al., Vectors for Plant Transformation, in: Methods in Plant Molecular Biology & Biotechnology" in Glich et al., (Eds. pp. 89-119, CRC Press, 1993).
84. Guerineau et al., Mol. Gen. Genet., 262:141 (1991).
85. Guerrero et al., Plant Mol. Biol., 15:11 (1990).
86. Gupta et al., PNAS, 90:1629 (1993).
87. Haines and Higgins (eds.), Nucleic Acid Hybridization, IRL Press, Oxford, U.K.
88. Hajdukiewicz et al. Plant Mol Biol 25:989-994 (1994)
89. Hammock et al., Nature, 344:458 (1990).
90. Hansen et al. Proc. Natl. Acad. Sci. USA 91:7603-7607 (1994)
91. Hayford et al. Plant Physiol. 86:1216 (1988)
92. Hemenway et al., EMBO Journal, 7:1273 (1988).
93. Henikoff & Henikoff, Proc. Natl. Acad. Sci. USA, 89:10915 (1989).
94. Hiei et al. Plant J 6: 271-282 (1994)
95. Higgins et al., Gene, 73:237 (1988).
96. Higo et al. (1999) Nucl Acids Res 27(1): 297-300
97. Hilder et al., Nature, 330:160 (1987).

98. Hille et al. Plant Mol. Biol. 7:171 (1986)
99. Hinchee et al. Bio/Technology 6:915 (1988).
100. Hoekema et al. (1983) Nature 303:179-181
101. Hoekema, In: The Binary Plant Vector System. Offset-drukkerij Kanters B. V.; Alblasserdam (1985).
102. Hood et al. J Bacteriol 168:1291-1301 (1986)
103. Huang et al., CABIOS, 8:155 (1992).
104. Ikeda et al., J. Bacteriol., 169:5612 (1987).
105. Ikuta et al., Biotech., 8:241 (1990).
106. Ingelbrecht et al., Plant Cell, 1:671 (1989).
107. Innis and Gelfand, eds., PCR Methods Manual (Academic Press, New York) (1999).
108. Innis et al., eds., PCR Protocols: A Guide to Methods and Applications (Academic Press, New York (1995).
109. Innis et al., PCR Protocols: A Guide to Methods and Applications, Academic Press, Inc., San Diego, Calif. (1990).
110. Ishida Y et al. Nature Biotech 745-750 (1996)
111. Jefferson et al. EMBO J 6:3901-3907 (1987)
112. Jefferson et al. Plant Mol Biol Rep 5:387-405 (1987)
113. Jenes B et al. Techniques for Gene Transfer, in: Recombinant Plants, Vol. 1, Engineering and Utilization, edited by S D Kung and R Wu, Academic Press, pp. 128-143 (1993)
114. Jobling et al., Nature, 325:622 (1987).
115. Johnson et al., PNAS USA, 86:9871 (1989)
116. Jones et al. Mol. Gen. Genet., 210:86 (1987)
117. Joshi et al., Nucleic Acid Res., 15:9627 (1987).
118. Kaasen et al., J. Bacteriol., 174:889 (1992).
119. Karlin and Altschul, Proc. Natl. Acad Sci. USA, 87:2264 (1990).
120. Karlin and Altschul, Proc. Natl. Acad. Sci. USA, 90:5873 (1993).
121. Karsten et al., Botanica Marina, 35:11 (1992).
122. Katz et al., J. Gen. Microbiol., 129:2703 (1983).
123. Keller et al., EMBO Journal, 8:1309 (1989).
124. Keller et al., Genes Dev., 3:1639 (1989)
125. Klapwijk et al. J. Bacteriol., 141, 128-136 (1980)
126. Klein et al., Bio/Technology, 6:559 (1988).
127. Klein et al., Plant Physiol., 91:440 (1988).
128. Klein et al., Proc. Natl. Acad. Sci. USA, 85:4305 (1988).
129. Knauf, et al., Genetic Analysis of Host Range Expression by *Agrobacterium* In: Molecular Genetics of the Bacteria-Plant Interaction, Puhler, A. ed., Springer-Verlag, New York, 1983.
130. Koncz & Schell Mol Gen Genet 204:383-396 (1986)
131. Koprek T et al. Plant J 19(6): 719-726 (1999)
132. Koster and Leopold, Plant Physiol., 88:829 (1988).
133. Koziel et al., Biotechnology, 11:194 (1993).
134. Kunkel et al., Methods in Enzymol., 154:367 (1987).
135. Kunkel, Proc. Natl. Acad. Sci. USA, 82:488 (1985).
136. Lam E und Chua N H, J Biol Chem; 266(26):17131-17135 (1991)
137. Laufs et al., PNAS, 87:7752 (1990).
138. Lawton et al., Mol. Cell Biol., 7:335 (1987).
139. Lee and Saier, J. Bacteriol., 153 (1982).
140. Leffel et al. Biotechniques 23(5):912-8 (1997)
141. Lescot et al. Nucleic Acids Res 30(1):325-7 (2002)
142. Levings, Science, 250:942 (1990).
143. Li et al. Plant Mol Biol 20:1037-1048 (1992)
144. Lindsey et al., Transgenic Research, 2:3347 (1993).
145. Liu et al. Plant J. 8, 457-463 (1995)
146. Lommel et al., Virology, 181:382 (1991).
147. Loomis et al., J. Expt. Zool., 252:9 (1989).
148. Lorz et al., Mol. Gen. Genet., 199:178 (1985).
149. Ma et al., Nature, 334:631 (1988).
150. Macejak et al., Nature, 353:90 (1991).
151. Maki et al., Methods in Plant Molecular Biology & Biotechnology, Glich et al., 67-88 CRC Press, (1993).
152. Maniatis T, Fritsch E F, and Sambrook J Molecular Cloning: A Laboratory Manual, Cold Spring Harbor Laboratory, Cold Spring Harbor (NY), (1989)
153. Mariani et al, Nature, 347:737 (1990).
154. Matzke et al. (2000) Plant Mol Biol 43:401-415;
155. McBride et al., PNAS USA, 91:7301 (1994).
156. McCabe et al., Bio/Technology, 6:923 (1988).
157. Meinkoth and Wahl, Anal. Biochem., 138:267 (1984).
158. Messing and Vierra, Gene, 19:259 (1982).
159. Michael et al., J. Mol. Biol., 26:585 (1990)
160. Millar et al. Plant Mol Biol Rep 10:324-414 (1992)
161. Mogen et al., Plant Cell, 2:1261 (1990).
162. Moore et al., J. Mol. Biol., 272:336 (1997).
163. Mozo & Hooykaas Plant Mol. Biol. 16:917-918 (1991)
164. Mundy and Chua, EMBO J., 7:2279 (1988).
165. Munroe et al., Gene, 91:151 (1990).
166. Murakami et al., Mol. Gen. Genet., 205:42 (1986).
167. Murata et al., FEBS Lett., 296:187 (1992).
168. Murdock et al., Phytochemistry, 29:85 (1990).
169. Murray et al., Nucleic Acids Res., 17:477 (1989).
170. Myers and Miller, CABIOS, 4:11 (1988).
171. Naested H Plant J 18:571-576 (1999)
172. Napoli et al., Plant Cell, 2:279 (1990).
173. Needleman and Wunsch, J. Mol. Biol., 48:443-453 (1970).
174. Nehra et al. Plant J. 5:285-297 (1994)
175. Niedz et al., Plant Cell Reports, 14:403 (1995).
176. Odell et al., Mol. Gen. Genet., 113:369 (1990).
177. Odell et al., Nature, 313:810 (1985).
178. Ohtsuka et al., J. Biol. Chem., 260:2605 (1985)
179. Olhoft et al. Plant Cell Rep 20: 706-711 (2001)
180. Ow et al., Science, 234:856 (1986).
181. Pacciotti et al., Bio/Technology, 3:241 (1985).
182. Park et al., J. Plant Biol., 38:365 (1985).
183. Paszkowski et al., EMBO J., 3:2717 (1984).
184. Pearson and Lipman, Proc. Natl. Acad. Sci., 85:2444 (1988).
185. Pearson et al., Meth. Mol. Biol., 24:307 (1994).
186. Perera R J et al. Plant Mol. Biol 23(4): 793-799 (1993)
187. Perlak et al., Proc. Natl. Acad. Sci. USA, 88:3324 (1991).
188. Phillips et al., In Corn & Corn Improvement, 3rd Edition Sprague et al. (Eds. pp. 345-387)(1988).
189. Phi-Van et al., Mol. Cell. Biol., 10:2302 (1990).
190. Piatkowski et al., Plant Physiol., 94:1682 (1990).
191. Potrykus et al., Mol. Gen. Genet., 199:183 (1985).
192. Potrykus, Trends Biotech., 7:269 (1989).
193. Prasher et al., Biochem. Biophys. Res. Comm., 126: 1259 (1985).
194. Proudfoot, Cell, 64:671 (1991).
195. Reed et al., J. Gen. Microbiol., 130:1 (1984).
196. Riggs et al., Proc. Natl. Acad. Sci. USA, 83:5602 (1986).
197. Rossolini et al., Mol. Cell. Probes, 8:91 (1994).
198. Ruiz, Plant Cell, 10:937 (1998).
199. Sambrook et al., Molecular Cloning: A Laboratory Manual (2d ed., Cold Spring Harbor Laboratory Press, Plainview, N.Y.) (1989).
200. Sanfacon et al., Genes Dev., 5:141 (1991).
201. Sanford et al., Particulate Science and Technology, 5:27 (1987).
202. Scheeren-Groot et al. J. Bacteriol 176: 6418-6426 (1994)
203. Schenborn and Groskreutz Mol Biotechnol 13(1): 29-44 (1999)
204. Schlaman and Hooykaas Plant J 11:1377-1385 (1997)

205. Schoffl F et al. (1989) Mol Gen Genetics 217(2-3):246-53
206. Shagan et al., Plant Physiol., 101:1397 (1993).
207. Shah et al. Science 233: 478 (1986)
208. Shapiro, Mobile Genetic Elements, Academic Press, N.Y. (1983).
209. Shimamoto et al., Nature, 338:274 (1989).
210. Silhavy T J, Berman M L, and Enquist L W Experiments with Gene Fusions, Cold Spring Harbor Laboratory Press, Cold Spring Harbor (NY), (1984)
211. Skuzeski et al., Plant Molec. Biol. 15: 65-79 (1990).
212. Smith et al., Adv. Appl. Math., 2:482 (1981).
213. Smith et al., Mol. Gen. Genet., 224:447 (1990).
214. Spencer et al., Theor. Appl. Genet, 79:625 (1990)
215. Stalker et al., Science, 242:419 (1988).
216. Staub et al., EMBO J., 12:601 (1993).
217. Staub et al., Plant Cell, 4:39 (1992).
218. Steifel et al., The Plant Cell, 2:785 (1990).
219. Stemmer, Nature, 370:389 (1994).
220. Stemmer, Proc. Natl. Acad. Sci. USA, 91:10747 (1994).
221. Stief et al., Nature, 341:343 (1989).
222. Stougaard Plant J 3:755-761 (1993)
223. Sukhapinda et al., Plant Mol. Biol., 8:209 (1987).
224. Sundaresan et al. Gene Develop 9: 1797-1810 (1995)
225. Sutcliffe, PNAS USA, 75:3737 (1978).
226. Svab et al., Plant Mol. Biol. 14:197 (1990)
227. Svab et al., Proc. Natl. Acad. Sci. USA, 87:8526 (1990).
228. Svab et al., Proc. Natl. Acad. Sci. USA, 90:913 (1993).
229. Tarczynski et al., PNAS USA, 89:2600 (1992).
230. Thillet et al., J. Biol. Chem., 263:12500 (1988).
231. Tijssen, Laboratory Techniques in Biochemistry and Molecular Biology-Hybridization with Nucleic Acid Probes, Elsevier, N.Y. (1993).
232. Tomes et al., Plant Cell, Tissue and Organ Culture: Fundamental Methods, Springer Verlag, Berlin (1995).
233. Tomic et al., NAR, 12:1656 (1990).
234. Thompson J D et al., NAR 22(22):4673-4680 (1994).
235. Turner et al., Molecular Biotechnology, 3:225 (1995).
236. Twell et al., Plant Physiol., 91:1270 (1989).
237. Ugaki et al., Nucl. Acids Res., 19:371 (1991).
238. Ulmasov et al., Plant Mol. Biol., 35:417 (1997).
239. Upender et al., Biotechniques, 18:29 (1995).
240. van der Krol et al., Plant Cell, 2:291 (1990).
241. Vanden Elzen et al. Plant Mol Biol. 5:299 (1985)
242. Vasil et al. Bio/Technology, 10:667-674 (1992)
243. Vasil et al. Bio/Technology, 11:1153-1158 (1993)
244. Vasil et al., Mol. Microbiol., 3:371 (1989).
245. Vasil et al., Plant Physiol., 91:1575 (1989).
246. Vernon and Bohnert, EMBO J., 11:2077 (1992).
247. Walker and Gaastra, eds., Techniques in Molecular Biology, MacMillan Publishing Company, New York (1983).
248. Wan & Lemaux (1994) Plant Physiol., 104:3748
249. Wang et al., Mol. Cell. Biol., 12:3399 (1992).
250. Waterman, M. S. Introduction to Computational Biology: Maps, sequences and genomes. Chapman & Hall. London (1995).
251. Watrud et al., in Engineered Organisms and the Environment (1985).
252. Watson et al. J. Bacteriol 123, 255-264 (1975)
253. Watson et al., Corn: Chemistry and Technology (1987).
254. Weeks et al. Plant Physiol 102:1077-1084 (1993)
255. Weissinger et al., Annual Rev. Genet., 22:421 (1988).
256. White et al, Nucl Acids Res, 18, 1062 (1990).
257. Wingender E et al. Nucleic Acids Res 29(1):281-3 (2001)
258. Wolter et al., EMBO Journal, 11:4685 (1992).
259. Wyn-Jones and Storey, Physiology and Biochemistry of Drought Resistance in Plants, Paleg et al. (eds.), pp. 171-204 (1981).
260. Yamaguchi-Shinozaki et al., Plant Cell Physiol., 33:217 (1992).
261. Zhang et al., Proc. Natl. Acad. Sci. USA, 94:4504 (1997).
262. Zukowsky et al., PNAS USA, 80:1101 (1983).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

The invention claimed is:

1. An expression cassette for regulating seed-specific or seed-preferential expression in plants comprising
   a) at least one transcription regulating nucleotide sequence of a *Linum usitatissimum* tonoplast intrinsic protein gene, wherein the at least one transcription regulating nucleotide sequence drives seed-specific or seed-preferential expression and is selected from the group of sequences consisting of
      i) the sequence described by SEQ ID NO: 6, 7, or 8,
      ii) a fragment of at least 250 consecutive bases of the sequence described by SEQ ID NO: 6, 7, or 8, and
      iii) a nucleotide sequence having at least 90% sequence identity to SEQ ID NO: 6, 7, or 8,
   and functionally linked thereto
   b) at least one nucleic acid sequence which is heterologous in relation to said at least one transcription regulating nucleotide sequence.

2. The expression cassette of claim 1, wherein the at least one transcription regulating nucleotide sequence drives seed-specific or seed-preferential expression and has at least 95% sequence identity to SEQ ID NO: 6, 7, or 8.

3. The expression cassette of claim 1, wherein expression in a plant of the at least one nucleic acid sequence results in expression of a protein, or expression of an antisense RNA, sense or double-stranded RNA.

4. The expression cassette of claim 1, wherein expression in a plant of the at least one nucleic acid sequence confers to the plant an agronomically valuable trait.

5. A vector comprising the expression cassette of claim 1.

6. A transgenic microorganism or plant host cell comprising the expression cassette of claim 1 or a vector comprising said expression cassette.

7. A seed-specific or seed-preferential promoter comprising an isolated nucleotide sequence selected from the group of sequences consisting of
   i) the sequence described by SEQ ID NO: 6, 7, or 8,
   ii) a fragment of at least 250 consecutive bases of the sequence described by SEQ ID NO: 6, 7, or 8, and
   iii) a nucleotide sequence having at least 90% sequence identity to SEQ ID NO: 6, 7, or 8.

8. The seed-specific or seed-preferential promoter of claim 7, wherein the isolated nucleotide sequence has at least 95% sequence identity to SEQ ID NO: 6, 7, or 8.

9. A vector comprising the seed-specific or seed-preferential promoter of claim 7.

10. A transgenic microorganism or plant host cell comprising the seed-specific or seed-preferential promoter of claim 7 or a vector comprising said seed-specific or seed-preferential promoter.

11. A transgenic plant or plant cell comprising the expression cassette of claim 1 or a vector comprising said expression cassette.

12. A transgenic plant or plant cell comprising the seed-specific or seed-preferential promoter of claim 7 or a vector comprising said seed-specific or seed-preferential promoter.

13. A method for producing a transgenic plant or plant cell, comprising transforming a plant or a plant cell with the expression cassette of claim 1 or a vector comprising said expression cassette.

14. A method for producing a transgenic plant or plant cell, comprising transforming a plant or a plant cell with the seed-specific or seed-preferential promoter of claim 7 or a vector comprising said seed-specific or seed-preferential promoter.

15. A method for identifying and/or isolating a transcription regulating nucleotide sequence with seed-specific or seed-preferential expression activity comprising
   a) preparing fragments of at least 250 consecutive bases of the sequence described by SEQ ID NO: 6, 7, or 8, or variants having at least 90% identity to the sequence described by SEQ ID NO: 6, 7, or 8,
   b) testing the fragments or variants obtained for seed-specific or seed-preferential expression activity, and
   c) identifying and/or isolating a fragment or a variant with seed-specific or seed-preferential expression activity.

16. An expression cassette for regulating seed-specific or seed-preferential expression in plants comprising at least one transcription regulating nucleotide sequence obtained by the method of claim 15 and functionally linked thereto at least one nucleic acid sequence which is heterologous in relation to said at least one transcription regulating nucleotide sequence, wherein the at least one transcription regulating nucleotide sequence comprises:

i) the sequence described by SEQ ID NO: 6, 7, or 8, ii) a fragment of at least 250 consecutive bases of the sequence described by SEQ ID NO: 6, 7, or 8, or iii) a nucleotide sequence having at least 90% identity to SEQ ID NO: 6, 7, or 8.

17. A method for preparing the expression cassette of claim 1 comprising a) obtaining at least one transcription regulating nucleotide sequence by:

i) providing the sequence described by SEQ ID NO: 6, 7, or 8;

ii) (1) obtaining fragments of at least 250 consecutive bases of the sequence described by SEQ ID NO: 6, 7, or 8, or obtaining variants having at least 90% identity to the sequence described by SEQ ID NO: 6, 7, or 8;

(2) testing the fragments or variants obtained in part (1) for seed-specific or seed-preferential expression; and (3) identifying and/or isolating a fragment or a variant with seed-specific or seed-preferential expression activity; and b) operably linking the at least one transcription regulating nucleotide sequence to at least one nucleic acid sequence which is heterologous in relation to said at least one transcription regulating nucleotide sequence.

18. A method for regulating seed-specific or seed-preferential expression in a plant comprising i) introducing into a plant cell the expression cassette of claim 1, ii) selecting a transgenic plant cell which comprises said expression cassette, and iii) regenerating a plant from the transgenic plant cell, wherein the at least one transcription regulating nucleotide sequence directs seed-specific or seed-preferential expression of the operably linked at least one nucleic acid sequence in the plant.

* * * * *

SEQUENCE LISTING

```
<160> NUMBER OF SEQ ID NOS: 254

<210> SEQ ID NO 1
<211> LENGTH: 529
<212> TYPE: DNA
<213> ORGANISM: Arabidopsis thaliana
<220> FEATURE:
<221> NAME/KEY: promoter
<222> LOCATION: (1)..(529)
<223> OTHER INFORMATION: transcription regulating nucleotide sequence
      from Arabidopsis thaliana gene At1g73190 (alpha tonoplast
      intrinsic protein) comprising 5'-untranslated region
<220> FEATURE:
<221> NAME/KEY: TATA_signal
<222> LOCATION: (260)..(267)
<223> OTHER INFORMATION: putative TATA-box
<220> FEATURE:
<221> NAME/KEY: 5'UTR
<222> LOCATION: (321)..(529)
<223> OTHER INFORMATION: putative 5'-untranslated region

<400> SEQUENCE: 1
ggttaaaagt gaaatcatt tgtcacatgt tatgcttgaa ctaagaaata attattgact    60
```

```
tgcagaatta tcaaacgatc aaatcataaa gaacatatta caatttcatt aacttccgat      120
taatctgccg tgaaaccgtg caatctcaca gttttcccaa ctctagaagg ttcatatgct      180
tgtttatcta cttggcacac atgcatgctt agtcaacaca acacatacac atacataaac      240
acgtacacga ggacatgtat tatatatccc gaacctaata aggttcgtcc aaaaataact      300
caccaagaga agataagaaa gcagcacgaa caccaactct taaggaaaac atctaagtta      360
tggttaagta attgcatgca atttaaagct acgtgtccag cttaagacac tcaagtctca      420
catctgtccc tttttacttc gacttcgctt cttttggttt cttttaaact ctctctatct      480
ctctctttct tcttcacact ttgttgttaa tttcaagtgt ttgatcata               529

<210> SEQ ID NO 2
<211> LENGTH: 320
<212> TYPE: DNA
<213> ORGANISM: Arabidopsis thaliana
<220> FEATURE:
<221> NAME/KEY: promoter
<222> LOCATION: (1)..(320)
<223> OTHER INFORMATION: transcription regulating nucleotide sequence
      (putative core promoter region) from Arabidopsis thaliana gene
      At1g73190 (alpha tonoplast intrinsic protein)
<220> FEATURE:
<221> NAME/KEY: TATA_signal
<222> LOCATION: (260)..(267)
<223> OTHER INFORMATION: putative TATA-box

<400> SEQUENCE: 2
ggttaaaagt gaaatcatt tgtcacatgt tatgcttgaa ctaagaaata attattgact       60
tgcagaatta tcaaacgatc aaatcataaa gaacatatta caatttcatt aacttccgat      120
taatctgccg tgaaaccgtg caatctcaca gttttcccaa ctctagaagg ttcatatgct      180
tgtttatcta cttggcacac atgcatgctt agtcaacaca acacatacac atacataaac      240
acgtacacga ggacatgtat tatatatccc gaacctaata aggttcgtcc aaaaataact      300
caccaagaga agataagaaa                                                  320

<210> SEQ ID NO 3
<211> LENGTH: 1510
<212> TYPE: DNA
<213> ORGANISM: Brassica napus
<220> FEATURE:
<221> NAME/KEY: promoter
<222> LOCATION: (1)..(1510)
<223> OTHER INFORMATION: transcription regulating nucleotide sequence
      (derivativ) from Brassica napus orthologous gene to Arabidopsis
      thaliana At1g73190 (alpha tonoplast intrinsic protein) comprising
      5'-untranslated region
<220> FEATURE:
<221> NAME/KEY: TATA_signal
<222> LOCATION: (1209)..(1212)
<223> OTHER INFORMATION: putative TATA-box

<400> SEQUENCE: 3
cttcagttat gcctggcttg tgtgacaatc tttgacaaga agtgcaagac gtcaaaattg       60
acaatgggta tgttaaaact ttttgccaaa atattgagtt tggtatctta gtctgcttca      120
gttgttcatt caaacagatt gagtggtgaa atgaatactg tgcataaatt gtatcttttc      180
atgaccgcct atgtaatgta tgaactgagt cactgttgca tttaaagttg tgagagatgg      240
tttctccttg gcttactatg cagaattgtg atatctcact gatatggact agtttgtgtt      300
atatcgtctt tgttctgtct gaaggattaa aatcttcaac tatgacagaa agcgttattt      360
caagaagatg ttcgagagac tgtaccaggt atacttctta acggctttaa agcataatta      420
```

| | | | | |
|---|---|---|---|---|
| caagtcgcct | tactaaggtt | ccatggttat | tcaccaacag | gctgaatgga | aaccggagtt | 480 |
| tccagacagg | ttcagtgaga | attagtgaac | ttgtcaaggc | agtcgattca | ttgaaactcg | 540 |
| aagatggcaa | atctcaaggt | ttgagtctat | tagttttaac | cctaaaacct | gtgtctgatt | 600 |
| ttgtaagaaa | ggtttacaaa | aacactattg | ttcttcaacg | gttatcttag | gacaaggatc | 660 |
| agctcagaag | aaagctgttg | cttccatccc | cactatacaa | aaaccggctg | aatatcggcc | 720 |
| tccgcagtcc | gcatgctaag | cacgcagctg | ccattcaagc | caaggtactc | aaaatagaac | 780 |
| ttctctatga | ttatcacaac | gatactaatt | actagttatc | aaacgtcatg | attgtggtac | 840 |
| aagctcatca | gaattggttc | tttaacataa | tttgcttgtt | catactgttt | tagattgaac | 900 |
| atagtcttca | catatcaatg | tctctgataa | ttacatgatt | tgcaaatgca | gttgctcgag | 960 |
| aggaaaccca | gcagggtaag | tgctctatct | tgcaatacat | acataatctt | ggaaacagtc | 1020 |
| ttccttatgt | tgatggatgc | tctgttgttc | gttcattaca | gagagatgag | caagaacgct | 1080 |
| cttaaaaaca | agaagaagaa | aggagccgag | gctgctgctt | ctggggctaa | caacgcctga | 1140 |
| ttaaagaggt | cacacccaag | ttatcaagtt | cactggagac | tacagttttg | agattccaac | 1200 |
| aaagattcta | tagaaattgc | acaatacata | cataatctcc | ttaaactta | tgcatgtact | 1260 |
| taaccatgag | attccaacaa | agattctttg | tcttaatccg | tccaaaaaat | taccaagaga | 1320 |
| agataaggag | gcggaggaaa | atgacataca | tggttaagta | acatgcatgc | agtttcaagc | 1380 |
| tacgtgtcca | tctcaagaca | ctcaagtatc | acatctgtcc | tttacttctt | ttaaattctc | 1440 |
| tgtctctctc | tttctacttc | tacctttgtt | catcacacat | ccttgttgat | tcagagtgtt | 1500 |
| tgtgattata | | | | | 1510 |

<210> SEQ ID NO 4
<211> LENGTH: 1112
<212> TYPE: DNA
<213> ORGANISM: Brassica napus
<220> FEATURE:
<221> NAME/KEY: promoter
<222> LOCATION: (1)..(1112)
<223> OTHER INFORMATION: transcription regulating nucleotide sequence
  (derivative; putative promoter region) from Brassica napus
  orthologous gene to Arabidopsis thaliana At1g73190 (alpha
  tonoplast intrinsic protein) comprising 5'-untranslated region
<220> FEATURE:
<221> NAME/KEY: TATA_signal
<222> LOCATION: (811)..(814)
<223> OTHER INFORMATION: putative TATA-box

<400> SEQUENCE: 4

| | | | | |
|---|---|---|---|---|
| taacggcttt | aaagcataat | tacaagtcgc | cttactaagg | ttccatggtt | attcaccaac | 60 |
| aggctgaatg | gaaaccggag | tttccagaca | ggttcagtga | gaattagtga | acttgtcaag | 120 |
| gcagtcgatt | cattgaaact | cgaagatggc | aaatctcaag | gtttgagtct | attagtttta | 180 |
| accctaaaac | ctgtgtctga | ttttgtaaga | aaggtttaca | aaaacactat | tgttcttcaa | 240 |
| cggttatctt | aggacaagga | tcagctcaga | gaaaagctgt | tgcttccatc | cccactatac | 300 |
| aaaaaccggc | tgaatatcgg | cctccgcagt | ccgcatgcta | agcacgcagc | tgccattcaa | 360 |
| gccaaggtac | tcaaaataga | acttctctat | gattatcaca | acgatactaa | ttactagtta | 420 |
| tcaaacgtca | tgattgtggt | acaagctcat | cagaattggt | tctttaacat | aatttgcttg | 480 |
| ttcatactgt | tttagattga | acatagtctt | cacatatcaa | tgtctctgat | aattacatga | 540 |
| tttgcaaatg | cagttgctcg | agaggaaacc | cagcagggta | agtgctctat | cttgcaatac | 600 |
| atacataatc | ttggaaacag | tcttccttat | gttgatggat | gctctgttgt | tcgttcatta | 660 |
| cagagagatg | agcaagaacg | ctcttaaaaa | caagaagaag | aaaggagccg | aggctgctgc | 720 |

```
ttctggggct aacaacgcct gattaaagag gtcacaccca agttatcaag ttcactggag      780
actacagttt tgagattcca acaaagattc tatagaaatt gcacaataca tacataatct      840
ccttaaactt tatgcatgta cttaaccatg agattccaac aaagattctt tgtcttaatc      900
cgtccaaaaa attaccaaga gaagataagg aggcggagga aaatgacata catggttaag      960
taacatgcat gcagtttcaa gctacgtgtc catctcaaga cactcaagta tcacatctgt     1020
cctttacttc ttttaaattc tctgtctctc tctttctact tctacctttg ttcatcacac     1080
atccttgttg attcagagtg tttgtgatta ta                                   1112
```

```
<210> SEQ ID NO 5
<211> LENGTH: 578
<212> TYPE: DNA
<213> ORGANISM: Brassica napus
<220> FEATURE:
<221> NAME/KEY: promoter
<222> LOCATION: (1)..(578)
<223> OTHER INFORMATION: transcription regulating nucleotide sequence
      (derivative; putative promoter region) from Brassica napus
      orthologous gene to Arabidopsis thaliana At1g73190 (alpha
      tonoplast intrinsic protein) comprising 5'-untranslated region
<220> FEATURE:
<221> NAME/KEY: TATA_signal
<222> LOCATION: (277)..(280)
<223> OTHER INFORMATION: putative TATA-box

<400> SEQUENCE: 5
acatgatttg caaatgcagt tgctcgagag gaaacccagc agggtaagtg ctctatcttg       60
caatacatac ataatcttgg aaacagtctt ccttatgttg atggatgctc tgttgttcgt      120
tcattacaga gagatgagca agaacgctct aaaaacaag aagaagaaag gagccgaggc       180
tgctgcttct ggggctaaca acgcctgatt aaagaggtca cacccaagtt atcaagttca      240
ctggagacta cagttttgag attccaacaa agattctata gaaattgcac aatacataca      300
taatctcctt aaactttatg catgtactta accatgagat tccaacaaag attctttgtc      360
ttaatccgtc aaaaaatta ccaagagaag ataaggaggc ggaggaaaat gacatacatg       420
gttaagtaac atgcatgcag tttcaagcta cgtgtccatc tcaagacact caagtatcac      480
atctgtcctt tacttctttt aaattctctg tctctctctt tctacttcta cctttgttca      540
tcacacatcc ttgttgattc agagtgtttg tgattata                              578
```

```
<210> SEQ ID NO 6
<211> LENGTH: 1521
<212> TYPE: DNA
<213> ORGANISM: Linum usitatissimum
<220> FEATURE:
<221> NAME/KEY: promoter
<222> LOCATION: (1)..(1521)
<223> OTHER INFORMATION: transcription regulating nucleotide sequence
      (derivative) from Linum usitatissimum orthologous gene to
      Arabidopsis thaliana At1g73190 (alpha tonoplast intrinsic protein)
      comprising 5'-untranslated region
<220> FEATURE:
<221> NAME/KEY: TATA_signal
<222> LOCATION: (1358)..(1361)
<223> OTHER INFORMATION: putative TATA-box

<400> SEQUENCE: 6
tcgacggata tattggattt ggagataatg cagtcgaggg aagggcacgg ggagatgttt       60
cagctgaccg atttggcgtt ggagtgtacc tgtgtgttgc cggagaagcg gccgaagatg      120
gcggaggttg tgaggaggat tgaggagatt gagcagagaa gtaaatgaaa tttgttgaaa      180
tgggtttgta aatgaagagg aaaagatttg atattggatt tgtttgtttt gttcataggc      240
```

```
tcatttgtgg gtggaggaag aaacagagtt gtgtgattct ttgtgaggga tccaaattgg    300
aatttgtgac atttgccagt gtaattaatg agataaatgt agaaaatcgg ttcatcctgt    360
tatgaatcga taagtaggaa aacgaaatta agatggattg aaaaagagaa gatataaatg    420
attttatgtg aaaaagtttt gatggaaaaa attatggatg catggtggcg ttgaaagctc    480
agctataata agagagtaca aatttaaaag atatttatga agattttaag atatcataat    540
cgataaaaca agagatgaat aaatgaatta ggaacggata atgcaacgaa agtaaaaagt    600
acgactcatc ataacccatt ctacataggg gaatttggat aaactaactt caacattgat    660
ttggtattcg ctgtaatcat catttaacct cgagtcttaa catatcaatt cgtttcactt    720
caggggtgga accaggggga gtcgcggtgt gagttctggc tcacacctct gttctgatct    780
cgagcatcaa aattaagtat attttgtga atttcttgaa tccggttata tgcaattta    840 attctgactc aacacttggc ccattacaaa attagaggga atcaagtaga tttatgggta    900
gctaataatt atatttaaaa tttggacgtt tttttaactc gagtttaata atatttgaag    960
ttttgcccct ttatttttgtt gtttaaacta aataatctat caaattaaac tcaataatta   1020
ccacttataa ctaaagttat cgaacagacg atcatgaatt gggttagacg ggttagaggt   1080
tagtcgagtt gaaagggaac cccagcagaa agaggttgca gacctgcaga aagagctagg   1140
ttacatttat tcctgtacgc ggcaaacaac cttagttttt gctgattgcc aatggatcaa   1200
acagagaaga acatgcattt acagaggata gggacgagaa tcgtcgtcac agcatcaaga   1260
caattagttt aattctacgt ggctatcccc atgcatgaaa ttccaaaaca ggtgtcccca   1320
aaacgatcag tccaaactct cccttcccaa cttcatctat aacacttcca cctcccatcc   1380
atgcataaac ctcatttctt tctctgttct cttctgtctc ttcgcttact atcttatcaa   1440
aaaccacatt cataactaca ttgacaatca cttccagatt tgctaagcca aaatactgat   1500
atcaacaaac aagtcatcat c                                             1521
```

<210> SEQ ID NO 7
<211> LENGTH: 1086
<212> TYPE: DNA
<213> ORGANISM: Linum usitatissimum
<220> FEATURE:
<221> NAME/KEY: promoter
<222> LOCATION: (1)..(1086)
<223> OTHER INFORMATION: transcription regulating nucleotide sequence
      (derivative; putative promoter region) from Linum usitatissimum
      orthologous gene to Arabidopsis thaliana At1g73190 (alpha
      tonoplast intrinsic protein) comprising 5'-untranslated region
<220> FEATURE:
<221> NAME/KEY: TATA_signal
<222> LOCATION: (923)..(926)
<223> OTHER INFORMATION: putative TATA-box

<400> SEQUENCE: 7

```
gttttgatgg aaaaaattat ggatgcatgg tggcgttgaa agctcagcta taataagaga     60
gtacaaattt aaaagatatt tatgaagatt ttaagatatc ataatcgata aaacaagaga    120
tgaataaatg aattaggaac ggataatgca acgaaagtaa aagtacgac tcatcataac    180 ccattctaca taggggaatt tggataaact aacttcaaca ttgatttggt attcgctgta    240
atcatcattt aacctcgagt cttaacatat caattcgttt cacttcaggg gtggaaccag    300
ggggagtcgc ggtgtgagtt ctggctcaca cctctgttct gatctcgagc atcaaaatta    360
agtatatttt gtgaatttc ttgaatccgg ttatatgcaa ttttaattct gactcaacac    420
ttggcccatt acaaaattag agggaatcaa gtagatttat gggtagctaa taattatatt    480
```

```
taaaatttgg acgttttttt aactcgagtt taataatatt tgaagttttg cccttttatt    540
ttgttgttta aactaaataa tctatcaaat taaactcaat aattaccact tataactaaa    600
gttatcgaac agacgatcat gaattgggtt agacgggtta gaggttagtc gagttgaaag    660 ggaacccag cagaaagagg ttgcagacct gcagaaagag ctaggttaca tttattcctg     720
tacgcggcaa acaaccttag tttttgctga ttgccaatgg atcaaacaga gaagaacatg    780
catttacaga ggatagggac gagaatcgtc gtcacagcat caagacaatt agtttaattc    840
tacgtggcta tccccatgca tgaaattcca aaacaggtgt ccccaaaacg atcagtccaa    900
actctccctt cccaacttca tctataacac ttccacctcc catccatgca taaacctcat    960
ttctttctct gttctcttct gtctcttcgc ttactatctt atcaaaaacc acattcataa    1020
ctacattgac aatcacttcc agatttgcta agccaaaata ctgatatcaa caaacaagtc    1080
atcatc                                                                1086
```

<210> SEQ ID NO 8
<211> LENGTH: 400
<212> TYPE: DNA
<213> ORGANISM: Linum usitatissimum
<220> FEATURE:
<221> NAME/KEY: promoter
<222> LOCATION: (1)..(400)
<223> OTHER INFORMATION: transcription regulating nucleotide sequence
      (derivative; putative promoter region) from Linum usitatissimum
      orthologous gene to Arabidopsis thaliana At1g73190 (alpha
      tonoplast intrinsic protein) comprising 5'-untranslated region
<220> FEATURE:
<221> NAME/KEY: TATA_signal
<222> LOCATION: (237)..(240)
<223> OTHER INFORMATION: putative TATA-box

<400> SEQUENCE: 8

```
acctgcagaa agagctaggt tacatttatt cctgtacgcg gcaaacaacc ttagttttg     60 ctgattgcca atggatcaaa cagaagaagaa catgcattta cagaggatag ggacgagaat    120
cgtcgtcaca gcatcaagac aattagttta attctacgtg gctatcccca tgcatgaaat    180
tccaaaacag gtgtccccaa aacgatcagt ccaaactctc ccttcccaac ttcatctata    240
acacttccac ctcccatcca tgcataaacc tcatttcttt ctctgttctc ttctgtctct    300
tcgcttacta tcttatcaaa aaccacattc ataactacat tgacaatcac ttccagattt    360
gctaagccaa aatactgata tcaacaaaca agtcatcatc                           400
```

<210> SEQ ID NO 9
<211> LENGTH: 1751
<212> TYPE: DNA
<213> ORGANISM: Linum usitatissimum
<220> FEATURE:
<221> NAME/KEY: promoter
<222> LOCATION: (1)..(1751)
<223> OTHER INFORMATION: transcription regulating nucleotide sequence
      (derivative) from Linum usitatissimum orthologous gene to
      Arabidopsis thaliana At1g73190 (alpha tonoplast intrinsic protein)
      comprising 5'-untranslated region
<220> FEATURE:
<221> NAME/KEY: TATA_signal
<222> LOCATION: (1600)..(1603)
<223> OTHER INFORMATION: putative TATA-box

<400> SEQUENCE: 9

```
gaggaatggg aagaatgccg ctagattgga cggcgaggct atcaataatc aaagacatag    60
ccaaaggact agcatatctc cacaattcac tcccctccca cagagctcct cacggcaacc    120
tcaaatcctc caacgtcctc gtccaaaggg aaggactaaa ctactactgc aagctcaccg    180
```

| | |
|---|---|
| actacggcca cctcccgctc ctccaatccc aaaaggtctc cgagaggctc gccgtcggta | 240 |
| ggtcgccgga gtacggcctg gggaagcggc tgacccacaa ggccgacgtc tactgcttcg | 300 |
| gaatcgtgct gctggaagcc atcaccggta agattcccga cgatgggccg ccgccgcagc | 360 |
| agagggacaa ggaagggacg acgtcgatgg aggatctgtc cggctgggtt cggtcggcgg | 420 |
| tgaacagtga ctggtcgact gatatattgg atttggagat aatgcagtcg agggaagggc | 480 |
| acggggagat gtttcagttg accgatttgg cgttggagtg tacctgtgtg ttgccggaga | 540 |
| aacggccgaa gatggcggag gttgtgagga ggattgagga gattgagcag agaaggaaat | 600 |
| gaaatttgtt gaaagggtt tgtaaatgaa gaggaaaaga tttgatattg gatttgtttg | 660 |
| ttttgtgggg aggaagaaac agagttgtgt gattctttgt gagggatcca aattggaatt | 720 |
| tgtaacattt gccaatgtaa ttaatgagat aaaggtagaa aaccggttca tcctgttatg | 780 |
| aatcgacaag taaaaaaaag aaattaagat ggatcgaaaa aagaaaatg taaaaaaatt | 840 |
| tacggaaaaa acatcataga cgtacgaaag cgaccaaagc tccattataa tcattgaaaa | 900 |
| tatatttgaa agggatttac aatgatttca agatagttca atcgatacaa agtttgacta | 960 |
| ttcctgcttt tctgattctt tttagtgaaa ggatttagat caactaactt aaacattgat | 1020 |
| ttagtatgtg atataaccac cattcaataa cgaagtttaa cattttcgag ttccggttca | 1080 |
| ccttactttg acccttgagc aatgaaattg tatatttatg attttcttga atccggatcg | 1140 |
| gtcaatttaa ttatggctga tcagtgttgg attattgcta aagacgaaat tagaaggaaa | 1200 |
| tattgagagt ttcatgtaca tcatatgtaa aatttgaaat tttttatgat ttgagttgaa | 1260 |
| tgatacttga agatatgttc cattatttct ttattaaaac aaaatgacct atcaaattta | 1320 |
| actccattac tattcataac ctgcaaaaac ttagttggaa gagaaacacc tgcagaaaga | 1380 |
| gcgaggttgc atttattcct gtacgcggca aacaaccttagttttttttt ggtcgatcgc | 1440 |
| caatggacaa acagagaaga agatgcattt cagaggata gggacgagaa aacttcgtca | 1500 |
| cggcatcaag acaattagtt tctacgtggc tatccacatg catgaaattc caaaacaggt | 1560 |
| gtccccaaaa tgagtccaaa ctctcccttc ccaacttcat atacaacact tccacctccc | 1620 |
| atcccatgca tacacctcaa ttgtttctct gttctcttct gcctcttcgc ttaccgtctt | 1680 |
| atcaaaaacc atacttgaca atcacttcca gatttgctaa gccaaaatac tgatatcaac | 1740 |
| aagtcatcat c | 1751 |

<210> SEQ ID NO 10
<211> LENGTH: 901
<212> TYPE: DNA
<213> ORGANISM: Linum usitatissimum
<220> FEATURE:
<221> NAME/KEY: promoter
<222> LOCATION: (1)..(901)
<223> OTHER INFORMATION: transcription regulating nucleotide sequence
      (derivative; putative promoter region) from Linum usitatissimum
      orthologous gene to Arabidopsis thaliana At1g73190 (alpha
      tonoplast intrinsic protein) comprising 5'-untranslated region
<220> FEATURE:
<221> NAME/KEY: TATA_signal
<222> LOCATION: (750)..(753)
<223> OTHER INFORMATION: putative TATA-box

<400> SEQUENCE: 10

| | |
|---|---|
| acatcataga cgtacgaaag cgaccaaagc tccattataa tcattgaaaa tatatttgaa | 60 |
| agggatttac aatgatttca agatagttca atcgatacaa agtttgacta ttcctgcttt | 120 |
| tctgattctt tttagtgaaa ggatttagat caactaactt aaacattgat ttagtatgtg | 180 |
| atataaccac cattcaataa cgaagtttaa cattttcgag ttccggttca ccttactttg | 240 |

```
accccttgagc aatgaaattg tatatttatg attttcttga atccggatcg gtcaatttaa    300
ttatggctga tcagtgttgg attattgcta aagacgaaat tagaaggaaa tattgagagt    360
ttcatgtaca tcatatgtaa aatttgaaat tttttatgat ttgagttgaa tgatacttga    420
agatatgttc cattatttct ttattaaaac aaaatgacct atcaaattta actccattac    480
tattcataac ctgcaaaaac ttagttggaa gagaaacacc tgcagaaaga gcgaggttgc    540
atttattcct gtacgcggca aacaacctta gttttttttt ggtcgatcgc caatggacaa    600
acagagaaga agatgcattt acagaggata gggacgagaa aacttcgtca cggcatcaag    660
acaattagtt tctacgtggc tatccacatg catgaaattc caaaacaggt gtccccaaaa    720
tgagtccaaa ctctcccttc caacttcat atacaacact tccacctccc atcccatgca     780
tacacctcaa ttgtttctct gttctcttct gcctcttcgc ttaccgtctt atcaaaaacc    840
atacttgaca atcacttcca gatttgctaa gccaaaatac tgatatcaac aagtcatcat    900
c                                                                     901
```

```
<210> SEQ ID NO 11
<211> LENGTH: 384
<212> TYPE: DNA
<213> ORGANISM: Linum usitatissimum
<220> FEATURE:
<221> NAME/KEY: promoter
<222> LOCATION: (1)..(384)
<223> OTHER INFORMATION: transcription regulating nucleotide sequence
      (derivative; putative promoter region) from Linum usitatissimum
      orthologous gene to Arabidopsis thaliana At1g73190 (alpha
      tonoplast intrinsic protein) comprising 5'-untranslated region
<220> FEATURE:
<221> NAME/KEY: TATA_signal
<222> LOCATION: (233)..(236)
<223> OTHER INFORMATION: putative TATA-box

<400> SEQUENCE: 11
```

```
acctgcagaa agagcgaggt tgcatttatt cctgtacgcg gcaaacaacc ttagtttttt     60
tttggtcgat cgccaatgga caaacagaga agaagatgca tttacagagg atagggacga    120
gaaaacttcg tcacggcatc aagacaatta gtttctacgt ggctatccac atgcatgaaa    180
ttccaaaaca ggtgtcccca aaatgagtcc aaactctccc ttcccaactt catatacaac    240
acttccacct cccatcccat gcatacacct caattgtttc tctgttctct tctgcctctt    300
cgcttaccgt cttatcaaaa accatacttg acaatcactt ccagatttgc taagccaaaa    360
tactgatatc aacaagtcat catc                                            384
```

```
<210> SEQ ID NO 12
<211> LENGTH: 1612
<212> TYPE: DNA
<213> ORGANISM: Arabidopsis thaliana
<220> FEATURE:
<221> NAME/KEY: CDS
<222> LOCATION: (210)..(1016)
<223> OTHER INFORMATION: coding for Arabidopsis thaliana At1g73190 gene
      product (alpha tonoplast intrinsic protein)

<400> SEQUENCE: 12
```

```
gcagcacgaa caccaactct aaggaaaac atctaagtta tggttaagta attgcatgca      60
atttaaagct acgtgtccag cttaagcac tcaagtctca catctgtccc tttttacttc    120
gacttcgctt cttttggttt cttttaaact ctctctatct ctctctttct tcttcacact    180
ttgttgttaa tttcaagtgt ttgatcata atg gca aca tca gct cgt aga gca     233
                                  Met Ala Thr Ser Ala Arg Arg Ala
                                   1               5
```

| | | | | | | | | | | | | | | | | |
|---|---|---|---|---|---|---|---|---|---|---|---|---|---|---|---|---|
| tac | ggt | ttc | ggt | aga | gcc | gat | gag | gct | aca | cac | cct | gac | tcc | att | aga | 281 |
| Tyr | Gly | Phe | Gly | Arg | Ala | Asp | Glu | Ala | Thr | His | Pro | Asp | Ser | Ile | Arg | |
| | 10 | | | | 15 | | | | | 20 | | | | | | |
| gca | act | tta | gct | gag | ttt | ctc | tcc | act | ttt | gtc | ttc | gtc | ttt | gca | gct | 329 |
| Ala | Thr | Leu | Ala | Glu | Phe | Leu | Ser | Thr | Phe | Val | Phe | Val | Phe | Ala | Ala | |
| 25 | | | | | 30 | | | | | 35 | | | | | 40 | |
| gaa | ggc | tct | atc | ctc | tct | ctc | gat | aag | ttg | tat | tgg | gaa | cat | gcg | gct | 377 |
| Glu | Gly | Ser | Ile | Leu | Ser | Leu | Asp | Lys | Leu | Tyr | Trp | Glu | His | Ala | Ala | |
| | | | | 45 | | | | | 50 | | | | | 55 | | |
| cat | gcg | ggg | aca | aac | aca | cca | gga | ggg | ctg | att | tta | gta | gcg | ttg | gct | 425 |
| His | Ala | Gly | Thr | Asn | Thr | Pro | Gly | Gly | Leu | Ile | Leu | Val | Ala | Leu | Ala | |
| | | 60 | | | | | 65 | | | | | 70 | | | | |
| cat | gcg | ttt | gct | ctg | ttt | gct | gct | gtt | tca | gca | gcc | att | aat | gtc | tcc | 473 |
| His | Ala | Phe | Ala | Leu | Phe | Ala | Ala | Val | Ser | Ala | Ala | Ile | Asn | Val | Ser | |
| | | 75 | | | | | 80 | | | | | 85 | | | | |
| ggc | gga | cac | gtt | aac | ccg | gca | gtc | act | ttt | ggt | gct | ctt | gtt | gga | ggc | 521 |
| Gly | Gly | His | Val | Asn | Pro | Ala | Val | Thr | Phe | Gly | Ala | Leu | Val | Gly | Gly | |
| | 90 | | | | | 95 | | | | | 100 | | | | | |
| aga | gtt | aca | gcg | atc | cgc | gcc | atc | tac | tac | tgg | atc | gct | cag | ctt | ctt | 569 |
| Arg | Val | Thr | Ala | Ile | Arg | Ala | Ile | Tyr | Tyr | Trp | Ile | Ala | Gln | Leu | Leu | |
| 105 | | | | | 110 | | | | | 115 | | | | | 120 | |
| gga | gcc | atc | ctc | gct | tgt | ctc | ttg | tta | agg | ctc | aca | aca | aac | ggc | atg | 617 |
| Gly | Ala | Ile | Leu | Ala | Cys | Leu | Leu | Leu | Arg | Leu | Thr | Thr | Asn | Gly | Met | |
| | | | | 125 | | | | | 130 | | | | | 135 | | |
| aga | cca | gtt | ggt | ttc | cgt | cta | gca | tca | ggt | gtt | gga | gcg | gtt | aat | gga | 665 |
| Arg | Pro | Val | Gly | Phe | Arg | Leu | Ala | Ser | Gly | Val | Gly | Ala | Val | Asn | Gly | |
| | | | 140 | | | | | 145 | | | | | 150 | | | |
| ctt | gta | tta | gag | atc | att | tta | aca | ttt | ggc | tta | gtc | tac | gta | gtg | tat | 713 |
| Leu | Val | Leu | Glu | Ile | Ile | Leu | Thr | Phe | Gly | Leu | Val | Tyr | Val | Val | Tyr | |
| | | | | 155 | | | | | 160 | | | | | 165 | | |
| tcc | act | ttg | att | gat | cca | aaa | cgt | gga | agc | ctc | ggg | atc | ata | gca | ccg | 761 |
| Ser | Thr | Leu | Ile | Asp | Pro | Lys | Arg | Gly | Ser | Leu | Gly | Ile | Ile | Ala | Pro | |
| | 170 | | | | | 175 | | | | | 180 | | | | | |
| ctt | gca | atc | gga | ctc | ata | gtt | ggg | gca | aac | atc | tta | gta | ggt | gga | cca | 809 |
| Leu | Ala | Ile | Gly | Leu | Ile | Val | Gly | Ala | Asn | Ile | Leu | Val | Gly | Gly | Pro | |
| 185 | | | | | 190 | | | | | 195 | | | | | 200 | |
| ttt | tct | ggt | gct | tcg | atg | aat | cca | gct | aga | gct | ttt | ggt | cca | gcg | ttg | 857 |
| Phe | Ser | Gly | Ala | Ser | Met | Asn | Pro | Ala | Arg | Ala | Phe | Gly | Pro | Ala | Leu | |
| | | | | 205 | | | | | 210 | | | | | 215 | | |
| gtg | gga | tgg | aga | tgg | cat | gac | cac | tgg | atc | tat | tgg | gtc | gga | cca | ttc | 905 |
| Val | Gly | Trp | Arg | Trp | His | Asp | His | Trp | Ile | Tyr | Trp | Val | Gly | Pro | Phe | |
| | | | 220 | | | | | 225 | | | | | 230 | | | |
| atc | ggt | agt | gct | tta | gcc | gcc | ctt | ata | tat | gag | tac | atg | gtc | ata | ccc | 953 |
| Ile | Gly | Ser | Ala | Leu | Ala | Ala | Leu | Ile | Tyr | Glu | Tyr | Met | Val | Ile | Pro | |
| | | 235 | | | | | 240 | | | | | 245 | | | | |
| acc | gaa | cca | cct | acc | cac | cac | gca | cat | ggt | gta | cac | cag | ccc | ttg | gcc | 1001 |
| Thr | Glu | Pro | Pro | Thr | His | His | Ala | His | Gly | Val | His | Gln | Pro | Leu | Ala | |
| | 250 | | | | | 255 | | | | | 260 | | | | | |
| cct | gaa | gat | tac | tag | atggaacttt | | cctcatgtca | | ccactgcttt | | tgttcgttgt | | | | | 1056 |
| Pro | Glu | Asp | Tyr | | | | | | | | | | | | | |
| 265 | | | | | | | | | | | | | | | | |

| | |
|---|---|
| tcaagctctc tttgtctgta tgatgagatc acttgcatag atactttttt tcttatgcta | 1116 |
| ctcttatgtt gtaataataa aaaataaaga acgatttcgc aatgctcgat atcttttac | 1176 |
| caaacatgaa tacaagtacc aatacctata ctctaatcta ttgactttct tctgtctatc | 1236 |
| agttttgtgt tcgtctgaaa cctgaaaaag aaagaaagaa gcttcttctc cttgttattg | 1296 |
| tgtcaaggtc ctctcatctt ttcaacaatc tgtctacttt ttcctcaac gtgacgtttc | 1356 |
| ttctcttcaa acttctctcc cactttcttc ctaaaatcga acatcctcgc ctttgctgcc | 1416 |

```
cccattttct tccttttga atttgaatca tcctcttcac ccgaaacagt cgacatagac    1476
ggtgattgac caatacccgg aattatatct cccgcactgc ctcctctcgc tattgtatca    1536
tgcttttcgc tgctttccag cagtggagtc ttgagttctt ctaaggattt gtcactctct    1596
actaggagag ctatgg                                                    1612
```

<210> SEQ ID NO 13
<211> LENGTH: 268
<212> TYPE: PRT
<213> ORGANISM: Arabidopsis thaliana

<400> SEQUENCE: 13

```
Met Ala Thr Ser Ala Arg Arg Ala Tyr Gly Phe Gly Arg Ala Asp Glu
1               5                   10                  15

Ala Thr His Pro Asp Ser Ile Arg Ala Thr Leu Ala Glu Phe Leu Ser
            20                  25                  30

Thr Phe Val Phe Val Phe Ala Ala Glu Gly Ser Ile Leu Ser Leu Asp
        35                  40                  45

Lys Leu Tyr Trp Glu His Ala Ala His Ala Gly Thr Asn Thr Pro Gly
    50                  55                  60

Gly Leu Ile Leu Val Ala Leu Ala His Ala Phe Ala Leu Phe Ala Ala
65                  70                  75                  80

Val Ser Ala Ala Ile Asn Val Ser Gly Gly His Val Asn Pro Ala Val
                85                  90                  95

Thr Phe Gly Ala Leu Val Gly Gly Arg Val Thr Ala Ile Arg Ala Ile
            100                 105                 110

Tyr Tyr Trp Ile Ala Gln Leu Leu Gly Ala Ile Leu Ala Cys Leu Leu
        115                 120                 125

Leu Arg Leu Thr Thr Asn Gly Met Arg Pro Val Gly Phe Arg Leu Ala
    130                 135                 140

Ser Gly Val Gly Ala Val Asn Gly Leu Val Leu Glu Ile Ile Leu Thr
145                 150                 155                 160

Phe Gly Leu Val Tyr Val Val Tyr Ser Thr Leu Ile Asp Pro Lys Arg
                165                 170                 175

Gly Ser Leu Gly Ile Ile Ala Pro Leu Ala Ile Gly Leu Ile Val Gly
            180                 185                 190

Ala Asn Ile Leu Val Gly Gly Pro Phe Ser Gly Ala Ser Met Asn Pro
        195                 200                 205

Ala Arg Ala Phe Gly Pro Ala Leu Val Gly Trp Arg Trp His Asp His
    210                 215                 220

Trp Ile Tyr Trp Val Gly Pro Phe Ile Gly Ser Ala Leu Ala Ala Leu
225                 230                 235                 240

Ile Tyr Glu Tyr Met Val Ile Pro Thr Glu Pro Thr His His Ala
                245                 250                 255

His Gly Val His Gln Pro Leu Ala Pro Glu Asp Tyr
            260                 265
```

<210> SEQ ID NO 14
<211> LENGTH: 135
<212> TYPE: DNA
<213> ORGANISM: Brassica napus
<220> FEATURE:
<221> NAME/KEY: CDS
<222> LOCATION: (1)..(135)
<223> OTHER INFORMATION: coding for Brassica napus ortholog of
      Arabidopsis thaliana At73190 gene product (alpha tonoplast
      intrinsic protein)

-continued

```
<400> SEQUENCE: 14 atg gca aca tcg gct cgt aga gca tac ggt ttc ggt aga gcc gac gag      48
Met Ala Thr Ser Ala Arg Arg Ala Tyr Gly Phe Gly Arg Ala Asp Glu
1               5                   10                  15 gct aca cac cct gac tcc att aga gcc acc tta gct gag ttc ctc tcc      96
Ala Thr His Pro Asp Ser Ile Arg Ala Thr Leu Ala Glu Phe Leu Ser
            20                  25                  30 act ttt gtc ttc gtc ttt gcc gct gaa ggc tct atc ctc                 135
Thr Phe Val Phe Val Phe Ala Ala Glu Gly Ser Ile Leu
        35                  40                  45

<210> SEQ ID NO 15
<211> LENGTH: 45
<212> TYPE: PRT
<213> ORGANISM: Brassica napus

<400> SEQUENCE: 15

Met Ala Thr Ser Ala Arg Arg Ala Tyr Gly Phe Gly Arg Ala Asp Glu
1               5                   10                  15

Ala Thr His Pro Asp Ser Ile Arg Ala Thr Leu Ala Glu Phe Leu Ser
            20                  25                  30

Thr Phe Val Phe Val Phe Ala Ala Glu Gly Ser Ile Leu
        35                  40                  45

<210> SEQ ID NO 16
<211> LENGTH: 57
<212> TYPE: DNA
<213> ORGANISM: Linum usitatissimum
<220> FEATURE:
<221> NAME/KEY: CDS
<222> LOCATION: (1)..(57)
<223> OTHER INFORMATION: coding for Linum usitatissimum ortholog of
      Arabidopsis thaliana At73190 gene product (tonoplast intrinsic
      protein)

<400> SEQUENCE: 16 atg cct cga aga tac gga ttt ggg agg gcg gac gag gcc acc cac cct      48
Met Pro Arg Arg Tyr Gly Phe Gly Arg Ala Asp Glu Ala Thr His Pro
1               5                   10                  15 gat tcc ttc                                                          57
Asp Ser Phe <210> SEQ ID NO 17
<211> LENGTH: 19
<212> TYPE: PRT
<213> ORGANISM: Linum usitatissimum

<400> SEQUENCE: 17

Met Pro Arg Arg Tyr Gly Phe Gly Arg Ala Asp Glu Ala Thr His Pro
1               5                   10                  15

Asp Ser Phe

<210> SEQ ID NO 18
<211> LENGTH: 57
<212> TYPE: DNA
<213> ORGANISM: Linum usitatissimum
<220> FEATURE:
<221> NAME/KEY: CDS
<222> LOCATION: (1)..(57)
<223> OTHER INFORMATION: coding for Linum usitatissimum ortholog of
      Arabidopsis thaliana At73190 gene product (tonoplast intrinsic
      protein)

<400> SEQUENCE: 18 atg cct aga aga tac gga ttt ggg aga gcg gaa gag gcc acc cac cct      48
```

```
Met Pro Arg Arg Tyr Gly Phe Gly Arg Ala Glu Glu Ala Thr His Pro
1               5                   10                  15 gat tcc ttc                                                         57
Asp Ser Phe <210> SEQ ID NO 19
<211> LENGTH: 19
<212> TYPE: PRT
<213> ORGANISM: Linum usitatissimum

<400> SEQUENCE: 19

Met Pro Arg Arg Tyr Gly Phe Gly Arg Ala Glu Glu Ala Thr His Pro
1               5                   10                  15

Asp Ser Phe

<210> SEQ ID NO 20
<211> LENGTH: 31
<212> TYPE: DNA
<213> ORGANISM: Artificial sequence
<220> FEATURE:
<223> OTHER INFORMATION: oligonucleotide primer

<400> SEQUENCE: 20
aaaatagtcg acggttaaaa gtgaaaatca t                                  31

<210> SEQ ID NO 21
<211> LENGTH: 29
<212> TYPE: DNA
<213> ORGANISM: Artificial sequence
<220> FEATURE:
<223> OTHER INFORMATION: oligonucleotide primer

<400> SEQUENCE: 21
aaaataggat cctatgatca aacacttga                                     29

<210> SEQ ID NO 22
<211> LENGTH: 33
<212> TYPE: DNA
<213> ORGANISM: Artificial sequence
<220> FEATURE:
<223> OTHER INFORMATION: oligonucleotide primer

<400> SEQUENCE: 22
aaaataggat cctttcttat cttctcttgg tga                                33

<210> SEQ ID NO 23
<211> LENGTH: 25
<212> TYPE: DNA
<213> ORGANISM: Artificial sequence
<220> FEATURE:
<223> OTHER INFORMATION: oligonucleotide primer

<400> SEQUENCE: 23
tttttaagct tcttcagtta tgcct                                         25

<210> SEQ ID NO 24
<211> LENGTH: 26
<212> TYPE: DNA
<213> ORGANISM: Artificial sequence
<220> FEATURE:
<223> OTHER INFORMATION: oligonucleotide primer

<400> SEQUENCE: 24
tttttggatc ctataatcac aaacac                                        26
```

-continued

```
<210> SEQ ID NO 25
<211> LENGTH: 29
<212> TYPE: DNA
<213> ORGANISM: Artificial sequence
<220> FEATURE:
<223> OTHER INFORMATION: oligonucleotide primer

<400> SEQUENCE: 25
tttttaagct ttaacggctt taaagcata                                    29

<210> SEQ ID NO 26
<211> LENGTH: 32
<212> TYPE: DNA
<213> ORGANISM: Artificial sequence
<220> FEATURE:
<223> OTHER INFORMATION: oligonucleotide primer

<400> SEQUENCE: 26
tttttaagct tacatgattt gcaaatgcag tt                                32

<210> SEQ ID NO 27
<211> LENGTH: 38
<212> TYPE: DNA
<213> ORGANISM: Artificial sequence
<220> FEATURE:
<223> OTHER INFORMATION: oligonucleotide primer

<400> SEQUENCE: 27 tttttttaagc tttcgacgga tatattggat ttggagat                         38

<210> SEQ ID NO 28
<211> LENGTH: 39
<212> TYPE: DNA
<213> ORGANISM: Artificial sequence
<220> FEATURE:
<223> OTHER INFORMATION: oligonucleotide primer

<400> SEQUENCE: 28
ttttttacta gtgatgatga cttgtttgtt gatatcagt                         39

<210> SEQ ID NO 29
<211> LENGTH: 36
<212> TYPE: DNA
<213> ORGANISM: Artificial sequence
<220> FEATURE:
<223> OTHER INFORMATION: oligonucleotide primer

<400> SEQUENCE: 29 tttttttaagc ttgttttgat ggaaaaaatt atggat                           36

<210> SEQ ID NO 30
<211> LENGTH: 33
<212> TYPE: DNA
<213> ORGANISM: Artificial sequence
<220> FEATURE:
<223> OTHER INFORMATION: oligonucleotide primer

<400> SEQUENCE: 30 tttttttaagc ttacctgcag aaagagctag gtt                              33

<210> SEQ ID NO 31
<211> LENGTH: 38
<212> TYPE: DNA
<213> ORGANISM: Artificial sequence
<220> FEATURE:
<223> OTHER INFORMATION: oligonucleotide primer

<400> SEQUENCE: 31
```

-continued tttttttaagc ttgaggaatg ggaagaatgc cgctagat                  38

<210> SEQ ID NO 32
<211> LENGTH: 42
<212> TYPE: DNA
<213> ORGANISM: Artificial sequence
<220> FEATURE:
<223> OTHER INFORMATION: oligonucleotide primer

<400> SEQUENCE: 32 tttttttacta gtgatgatga cttgttgata tcagtatttt gg             42

<210> SEQ ID NO 33
<211> LENGTH: 29
<212> TYPE: DNA
<213> ORGANISM: Artificial sequence
<220> FEATURE:
<223> OTHER INFORMATION: oligonucleotide primer

<400> SEQUENCE: 33 tttttttaagc ttacatcata gacgtacga                            29

<210> SEQ ID NO 34
<211> LENGTH: 33
<212> TYPE: DNA
<213> ORGANISM: Artificial sequence
<220> FEATURE:
<223> OTHER INFORMATION: oligonucleotide primer

<400> SEQUENCE: 34 tttttttaagc ttacctgcag aaagagcgag gtt                       33

<210> SEQ ID NO 35
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 35 aaca                                                        4

<210> SEQ ID NO 36
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 36 agaa                                                        4

<210> SEQ ID NO 37
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 37 tgaa                                                        4

<210> SEQ ID NO 38
<211> LENGTH: 4
<212> TYPE: DNA
<213> ORGANISM: Artificial sequence

```
<220> FEATURE:
<223> OTHER INFORMATION: promoter motif - core sequence

<400> SEQUENCE: 38 acgt                                                                    4

<210> SEQ ID NO 39
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 39 acgt                                                                    4

<210> SEQ ID NO 40
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 40 acac                                                                    4

<210> SEQ ID NO 41
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 41 acgt                                                                    4

<210> SEQ ID NO 42
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 42 ccgt                                                                    4

<210> SEQ ID NO 43
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 43 aaag                                                                    4

<210> SEQ ID NO 44
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 44 catg                                                                    4
```

```
<210> SEQ ID NO 45
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 45 agtt                                                                      4

<210> SEQ ID NO 46
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 46 tgag                                                                      4

<210> SEQ ID NO 47
<211> LENGTH: 4
<212> TYPE: DNA
<213> ORGANISM: Artificial sequence
<220> FEATURE:
<223> OTHER INFORMATION: promoter motif - core sequence
<220> FEATURE:
<221> NAME/KEY: misc_feature
<222> LOCATION: (3)..(3)
<223> OTHER INFORMATION: n is a, c, g, or t

<400> SEQUENCE: 47 acnt                                                                      4

<210> SEQ ID NO 48
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 48 acat                                                                      4

<210> SEQ ID NO 49
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 49 acgt                                                                      4

<210> SEQ ID NO 50
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 50 atct                                                                      4

<210> SEQ ID NO 51
<211> LENGTH: 4
<212> TYPE: DNA
<213> ORGANISM: Artificial sequence
```

```
<220> FEATURE:
<223> OTHER INFORMATION: promoter motif - core sequence

<400> SEQUENCE: 51 ttga                                                                       4

<210> SEQ ID NO 52
<211> LENGTH: 4
<212> TYPE: DNA
<213> ORGANISM: Artificial sequence
<220> FEATURE:
<223> OTHER INFORMATION: promoter motif - core sequence
<220> FEATURE:
<221> NAME/KEY: misc_feature
<222> LOCATION: (3)..(3)
<223> OTHER INFORMATION: n is a, c, g, or t

<400> SEQUENCE: 52 atna                                                                       4

<210> SEQ ID NO 53
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 53 caaa                                                                       4

<210> SEQ ID NO 54
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 54 taaa                                                                       4

<210> SEQ ID NO 55
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 55 tgtc                                                                       4

<210> SEQ ID NO 56
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 56 atta                                                                       4

<210> SEQ ID NO 57
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 57
```

```
atga                                                              4

<210> SEQ ID NO 58
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 58 ccat                                                              4

<210> SEQ ID NO 59
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 59 ccgt                                                              4

<210> SEQ ID NO 60
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 60 gcat                                                              4

<210> SEQ ID NO 61
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 61 cctt                                                              4

<210> SEQ ID NO 62
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 62 tcat                                                              4

<210> SEQ ID NO 63
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 63 acgt                                                              4

<210> SEQ ID NO 64
<211> LENGTH: 4
<212> TYPE: DNA
<213> ORGANISM: Artificial sequence
```

```
<220> FEATURE:
<223> OTHER INFORMATION: promoter motif

<400> SEQUENCE: 64 ttat                                                                     4

<210> SEQ ID NO 65
<211> LENGTH: 4
<212> TYPE: DNA
<213> ORGANISM: Artificial sequence
<220> FEATURE:
<223> OTHER INFORMATION: promoter motif

<400> SEQUENCE: 65 ccat                                                                     4

<210> SEQ ID NO 66
<211> LENGTH: 4
<212> TYPE: DNA
<213> ORGANISM: Artificial sequence
<220> FEATURE:
<223> OTHER INFORMATION: promoter motif

<400> SEQUENCE: 66 tcaa                                                                     4

<210> SEQ ID NO 67
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 67 accc                                                                     4

<210> SEQ ID NO 68
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 68 aaat                                                                     4

<210> SEQ ID NO 69
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 69 aaac                                                                     4

<210> SEQ ID NO 70
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 70 aaaa                                                                     4
```

```
<210> SEQ ID NO 71
<211> LENGTH: 4
<212> TYPE: DNA
<213> ORGANISM: Artificial sequence
<220> FEATURE:
<223> OTHER INFORMATION: promoter motif

<400> SEQUENCE: 71 aaag                                                                    4

<210> SEQ ID NO 72
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 72 tttt                                                                    4

<210> SEQ ID NO 73
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 73 acgt                                                                    4

<210> SEQ ID NO 74
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 74 cgcg                                                                    4

<210> SEQ ID NO 75
<211> LENGTH: 4
<212> TYPE: DNA
<213> ORGANISM: Artificial sequence
<220> FEATURE:
<223> OTHER INFORMATION: promoter motif - core sequence

<400> SEQUENCE: 75 gtta                                                                    4

<210> SEQ ID NO 76
<211> LENGTH: 4
<212> TYPE: DNA
<213> ORGANISM: Artificial sequence
<220> FEATURE:
<223> OTHER INFORMATION: promoter motif - core sequence
<220> FEATURE:
<221> NAME/KEY: misc_feature
<222> LOCATION: (2)..(2)
<223> OTHER INFORMATION: n is a, c, g, or t

<400> SEQUENCE: 76 gngg                                                                    4

<210> SEQ ID NO 77
<211> LENGTH: 12
<212> TYPE: DNA
<213> ORGANISM: Artificial sequence
```

-continued

```
<220> FEATURE:
<223> OTHER INFORMATION: promoter motif - conserved sequence
<220> FEATURE:
<221> NAME/KEY: misc_feature
<222> LOCATION: (3)..(3)
<223> OTHER INFORMATION: n is a, c, g, or t

<400> SEQUENCE: 77
tcnaacactt ga                                                            12

<210> SEQ ID NO 78
<211> LENGTH: 13
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 78
gannnnaana gaa                                                           13

<210> SEQ ID NO 79
<211> LENGTH: 13
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 79
aannnntana gaa                                                           13

<210> SEQ ID NO 80
<211> LENGTH: 13
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (3)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 80
tannnntana gaa                                                           13

<210> SEQ ID NO 81
<211> LENGTH: 13
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
```

```
<222> LOCATION: (3)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 81
gannnntnnt gaa                                                        13

<210> SEQ ID NO 82
<211> LENGTH: 5
<212> TYPE: DNA
<213> ORGANISM: Artificial sequence
<220> FEATURE:
<223> OTHER INFORMATION: promoter motif - conserved sequence

<400> SEQUENCE: 82 cacgt                                                                  5

<210> SEQ ID NO 83
<211> LENGTH: 5
<212> TYPE: DNA
<213> ORGANISM: Artificial sequence
<220> FEATURE:
<223> OTHER INFORMATION: promoter motif - conserved sequence

<400> SEQUENCE: 83 tacgt                                                                  5

<210> SEQ ID NO 84
<211> LENGTH: 5
<212> TYPE: DNA
<213> ORGANISM: Artificial sequence
<220> FEATURE:
<223> OTHER INFORMATION: promoter motif - conserved sequence

<400> SEQUENCE: 84 cacgt                                                                  5

<210> SEQ ID NO 85
<211> LENGTH: 11
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t

<400> SEQUENCE: 85
gnacacgtag c                                                          11

<210> SEQ ID NO 86
<211> LENGTH: 9
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(4)
<223> OTHER INFORMATION: n is a, c, g, or t

<400> SEQUENCE: 86 annnacgtg                                                              9
```

```
<210> SEQ ID NO 87
<211> LENGTH: 9
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(4)
<223> OTHER INFORMATION: n is a, c, g, or t

<400> SEQUENCE: 87 tnnnacgtg                                                                    9

<210> SEQ ID NO 88
<211> LENGTH: 17
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (12)..(16)
<223> OTHER INFORMATION: n is a, c, g, or t

<400> SEQUENCE: 88
gntgccgtga cnnnnnt                                                          17

<210> SEQ ID NO 89
<211> LENGTH: 5
<212> TYPE: DNA
<213> ORGANISM: Artificial sequence
<220> FEATURE:
<223> OTHER INFORMATION: promoter motif - conserved sequence

<400> SEQUENCE: 89 aaagc                                                                        5

<210> SEQ ID NO 90
<211> LENGTH: 6
<212> TYPE: DNA
<213> ORGANISM: Artificial sequence
<220> FEATURE:
<223> OTHER INFORMATION: promoter motif - conserved sequence

<400> SEQUENCE: 90 catgca                                                                       6

<210> SEQ ID NO 91
<211> LENGTH: 8
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t

<400> SEQUENCE: 91 angagttg                                                                     8

<210> SEQ ID NO 92
<211> LENGTH: 8
<212> TYPE: DNA
<213> ORGANISM: Artificial sequence
```

```
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t

<400> SEQUENCE: 92 tngagttg                                                                  8

<210> SEQ ID NO 93
<211> LENGTH: 8
<212> TYPE: DNA
<213> ORGANISM: Artificial sequence
<220> FEATURE:
<223> OTHER INFORMATION: promoter motif - conserved sequence

<400> SEQUENCE: 93 gtgagtta                                                                  8

<210> SEQ ID NO 94
<211> LENGTH: 8
<212> TYPE: DNA
<213> ORGANISM: Artificial sequence
<220> FEATURE:
<223> OTHER INFORMATION: promoter motif

<400> SEQUENCE: 94 ctgagtca                                                                  8

<210> SEQ ID NO 95
<211> LENGTH: 8
<212> TYPE: DNA
<213> ORGANISM: Artificial sequence
<220> FEATURE:
<223> OTHER INFORMATION: promoter motif

<400> SEQUENCE: 95 ttgagtca                                                                  8

<210> SEQ ID NO 96
<211> LENGTH: 8
<212> TYPE: DNA
<213> ORGANISM: Artificial sequence
<220> FEATURE:
<223> OTHER INFORMATION: promoter motif

<400> SEQUENCE: 96 atgagtcg                                                                  8

<210> SEQ ID NO 97
<211> LENGTH: 10
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 97
``` gnacntgnnt					10

<210> SEQ ID NO 98
<211> LENGTH: 10
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 98 tnacntgnnt					10

<210> SEQ ID NO 99
<211> LENGTH: 10
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 99 tnacntannt					10

<210> SEQ ID NO 100
<211> LENGTH: 10
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 100 cnacntgnnt					10

<210> SEQ ID NO 101
<211> LENGTH: 14
<212> TYPE: DNA
<213> ORGANISM: Artificial sequence

```
<220> FEATURE:
<223> OTHER INFORMATION: promoter motif - conserved sequence
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 101
gtacnngnnn acat                                                           14

<210> SEQ ID NO 102
<211> LENGTH: 14
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 102
atcannannn acat                                                           14

<210> SEQ ID NO 103
<211> LENGTH: 14
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 103
ttcanncnnn acat                                                           14

<210> SEQ ID NO 104
<211> LENGTH: 14
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (5)..(6)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 104
gtccnngnnn acgt                                                           14

<210> SEQ ID NO 105
<211> LENGTH: 11
<212> TYPE: DNA
<213> ORGANISM: Artificial sequence
```

```
<220> FEATURE:
<223> OTHER INFORMATION: promoter motif - conserved sequence

<400> SEQUENCE: 105
ttatctactt g                                                          11

<210> SEQ ID NO 106
<211> LENGTH: 5
<212> TYPE: DNA
<213> ORGANISM: Artificial sequence
<220> FEATURE:
<223> OTHER INFORMATION: promoter motif - conserved sequence

<400> SEQUENCE: 106 ttgac                                                                  5

<210> SEQ ID NO 107
<211> LENGTH: 7
<212> TYPE: DNA
<213> ORGANISM: Artificial sequence
<220> FEATURE:
<223> OTHER INFORMATION: promoter motif - conserved sequence

<400> SEQUENCE: 107 aataatt                                                                7

<210> SEQ ID NO 108
<211> LENGTH: 7
<212> TYPE: DNA
<213> ORGANISM: Artificial sequence
<220> FEATURE:
<223> OTHER INFORMATION: promoter motif - conserved sequence

<400> SEQUENCE: 108 aattatt                                                                7

<210> SEQ ID NO 109
<211> LENGTH: 7
<212> TYPE: DNA
<213> ORGANISM: Artificial sequence
<220> FEATURE:
<223> OTHER INFORMATION: promoter motif - conserved sequence

<400> SEQUENCE: 109 aatcatt                                                                7

<210> SEQ ID NO 110
<211> LENGTH: 7
<212> TYPE: DNA
<213> ORGANISM: Artificial sequence
<220> FEATURE:
<223> OTHER INFORMATION: promoter motif - conserved sequence

<400> SEQUENCE: 110 aatgatt                                                                7

<210> SEQ ID NO 111
<211> LENGTH: 9
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (5)..(5)
<223> OTHER INFORMATION: n is a, c, g, or t

<400> SEQUENCE: 111
```

```
caaanaatt                                                            9

<210> SEQ ID NO 112
<211> LENGTH: 9
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (5)..(5)
<223> OTHER INFORMATION: n is a, c, g, or t

<400> SEQUENCE: 112 taaanaatc                                                            9

<210> SEQ ID NO 113
<211> LENGTH: 9
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (5)..(5)
<223> OTHER INFORMATION: n is a, c, g, or t

<400> SEQUENCE: 113 taaanaatt                                                            9

<210> SEQ ID NO 114
<211> LENGTH: 6
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (5)..(5)
<223> OTHER INFORMATION: n is a, c, g, or t

<400> SEQUENCE: 114 tgtcnc                                                               6

<210> SEQ ID NO 115
<211> LENGTH: 10
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 115 attaananna                                                          10

<210> SEQ ID NO 116
<211> LENGTH: 10
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
```

```
<222> LOCATION: (6)..(6)
<223> OTHER INFORMATION: n is a, c, g, or t
<220> FEATURE:
<221> NAME/KEY: misc_feature
<222> LOCATION: (8)..(9)
<223> OTHER INFORMATION: n is a, c, g, or t

<400> SEQUENCE: 116 atgaananna                                                                  10

<210> SEQ ID NO 117
<211> LENGTH: 25
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 117
acttaaccat gagntnccaa caaag                                                 25

<210> SEQ ID NO 118
<211> LENGTH: 25
<212> TYPE: DNA
<213> ORGANISM: Artificial sequence
<220> FEATURE:
<223> OTHER INFORMATION: promoter motif
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 118
gaataaccat ggancnttag taagg                                                 25

<210> SEQ ID NO 119
<211> LENGTH: 25
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 119
agataaccgt tgangnacaa tagtg                                                 25

<210> SEQ ID NO 120
<211> LENGTH: 25
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
```

```
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 120
ccacatgcat gaantnccaa aacag                                              25

<210> SEQ ID NO 121
<211> LENGTH: 25
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (14)..(14)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 121
ctaaatcctt tcantnaaaa gaatc                                              25

<210> SEQ ID NO 122
<211> LENGTH: 15
<212> TYPE: DNA
<213> ORGANISM: Artificial sequence
<220> FEATURE:
<223> OTHER INFORMATION: promoter motif - conserved sequence

<400> SEQUENCE: 122
tcattacaga gagat                                                         15

<210> SEQ ID NO 123
<211> LENGTH: 9
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (3)..(4)
<223> OTHER INFORMATION: n is a, c, g, or t

<400> SEQUENCE: 123 canntcatc                                                                9

<210> SEQ ID NO 124
<211> LENGTH: 15
<212> TYPE: DNA
<213> ORGANISM: Artificial sequence
<220> FEATURE:
<223> OTHER INFORMATION: promoter motif - conserved sequence

<400> SEQUENCE: 124
tcattcaact caaat                                                         15

<210> SEQ ID NO 125
<211> LENGTH: 15
<212> TYPE: DNA
<213> ORGANISM: Artificial sequence
<220> FEATURE:
<223> OTHER INFORMATION: promoter motif

<400> SEQUENCE: 125
```

```
tcattgaaaa tatat                                            15

<210> SEQ ID NO 126
<211> LENGTH: 15
<212> TYPE: DNA
<213> ORGANISM: Artificial sequence
<220> FEATURE:
<223> OTHER INFORMATION: promoter motif

<400> SEQUENCE: 126
tcatttaacc tcgag                                            15

<210> SEQ ID NO 127
<211> LENGTH: 5
<212> TYPE: DNA
<213> ORGANISM: Artificial sequence
<220> FEATURE:
<223> OTHER INFORMATION: promoter motif - conserved sequence

<400> SEQUENCE: 127 acgta                                                        5

<210> SEQ ID NO 128
<211> LENGTH: 15
<212> TYPE: DNA
<213> ORGANISM: Artificial sequence
<220> FEATURE:
<223> OTHER INFORMATION: promoter motif

<400> SEQUENCE: 128
ttatttcaag aagat                                            15

<210> SEQ ID NO 129
<211> LENGTH: 15
<212> TYPE: DNA
<213> ORGANISM: Artificial sequence
<220> FEATURE:
<223> OTHER INFORMATION: promoter motif

<400> SEQUENCE: 129
ccattctaca taggg                                            15

<210> SEQ ID NO 130
<211> LENGTH: 15
<212> TYPE: DNA
<213> ORGANISM: Artificial sequence
<220> FEATURE:
<223> OTHER INFORMATION: promoter motif

<400> SEQUENCE: 130
tcaatccatc ttaat                                            15

<210> SEQ ID NO 131
<211> LENGTH: 9
<212> TYPE: DNA
<213> ORGANISM: Artificial sequence
<220> FEATURE:
<223> OTHER INFORMATION: promoter motif

<400> SEQUENCE: 131 catttcaac                                                    9

<210> SEQ ID NO 132
<211> LENGTH: 8
<212> TYPE: DNA
<213> ORGANISM: Artificial sequence
```

```
<220> FEATURE:
<223> OTHER INFORMATION: promoter motif - conserved sequence
<220> FEATURE:
<221> NAME/KEY: misc_feature
<222> LOCATION: (7)..(7)
<223> OTHER INFORMATION: n is a, c, g, or t

<400> SEQUENCE: 132 aacccanc                                                                        8

<210> SEQ ID NO 133
<211> LENGTH: 8
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (7)..(7)
<223> OTHER INFORMATION: n is a, c, g, or t

<400> SEQUENCE: 133 aacccant                                                                        8

<210> SEQ ID NO 134
<211> LENGTH: 16
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t

<400> SEQUENCE: 134
tgnnntgcaa atnnng                                                              16

<210> SEQ ID NO 135
<211> LENGTH: 16
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t

<400> SEQUENCE: 135
tgnnntttaa acnnna                                                              16

<210> SEQ ID NO 136
<211> LENGTH: 16
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
```

```
<222> LOCATION: (13)..(15)
<223> OTHER INFORMATION: n is a, c, g, or t

<400> SEQUENCE: 136
tcnnntgtaa aannng                                                    16

<210> SEQ ID NO 137
<211> LENGTH: 16
<212> TYPE: DNA
<213> ORGANISM: Artificial sequence
<220> FEATURE:
<223> OTHER INFORMATION: promoter motif
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t

<400> SEQUENCE: 137
tgnnntgaaa aannna                                                    16

<210> SEQ ID NO 138
<211> LENGTH: 16
<212> TYPE: DNA
<213> ORGANISM: Artificial sequence
<220> FEATURE:
<223> OTHER INFORMATION: promoter motif
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t

<400> SEQUENCE: 138
ggnnntgaaa agnnnc                                                    16

<210> SEQ ID NO 139
<211> LENGTH: 16
<212> TYPE: DNA
<213> ORGANISM: Artificial sequence
<220> FEATURE:
<223> OTHER INFORMATION: promoter motif
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (13)..(15)
<223> OTHER INFORMATION: n is a, c, g, or t

<400> SEQUENCE: 139
tgnnnttgaa agnnna                                                    16

<210> SEQ ID NO 140
<211> LENGTH: 6
<212> TYPE: DNA
<213> ORGANISM: Artificial sequence
<220> FEATURE:
<223> OTHER INFORMATION: promoter motif - conserved sequence

<400> SEQUENCE: 140 tttttg                                                                6
```

```
<210> SEQ ID NO 141
<211> LENGTH: 7
<212> TYPE: DNA
<213> ORGANISM: Artificial sequence
<220> FEATURE:
<223> OTHER INFORMATION: promoter motif - conserved sequence

<400> SEQUENCE: 141 acgtggc                                                                       7

<210> SEQ ID NO 142
<211> LENGTH: 6
<212> TYPE: DNA
<213> ORGANISM: Artificial sequence
<220> FEATURE:
<223> OTHER INFORMATION: promoter motif - conserved sequence

<400> SEQUENCE: 142 cgcgta                                                                        6

<210> SEQ ID NO 143
<211> LENGTH: 11
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(3)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t

<400> SEQUENCE: 143
tnngttacnn t                                                                 11

<210> SEQ ID NO 144
<211> LENGTH: 13
<212> TYPE: DNA
<213> ORGANISM: Artificial sequence
<220> FEATURE:
<223> OTHER INFORMATION: promoter motif - conserved sequence
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t
<220> FEATURE:
<221> NAME/KEY: misc_feature
<222> LOCATION: (10)..(12)
<223> OTHER INFORMATION: n is a, c, g, or t

<400> SEQUENCE: 144
gnggtnngtn nng                                                               13

<210> SEQ ID NO 145
<211> LENGTH: 19
<212> TYPE: DNA
<213> ORGANISM: Artificial sequence
<220> FEATURE:
<223> OTHER INFORMATION: promoter motif - matrix

<400> SEQUENCE: 145
atgatcaaac acttgaaat                                                         19
```

```
<210> SEQ ID NO 146
<211> LENGTH: 15
<212> TYPE: DNA
<213> ORGANISM: Artificial sequence
<220> FEATURE:
<223> OTHER INFORMATION: promoter motif - matrix

<400> SEQUENCE: 146
agaaaccaaa agaag                                                    15

<210> SEQ ID NO 147
<211> LENGTH: 15
<212> TYPE: DNA
<213> ORGANISM: Artificial sequence
<220> FEATURE:
<223> OTHER INFORMATION: promoter motif - matrix

<400> SEQUENCE: 147
agaatttaaa agaag                                                    15

<210> SEQ ID NO 148
<211> LENGTH: 15
<212> TYPE: DNA
<213> ORGANISM: Artificial sequence
<220> FEATURE:
<223> OTHER INFORMATION: promoter motif - matrix

<400> SEQUENCE: 148
caaatcataa agaac                                                    15

<210> SEQ ID NO 149
<211> LENGTH: 15
<212> TYPE: DNA
<213> ORGANISM: Artificial sequence
<220> FEATURE:
<223> OTHER INFORMATION: promoter motif - matrix

<400> SEQUENCE: 149
ataatcatag agaag                                                    15

<210> SEQ ID NO 150
<211> LENGTH: 15
<212> TYPE: DNA
<213> ORGANISM: Artificial sequence
<220> FEATURE:
<223> OTHER INFORMATION: promoter motif - matrix

<400> SEQUENCE: 150
tgaactatct tgaaa                                                    15

<210> SEQ ID NO 151
<211> LENGTH: 17
<212> TYPE: DNA
<213> ORGANISM: Artificial sequence
<220> FEATURE:
<223> OTHER INFORMATION: promoter motif - matrix

<400> SEQUENCE: 151
gctggacacg tagcttt                                                  17

<210> SEQ ID NO 152
<211> LENGTH: 17
<212> TYPE: DNA
<213> ORGANISM: Artificial sequence
<220> FEATURE:
<223> OTHER INFORMATION: promoter motif - matrix

<400> SEQUENCE: 152
```
gatggacacg tagcttg                                                          17

<210> SEQ ID NO 153
<211> LENGTH: 21
<212> TYPE: DNA
<213> ORGANISM: Artificial sequence
<220> FEATURE:
<223> OTHER INFORMATION: promoter motif - matrix

<400> SEQUENCE: 153
ttaaagctac gtgtccagct t                                                     21

<210> SEQ ID NO 154
<211> LENGTH: 21
<212> TYPE: DNA
<213> ORGANISM: Artificial sequence
<220> FEATURE:
<223> OTHER INFORMATION: promoter motif - matrix

<400> SEQUENCE: 154
ttcaagctac gtgtccatct c                                                     21

<210> SEQ ID NO 155
<211> LENGTH: 21
<212> TYPE: DNA
<213> ORGANISM: Artificial sequence
<220> FEATURE:
<223> OTHER INFORMATION: promoter motif - matrix

<400> SEQUENCE: 155
ttcaagctac gtgtccatct c                                                     21

<210> SEQ ID NO 156
<211> LENGTH: 21
<212> TYPE: DNA
<213> ORGANISM: Artificial sequence
<220> FEATURE:
<223> OTHER INFORMATION: promoter motif - matrix

<400> SEQUENCE: 156
agctggacac gtagctttaa a                                                     21

<210> SEQ ID NO 157
<211> LENGTH: 21
<212> TYPE: DNA
<213> ORGANISM: Artificial sequence
<220> FEATURE:
<223> OTHER INFORMATION: promoter motif - matrix

<400> SEQUENCE: 157
agatggacac gtagcttgaa a                                                     21

<210> SEQ ID NO 158
<211> LENGTH: 21
<212> TYPE: DNA
<213> ORGANISM: Artificial sequence
<220> FEATURE:
<223> OTHER INFORMATION: promoter motif - matrix

<400> SEQUENCE: 158
ggatagccac gtagaattaa a                                                     21

<210> SEQ ID NO 159
<211> LENGTH: 21
<212> TYPE: DNA
<213> ORGANISM: Artificial sequence

```
<220> FEATURE:
<223> OTHER INFORMATION: promoter motif - matrix

<400> SEQUENCE: 159
ggatagccac gtagaaacta a                                              21

<210> SEQ ID NO 160
<211> LENGTH: 27
<212> TYPE: DNA
<213> ORGANISM: Artificial sequence
<220> FEATURE:
<223> OTHER INFORMATION: promoter motif - matrix

<400> SEQUENCE: 160
cttaagctgg acacgtagct ttaaatt                                        27

<210> SEQ ID NO 161
<211> LENGTH: 27
<212> TYPE: DNA
<213> ORGANISM: Artificial sequence
<220> FEATURE:
<223> OTHER INFORMATION: promoter motif - matrix

<400> SEQUENCE: 161
cttgagatgg acacgtagct tgaaact                                        27

<210> SEQ ID NO 162
<211> LENGTH: 27
<212> TYPE: DNA
<213> ORGANISM: Artificial sequence
<220> FEATURE:
<223> OTHER INFORMATION: promoter motif - matrix

<400> SEQUENCE: 162
caatttaaag ctacgtgtcc agcttaa                                        27

<210> SEQ ID NO 163
<211> LENGTH: 27
<212> TYPE: DNA
<213> ORGANISM: Artificial sequence
<220> FEATURE:
<223> OTHER INFORMATION: promoter motif - matrix

<400> SEQUENCE: 163
cagtttcaag ctacgtgtcc atctcaa                                        27

<210> SEQ ID NO 164
<211> LENGTH: 27
<212> TYPE: DNA
<213> ORGANISM: Artificial sequence
<220> FEATURE:
<223> OTHER INFORMATION: promoter motif - matrix

<400> SEQUENCE: 164
tagtttaatt ctacgtggct atcccca                                        27

<210> SEQ ID NO 165
<211> LENGTH: 27
<212> TYPE: DNA
<213> ORGANISM: Artificial sequence
<220> FEATURE:
<223> OTHER INFORMATION: promoter motif - matrix

<400> SEQUENCE: 165
caattagttt ctacgtggct atccaca                                        27
```

```
<210> SEQ ID NO 166
<211> LENGTH: 27
<212> TYPE: DNA
<213> ORGANISM: Artificial sequence
<220> FEATURE:
<223> OTHER INFORMATION: promoter motif - matrix

<400> SEQUENCE: 166
attgtcttga tgccgtgacg aagtttt                                          27

<210> SEQ ID NO 167
<211> LENGTH: 17
<212> TYPE: DNA
<213> ORGANISM: Artificial sequence
<220> FEATURE:
<223> OTHER INFORMATION: promoter motif - matrix

<400> SEQUENCE: 167
tgcaatttaa agctacg                                                     17

<210> SEQ ID NO 168
<211> LENGTH: 17
<212> TYPE: DNA
<213> ORGANISM: Artificial sequence
<220> FEATURE:
<223> OTHER INFORMATION: promoter motif - matrix

<400> SEQUENCE: 168
gaatcagaaa agcagga                                                     17

<210> SEQ ID NO 169
<211> LENGTH: 27
<212> TYPE: DNA
<213> ORGANISM: Artificial sequence
<220> FEATURE:
<223> OTHER INFORMATION: promoter motif - matrix

<400> SEQUENCE: 169
agtaattgca tgcaatttaa agctacg                                          27

<210> SEQ ID NO 170
<211> LENGTH: 27
<212> TYPE: DNA
<213> ORGANISM: Artificial sequence
<220> FEATURE:
<223> OTHER INFORMATION: promoter motif - matrix

<400> SEQUENCE: 170
ttaaattgca tgcaattact taaccat                                          27

<210> SEQ ID NO 171
<211> LENGTH: 27
<212> TYPE: DNA
<213> ORGANISM: Artificial sequence
<220> FEATURE:
<223> OTHER INFORMATION: promoter motif - matrix

<400> SEQUENCE: 171
ttggcacaca tgcatgctta gtcaaca                                          27

<210> SEQ ID NO 172
<211> LENGTH: 27
<212> TYPE: DNA
<213> ORGANISM: Artificial sequence
<220> FEATURE:
<223> OTHER INFORMATION: promoter motif - matrix

<400> SEQUENCE: 172
```
tgactaagca tgcatgtgtg ccaagta                                              27

<210> SEQ ID NO 173
<211> LENGTH: 27
<212> TYPE: DNA
<213> ORGANISM: Artificial sequence
<220> FEATURE:
<223> OTHER INFORMATION: promoter motif - matrix

<400> SEQUENCE: 173
gtaacatgca tgcagtttca agctacg                                              27

<210> SEQ ID NO 174
<211> LENGTH: 27
<212> TYPE: DNA
<213> ORGANISM: Artificial sequence
<220> FEATURE:
<223> OTHER INFORMATION: promoter motif - matrix

<400> SEQUENCE: 174
ttaagtaaca tgcatgcagt ttcaagc                                              27

<210> SEQ ID NO 175
<211> LENGTH: 27
<212> TYPE: DNA
<213> ORGANISM: Artificial sequence
<220> FEATURE:
<223> OTHER INFORMATION: promoter motif - matrix

<400> SEQUENCE: 175
tgaaactgca tgcatgttac ttaacca                                              27

<210> SEQ ID NO 176
<211> LENGTH: 27
<212> TYPE: DNA
<213> ORGANISM: Artificial sequence
<220> FEATURE:
<223> OTHER INFORMATION: promoter motif - matrix

<400> SEQUENCE: 176
gttaagtaca tgcataaagt ttaagga                                              27

<210> SEQ ID NO 177
<211> LENGTH: 27
<212> TYPE: DNA
<213> ORGANISM: Artificial sequence
<220> FEATURE:
<223> OTHER INFORMATION: promoter motif - matrix

<400> SEQUENCE: 177
ctcccatcca tgcataaacc tcatttc                                              27

<210> SEQ ID NO 178
<211> LENGTH: 27
<212> TYPE: DNA
<213> ORGANISM: Artificial sequence
<220> FEATURE:
<223> OTHER INFORMATION: promoter motif - matrix

<400> SEQUENCE: 178
gctatcccca tgcatgaaat tccaaaa                                              27

<210> SEQ ID NO 179
<211> LENGTH: 27
<212> TYPE: DNA
<213> ORGANISM: Artificial sequence

```
<220> FEATURE:
<223> OTHER INFORMATION: promoter motif - matrix

<400> SEQUENCE: 179
tggaatttca tgcatgggga tagccac                                              27

<210> SEQ ID NO 180
<211> LENGTH: 27
<212> TYPE: DNA
<213> ORGANISM: Artificial sequence
<220> FEATURE:
<223> OTHER INFORMATION: promoter motif - matrix

<400> SEQUENCE: 180
gagaagaaca tgcatttaca gaggata                                              27

<210> SEQ ID NO 181
<211> LENGTH: 27
<212> TYPE: DNA
<213> ORGANISM: Artificial sequence
<220> FEATURE:
<223> OTHER INFORMATION: promoter motif - matrix

<400> SEQUENCE: 181
tcccatccca tgcatacacc tcaattg                                              27

<210> SEQ ID NO 182
<211> LENGTH: 27
<212> TYPE: DNA
<213> ORGANISM: Artificial sequence
<220> FEATURE:
<223> OTHER INFORMATION: promoter motif - matrix

<400> SEQUENCE: 182
gctatccaca tgcatgaaat tccaaaa                                              27

<210> SEQ ID NO 183
<211> LENGTH: 27
<212> TYPE: DNA
<213> ORGANISM: Artificial sequence
<220> FEATURE:
<223> OTHER INFORMATION: promoter motif - matrix

<400> SEQUENCE: 183
tggaatttca tgcatgtgga tagccac                                              27

<210> SEQ ID NO 184
<211> LENGTH: 27
<212> TYPE: DNA
<213> ORGANISM: Artificial sequence
<220> FEATURE:
<223> OTHER INFORMATION: promoter motif

<400> SEQUENCE: 184
aacgccacca tgcatccata atttttt                                              27

<210> SEQ ID NO 185
<211> LENGTH: 15
<212> TYPE: DNA
<213> ORGANISM: Artificial sequence
<220> FEATURE:
<223> OTHER INFORMATION: promoter motif - matrix

<400> SEQUENCE: 185
ccttaagagt tggtg                                                           15
```

```
<210> SEQ ID NO 186
<211> LENGTH: 15
<212> TYPE: DNA
<213> ORGANISM: Artificial sequence
<220> FEATURE:
<223> OTHER INFORMATION: promoter motif - matrix

<400> SEQUENCE: 186
cttctagagt tggga                                              15

<210> SEQ ID NO 187
<211> LENGTH: 15
<212> TYPE: DNA
<213> ORGANISM: Artificial sequence
<220> FEATURE:
<223> OTHER INFORMATION: promoter motif - matrix

<400> SEQUENCE: 187
ttagtcgagt tgaaa                                              15

<210> SEQ ID NO 188
<211> LENGTH: 17
<212> TYPE: DNA
<213> ORGANISM: Artificial sequence
<220> FEATURE:
<223> OTHER INFORMATION: promoter motif - matrix

<400> SEQUENCE: 188
tcttggtgag ttatttt                                            17

<210> SEQ ID NO 189
<211> LENGTH: 17
<212> TYPE: DNA
<213> ORGANISM: Artificial sequence
<220> FEATURE:
<223> OTHER INFORMATION: promoter motif

<400> SEQUENCE: 189
atgaactgag tcactgt                                            17

<210> SEQ ID NO 190
<211> LENGTH: 17
<212> TYPE: DNA
<213> ORGANISM: Artificial sequence
<220> FEATURE:
<223> OTHER INFORMATION: promoter motif

<400> SEQUENCE: 190
aagtgttgag tcagaat                                            17

<210> SEQ ID NO 191
<211> LENGTH: 17
<212> TYPE: DNA
<213> ORGANISM: Artificial sequence
<220> FEATURE:
<223> OTHER INFORMATION: promoter motif

<400> SEQUENCE: 191
ttatgatgag tcgtact                                            17

<210> SEQ ID NO 192
<211> LENGTH: 17
<212> TYPE: DNA
<213> ORGANISM: Artificial sequence
<220> FEATURE:
<223> OTHER INFORMATION: promoter motif - matrix

<400> SEQUENCE: 192
```

```
cacgaggaca tgtatta                                                      17

<210> SEQ ID NO 193
<211> LENGTH: 17
<212> TYPE: DNA
<213> ORGANISM: Artificial sequence
<220> FEATURE:
<223> OTHER INFORMATION: promoter motif - matrix

<400> SEQUENCE: 193
gttaagtaca tgcataa                                                      17

<210> SEQ ID NO 194
<211> LENGTH: 17
<212> TYPE: DNA
<213> ORGANISM: Artificial sequence
<220> FEATURE:
<223> OTHER INFORMATION: promoter motif - matrix

<400> SEQUENCE: 194
ttaagtaaca tgcatgc                                                      17

<210> SEQ ID NO 195
<211> LENGTH: 17
<212> TYPE: DNA
<213> ORGANISM: Artificial sequence
<220> FEATURE:
<223> OTHER INFORMATION: promoter motif - matrix

<400> SEQUENCE: 195
gatgatgact tgtttgt                                                      17

<210> SEQ ID NO 196
<211> LENGTH: 17
<212> TYPE: DNA
<213> ORGANISM: Artificial sequence
<220> FEATURE:
<223> OTHER INFORMATION: promoter motif - matrix

<400> SEQUENCE: 196
gaaaatgaca tacatgg                                                      17

<210> SEQ ID NO 197
<211> LENGTH: 17
<212> TYPE: DNA
<213> ORGANISM: Artificial sequence
<220> FEATURE:
<223> OTHER INFORMATION: promoter motif - matrix

<400> SEQUENCE: 197
taattctacg tggctat                                                      17

<210> SEQ ID NO 198
<211> LENGTH: 17
<212> TYPE: DNA
<213> ORGANISM: Artificial sequence
<220> FEATURE:
<223> OTHER INFORMATION: promoter motif - matrix

<400> SEQUENCE: 198
gctatccaca tgcatga                                                      17

<210> SEQ ID NO 199
<211> LENGTH: 17
<212> TYPE: DNA
<213> ORGANISM: Artificial sequence
```

```
<220> FEATURE:
<223> OTHER INFORMATION: promoter motif - matrix

<400> SEQUENCE: 199
agtttctacg tggctat                                                  17

<210> SEQ ID NO 200
<211> LENGTH: 21
<212> TYPE: DNA
<213> ORGANISM: Artificial sequence
<220> FEATURE:
<223> OTHER INFORMATION: promoter motif - matrix

<400> SEQUENCE: 200
acacgtacac gaggacatgt a                                             21

<210> SEQ ID NO 201
<211> LENGTH: 21
<212> TYPE: DNA
<213> ORGANISM: Artificial sequence
<220> FEATURE:
<223> OTHER INFORMATION: promoter motif - matrix

<400> SEQUENCE: 201
tcaaatcata aagaacatat t                                             21

<210> SEQ ID NO 202
<211> LENGTH: 21
<212> TYPE: DNA
<213> ORGANISM: Artificial sequence
<220> FEATURE:
<223> OTHER INFORMATION: promoter motif - matrix

<400> SEQUENCE: 202
ttagttcaag cataacatgt g                                             21

<210> SEQ ID NO 203
<211> LENGTH: 21
<212> TYPE: DNA
<213> ORGANISM: Artificial sequence
<220> FEATURE:
<223> OTHER INFORMATION: promoter motif - matrix

<400> SEQUENCE: 203
acatgtcctc gtgtacgtgt t                                             21

<210> SEQ ID NO 204
<211> LENGTH: 11
<212> TYPE: DNA
<213> ORGANISM: Artificial sequence
<220> FEATURE:
<223> OTHER INFORMATION: promoter motif - matrix

<400> SEQUENCE: 204
ttatctactt g                                                        11

<210> SEQ ID NO 205
<211> LENGTH: 17
<212> TYPE: DNA
<213> ORGANISM: Artificial sequence
<220> FEATURE:
<223> OTHER INFORMATION: promoter motif - matrix

<400> SEQUENCE: 205
aattattgac ttgcaga                                                  17
```

```
<210> SEQ ID NO 206
<211> LENGTH: 17
<212> TYPE: DNA
<213> ORGANISM: Artificial sequence
<220> FEATURE:
<223> OTHER INFORMATION: promoter motif - matrix

<400> SEQUENCE: 206
ttactttgac ccttgag                                                  17

<210> SEQ ID NO 207
<211> LENGTH: 17
<212> TYPE: DNA
<213> ORGANISM: Artificial sequence
<220> FEATURE:
<223> OTHER INFORMATION: promoter motif - matrix

<400> SEQUENCE: 207
aaagtttgac tattcct                                                  17

<210> SEQ ID NO 208
<211> LENGTH: 13
<212> TYPE: DNA
<213> ORGANISM: Artificial sequence
<220> FEATURE:
<223> OTHER INFORMATION: promoter motif - matrix

<400> SEQUENCE: 208
tcaataatta ttt                                                      13

<210> SEQ ID NO 209
<211> LENGTH: 13
<212> TYPE: DNA
<213> ORGANISM: Artificial sequence
<220> FEATURE:
<223> OTHER INFORMATION: promoter motif - matrix

<400> SEQUENCE: 209
gaaataatta ttg                                                      13

<210> SEQ ID NO 210
<211> LENGTH: 13
<212> TYPE: DNA
<213> ORGANISM: Artificial sequence
<220> FEATURE:
<223> OTHER INFORMATION: promoter motif - matrix

<400> SEQUENCE: 210
ataattattt ctt                                                      13

<210> SEQ ID NO 211
<211> LENGTH: 13
<212> TYPE: DNA
<213> ORGANISM: Artificial sequence
<220> FEATURE:
<223> OTHER INFORMATION: promoter motif - matrix

<400> SEQUENCE: 211
aaaatcattt gtc                                                      13

<210> SEQ ID NO 212
<211> LENGTH: 13
<212> TYPE: DNA
<213> ORGANISM: Artificial sequence
<220> FEATURE:
<223> OTHER INFORMATION: promoter motif - matrix

<400> SEQUENCE: 212
```

```
caaatgattt tca                                                          13

<210> SEQ ID NO 213
<211> LENGTH: 15
<212> TYPE: DNA
<213> ORGANISM: Artificial sequence
<220> FEATURE:
<223> OTHER INFORMATION: promoter motif - matrix

<400> SEQUENCE: 213
gtccaaaaaa ttacc                                                        15

<210> SEQ ID NO 214
<211> LENGTH: 15
<212> TYPE: DNA
<213> ORGANISM: Artificial sequence
<220> FEATURE:
<223> OTHER INFORMATION: promoter motif - matrix

<400> SEQUENCE: 214
aactaaataa tctat                                                        15

<210> SEQ ID NO 215
<211> LENGTH: 15
<212> TYPE: DNA
<213> ORGANISM: Artificial sequence
<220> FEATURE:
<223> OTHER INFORMATION: promoter motif - matrix

<400> SEQUENCE: 215
tcataaaaaa tttca                                                        15

<210> SEQ ID NO 216
<211> LENGTH: 13
<212> TYPE: DNA
<213> ORGANISM: Artificial sequence
<220> FEATURE:
<223> OTHER INFORMATION: promoter motif - matrix

<400> SEQUENCE: 216
atttgtcaca tgt                                                          13

<210> SEQ ID NO 217
<211> LENGTH: 15
<212> TYPE: DNA
<213> ORGANISM: Artificial sequence
<220> FEATURE:
<223> OTHER INFORMATION: promoter motif - matrix

<400> SEQUENCE: 217
acggattaag acaaa                                                        15

<210> SEQ ID NO 218
<211> LENGTH: 15
<212> TYPE: DNA
<213> ORGANISM: Artificial sequence
<220> FEATURE:
<223> OTHER INFORMATION: promoter motif - matrix

<400> SEQUENCE: 218
ggttatgaat agtaa                                                        15

<210> SEQ ID NO 219
<211> LENGTH: 27
<212> TYPE: DNA
<213> ORGANISM: Artificial sequence
```

```
<220> FEATURE:
<223> OTHER INFORMATION: promoter motif - matrix

<400> SEQUENCE: 219
tacttaacca tgagattcca acaaaga                                               27

<210> SEQ ID NO 220
<211> LENGTH: 27
<212> TYPE: DNA
<213> ORGANISM: Artificial sequence
<220> FEATURE:
<223> OTHER INFORMATION: promoter motif

<400> SEQUENCE: 220
tgaataacca tggaaccttta gtaaggc                                              27

<210> SEQ ID NO 221
<211> LENGTH: 27
<212> TYPE: DNA
<213> ORGANISM: Artificial sequence
<220> FEATURE:
<223> OTHER INFORMATION: promoter motif - matrix

<400> SEQUENCE: 221
aagataaccg ttgaagaaca atagtgt                                               27

<210> SEQ ID NO 222
<211> LENGTH: 27
<212> TYPE: DNA
<213> ORGANISM: Artificial sequence
<220> FEATURE:
<223> OTHER INFORMATION: promoter motif - matrix

<400> SEQUENCE: 222
tccacatgca tgaaattcca aaacagg                                               27

<210> SEQ ID NO 223
<211> LENGTH: 27
<212> TYPE: DNA
<213> ORGANISM: Artificial sequence
<220> FEATURE:
<223> OTHER INFORMATION: promoter motif - matrix

<400> SEQUENCE: 223
tctaaatcct ttcactaaaa agaatca                                               27

<210> SEQ ID NO 224
<211> LENGTH: 17
<212> TYPE: DNA
<213> ORGANISM: Artificial sequence
<220> FEATURE:
<223> OTHER INFORMATION: promoter motif - matrix

<400> SEQUENCE: 224
tcattacaga gagatga                                                          17

<210> SEQ ID NO 225
<211> LENGTH: 17
<212> TYPE: DNA
<213> ORGANISM: Artificial sequence
<220> FEATURE:
<223> OTHER INFORMATION: promoter motif - matrix

<400> SEQUENCE: 225
aacaaacaag tcatcat                                                          17
```

```
<210> SEQ ID NO 226
<211> LENGTH: 17
<212> TYPE: DNA
<213> ORGANISM: Artificial sequence
<220> FEATURE:
<223> OTHER INFORMATION: promoter motif - matrix

<400> SEQUENCE: 226
tatcaacaag tcatcat                                                    17

<210> SEQ ID NO 227
<211> LENGTH: 17
<212> TYPE: DNA
<213> ORGANISM: Artificial sequence
<220> FEATURE:
<223> OTHER INFORMATION: promoter motif - matrix

<400> SEQUENCE: 227
tcattcaact caaatca                                                    17

<210> SEQ ID NO 228
<211> LENGTH: 17
<212> TYPE: DNA
<213> ORGANISM: Artificial sequence
<220> FEATURE:
<223> OTHER INFORMATION: promoter motif

<400> SEQUENCE: 228
tcattgaaaa tatattt                                                    17

<210> SEQ ID NO 229
<211> LENGTH: 17
<212> TYPE: DNA
<213> ORGANISM: Artificial sequence
<220> FEATURE:
<223> OTHER INFORMATION: promoter motif

<400> SEQUENCE: 229
tcatttaacc tcgagtc                                                    17

<210> SEQ ID NO 230
<211> LENGTH: 17
<212> TYPE: DNA
<213> ORGANISM: Artificial sequence
<220> FEATURE:
<223> OTHER INFORMATION: promoter motif - matrix

<400> SEQUENCE: 230
gatagccacg tagaatt                                                    17

<210> SEQ ID NO 231
<211> LENGTH: 17
<212> TYPE: DNA
<213> ORGANISM: Artificial sequence
<220> FEATURE:
<223> OTHER INFORMATION: promoter motif - matrix

<400> SEQUENCE: 231
gatagccacg tagaaac                                                    17

<210> SEQ ID NO 232
<211> LENGTH: 17
<212> TYPE: DNA
<213> ORGANISM: Artificial sequence
<220> FEATURE:
<223> OTHER INFORMATION: promoter motif

<400> SEQUENCE: 232
```
ttatttcaag aagatgt                                                  17

<210> SEQ ID NO 233
<211> LENGTH: 17
<212> TYPE: DNA
<213> ORGANISM: Artificial sequence
<220> FEATURE:
<223> OTHER INFORMATION: promoter motif

<400> SEQUENCE: 233
ccattctaca tagggga                                                  17

<210> SEQ ID NO 234
<211> LENGTH: 17
<212> TYPE: DNA
<213> ORGANISM: Artificial sequence
<220> FEATURE:
<223> OTHER INFORMATION: promoter motif

<400> SEQUENCE: 234
tcaatccatc ttaattt                                                  17

<210> SEQ ID NO 235
<211> LENGTH: 17
<212> TYPE: DNA
<213> ORGANISM: Artificial sequence
<220> FEATURE:
<223> OTHER INFORMATION: promoter motif

<400> SEQUENCE: 235
caaacccatt tcaacaa                                                  17

<210> SEQ ID NO 236
<211> LENGTH: 15
<212> TYPE: DNA
<213> ORGANISM: Artificial sequence
<220> FEATURE:
<223> OTHER INFORMATION: promoter motif - matrix

<400> SEQUENCE: 236
aggaaaccca gcagg                                                    15

<210> SEQ ID NO 237
<211> LENGTH: 15
<212> TYPE: DNA
<213> ORGANISM: Artificial sequence
<220> FEATURE:
<223> OTHER INFORMATION: promoter motif

<400> SEQUENCE: 237
accgaaccca gccgg                                                    15

<210> SEQ ID NO 238
<211> LENGTH: 15
<212> TYPE: DNA
<213> ORGANISM: Artificial sequence
<220> FEATURE:
<223> OTHER INFORMATION: promoter motif - matrix

<400> SEQUENCE: 238
gtctaaccca attca                                                    15

<210> SEQ ID NO 239
<211> LENGTH: 15
<212> TYPE: DNA
<213> ORGANISM: Artificial sequence

```
<220> FEATURE:
<223> OTHER INFORMATION: promoter motif

<400> SEQUENCE: 239
tcataaccca ttcta                                                   15

<210> SEQ ID NO 240
<211> LENGTH: 15
<212> TYPE: DNA
<213> ORGANISM: Artificial sequence
<220> FEATURE:
<223> OTHER INFORMATION: promoter motif

<400> SEQUENCE: 240
tacaaaccca tttca                                                   15

<210> SEQ ID NO 241
<211> LENGTH: 17
<212> TYPE: DNA
<213> ORGANISM: Artificial sequence
<220> FEATURE:
<223> OTHER INFORMATION: promoter motif - matrix

<400> SEQUENCE: 241
tgatttgcaa atgcagt                                                 17

<210> SEQ ID NO 242
<211> LENGTH: 17
<212> TYPE: DNA
<213> ORGANISM: Artificial sequence
<220> FEATURE:
<223> OTHER INFORMATION: promoter motif - matrix

<400> SEQUENCE: 242
tgttgtttaa actaaat                                                 17

<210> SEQ ID NO 243
<211> LENGTH: 17
<212> TYPE: DNA
<213> ORGANISM: Artificial sequence
<220> FEATURE:
<223> OTHER INFORMATION: promoter motif - matrix

<400> SEQUENCE: 243
tcatatgtaa aatttga                                                 17

<210> SEQ ID NO 244
<211> LENGTH: 17
<212> TYPE: DNA
<213> ORGANISM: Artificial sequence
<220> FEATURE:
<223> OTHER INFORMATION: promoter motif

<400> SEQUENCE: 244
tggattgaaa aagagaa                                                 17

<210> SEQ ID NO 245
<211> LENGTH: 17
<212> TYPE: DNA
<213> ORGANISM: Artificial sequence
<220> FEATURE:
<223> OTHER INFORMATION: promoter motif

<400> SEQUENCE: 245
ggtcatgaaa agataca                                                 17
```

```
<210> SEQ ID NO 246
<211> LENGTH: 17
<212> TYPE: DNA
<213> ORGANISM: Artificial sequence
<220> FEATURE:
<223> OTHER INFORMATION: promoter motif

<400> SEQUENCE: 246
tggcgttgaa agctcag                                                  17

<210> SEQ ID NO 247
<211> LENGTH: 11
<212> TYPE: DNA
<213> ORGANISM: Artificial sequence
<220> FEATURE:
<223> OTHER INFORMATION: promoter motif - matrix

<400> SEQUENCE: 247
ggtttttgat a                                                        11

<210> SEQ ID NO 248
<211> LENGTH: 11
<212> TYPE: DNA
<213> ORGANISM: Artificial sequence
<220> FEATURE:
<223> OTHER INFORMATION: promoter motif - matrix

<400> SEQUENCE: 248
ggtttttgat a                                                        11

<210> SEQ ID NO 249
<211> LENGTH: 21
<212> TYPE: DNA
<213> ORGANISM: Artificial sequence
<220> FEATURE:
<223> OTHER INFORMATION: promoter motif - matrix

<400> SEQUENCE: 249
ttaattctac gtggctatcc c                                             21

<210> SEQ ID NO 250
<211> LENGTH: 21
<212> TYPE: DNA
<213> ORGANISM: Artificial sequence
<220> FEATURE:
<223> OTHER INFORMATION: promoter motif - matrix

<400> SEQUENCE: 250
tagtttctac gtggctatcc a                                             21

<210> SEQ ID NO 251
<211> LENGTH: 11
<212> TYPE: DNA
<213> ORGANISM: Artificial sequence
<220> FEATURE:
<223> OTHER INFORMATION: promoter motif - matrix

<400> SEQUENCE: 251
tgccgcgtac a                                                        11

<210> SEQ ID NO 252
<211> LENGTH: 11
<212> TYPE: DNA
<213> ORGANISM: Artificial sequence
<220> FEATURE:
<223> OTHER INFORMATION: promoter motif - matrix

<400> SEQUENCE: 252
```

```
tgccgcgtac a                                                        11

<210> SEQ ID NO 253
<211> LENGTH: 17
<212> TYPE: DNA
<213> ORGANISM: Artificial sequence
<220> FEATURE:
<223> OTHER INFORMATION: promoter motif - matrix

<400> SEQUENCE: 253
agctaggtta catttat                                                  17

<210> SEQ ID NO 254
<211> LENGTH: 15
<212> TYPE: DNA
<213> ORGANISM: Artificial sequence
<220> FEATURE:
<223> OTHER INFORMATION: promoter motif - matrix

<400> SEQUENCE: 254
tagaggttag tcgag                                                    15
```